United States Patent [19]
Hatton et al.

[11] Patent Number: 5,547,974
[45] Date of Patent: Aug. 20, 1996

[54] DERIVATIVES OF N-PHENYLPYRAZOLES

[75] Inventors: Leslie R. Hatton, Essex; Ian G. Buntain, Chelmsford; David W. Hawkins, Upminster; Edgar W. Parnell, Essex; Christopher J. Pearson, Essex; David A. Roberts, Essex, all of England

[73] Assignee: Rhone-Poulenc Agriculture Ltd., Essex, England

[21] Appl. No.: 57,669

[22] Filed: May 5, 1993

Related U.S. Application Data

[60] Division of Ser. No. 520,290, May 7, 1990, Pat. No. 5,232,940, which is a continuation-in-part of Ser. No. 445,153, Dec. 5, 1989, abandoned, and a continuation of Ser. No. 380,333, Jul. 17, 1989, abandoned, and Ser. No. 413,134, Sep. 27, 1989, abandoned, which is a continuation of Ser. No. 205,238, Jun. 10, 1988, abandoned, said Ser. No. 445,153, is a continuation of Ser. No. 943,132, Dec. 18, 1986, abandoned, said Ser. No. 380,333, is a continuation of Ser. No. 205,299, Jun. 10, 1988, abandoned.

[30] Foreign Application Priority Data

Dec. 20, 1985 [GB] United Kingdom ............. 85/31485
Jun. 12, 1987 [GB] United Kingdom ............. 87/13768
Jun. 12, 1987 [GB] United Kingdom ............. 87/13769

[51] Int. Cl.$^6$ ................. A61K 31/41; C07D 231/10
[52] U.S. Cl. ............. 514/406; 514/63; 514/407; 548/110; 548/369.4; 548/366.1; 548/371.4; 548/372.5; 548/373.1; 548/374.1; 548/375.1; 548/376.1; 548/377.1
[58] Field of Search .............. 548/369.4, 366.1, 548/371.4, 372.5, 373.1, 374.1, 375.1, 376.1, 377.1, 110; 514/406, 407, 63

[56] References Cited

U.S. PATENT DOCUMENTS

| | | | |
|---|---|---|---|
| 2,998,419 | 8/1961 | Dickinson, Jr. et al. | 548/377.1 |
| 3,254,093 | 5/1966 | Huisgen et al. | 548/377.1 |
| 3,282,954 | 11/1966 | Stein et al. | 514/406 |
| 3,423,424 | 1/1969 | Trepanier | 514/406 |
| 3,478,032 | 11/1969 | Arya | 548/377.1 |
| 3,760,084 | 9/1973 | Marsico, Jr. et al. | 548/373.1 |
| 3,869,274 | 3/1975 | Crovetti et al. | 548/376.1 |
| 4,008,249 | 2/1977 | Fischer et al. | 548/374.1 |
| 4,066,776 | 1/1978 | Jones et al. | 514/406 |
| 4,134,987 | 1/1979 | Huppatz | 548/377.1 |

(List continued on next page.)

FOREIGN PATENT DOCUMENTS

| | | | |
|---|---|---|---|
| 508225 | 11/1986 | Australia | 548/371.4 |
| 610085 | 4/1988 | Australia | 514/404 |
| 6680686 | 12/1988 | Australia | 548/362 |
| 87780 | 11/1986 | European Pat. Off. | 548/371.4 |
| 202169 | 11/1986 | European Pat. Off. | 548/371.4 |
| 0200872 | 11/1986 | European Pat. Off. | 548/371.4 |
| 0201852 | 11/1986 | European Pat. Off. | 548/371.4 |
| 204242 | 12/1986 | European Pat. Off. | 514/407 |
| 0216102 | 4/1987 | European Pat. Off. | 260/310 |

(List continued on next page.)

OTHER PUBLICATIONS

*J. Het. Chem.* 12, pp. 1199–1205 (1975), Southwick et al.
*II Farmaco Ed Scientifica* XXXVIII, pp. 274–282 (1983), Giori et al.
Chemical Abstract 91205651p (JP 7984032), 1980.
Elguero et al, *Bull. Soc. Chim. Fr.*, pp. 610–624, 2832–2845, 3727–3743 (1966), 3744–3752, 2617–2618.
Bouchet et al, *Tetrachedron* 35, pp. 1331–1338 (1979).
Bouchet et al, *Bull. Soc. Chim. Fr.*, pp. 4716–4728 (1967), 184–191 (1976).
Jacquier et al, *Bull. Soc. Chim. Fr.*, pp. 2977–2981 (1966).
Elguero et al, *J. Chim. Phys.* 63(9), pp. 1242–1246, 1967.
Katrizky et al, *J. Chem. Soc. Perkin Trans.* 2, pp. 1632–1636 (1975).
Shawali et al, *Indian J. Chem.* 14B, pp. 549–550 (1976).
Kreutzberger et al, *Arch. Pharm.* 313, pp. 906–912 (1980).
Tanaka et al, *J. Heterocycl. Chem.* 23, pp. 1535–1538 (1986).
Tominaga, *Yakugaku Zasshi* 95, pp. 378–382 (1975).
Bauer et al, *J. Flourine Chem.* 16, pp. 129–136 (1980).
Bouchet et al, *Tetrahedron Letters* 45, pp. 3317–3322 (1964).
Chemical Abstracts 113: 191343y (D'Silva et al), 1988.
Chemical Abstracts 114: 185494c (Roberts et al), 1990.
Chemical Abstracts 113: 59172n (Buntain et al), 1988.
CA 108: 167465r Preparation of . . . regulators. Stetter et al., p. 651, 1988.
CA 112: 35845n N–phenylpyrazole . . . and use. Buntain et al., p. 580, 1990.

*Primary Examiner*—Joseph K. McKane
*Attorney, Agent, or Firm*—Burns, Doane, Swecker & Mathis, L.L.P.

[57] ABSTRACT

N-Phenylpyrazole derivatives of the formula:

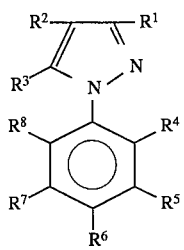

wherein $R^1$ represents cyano, nitro, halogen, acetyl or formyl;

$R^2$ represents $R^5SO_2$, $R^5SO$ or $R^5S$ in which $R^5$ is optionally halogen substituted alkyl, alkenyl or alkynyl;

$R^3$ represents a hydrogen atom or a group $NR^6R^7$ wherein $R^6$ and $R^7$ each represent hydrogen, alkyl, alkenylalkyl, alkynylalkyl, formyl, optionally halogen substituted alkanoyl, optionally halogen substituted alkoxycarbonyl, or alkoxymethyleneamino, halogen, or $R^6$ and $R^7$ together form a cyclic imide and $R^4$ represents a substituted phenyl group possess arthropodicidal, plant nematocidal, anthelmintic and anti-protozoal properties; their preparation, compositions containing them and their use are described.

18 Claims, No Drawings

U.S. PATENT DOCUMENTS

| | | | |
|---|---|---|---|
| 4,145,554 | 3/1979 | Jones et al. | 548/372.1 |
| 4,260,775 | 4/1981 | Plath et al. | 548/362 |
| 4,307,107 | 12/1981 | Maurer et al. | 548/372.1 |
| 4,382,947 | 5/1983 | Maurer et al. | 548/372.1 |
| 4,418,073 | 11/1983 | Maurer et al. | 548/372.1 |
| 4,614,533 | 9/1986 | Schallner et al. | 71/92 |
| 4,622,330 | 11/1986 | Bochis et al. | 514/313 |
| 4,746,354 | 5/1988 | Gehring et al. | 71/92 |
| 4,747,867 | 5/1988 | Gehring et al. | 71/92 |
| 4,752,326 | 6/1988 | Ohyama et al. | 548/362 |
| 4,764,202 | 8/1988 | Gehring et al. | 548/362 |
| 4,770,692 | 9/1988 | Stetter et al. | 71/92 |
| 4,771,066 | 9/1988 | Gehring et al. | 514/404 |
| 4,772,310 | 9/1988 | Stetter et al. | 71/92 |
| 4,803,215 | 2/1989 | Jensen-Korte et al. | 514/407 |
| 4,804,398 | 2/1989 | Gehring et al. | 71/92 |
| 4,804,675 | 2/1989 | Jensen-Korte et al. | 548/362 |
| 4,810,720 | 3/1989 | Jensen-Korte et al. | 514/407 |
| 4,820,725 | 4/1989 | Jensen-Korte et al. | 514/407 |
| 4,820,847 | 4/1989 | Gallenkamp et al. | 548/362 |
| 4,845,089 | 7/1989 | Lindig et al. | 514/404 |
| 4,918,085 | 4/1990 | D'Silva et al. | 514/407 |
| 4,945,165 | 7/1990 | Jensen-Korte et al. | 548/362 |

FOREIGN PATENT DOCUMENTS

| | | | |
|---|---|---|---|
| 216102 | 11/1987 | European Pat. Off. | 514/404 |
| 249033 | 2/1988 | European Pat. Off. | 514/404 |
| 2409753 | 9/1975 | Germany | 548/362 |
| 2922591 | 4/1980 | Germany | 548/362 |
| 3415385 | 11/1985 | Germany | 514/404 |
| 3606476 | 3/1986 | Germany | 548/362 |
| 3509567 | 9/1986 | Germany | 514/407 |
| 3602728 | 11/1986 | Germany | 548/372.1 |
| 3517843 | 11/1986 | Germany | 548/372.1 |
| 3520329 | 12/1986 | Germany | 71/92 |
| 3529829 | 2/1987 | Germany | 548/362 |
| 3600287 | 7/1987 | Germany | 514/407 |
| 3617554 | 11/1987 | Germany | 548/362 |
| 3625686 | 2/1988 | Germany | 548/362 |
| 12644 | 7/1964 | Japan | 514/407 |
| 5143758 | 4/1972 | Japan | 514/404 |
| 54-84032 | 7/1979 | Japan | 514/407 |
| 57167972 | 11/1987 | Japan | 548/362 |
| 64-12644 | 2/1988 | Japan | 514/404 |
| 158874 | 3/1986 | United Kingdom | 548/362 |

DERIVATIVES OF N-PHENYLPYRAZOLES

This application is a divisional of application Ser. No. 07/520,290, filed May 7, 1990, now U.S. Pat. No. 5,232,940, which is a continuation-in-part of application Ser. No. 07/445,153, filed Dec. 5, 1989, and now abandoned, which is in turn a continuation of Ser. No. 06/943,132, filed Dec. 18, 1986, and now abandoned; Ser. No. 07/520,290 further being a continuation of Ser. No. 07/380,333, filed Jul. 17, 1989, and now abandoned, which is in turn a continuation of Ser. No. 07/205,299, filed Jun. 10, 1988, and now abandoned; and Ser. No. 07/520,290 further being a continuation of Ser. No. 07/413,134, filed Sep. 27, 1989, and now abandoned, which is in turn a continuation of Ser. No. 07/205,238, filed Jun. 10, 1988, and now abandoned.

BACKGROUND OF THE INVENTION

This invention relates to N-phenylpyrazole derivatives, to compositions containing them and to the use of N-phenylpyrazole derivatives against arthropod, plant nematode, helminth and protozoan pests.

In J. Heter, Chem., 12 (1975) 1199–1205, P. L. Southwick and B. Dhawan have described experiments for the preparation of 4,6-diamino-pyrazolo[3,4-d]pyrimidines in the expectation that such pyrimidine derivatives would have useful pharmacological properties. They employed as starting materials 5-amino-4-cyanopyrazoles carrying on the 1-position a hydrogen atom, a methyl group, a hydroxyethyl group or a phenyl group substituted by one or more chlorine atoms and/or methyl groups, and on the 3-position a hydrogen atom, a methyl group or a phenyl or benzyl group. This publication contains no suggestion that compounds of general formula I possess or would be expected to possess activity against arthropods, helminths or plant nematodes.

Apparently these pyrazole compounds did not lead (according to the authors of the article) to useful therapeutic (viz. antimalarial) 4,6-diaminopyrazolo[3,4-d]pyrimidines.

U.S. Pat. No. 3,760,084 describes certain 5-amino-1-phenyl-pyrazoles as being useful for ameliorating inflammation in warm-blooded animals: the compounds carry on the 3-position hydrogen or a lower alkyl group and on the 4-position a carbamoyl or cyano group.

U.S. Pat. No. 3,869,274 describes certain 4-nitropyrazoles as being useful for the induction of abscission of fruit from fruit-bearing plants.

U.S. Pat. No. 4,066,776 describes a very extensive group of 1,4-disubstituted-3-nitropyrazoles as having antimicrobial, parasiticidal and herbicidal properties: the great biological activity of the compounds is stated to be limited to the 3-nitropyrazoles disclosed, the characterizing feature of the compounds being the 3-nitropyrazole nucleus.

Japanese Patent Publication No. 12644/64 describes a process for the preparation of 4-thiocyanatopyrazole derivatives which are stated to be useful as germicides.

Japanese Patent Publication No. 49-117502 describes certain pyrazole sulphonamides having anti-thrombogenic properties.

None of the foregoing publications describes or suggests that compounds of general formula I possess or would be expected to possess the activity against arthropods, helminths or plant nematodes which has been discovered by the inventors.

DETAILED DESCRIPTION OF THE PREFERRED EMBODIMENTS

The present invention provides N-phenylpyrazole derivatives of the general formula I wherein $R^1$ represents a cyano or nitro group, a halogen, i.e. fluorine, chlorine, bromine or iodine atom, an acetyl or formyl group, a straight- or branched-chain alkyl group containing from 1 to 4 carbon atoms which may be unsubstituted or substituted by one or more halogen atoms or a cycloalkyl group containing from 3 to 6 carbon atoms; $R^2$ represents a group R'SO$_2$, R'SO, or R'S in which R represents a straight- or branched-chain alkyl, alkenyl or alkynyl (preferably 1-(alkynyl)alkyl and more preferably alk-2-ynyl) group containing up to 6 carbon atoms which may be unsubstituted or substituted by one or more halogen atoms which may be the same or different or $R^2$ is a halogen, i.e., fluorine, chlorine, bromine or iodine atom, the cyano or nitro group, a cycloalkyl group containing from 3 to 5 carbon atoms, a straight- or branched-chain alkenyl group containing from 2 to 6 carbon atoms, the thiocyanato group, the sulphamoyl group which may be unsubstituted or substituted by one or two straight- or branched-chain alkyl groups which may be the same or different and contain from 1 to 6 carbon atoms, the carbamoyl group which may be unsubstituted or substituted by one or two straight- or branched-chain alkyl groups which may be the same or different and contain from 1 to 6 carbon atoms, a straight- or branched-chain alkoxycarbonyl containing from 2 to 7 carbon atoms, a straight- or branched-chain alkanoyl group containing from 2 to 7 carbon atoms, or a straight- or branched-chain alkyl group containing from 1 to 6 carbon atoms which may be unsubstituted or substituted by one or more halogen atoms; $R^3$ represents a hydrogen atom, or an amino group —NR"R''' wherein R" and R''', which may be the same or different, each represent a hydrogen atom or a straight- or branched-chain alkenylalkyl or alkynylalkyl group containing up to 5 carbon atoms, a straight- or branched-chain alkyl group (containing from 1 to 6 carbon atoms, and which may be unsubstituted or substituted by straight- or branched-chain alkoxycarbonyl of 2 to 5 carbon atoms), a formyl group, a straight- or branched-chain alkanoyl group (which contains from 2 to 7 carbon atoms and which may be optionally substituted with one or more halogen atoms) or R" and R''', together with the nitrogen atom to which they are attached, form a 5 to 6 membered cyclic imide and is unsubstituted or substituted with one or more halogen atoms, or $R^3$ represents a straight- or branched-chain alkoxycarbonyl group (which contains from 2 to 7 carbon atoms and is unsubstituted or substituted by one or more halogen atoms), or $R^3$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms, or $R^3$ represents a halogen, i.e., fluorine, chlorine, bromine or iodine, atom, cycloalkyl group containing from 3 to 6 carbon atoms, or cycloalkylcarbonyl group (which contains from 4 to 7 carbon atoms) or straight- or branched-chain alkoxy carbonyl group (which contains from 2 to 7 carbon atoms and themselves are unsubstituted or substituted by one or more halogen atoms), or $R^3$ represents a straight- or branched-chain alkylsulphenylamino group containing from 1 to 4 carbon atoms, or $R^3$ represents a straight- or branched-chain alkyl group containing from 1 to 4 carbon atoms, the carboxy group or a straight- or branched-chain alkylthio, alkylsulphinyl or alkylsulphonyl group containing from 1 to 6 carbon atoms which may be unsubstituted or substituted by one or more halogen atoms, or $R^3$ represents a straight- or branched-chained trialkylsilylmethyl group containing from 1 to 6 carbon atoms in each alkyl group which may be the same or different, a trialkylsilyl group containing from 1 to 6 carbon atoms in each alkyl group which may be the same or different, or the cyano or nitro group; $R^4$, $R^5$, $R^6$, $R^7$ and $R^8$ may be the same or different and represent a halogen, i.e., fluorine, chlorine, bromine or iodine, atom, a straight- or branched-chain alkyl or alkoxy group containing from 1 to 4 carbon atoms which may be unsubstituted or substituted by one or more halogen atoms (e.g. a trifluoromethyl or trifluoromethoxy group), a straight- or branched-chain alkylthio or alkylsulphinyl group containing from 1 to 4 carbon atoms which is substituted by one or more halogen atoms (e.g. a trifluoromethylthio or trifluoromethylsulphinyl group), the nitro or cyano group or a straight- or branched-chain alkylsulphonyl group containing from 1 to 4 carbon atoms which may be unsubstituted or substituted by one or more halogen atoms (e.g. the trifluoromethylsulphonyl group).

Compounds of general formula I, processes for their preparation, compositions containing them and methods for their use constitute features of the present invention.

It is to be understood that the halogen atoms on the phenyl group may be the same or different. When groups are substituted by more than one halogen atom it is to be understood that the halogen atoms may be the same or different.

In a preferred embodiment, the present invention provides N-phenylpyrazole derivatives of the general formula I wherein $R^1$ represents a cyano or nitro group, a halogen, i.e. fluorine, chlorine, bromine or iodine, atom, or an acetyl or formyl group; $R^2$ represents a group $R'SO_2$, $R'SO$, or $R'S$ in which $R'$ represents a straight or branched chain alkyl, alkenyl or alkynyl (preferably 1-(alkynyl)alkyl and more preferably alk-2-ynyl) group containing up to 4 carbon atoms which may be unsubstituted or substituted by one or more halogen atoms which may be the same or different; $R^3$ represents a hydrogen atom, or an amino group —NR"R"' wherein R" and R"', which may be the same or different, each represent a hydrogen atom or a straight or branched chain alkyl, alkenylalkyl or alkynylalkyl group containing up to 5 carbon atoms, a formyl group, a straight or branched chain alkanoyl group (which contains from 2 to 5 carbon atoms and which may be optionally substituted by one or more halogen atoms) or R" and R"' together with the nitrogen atom to which they are attached form a 5 or 6 membered cyclic imide, or represents a straight or branched-chain alkoxycarbonyl group (which contains from 2 to 5 carbon atoms and is unsubstituted or substituted by one or more halogen atoms), or $R^3$ represents a straight or branched-chain alkoxymethyleneamino group containing from 2 to 5 carbon atoms which may be unsubstituted or substituted on methylene by a straight or branched-chain alkyl group containing from 1 to 4 carbon atoms, or represents a halogen, i.e. fluorine, chlorine, bromine or iodine, atom; and $R^4$ is a fluorine, chlorine, bromine or iodine atom; $R^6$ is a straight or branched chain alkyl or alkoxy group containing from 1 to 4 carbon atoms which may be unsubstituted or substituted by one or more halogen atoms which may be the same or different (the trifluoromethyl and trifluoromethoxy groups are preferred), or a chlorine or bromine atom; and $R^8$ is hydrogen or a fluorine, chlorine, bromine or iodine atom, with the exclusion of the compound wherein $R^1$ represents cyano, $R^2$ represents methanesulphonyl, $R^3$ represents amino, $R^4$ and $R^8$ are chloro and $R^6$ is trifluoromethyl (i.e., the phenyl ring is 2,6-dichloro-4-trifluoromethylphenyl), which have valuable activity against arthropod, plant nematode, helminth and protozoan pests, more particularly by ingestion of above preferred compound(s) by the arthropods.

Highly preferred compounds of the first embodiment of general formula I are those wherein $R^2$ represents an alkyl-sulphonyl/sulphinyl/thio group which is optionally halogen substituted containing from 1 to 4 carbon atoms, or an alkenyl- or alkynyl-sulphonyl/sulphinyl/thio group which is optionally halogen substituted and contains up to 4 carbon atoms, preferably a trifluoromethylthio or trifluoro methylsulphinyl group, $R^3$ represents the hydrogen atom, an amino or methylamino group and $R^1$ represents a halogen atom or preferably the cyano or nitro group.

Compounds of general formula I wherein the phenyl group contains the trifluoromethyl or trifluoromethoxy group, and $R^2$ represents an optionally halogenated alkyl-sulphonyl/sulphinyl/thio group containing from 1 to 4 carbon atoms are highly preferred. Trifluoromethylthio, trifluoromethylsulphinyl and trifluoromethanesulphonyl are especially preferred for $R^2$.

Highly preferred compounds of the first embodiment of general formula I are those with phenyl substitution which is 2,4,6-trichloro, 2,6-dichloro-4-difluoromethoxy, 2-chloro-4-trifluoromethyl, 2-bromo-6-chloro-4-trifluoromethyl, 2,6-dibromo-4-trifluoromethyl or 2-bromo-4-trifluoromethyl.

Compounds of general formula I with 2,6-dichloro-4-trifluoromethyl or 2,6-dichloro-4-trifluoromethoxy substitution of the phenyl group are especially preferred.

Compounds of the first embodiment of general formula I which are of particular interest are:
1. 5-Amino-3-cyano-1-(2,6-dichloro-4-trifluoromethylphenyl)- 4-trifluoromethylthiopyrazole.
2. 5-Amino-3-cyano-1-(2,6-dichloro-4-trifluoromethoxyphenyl)- 4-trifluoromethylthiopyrazole.
3. 5-Amino-3-cyano-1-(2,6-dichloro-4-difluoromethoxyphenyl)- 4-trifluoromethylthiopyrazole.
4. 5-Amino-1-(2-chloro-4-trifluoromethylphenyl)-3 -cyano-4-trifluoromethylthiopyrazole.
5. 5-Amino-3-cyano-1-(2,4,6-trichlorophenyl)-4-trifluoromethylthiopyrazole.
6. 5-Amino-3-cyano-1-(2,6-dibromo-4 -trifluoromethylphenyl)-4-trifluoromethylthiopyrazole.
7. 5-Amino-1-(2-bromo-4-trifluoromethylphenyl)-3 -cyano-4-trifluoromethylthiopyrazole.
8. 5-Amino-3-cyano-1-(2,6-dichloro-4 -trifluoromethylphenyl)-4-difluoromethylthiopyrazole.
9. 5-Amino-3-cyano-1-(2,6-dichloro-4 -trifluoromethylphenyl)-4-heptafluoropropylthiopyrazole.
10. 5-Amino-1-(2-bromo-6-chloro-4 -trifluoromethylphenyl)-3-cyano-4-trifluoromethylthiopyrazole.
11. 5-Amino-3-cyano-1-(2,6-dichloro-4 -trifluoromethylphenyl)-4-trichloromethylthiopyrazole.
12. 5-Amino-3-chloro-1-(2,6-dichloro-4 -trifluoromethylphenyl)-4-trifluoromethylthiopyrazole.
13. 5-Amino-3-bromo-1-(2,6-dichloro-4 -trifluoromethylphenyl)-4-trifluoromethylthiopyrazole.
14. 5-Amino-1-(2,6-dichloro-4-trifluoromethylphenyl)-3 -fluoro-4-trifluoromethylthiopyrazole.
15. 5-Amino-4-chlorodifluoromethylthio-3-cyano-1-(2,6 -dichloro-4-trifluoromethylphenyl)pyrazole.
16. 5-Chloro-3-cyano-1-(2,6-dichloro-4-trifluoromethylphenyl)- 4-trifluoromethylthiopyrazole.
17. 5-Amino-3-chloro-1-(2,6-dichloro-4 -trifluoromethylphenyl)-4-methanesulphonylpyrazole.
18. 3-Cyano-1-(2,6-dichloro-4-trifluoromethylphenyl)-5 -ethoxymethyleneamino-4-trifluoromethylthiopyrazole.
19. 3-Cyano-1-(2,6-dichloro-4-trifluoromethylphenyl)-5 -ethoxyethylideneamino-4-trifluoromethylthiopyrazole.
20. 3-Cyano-1-(2,6-dichloro-4-trifluoromethylphenyl)-5 -ethoxymethyleneamino-4-methanesulphonylpyrazole.
21. 5-Acetamido-3-cyano-1-(2,6-dichloro-4-trifluoromethylphenyl)- 4-trifluoromethylthiopyrazole.

22. 3-Cyano-1-(2,6-dichloro-4-trifluoromethylphenyl)-5-bis(propionyl)amino-4-trifluoromethylthiopyrazole.
23. 3-Cyano-1-(2,6-dichloro-4-trifluoromethylphenyl)-5-propionamido-4-trifluoromethylthiopyrazole.
24. 5-Acetamido-3-cyano-1-(2,6-dichloro-4-trifluoromethylphenyl)-4-methanesulphonylpyrazole.
25. 3-Cyano-1-(2,6-dichloro-4-trifluoromethylphenyl)-4-trifluoromethylthio-5-trimethylacetamidopyrazole.
26. 3-Cyano-1-(2,6-dichloro-4-trifluoromethylphenyl)-5-bis(methoxycarbonyl)amino-4-trifluoromethylthiopyrazole.
27. 3-Cyano-1-(2,6-dichloro-4-trifluoromethylphenyl)-5-bis(ethoxycarbonyl)amino-4-trifluoromethylthiopyrazole.
28. 5-Chloroacetamido-3-cyano-1-(2,6-dichloro-4-trifluoromethylphenyl)-4-trifluoromethylthiopyrazole.
29. 3-Cyano-1-(2,6-dichloro-4-trifluoromethylphenyl)-5-bis(ethoxycarbonyl)amino-4-methanesulphonylpyrazole.
30. 3-Cyano-1-(2,6-dichloro-4-trifluoromethylphenyl)-4-methanesulphonyl-5-trimethylacetamidopyrazole.
31. 3-Cyano-1-(2,6-dichloro-4-trifluoromethylphenyl)-5-dimethylamino-4-trifluoromethylthiopyrazole.
32. 3-Cyano-1-(2,6-dichloro-4-trifluoromethylphenyl)-5-isopropylamino-4-trifluoromethylthiopyrazole.
33. 3-Cyano-1-(2,6-dichloro-4-trifluoromethylphenyl)-5-propylamino-4-trifluoromethylthiopyrazole.
34. 3-Cyano-1-(2,6-dichloro-4-trifluoromethylphenyl)-5-dipropylamino-4-trifluoromethylthiopyrazole.
35. 3-Cyano-1-(2,6-dichloro-4-trifluoromethylphenyl)-5-bis(propargyl)amino-4-trifluoromethylthiopyrazole.
36. 3-Cyano-1-(2,6-dichloro-4-trifluoromethylphenyl)-5-methylamino-4-methanesulphonylpyrazole.
37. 5-Bromo-3-cyano-1-(2,6-dichloro-4-trifluoroethylphenyl)-4-trifluoromethanesulphonylpyrazole.
38. 5-Bromo-3-cyano-1-(2,6-dichloro-4-trifluoromethylphenyl)-4-trifluoromethylthiopyrazole.
39. 5-Bromo-3-cyano-1-(2,6-dichloro-4-trifluoromethylphenyl)-4-methanesulphonylpyrazole.
40. 5-Amino-3-bromo-1-(2,6-dichloro-4-trifluoromethylphenyl)-4-methanesulphonylpyrazole.
41. 3-Bromo-1-(2,6-dichloro-4-trifluoromethylphenyl)-4-methanesulphonylpyrazole.
42. 3-Cyano-1-(2,6-dichloro-4-trifluoromethylphenyl)-4-trifluoromethylthiopyrazole.
43. 3-Cyano-1-(2,6-dichloro-4-trifluoromethylphenyl)-4-trifluoromethanesulphonylpyrazole.
44. 3-Cyano-1-(2,6-dichloro-4-trifluoromethoxyphenyl)-4-trifluoromethylthiopyrazole.
45. 3-Cyano-1-(2,6-dichloro-4-trifluoromethylphenyl)-4-methanesulphonylpyrazole.
46. 3-Cyano-1-(2,6-dichloro-4-trifluoromethylphenyl)-5-iodo-4-trifluoromethylthiopyrazole.
47. 3-Cyano-1-(2,6-dichloro-4-trifluoromethylphenyl)-5-iodo-4-trifluoromethanesulphonylpyrazole.
48. 5-Amino-1-(2,6-dichloro-4-trifluoromethylphenyl)-3-iodo-4-methanesulphonylpyrazole.
49. 1-(2,6-Dichloro-4-trifluoromethylphenyl)-3-iodo-4-methanesulphonylpyrazole.
50. 1-(2,6-Dichloro-4-trifluoromethylphenyl)-3-iodo-4-trifluoromethylthiopyrazole.
51. 5-Amino-3-cyano-1-(2,6-dichloro-4-trifluoromethylphenyl)-4-trifluoromethanesulphonylpyrazole.
52. 5-Amino-3-cyano-1-(2,6-dichloro-4-trifluoromethylphenyl)-4-trifluoromethylsulphinylpyrazole.
53. 5-Amino-3-cyano-1-(2,6-dichloro-4-trifluoromethoxyphenyl)-4-trifluoromethanesulphonylpyrazole.
54. 5-Amino-3-cyano-1-(2,6-dichloro-4-trifluoromethoxyphenyl)-4-trifluoromethylsulphinylpyrazole.
55. 3-Cyano-1-(2,6-dichloro-4-trifluoromethylphenyl)-4-trifluoromethylsulphinylpyrazole.
56. 5-Amino-3-cyano-1-(2,6-dichloro-4-trifluoromethylphenyl)-4-(1-methylprop-2-ynylsulphinyl)pyrazole.
57. 5-Amino-3-cyano-1-(2,6-dichloro-4-trifluoromethylphenyl)-4-methylsulphinylpyrazole.
58. 5-Amino-3-cyano-1-(2,6-dichloro-4-trifluoromethylphenyl)-4-isopropylsulphinylpyrazole.
59. 5-Amino-3-bromo-1-(2,6-dichloro-4-trifluoromethylphenyl)-4-trifluoromethylsulphinylpyrazole.
60. 5-Amino-4-tert-butanesulphonyl-3-cyano-1-(2,6-dichloro-4-trifluoromethylphenyl)pyrazole.
61. 3-Cyano-1-(2,6-dichloro-4-trifluoromethylphenyl)-5-propylamino-4-trifluoromethylsulphonylpyrazole.
62. 5-Acetamido-3-cyano-1-(2,6-dichloro-4-trifluoromethylphenyl)-4-trifluoromethanesulphonylpyrazole.
63. 1-(2,6-Dichloro-4-trifluoromethylphenyl)-4-methanesulphonyl-3-nitropyrazole.
64. 5-Amino-1-(2,6-dichloro-4-trifluoromethylphenyl)-4-methanesulphonyl-3-nitropyrazole.
65. 1-(2,6-Dichloro-4-trifluoromethylphenyl)-3-nitro-4-trifluoromethylsulphinylpyrazole.
66. 5-Amino-1-(2-bromo-6-chloro-4-trifluoromethylphenyl)-3-cyano-4-methanesulphonylpyrazole.
67. 5-Amino-1-(2,6-dichloro-4-trifluoromethoxyphenyl)-3-cyano-4-methanesulphonylpyrazole.
68. 3-Acetyl-5-amino-1-(2,6-dichloro-4-trifluoromethylphenyl)-4-methanesulphonylpyrazole.
69. 5-Amino-3-cyano-1-(2,6-dichloro-4-trifluoromethylphenyl)-4-methylthiopyrazole.
70. 5-Amino-3-cyano-1-(2,6-dichloro-4-trifluoromethylphenyl)-4-ethylthiopyrazole.
71. 5-Amino-3-cyano-1-(2,6-dichloro-4-trifluoromethylphenyl)-4-propylthiopyrazole.
72. 5-Amino-3-cyano-1-(2,6-dichloro-4-trifluoromethylphenyl)-4-isopropylthiopyrazole.
73. 5-Amino-3-cyano-1-(2,6-dichloro-4-trifluoromethylphenyl)-4-(2-methylpropylthio)pyrazole.
74. 5-Amino-3-cyano-1-(2,6-dichloro-4-trifluoromethylphenyl)-4-(1-methylpropylthio)pyrazole.
75. 4-Allylthio-5-amino-3-cyano-1-(2,6-dichloro-4-trifluoromethylphenyl)pyrazole.
76. 5-Amino-3-cyano-1-(2,6-dichloro-4-trifluoromethylphenyl)-4-(prop-2-ynylthio)pyrazole.
77. 5-Amino-3-cyano-1-(2,6-dichloro-4-trifluoromethylphenyl)-4-(1-methylprop-2-ynylthio)pyrazole.
78. 5-Amino-3-bromo-1-(2,6-dichloro-4-trifluoromethylphenyl)-4-methylthiopyrazole.
79. 5-Amino-3-cyano-1-(2,6-dichloro-4-trifluoromethylphenyl)-4-tert-butylthiopyrazole.
80. 5-Amino-3-bromo-1-(2,6-dichloro-4-trifluoromethylphenyl)-4-methylsulphinylpyrazole.
81. 5-Amino-3-cyano-1-(2,6-dichloro-4-trifluoromethylphenyl)-4-ethanesulphonylpyrazole.
82. 3-Cyano-1-(2,6-dichloro-4-trifluoromethylphenyl)-5-methylamino-4-trifluoromethylthiopyrazole.
83. 3-Cyano-1-(2,6-dichloro-4-trifluoromethylphenyl)-5-(N-ethoxycarbonyl-N-methyl)amino-4-trifluoromethylthiopyrazole.
84. 3-Cyano-1-(2,6-dichloro-4-trifluoromethylphenyl)-5-trifluoroacetamido-4-trifluoromethylthiopyrazoie.
85. 3-Cyano-1-(2,6-dichloro-4-trifluoromethylphenyl)-5-(ethoxycarbonylamino)-4-trifluoromethylthiopyrazole.
86. 3-Acetyl-1-(2,6-dichloro-4-trifluoromethylphenyl)-4-trifluoromethylthiopyrazole.

87. 1-(2,6-Dichloro-4-trifluoromethylphenyl)-3-formyl-4-trifluoromethylthiopyrazole.
88. 5-Amino-1-(2,6-dichloro-4-trifluoromethylphenyl)-3-formyl-4-trifluoromethylthiopyrazole.
89. 3-Cyano-1-(2,6-dichloro-4-trifluoromethylphenyl)-5-fluoro-4-trifluoromethanesulphonylpyrazole.
90. 5-Amino-3-cyano-4-dichlorofluoromethylthio-1-(2,6-dichloro-4-trifluoromethylphenyl)pyrazole.
91. 5-Amino-3-chloro-1-(2,6-dichloro-4-trifluoromethylphenyl)- 4-trifluoromethanesulphonylpyrazole.
92. 5-Amino-3-cyano-1-(2,6-dichloro-4-trifluoromethylphenyl)- 4-pentafluoroethylthiopyrazole.
93. 3-Cyano-1-(2,6-dichloro-4-trifluoromethylphenyl)-5-dimethylamino-4-trifluoromethylsulphinylpyrazole.
94. 3-Cyano-1-(2,6-dichloro-4-trifluoromethylphenyl)-5-iodo-4-trifluoromethylsulphinylpyrazole.
95. 5-Bromo-3-cyano-1-(2,6-dichloro-4-trifluoromethylphenyl)- 4-trifluoromethylsulphinylpyrazole.
96. 5-Acetamido-3-cyano-1-(2,6-dichloro-4-trifluoromethylphenyl)- 4-trifluoromethylsulphinylpyrazole.
97. 3-Cyano-1-(2,6-dichloro-4 -trifluoromethylphenl)-5-bis(ethoxycarbonyl)amino-4-trifluoromethanesulphonylpyrazole.
98. 3-Cyano-1-(2,6,dichloro-4-trifluoromethylphenyl)-5-ethoxycarbonylamino-4-trifluoromethanesulphonylpyrazole.
99. 3-Cyano-1-(2,6-dichloro-4-trifluoromethylphenyl)-5-ethoxymethyleneamino-4-trifluoromethanesulphonylpyrazole.
100. 5-Amino-4-(2-chloro-1,1,2-trifluoroethylthio)-3 -cyano-1-(2,6-dichloro-4-trifluoromethylphenyl)pyrazole.
101. 3-Cyano-1-(2,6-dichloro-4-trifluoromethylphenyl)-5-dimethylamino-4-trifluoromethanesulphonylpyrazole.

The numbers 1 to 101 are assigned to the above compounds for identification and reference hereinafter.

In a second embodiment, the invention provides 4 -nitro-N-phenylpyrazole derivatives of the formula XXVI wherein $R^8$ represents a fluorine, chlorine or bromine atom, $R^6$ represents a chlorine or bromine atom, or a straight- or branched-chain alkyl or alkoxy group containing from 1 to 4 carbon atoms which may be unsubstituted or substituted by one or more halogen atoms (e.g. a trifluoromethyl or trifluoromethoxy group), $R^4$ is as defined for $R^8$ or represents the hydrogen atom, $R^1$ represents a halogen, i.e. fluorine, chlorine, bromine or iodine, atom, or the cyano or nitro group, $R^3$ represents the hydrogen atom or the amino group —NR"R'" wherein R" and R'", which may be the same or different, each represents the hydrogen atom or a straight- or branched-chain alkyl group containing from 1 to 6 carbon atoms, the formyl group, a straight- or branched-chain alkanoyl group containing from 2 to 7 carbon atoms (or R" and R'" together form a 5 or 6 membered cyclic imide with the nitrogen atom to which they are attached) which may be unsubstituted or substituted by one or more halogen atoms, or a straight- or branched-chain alkoxycarbonyl group containing from 2 to 7 carbon atoms, which may be unsubstituted or substituted by one or more halogen atoms, or $R^3$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms, or represents a fluorine, chlorine, bromine or iodine atom, have valuable activity against arthropod, plant nematode, helminth and protozoan pests, more particularly by ingestion of the compound(s) of formula XXVI by the arthropods.

Highly preferred compounds of the second embodiment of formula XXVI are those wherein $R^4$, $R^6$ and $R^8$ together represent 2,4,6-trichloro, 2,6-dichloro-4-trifluoromethyl or 2,6-dichloro-4-trifluoromethoxy substitution of the phenyl group.

Highly preferred compounds of the second embodiment are those wherein $R^3$ represents the hydrogen atom or —NR"R'", preferably an amino or acetamido group, $R^4$, $R^6$ and $R^8$ together represent 2-6-dichloro-4-trifluoromethyl or 2,6-dichloro-4-trifluoromethoxy substitution of the phenyl group, and $R^1$ is as hereinbefore defined.

The following compounds of formula XXVI are of particular interest as insecticides:
102. 5-Acetamido-3-bromo-1-(2,6-dichloro-4-trifluoromethylphenyl)- 4-nitropyrazole.
103. 5-Acetamido-3-chloro-1-(2,6-dichloro-4-trifluoromethylphenyl)- 4-nitropyrazole.
104. 5-Acetamido-3-cyano-1-(2,6-dichloro-4-trifluoromethylphenyl)- 4-nitropyrazole.
105. 5-Amino-3-bromo-1-(2,6-dichloro-4-trifluoromethylphenyl)- 4-nitropyrazole.
106. 5-Amino-3-chloro-1-(2,6-dichloro-4-trifluoromethylphenyl)- 4-nitropyrazole.
107. 5-Amino-3-cyano-1-(2,6-dichloro-4-trifluoromethylphenyl)- 4-nitropyrazole.
108. 5-Bromo-3-cyano-1-(2,6-dichloro-4-trifluoromethylphenyl)- 4-nitropyrazole.

The numbers 102 to 108 are assigned to the above compounds for identification and reference hereinafter.

In a third preferred embodiment, the N-phenylpyrazole derivatives of the general formula I depicted hereinafter include compounds wherein $R^2$ represents a halogen, i.e. fluorine, chlorine, bromine or iodine, atom, the cyano or nitro group or a group $R'SO_2$, R'SO or R'S in which R' represents a straight- or branched-chain alkyl group containing from 1 to 6 carbon atoms which may be unsubstituted or substituted by one or more halogen atoms, a cycloalkyl group containing from 3 to 5 carbon atoms, a straight- or branched-chain alkenyl group containing from 2 to 6 carbon atoms, the thiocyanato group, the sulphamoyl group which may be unsubstituted or substituted by one or two straight- or branched-chain alkyl groups which may be the same or different and contain from 1 to 6 atoms, the carbamoyl group which may be unsubstituted or substituted by one or two straight- or branched-chain alkyl groups which may be the same or different and contain from 1 to 6 carbon atoms, a straight- or branched-chain alkoxycarbonyl group containing from 2 to 7 carbon atoms, a straight- or branched-chain alkanoyl group containing from 2 to 7 carbon atoms, or a straight- or branched-chain alkyl group containing from 1 to 6 carbon atoms which may be unsubstituted or substituted by one or more halogen atoms, $R^3$ represents the hydrogen atom, or the amino group —NR"R'" wherein R" and R'", which may be the same or different, each represents a hydrogen atom or a straight- or branched-chain alkyl group (containing from 1 to 6 carbon atoms, and which may be unsubstituted or substituted by straight- or branched-chain alkoxycarbonyl of 2 to 5 carbon atoms), cycloalkyl group containing from 3 to 6 carbon atoms, formyl group, straight- or branched-chain alkanoyl group (which contain from 2 to 7 carbon atoms or together form a 5 or 6 membered cyclic imide with the nitrogen atom to which they are attached and themselves may be unsubstitued or substituted by one or more halogen atoms) or cycloalkylcarbonyl group (which contain from 4 to 7 carbon atoms) or straight- or branched-chain alkoxycarbonyl groups (which contain from 2 to 7 carbon atoms and themselves are unsubstituted or substituted by one or more halogen atoms), or $R^3$ represents a straight- or branched-chain alkylsulphenylamino group containing from 1 to 4 carbon atoms, a straight- or branched-chain alkoxymethyleneamino group containing from 2 to 5 carbon atoms which may be unsubstituted or substituted on methylene by a straight- or branched-chain alkyl group containing from 1 to 4 carbon atoms, or represents a halogen, i.e. fluorine, chlorine, bromine or iodine, atom, a straight- or branched-chain alkyl group containing from 1 to 4 carbon atoms, the carboxy group, or a straight- or branched-chain alkylthio, alkylsulphinyl or alkylsulphonyl group containing from 1 to 6 carbon atoms which may be unsubstituted or substituted by one or more halogen atoms, or represents a straight- or branched-chain trialkylsilylmethyl group containing from 1 to 6 carbon atoms in each alkyl group which may be the same or different, a trialkylsilyl group containing from 1 to 6 carbon atoms in each alkyl group which may be the same or different or the cyano or nitro group, $R^4$—$R^8$ each represent a halogen, i.e. fluorine, chlorine, bromine or iodine atom, a straight- or branched-chain alkyl or alkoxy group containing from 1 to 4 carbon atoms which may be unsubstituted or substituted by one or more halogen atoms (e.g. a trifluoromethyl or trifluoromethoxy group), a straight- or branched-chain alkylthio or alkylsulphinyl group containing from 1 to 4 carbon atoms which is substituted by one or more halogen atoms (e.g. a trifluoromethylthio or trifluoromethylsulphinyl group), the nitro or cyano group or a straight- or branched-chain alkylsulphonyl group containing from 1 to 4 carbon atoms which may be unsubstituted or substituted by one or more halogen atoms (e.g. the trifluoromethylsulphonyl group), and $R^1$ represents a halogen, i.e. fluorine, chlorine, bromine or iodine, atom, a cyano or nitro group or a straight- or branched-chain alkyl group containing from 1 to 4 carbon atoms which may be unsubstituted or substituted by one or more halogen atoms, or a cycloalkyl group containing from 3 to 6 carbon atoms, and, when $R^3$ represents a carboxy group, salts thereof with pesticidally-acceptable bases provided that $R^1$, $R^2$ and $R^3$ do not simultaneously represent three groups of the same genus selected from the genera (i) nitro, (ii) cyano, (iii) halogen and (iv) unsubstituted alkyl, have valuable activity against arthropod, plant nematode and helminth pests, more particularly by ingestion of the compound(s) of general formula I by the arthropods.

By the term "salts with pesticidally-acceptable bases" is meant salts the cations of which are known and accepted in the art for the formation of salts of pesticidally active acids for agricultural or horticultural use. When intended for application to vertebrates to combat infection or infestation by arthropods or helminths, the salts with bases used will be non-toxic. By the term "non-toxic" is meant salts with bases the cations of which are innocuous to the vertebrates at the doses administered and which do not vitiate the beneficial effects produced by the anion.

Preferably, the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. It is to be understood that where reference is made in the present specification to the compounds of general formula I such reference is intended to include also the salts with pesticidally-acceptable bases of compounds of general formula I where appropriate.

Preferred compounds of general formula I are those with phenyl substitution which is 2,4,6-trichloro, 2,3,5,6-tetrachloro, 2-chloro-4-trifluoromethyl, 2,3,5,6-tetrafluoro- 4-trifluoromethyl, 2,6-dichloro-4-trifluoromethylthio, 2-chloro-3,5,6-trifluoro-4-trifluoromethyl, 2,6 -dichloro-3,5-difluoro-4-trifluoromethyl, 2,6-dichloro-4-nitro, 2,6-dichloro-4-trifluoromethylsulphinyl, 2,6 -dichloro-4-methanesulphonyl and 2,6-dichloro-4-trifluoromethanesulphonyl.

Compounds of general formula I wherein $R^4$—$R^8$ represent 2,6-dichloro-4-trifluoromethyl or 2,6-dichloro-4-trifluoromethoxy substitution of the phenyl group are especially preferred.

Preferred compounds are those where (a) $R^2$ and $R^1$ each represent a cyano group and $R^3$ represents the hydrogen atom, the amino group —NR"R"' or an alkylsulphenylamino group, an alkoxymethyleneamino group which may be unsubstituted or substituted on methylene by an alkyl group, a halogen atom, an alkyl group, the carboxy group, an alkylthio, alkylsulphinyl or alkylsulphonyl group which is optionally halogen substituted, a trialkylsilylmethyl group, a trialkylsilyl group or the nitro group;

(b) $R^2$ represents an alkylsulphonyl group which is optionally halogen substituted, a cycloalkylsulphonyl group or an alkenylsulphonyl group, $R^3$ represents the hydrogen atom, the amino group —NR"R"' or an alkylsulphenylamino group, an alkoxymethyleneamino group which is unsubstituted or substituted on methylene by an alkyl group, a halogen atom, an alkyl group, the carboxy group, an alkylthio, alkylsulphinyl or alkylsulphonyl group which is optionally halogen substituted, a trialkylsilylmethyl group, a trialkylsilyl group or the cyano or nitro group and $R^1$ represents a halogen atom or the cyano or nitro group;

(c) $R^1$ represents the nitro group, $R^2$ represents the cyano or nitro group, a carbamoyl group or an alkoxycarbonyl group and $R^3$ represents the hydrogen atom, a halogen atom, an alkyl group, the carboxy group, an alkylthio, alkylsulphinyl or alkylsulphony group which is optionally halogen substituted, a trialkylsilylmethyl group, a trialkylsilyl group or the nitro group;

(d) $R^1$ represents a halogen atom, $R^2$ represents the cyano or nitro group, a carbamoyl group or an alkoxycarbonyl group and $R^3$ represents the hydrogen atom, the amino group —NR"R"' or an alkylsulphenylamino group, an alkoxymethyleneamino group which is unsubstituted or substituted on methylene by an alkyl group, a halogen atom, an alkyl group, the carboxy group, an alkylthio, alkylsulphinyl or alkylsulphonyl group which is optionally halogen substituted, a trialkylsilylmethyl group, a trialkylsilyl group or the nitro group; and (e) $R^1$ represents an alkyl group which is unsubstituted or substituted by one or more halogen atoms or a cycloalkyl group, $R^2$ represents a halogen atom, the cyano or nitro group, a group R'SO$_2$, R'SO or R'S, the thiocyanato group, a sulphamoyl group, a carbamoyl group, an alkoxycarbonyl group, an alkanoyl group or an alkyl group which is unsubstituted or substituted by one or more halogen atoms. $R^3$ represents the hydrogen atom, the amino group —NR"R"' or an alkylsulphenylamino group, an alkoxymethyleneamino group which is unsubstituted or substituted on methylene by an alkyl group, a halogen atom, an alkyl group, the carboxy group, an alkylthio, alkylsulphinyl or alkylsuphonyl group which is optionally halogen substituted, a trialkylsilylmethyl group, a trialkylsilyl group or the cyano or nitro group.

It will be appreciated that the groups listed above are as hereinbefore defined earlier in the specification.

Compounds of general formula I wherein $R^1$ represents a trifluoromethyl or methyl group are also preferred in this third embodiment.

Compounds of the third embodiment of general formula I which are of particular interest against arthropods are:

109. 5-Amino-3,4-dicyano-1-(2,4,6-trichlorophenyl)pyrazole
110. 5-Amino-1-(2,6-dichloro-4-trifluoromethylphenyl)- 3,4-dicyanopyrazole
111. 5-Amino-3,4-dicyano-1-(2,3,5,6-tetrachlorophenyl)pyrazole
112. 5-Amino-4-cyano-1-(2,6-dichloro-4-trifluoromethylphenyl)- 3-methylpyrazole
113. 5-Amino-4-cyano-1-(2,6-dichloro-4-trifluoromethylphenyl)- 3-trifluoromethylpyrazole
114. 5-Amino-3-chloro-4-cyano-1-(2,6-dichloro-4-trifluoromethylphenyl)pyrazole
115. 5-Amino-3-bromo-4-cyano-1-(2,6-dichloro-4-trifluoromethylphenyl)pyrazole
116. 5-Amino-3-iodo-4-cyano-1-(2,6-dichloro-4-trifluoromethylphenyl)pyrazole
117. 4-Cyano-1-(2,6-dichloro-4-trifluoromethylphenyl)-3 -methyl-5-ethanesulphenylaminopyrazole
118. 4-Cyano-1-(2,6-dichloro-4-trifluoromethylphenyl)-3 -methyl-5-methoxymethyleneaminopyrazole
119. 4-Cyano-1-(2,6-dichloro-4-trifluoromethylphenyl)-3 -methyl-5-propoxymethyleneaminopyrazole
120. 5-Acetamido-1-(2,6-dichloro-4-trifluoromethylphenyl)- 3,4-dicyanopyrazole
121. 5-Dichloroacetamido-1-(2,6-dichlcro-4 -trifluoromethylphenyl)-3,4-dicyanopyrazole
122. 5-Cyclopropylcarbonamido-1-(2,6-dichloro-4 -trifluoromethylphenyl)-3,4-dicyanopyrazole
123. 5-Pentanamido-1-(2,6-dichloro-4-trifluoromethylphenyl)- 3,4-dicyanopyrazole
124. 5-Propionamido-1-(2,6-dichloro-4-trifluoromethylphenyl)- 3,4-dicyanopyrazole
125. 5-Amino-1-(2-chloro-4-trifluoromethylphenyl)-3,4-dicyanopyrazole
126. 5-Amino-3,4-dicyano-1-(2,3,5,6-tetrafluoro-4-trifluoromethylphenyl)pyrazole
127. 5-Amino-4-cyano-1-(2,6-dichloro-4-trifluoromethylphenyl)- 3-pentafluoroethylpyrazole
128. 5-Amino-3-chlorodifluoromethyl-1-(2,6-dichloro-4 -trifluoromethylphenyl)-4-cyanopyrazole
129. 5-Amino-1-(2,6-dichloro-4-trifluoromethylphenyl)-4 -cyano-3-difluoromethylpyrazole
130. 5-Amino-1-(2,6-dichloro-4-trifluoromethylphenyl)-4 -methanesulphonyl-3-trifluoromethylpyrazole
131. 5-Amino-4-carbamoyl-1-(2,6-dichloro-4 -trifluoromethylphenyl)-3-trifluoromethylpyrazole
132. 5-Amino-1-(2,6-dichloro-4-trifluoromethylphenyl)-4 -methoxycarbonyl-3-trifluoromethylpyrazole
133. 5-Acetamido-4-cyano-1-(2,6-dichloro-4 -trifluoromethylphenyl)-3-trifluoromethylpyrazole
134. 1-(2,6-Dichloro-4-trifluoromethylphenyl)-3,4 -dicyano-5-(2,2-dimethylpropionamido)-pyrazole
135. 4-Cyano-1-(2,6-dichloro-4-trifluoromethylphenyl)-5 -ethoxymethyleneamino-3-trifluoromethylpyrazole
136. 4-Cyano-1-(2,6-dichloro-4-trifluoromethylphenyl)-5 -dimethylamino-3-trifluoromethylpyrazole
137. 4-Cyano-1-(2,6-dichloro-4-trifluoromethylphenyl)-5 -ethoxycarbonylmethylamino-3-trifluoromethylpyrazole
138. 4-Cyano-5-methylamino-1-(2,6-dichloro-4-trifluoromethylphenyl)-3-trifluoromethylpyrazole
139. 4-Cyano-1-(2,6-dichloro-4-trifluoromethylphenyl)-5 -(2,2-dimethylpropionamido)-3-trifluoromethylpyrazole
140. 5-Amino-4-bromo-1-(2,6-dichloro-4-trifluoromethylphenyl)- 3-trifluoromethylpyrazole
141. 5-Bromo-4-cyano-1-(2,6-dichloro-4-trifluoromethylphenyl)- 3-trifluoromethylpyrazole
142. 5-Amino-4-cyano-1-(2,6-dichloro-4-trifluoromethylphenyl)- 3-fluoromethylpyrazole
143. 5-Amino-1-(2,6-dichloro-4-trifluoromethylphenyl)-4 -nitro-3-trifluoromethylpyrazole
144. 5-Amino-4-cyano-1-(2,6-dichloro-4-trifluoromethoxyphenyl)- 3-trifluoromethylpyrazole
145. 4-Cyano-1-(2,6-dichloro-4-trifluoromethylphenyl)-5 -bis(ethoxycarbonyl)amino-3-trifluoromethylpyrazole
146. 4-Cyano-1-(2,6-dichloro-4-trifluoromethylphenyl)-5 -bis(cyclopropanecarbonyl)amino-3-trifluoromethylpyrazole
147. 4-Cyano-1-(2,6-dichloro-4-trifluoromethylphenyl)-5 -cyclopropanecarbonamido-3-trifluoromethylpyrazole
148. 5-Amino-4-chloro-1-(2,6-dichloro-4-trifluoromethylphenyl)- 3-trifluoromethylpyrazole
149. 4-Cyano-1-(2,6-dichloro-4-trifluoromethylphenyl)-5 -ethoxycarbonylamino-3-trifluoromethylpyrazole
150. 4-Cyano-1-(2,6-dichloro-4-trifluoromethylphenyl)-3-trifluoromethylpyrazole
151. 4-Cyano-1-(2,6-dichloro-4-trifluoromethylphenyl)-5 -iodo-3-trifluoromethylpyrazole
152. 4-Cyano-1-(2,6-dichloro-4-trifluoromethylphenyl)-5 -methyl-3-trifluoromethylpyrazole
153. 5-Amino-1-(2,6-dichloro-4-trifluoromethylphenyl)-4 -(N,N-dimethylsulphamoyl)-3-trifluoromethylpyrazole
154. 5-Amino-4-cyano-3-cyclopropyl-1-(2,6-dichloro-4-trifluoromethylphenyl)pyrazole
155. 5-Amino-4-cyano-1-(2,6-dichloro-4-trifluoromethylphenyl)- 3-heptafluoropropylpyrazole
156. 5-Amino-3,4-dicyano-1-(2,6-dichloro-4-trifluoromethylthiophenyl)pyrazole
157. 5-Amino-1-(2-chloro-3,5,6-trifluoro-4-trifluoromethylphenyl)- 3,4-dicyanopyrazole
158. 5-Amino-1-(2,6-dichloro-3,5-difluoro-4-trifluoromethylphenyl)- 3,4-dicyanopyrazole
159. 5-Amino-1-(2,6-dichloro-4-trifluoromethoxyphenyl) 3,4-dicyanopyrazole
160. 5-Amino-4-cyano-3-ethyl-1-(2,6-dichloro-4-trifluoromethylphenyl)pyrazole
161. 5-Amino-1-(2,6-dichloro-4-trifluoromethylphenyl)-4 -methanesulphonyl-3-methylpyrazole
162. 5-Amino-1-(2,6-dichloro-4-trifluoromethylphenyl)-3 -methyl-4-ethoxycarbonylpyrazole
163. 5-Amino-1-(2,6-dichloro-4-trifluoromethoxyphenyl)-4 -methanesulphonyl-3-methylpyrazole
164. 5-Amino-1-(2-chloro-3,5,6-trifluoro-4 -trifluoromethylphenyl)-4-cyano-3-trifluoromethylpyrazole
165. 5-Amino-4-cyano-1-(2,6-dichloro-4 -trifluoromethylthiophenyl)-3-trifluoromethylpyrazole
166. 5-Amino-3-chlorofluoromethyl-4-cyano-1-(2,6 -dichloro-4-trifluoromethylphenyl)pyrazole
167. 5-Amino-4-cyano-1-(2,6-dichloro-3,5-difluoro-4 -trifluoromethylphenyl)-3-trifluoromethylpyrazole
168. 4-Cyano-1-(2,6-dichloro-4-trifluoromethylphenyl)-5(1-ethoxyethylideneamino)-3-methylpyrazole
169. 4-Cyano-1-(2,6-dichloro-4-trifluoromethylphenyl)-3 -methyl-5-succinimidopyrazole
170. 5-Acetamido-1-(2,6-dichloro-4-trifluoromethylphenyl)- 4-methanesulphonyl-3-trifluoromethylpyrazole
171. 5-Acetamido-1-(2,6-dichloro-4-trifluoromethylphenyl)- 3-methyl-4-methanesulphonylpyrazole
172. 5-Amino-1-(2,6-dichloro-4-nitrophenyl)-3,4-dicyanopyrazole 173. 1-(2,6-Dichloro-4-trifluoromethylphenyl)-3,4-dicyano-5-methylaminopyrazole
174. 1-(2,6-Dichloro-4-trifluoromethylphenyl)-3,4-dicyano-5-ethylaminopyrazole
175. 4-Cyano-1-(2,6-dichloro-4-trifluoromethylphenyl)-5-(N-methyl-N-ethoxycarbonylamino)-3-trifluoromethylpyrazole
176. 4-Cyano-1-(2,6-dichloro-4-trifluoromethylphenyl)-5-(N-acetyl-N-trimethylacetylamino)-3-trifluoromethylpyrazole
177. 4-Cyano-1-(2,6-dichloro-4-trifluoromethylphenyl)-5-(N-propionyl-N-trimethylacetylamino)-3-trifluoromethylpyrazole
178. 1-(2,6-Dichloro-4-trifluoromethylphenyl)-4-nitro-3-trifluoromethyl-5-trimethylacetylaminopyrazole
179. 1-(2,6-Dichloro-4-trifluoromethylphenyl)-5-ethoxycarbonylamino-4-nitro-3-trifluoromethylpyrazole
180. 3-Chloro-1-(2,6-dichloro-4-trifluoromethylphenyl)-4-cyano-5-trimethylacetylaminopyrazole
181. 3-Chloro-1-(2,6-dichloro-4-trifluoromethylphenyl)-4-cyano-5-bis(ethoxycarbonyl)aminopyrazole
182. 3-Chloro-1-(2,6-dichloro-4-trifluoromethylphenyl)-4-cyano-5-ethoxycarbonylaminopyrazole
183. 4-Cyano-diacetylamino-1-(2,6-dichloro-4-trifluoromethylphenyl)-3-trifluoromethylpyrazole
184. 5-(N-Acetyl-N-ethoxycarbonylamino)-4-cyano-1-(2,6-dichloro-4-trifluoromethylphenyl)-3-trifluoromethylpyrazole
185. 1-(2,6-Dichloro-4-trifluoromethylphenyl)-5-bis(ethoxycarbonyl)amino-3,4-dicyanopyrazole
186. 1-(2,6-Dichloro-4-trifluoromethylphenyl)-5-bis(ethoxycarbonyl)amino-4-methanesulphonyl-3-trifluoromethylpyrazole
187. 1-(2,6-Dichloro-4-trifluoromethylphenyl)-5-ethoxycarbonylamino-4-methanesulphonyl-3-trifluoromethylpyrazole
188. 1-(2,6-Dichloro-4-trifluoromethylphenyl)-3,4-dicyano-5-ethoxycarbonylaminopyrazole
189. 5-Amino-1-(2,6-dichloro-4-trifluoromethylphenyl)-4-iodo-3-trifluoromethylpyrazole
190. 5-Amino-1-(2,6-dichloro-4-trifluoromethylphenyl)-4-iodo-3-methylpyrazole
191. 5-Amino-1-(2,6-dichloro-4-trifluoromethylphenyl)-3-methyl-4-nitropyrazole
192. 5-Acetamido-1-(2,6-dichloro-4-trifluoromethylphenyl)-4-nitro-3-trifluoromethylpyrazole
193. 1-(2,6-Dichloro-4-trifluoromethylphenyl)-4-nitro-3-trifluoromethylpyrazole
194. 1-(2,6-Dichloro-4-trifluoromethylphenyl)-3-methyl-4-methanesulphonylpyrazole
195. 4-Cyano-1-(2,6-dichloro-4-trifluoromethylphenyl)-3-fluoropyrazole
196. 1-(2,6-Dichloro-4-trifluoromethylphenyl)-4-methanesulphonyl-3-trifluoromethylpyrazole
197. 5-Chloro-1-(2,6-dichloro-4-trifluoromethylphenyl)-4-cyano-3-trifluoromethylpyrazole
198. 5-Amino-1-(2,6-dichloro-4-trifluoromethylphenyl)-4-(N-ethylsulphamoyl)-3-trifluoromethylpyrazole
199. 5-Amino-1-(2,6-dichloro-4-trifluoromethylphenyl)-4-(N-methylsulphamoyl)-3-trifluoromethylpyrazole
200. 1-(2,6-Dichloro-4-trifluoromethylphenyl)-4-cyano-3-nitropyrazole
201. 1-(2,6-Dichloro-4-trifluoromethylphenyl)-3,4-dicyano-5-nitropyrazole
202. 5-Amino-1-(2,6-dichloro-4-trifluoromethylphenyl)-4-cyano-3-fluoropyrazole
203. 5-Amino-3-chloro-1-(2,6-dichloro-4-trifluoromethoxyphenyl)-4-cyanopyrazole
204. 5-Amino-3-chloro-4-cyano-1-(2,6-dichloro-3,5-difluoro-4-trifluoromethylphenyl)pyrazole
205. 4-Cyano-1-(2,6-dichloro-4-trifluoromethylphenyl)-3-trifluoromethyl-5-trimethylsilylpyrazole
206. 5-tert.-Butyldimethylsilyl-4-cyano-1-(2,6-dichloro-4-trifluoromethylphenyl)-3-trifluoromethylpyrazole
207. 4-Cyano-1-(2,6-dichloro-4-trifluoromethylphenyl)-5-methylthio-3-trifluoromethylpyrazole
208. 4-Cyano-1-(2,6-dichloro-4-trifluoromethylphenyl)-3-trifluoromethyl-5-trifluoromethylthiopyrazole
209. 5-Carboxy-4-cyano-1-(2,6-dichloro-4-trifluoromethylphenyl)-3-trifluoromethylpyrazole
210. 1-(2,6-Dichloro-4-trifluoromethylphenyl)-4-nitro-3-trifluoromethyl-5-trimethylsilylpyrazole
211. 4-Cyano-1-(2,6-dichloro-4-trifluoromethylphenyl)-3-trifluoromethyl-5-trimethylsilylmethylpyrazole
212. 4-Cyano-1-(2,6-dichloro-4-trifluoromethylphenyl)-5-methoxycarbonylamino-3-trifluoromethylpyrazole
213. 1-(2,6-Dichloro-4-trifluoromethylphenyl)-4,5-dicyano-3-trifluoromethylpyrazole
214. 5-Amino-3-cyano-1-(2,6-dichloro-4-trifluoromethylphenyl)-4-methanesulphonylpyrazole
215. 4-Acetyl-1-(2,6-dichloro-4-trifluoromethylphenyl)-3-trifluoromethylpyrazole
216. 5-Amino-1-(2,6-dichloro-4-trifluoromethylphenyl)-4-methylsulphinyl-3-trifluoromethylpyrazole
217. 5-Amino-1-(2,6-dichloro-4-trifluoromethylphenyl)-4-ethylsulphinyl-3-trifluoromethylpyrazole
218. 5-Amino-1-(2,6-dichloro-4-trifluoromethylphenyl)-4-ethylsulphinyl-3-methylpyrazole
219. 5-Amino-4-cyano-1-(2,6-dichloro-4-trifluoromethylsulphinylphenyl)-3-trifluoromethylpyrazole
220. 4-Cyano-1-(2,6-dichloro-4-trifluoromethylphenyl)-5-methylsulphinyl-3-trifluoromethylpyrazole
221. 5-Amino-1-(2,6-dichloro-4-trifluoromethylphenyl)-4-ethylsulphonyl-3-trifluoromethylpyrazole
222. 5-Amino-1-(2,6-dichloro-4-trifluoromethylphenyl)-4-ethylsulphonyl-3-methylpyrazole
223. 5-Amino-1-(2,6-dichloro-4-trifluoromethylphenyl)-3-methyl-4-propanesulphonylpyrazole
224. 5-Amino-1-(2,6-dichloro-4-trifluoromethylphenyl)-4-trichloromethanesulphonyl-3-methylpyrazole
225. 5-Amino-1-(2,6-dichloro-4-trifluoromethylphenyl)-4-ethylthio-3-methylpyrazole
226. 5-Amino-1-(2,6-dichloro-4-trifluoromethylphenyl)-3-methyl-4-methylthiopyrazole
227. 5-Amino-1-(2,6-dichloro-4-trifluoromethylphenyl)-4-n-propylthio-3-methylpyrazole
228. 5-Amino-1-(2,6-dichloro-4-trifluoromethylphenyl)-4-ethylthio-3-trifluoromethylpyrazole
229. 5-Amino-1-(2,6-dichloro-4-trifluoromethylphenyl)-4-methylthio-3-trifluoromethylpyrazole
230. 5-Amino-1-(2,6-dichloro-4-trifluoromethylphenyl)-4-thiocyanato-3-trifluoromethylpyrazole
231. 5-Amino-1-(2,6-dichloro-4-trifluoromethylphenyl)-3-methyl-4-thiocyanatopyrazole
232. 5-Amino-4-cyano-1-(2,6-dichloro-4-methanesulphonylphenyl)-3-trifluoromethylpyrazole
233. 5-Amino-1-(2,6-dichloro-4-trifluoromethylphenyl)-3-methyl-4-trichloromethylthiopyrazole
234. 4-Cyano-1-(2,6-dichloro-4-trifluoromethanesulphonylphenyl)-5-nitro-3-trifluoromethylpyrazole
235. 1-(2,6-Dichloro-4-trifluoromethylphenyl)-4-difluoromethyl-3-trifluoromethylpyrazole
236. 5-Amino-1-(2,6-dichloro-4-trifluoromethylphenyl)-4-methyl-3-trifluoromethylpyrazole.

The numbers 109 and 236 are assigned to the above compounds for identification and reference hereinafter.

Especially preferred compounds of the third embodiment of general formula I are numbered: 110, 130, 145, 161, 179, 214 and 226.

According to a feature of the present invention, there is provided a method for the control of arthropod, plant nematode, helminth or protozoan pests at a locus which comprises the treatment of the locus (e.g. by application or administration) with an effective amount of a compound of general formula I, wherein the various symbols are as hereinbefore defined. The compounds of general formula I may, in particular, be used in the field of veterinary medicine and livestock husbandry and in the maintenance of public health against arthropods, helminths or protozoa which are parasitic internally or externally upon vertebrates, particularly warm,blooded vertebrates, for example man and domestic animals, e.g. cattle, sheep, goats, equines, swine, poultry, dogs, cats and fishes, for example Acarina, including ticks (e.g. *Ixodes* spp., *Boophilus* spp. e.g. *Boophilus microplus.*, *Amblyomma* spp., *Hyalomma* spp., *Rhipicephalus* spp. e.g. *Rhipicephalus appendiculatus*, *Haemaphysalis* spp., *Dermacemtor* spp., *Ornithodorus* spp. (e.g. *Ornithodorus moubata* and mites (e.g. *Damalinia* spp., *Dermahyssus gallinae*, *Sarcoptes* spp. e.g. *Sarcoptes scabiei*, *Psoroptes* spp., *Chorioptes* spp., *Demodex* spp., *Eutrombicula* spp.,); Diptera (e.g. *Aedes* spp., *Anopheles* spp., *Musca* spp., *Hypoderma* spp., *Gasterophilus* spp., *Simulium* spp.); Hemiptera (e.g. *Triatoma* spp.); Phthiraptera (e.g. *Damalinia* spp., *Linognathus* spp.); Siphonaptera (e.g. *Ctenocephalides* spp.); Dictyoptera (e.g. *Periplaneta* spp., *Blatella* spp.); Hymenoptera (e.g. *Monomorium pharaonis*); for example against infections of the gastro-intestinal tract caused by parasitic nematode worms, for example members of the family Trichostrongylidae, *Nippostrongylus brasiliensis*, *Trichinella spiralis*, *Haemonchus contortus*, *Trichostrongylus colubriformis*, *Nematodirus battus*, *Ostertagia circumcincta*, *Trichostrongylus axei*, *Cooperia* spp. and *Hymenolepis nana;* in the control and treatment of protozoal diseases caused by, for example, *Eimeria* spp. e.g. *Eimeria tenella*, *Eimeria acervulina*, *Eimeria brunetti*, *Eimeria maxima* and *Eimeria necatrix*, *Trypanosoma cruzi*, *Leishmania* spp., *Plasmodium* spp., *Babesia* spp., *Trichomonadidae* spp., *Histomonas* spp., *Giardia* spp., *Toxoplasma* spp., *Entamoeba histolytica* and *Theileria* spp.; in the protection of stored products, for example cereals, including grain and flour, groundnuts, animal feedstuffs, timber and household goods, e.g. carpets and textiles, against attack by arthropods, more especially beetles, including weevils, moths and mites, for example *Ephestia* spp. (flour moths), *Anthrenus* spp. (carpet beetles), *Tribolium* spp. (flour beetles), *Sitophilus* spp. (grain weevils) and *Acarus* spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, *Reticulitermes* spp., *Heterotermes* spp., *Coptotermes* spp.; in agriculture, against adults, larvae and eggs of Lepidoptera (butterflies and moths), e.g. *Heliothis* spp. such as *Heliothis virescens* (tobacco budworm), *Heliothis armigera* and *Heliothis zea*, *Spodoptera* spp. such as *S. exempta*, *S. littoralis* (Egyptian cotton worm), *S. eridania* (southern army worm), *Mamestra configurata* (bertha army worm); *Earias* spp. e.g. *E. insulana* (Egyptian bollworm), *Pectinophora* spp. e.g. *Pectinophora gossypiella* (pink bollworm), *Ostrinia* spp. such as *O. nubilalis* (European cornborer), *Trichoplusia ni* (cabbage looper), *Pieris* spp. (cabbage worms), *Laphygma* spp. (army worms), *Agrotis* and *Amathes* spp. (cutworms), *Wiseana* spp. (porina moth), *Chilo* spp. (rice stem borer), *Tryporyza* spp. and *Diatraea* spp. (sugar cane borers and rice borers), *Sparganothis pilleriana* (grape berry moth), *Cydia pomonella* (codling moth), *Archips* spp. (fruit tree tortrix moths), *Plutella xylostella* (diamond back moth); against adult and larvae of Coleoptera (beetles) e.g. *Hypothenemus hampei* (coffee berry borer), *Hylesinus* spp. (bark beetles), *Anthonomus grandis* (cotton boll weevil), *Acalymma* spp. (cucumber beetles), *Lema* spp., *Psylliodes* spp., *Leptinotarsa decemlineata* (Colorado potato beetle), *Diabrotica* spp. (corn rootworms), *Gonocephalum* spp. (false wire worms), *Agriotes* spp. (wireworms), *Dermolepida* and *Heteronychus* spp. (white grubs), *Phaedon cochleariae* (mustard beetle), *Lissorhoptrus oryzophilus* (rice water weevil), *Meligethes* spp. (pollen beetles), *Ceutorhynchus* spp., *Rhynchophorus* and *Cosmopolites* spp. (root weevils); against Hemiptera e.g. *Psylla* spp., *Bemisia* spp., *Trialeurodes* spp., *Aphis* spp., *Myzus* spp., *Megoura viciae*, *Phylloxera* spp., *Adelges* spp., *Phorodon humuli* (hop damson aphid), *Aeneolamia* spp., *Nephotettix* spp. (rice leaf hoppers), *Empoasca* spp., *Nilaparvata* spp., *Perkinsiella* spp., *Pyrilla* spp., *Aonidiella* spp. (red scales), *Coccus* spp., *Pseucoccus* spp., *Helopeltis* spp. (mosquito bugs), *Lygus* spp., *Dysdercus* spp., *Oxycarenus* spp., *Nezara* spp.; Hymenoptera e.g. *Athalia* spp. and *Cephus* spp. (saw flies), *Atta* spp. (leaf cutting ants); Diptera e.g. *Hylemyia* spp. (root flies), *Atherigona* spp. and *Chlorops* spp. (shoot flies), *Phytomyza* spp. (leaf miners), *Ceratitis* spp. (fruit flies); Thysanoptera such as *Thrips tabaci;* Orthoptera such as *Locusta* and *Schistocerca* spp. (locusts) and crickets e.g. *Gryllus* spp. and *Acheta* spp.; Collembola e.g. *Sminthurus* spp. and *Onychiurus* spp. (springtails), Isoptera e.g. *Odontotermes* spp. (termites), Dermaptera e.g. *Forficula* spp. (earwigs) and also other arthropods of agricultural significance such as Acari (mites) e.g. *Tetranychus* spp., *Panonychus* spp. and *Bryobia* spp. (spider mites), *Eriophyes* spp. (gall mites), *Polyphacotarsonemus* spp.; *Blaniulus* spp. (millipedes), *Scutigerella* spp. (symphilids), *Oniscus* spp. (woodlice) and *Triops* spp. (crustacea); nematodes which attack plants and trees of importance to agriculture, forestry and horticulture either directly or by spreading bacterial, viral, mycoplasma or fungal diseases of the plants, root-knot nematodes such as *Meloidogyne* spp. (e.g. *M. incognita*); cyst nematodes such as *Globodera* spp. (e.g. *G. rostochiensis*); *Heterodera* spp. (e.g. *H. avenae*); *Radopholus* spp. (e.g. *R. similis*); lesion nematodes such as *Pratylenchus* spp. (e.g. *P. pratensis*); *Belonolaimus* spp. (e.g. *B. gracilis*); *Tylenchulus* spp. (e.g. *T. semipenetrans*); *Rotylenchulus* spp. (e.g. *R. reniformis*); *Rotylenchus* spp. (e.g. *R. robustus*); *Helicotylenchus* spp. (e.g. *H. multicinctus*); *Hemicycliophora* spp. (e.g. *H. gracilis*); *Criconemoides* spp. (e.g. *C. similis*); *Trichodorus* spp. (e.g. *T. primitivus*); dagger nematodes such as *Xiphinema* spp. (e.g. *X. diversicaudatum*), *Longidorus* spp. (e.g. *L. elongatus*); *Hoplolaimus* spp. (e.g *H. coronatus*); *Aphelenchoides* spp. (e.g. *A. ritzema-bosi, A. besseyi*); stem and bulb eelworms such as *Ditylenchus* spp. (e.g. *D. dipsaci*).

The invention also provides a method for the control of arthropod or nematode pests of plants which comprises the application to the plants or to the medium in which they grow of an effective amount of a compound of general formula I or a pesticidally acceptable salt thereof.

For the control of arthropods and nematodes, the active compound is generally applied to the locus in which arthropod or nematode infestation is to be controlled at a rate of about 0.1 kg to about 25 kg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 1 g to 1000 g/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of general formula I may be applied in solid or liquid compositions to the soil principally to contol those nematodes dwelling therein but also to the foliage principally to control those nematodes attacking the aerial parts of the plants (e.g. *Aphelenchoides* spp. and *Ditylenchus* spp. listed above).

The compounds of general formula I are of value in controlling pests which feed on parts of the plant remote from the point of application, e.g. leaf feeding insects are killed by the subject compounds applied to roots.

In addition the compounds may reduce attacks on the plant by means of antifeeding or repellent effects.

The compounds of general formula I are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids), or termites, for example, *Reticulitermes* spp., *Heterotermes* spp., *Coptotermes* spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies. The compounds of general formula I are particularly useful in controlling arthropods, helminths or protozoa which are present inside domestic host animals or which feed in or on the skin or suck the blood of the animal, for which purpose they may be administered orally, parenterally, percutaneously or topically.

Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection.

Administration of a small amount of a compound of general formula I preferably by combination with poultry feed is effective in preventing or greatly reducing the incidence of coccidiosis. The compounds are effective against both the cecal form (caused by *E. tenella*) and the intestinal forms (principally caused by *E. acervulina, E. brunetti, E. maxima* and *E. necatrix*).

The compounds of general formula I also exert an inhibitory effect on the oocysts by greatly reducing the number and or the sporulation of those produced.

The compositions hereinafter described for topical application to man and animals and in the protection of stored products, household goods, property and areas of the general environment may, in general, alternatively be employed for application to growing crops and crop growing loci and as a seed dressing.

Suitable means of applying the compounds of general formula I include:

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their faeces;

to growing crops as foliar sprays, dusts, granules, fogs and foams; also as suspensions of finely divided and encapsulated compounds of general formula I;

as soil and root treatments by liquid drenches, dusts, granules, smokes and foams; and as seed dressings by liquid slurries and dusts.

The compounds of general formula I may be applied to control arthropods, helminths or protozoa in compositions of any type known to the art suitable for internal or external administration to vertebrates or application for the control of arthropods in any premises or indoor or outdoor area, containing as active ingredient at least one compound of general formula I in association with one or more compatible diluents or adjuvants appropriate for the intended use. All such compositions may be prepared in any manner known to the art.

Compositions suitable for administration to vertebrates or man include preparations suitable for oral, parenteral, percutaneous, e.g. pour-on, or topical administration.

Compositions for oral administration comprise one or more of the compounds of general formula I in association with pharmaceutically acceptable carriers or coatings and include, for example, tablets, pills, capsules, pastes, gels, drenches, mediocated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Solid or liquid baits suitable for controlling arthropods comprise one or more compounds of general formula I and a carrier or diluent which may include a food substance or some other substance to induce comsumption by the arthropod.

Liquid compositions include water miscible concentrates, emulsifiable concentrates, flowable suspensions, wettable or soluble powders containing one or more compounds of general formula I which may be used to treat substrates or sites infested or liable to infestation by arthropods including premises, outdoor or indoor storage or processing areas, containers or equipment and standing or running water.

Solid homogenous or heterogenous compositions containing one or more compounds of general formula I, for example granules, pellets, briquettes or capsules, may be used to treat standing or running water over a period of time. A similar effect may be achieved using trickle or intermittent feeds of water dispersible concentrates as described herein.

Compositions in the form of aerosols and aqueous or non-aqueous solutions or dispersions suitable for spraying, fogging and low- or ultra-low volume spraying may also be used.

Suitable solid diluents which may be used in the preparation of compositions suitable for applying the compounds of general formula I include aluminium silicate, kieselguhr, corn husks, tricalcium phosphate, powdered cork, absorbent carbon black, magnesium silicate, a clay such as kaolin, bentonite or attapulgite, and water soluble polymers and such solid compositions may, if desired, contain one or more compatible wetting, dispersing, emulsifying or colouring agents which, when solid, may also serve as diluent.

Such solid compositions, which may take the form of dusts, granules or wettable powders, are generally prepared by impregnating the solid diluents with solutions of the compound of general formula I in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g. gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octylphenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of general formula I may take the form of solutions, suspensions and emulsions of the compounds of general formula I optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of general formula I may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of general formula I which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavouring agents, dyes and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with, the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetridazole.

The compositions for application to control arthropod, plant nematode, helminth or protozoan pests usually contain from 0.00001% to 95%, more particularly from 0.0005% to 50%, by weight of one or more compounds of general formula I or of total active ingredients (that is to say the compound(s) of general formula I together with other substances toxic to arthropods and plant nematodes, anthelmintics, anticoccidials, synergists, trace elements or stabilisers). The actual compositions employed and their rate of application will be selected to achieve the desired effect(s) by the farmer, livestock producer, medical or veterinary practitioner, pest control operator or other person skilled in the art. Solid and liquid compositions for application topically to animals, timber, stored products or household goods usually contain from 0.00005% to 90%, more particularly from 0.001% to 10%, by weight of one or more compounds of general formula I. For administration to animals orally or parenterally, including percutaneously solid and liquid compositions normally contain from 0.1% to 90% by weight of one or more compound of general formula I. Medicated feedstuffs normally contain from 0.001% to 3% by weight of one or more compounds of general formula I. Concentrates and supplements for mixing with feedstuffs normally contain from 5% to 90%, and preferably from 5% to 50%, by weight of one or more compounds of general formula I. Mineral salt licks normally contain from 0.1% to 10% by weight of one or more compounds of general formula I.

Dusts and liquid compositions for application to livestock, persons, goods, premises or outdoor areas may contain 0.0001% to 15%, and more especially 0.005% to 2.0%, by weight of one or more compounds of general formula I. Suitable concentrations in treated waters are between 0.0001 ppm and 20 ppm, and more especially 0.001 ppm to 5.0 ppm. of one or more compounds of general formula I and may also be used therapeutically in fish farming with appropriate exposure times. Edible baits may contain from 0.01% to 5% and preferably 0.01% to 1.0%, by weight of one or more compounds of general formula I.

When administered to vertebrates parenterally, orally or by percutaneous or other means, the dosage of compounds of general formula I will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

In experiments on activity against arthropods carried out on representative compounds of the first preferred embodiment, the following results (wherein ppm indicates the concentration of the compound in parts per million of the test solution applied) have been obtained:

Test 1

One or more dilutions of the compounds to be tested were made in 50% aqueous acetone.

(a) Test species: *Plutella xylostella* (Diamond-back Moth) and *Phaedon cochleariae* (Mustard Beetle)

Turnip leaf discs were set in agar in petri-dishes and infected with 10 larvae (2nd instar Plutella or 3rd instar Phaedon). Four replicate dishes were assigned to each treatment and were sprayed under a Potter Tower with the appropriate test dilution. Four or five days after treatment the dishes were removed from the constant temperature (25° C.) room in which they had been held and the mean percentage mortalities of larvae were determined. These data were corrected against the mortalities in dishes treated with 50% aqueous acetone alone which served as controls.

(b) *Megoura viciae* (Vetch Aphid)

Potted tic bean plants previously infected with mixed stages of Megoura were sprayed to run-off using a laboratory turntable sprayer. Treated plants were held in a greenhouse for 2 days and were assessed for aphid mortality using a scoring system, judging the response in comparison with plants treated with 50% aqueous acetone alone, as controls. Each treatment was replicated 4 times.

| Score | |
|---|---|
| 3 | all aphids dead |
| 2 | few aphids alive |
| 1 | most aphids alive |
| 0 | no significant mortality |

(c) Test species: *Spodoptera littoralis*

French bean leaf discs were set in agar in petri-dishes and infected with 5 larvae (2nd instar). Four replicate dishes were assigned to each treatment and were sprayed under a Potter Tower with the appropriate test dilution. After 2 days live larvae were transferred to similar dishes containing untreated leaves set in agar. Two or three days later the dishes were removed from the constant temperature (25° C.) room in which they had been held and the mean percentage mortalities of larvae were determined. These data were corrected against the mortalities in dishes treated with 50% aqueous acetone alone which served as controls.

According to the above method an application of the following compounds was effective against the larvae of *Plutella xylostella* producing at least 65% mortality at less than 500 ppm: 1–10, 12–23, 25–27, 31–57, 59–70, 76–79, 81–88, 90–92, 96, 101.

According to the above method an application of the following compounds was effective against all stages of *Megoura viciae* producing a score of 7/12 at 50 ppm: 11, 58, 71, 72, 73, 74, 75

According to the above method an application of the following compounds was effective against the larvae of *Phaedon cochleariae* producing at least 90% mortality at less than 5 ppm: 24, 29, 80, 89.

According to the above method an application of the following compounds was effective against the larvae of *Spodoptera littoralis* producing at least 70% mortality at less than 500 ppm: 28, 30.

The following Composition Examples illustrate compositions for use against arthropod, plant nematode, helminth or protozoan pests which comprise, as active ingredient, compounds of general formula I. The compositions described in Composition Examples 1 to 6 can each be diluted in water to give a sprayable composition at concentrations suitable for use in the field.

COMPOSITION EXAMPLE 1

| | |
|---|---|
| 5-Amino-3-cyano-1-(2,6-dichloro-4-trifluoro-methylphenyl)-4-trifluoromethylthiopyrazole | 7% w/v |
| Ethylan BCP | 10% w/v |
| and N-methylpyrrolidone | to 100% by volume | by dissolving the Ethylan BCP in a portion of N-methylpyrrolidone, and then adding the active ingredient with heating and stirring until dissolved. The resulting solution was made up to volume by adding the remainder of the solvent.

COMPOSITION EXAMPLE 2

An emulsifiable concentrate was prepared from

| | |
|---|---|
| 5-Amino-3-cyano-1-(2,6-dichloro-4-trifluoro-methylphenyl)-4-trifluoromethylthiopyrazole | 7% w/v |
| Soprophor BSU | 4% w/v |
| Arylan CA | 4% w/v |
| N-methylpyrrolidone | 50% w/v |
| and Solvesso 150 | to 100% by volume | by dissolving Soprophor BSU, Arylan CA and the active ingredient in N-methylpyrrolidone, and then adding Solvesso 150 to volume.

COMPOSITION EXAMPLE 3

A wettable powder was prepared from

| | |
|---|---|
| 5-Amino-3-cyano-1-(2,6-dichloro-4-trifluoro-methylphenyl)-4-trifluoromethylthiopyrazole | 40% w/w |
| Arylan S | 2% w/w |
| Darvan No. 2 | 5% w/w |
| and Celite PF | to 100% by weight | by mixing the ingredients, and grinding the mixture in a hammer-mill to a particle size less than 50 microns.

COMPOSITION EXAMPLE 4

An aqueous flowable formulation was prepared from

| | |
|---|---|
| 5-Amino-3-cyano-1-(2,6-dichloro-4-trifluoro-methylphenyl)-4-trifluoromethylthiopyrazole | 30% w/v |
| Ethylan BCP | 1% w/v |
| Sopropon T36 | 0.2% w/v |
| Ethylene glycol | 5% w/v |
| Rhodigel 23 | 0.15% w/v |
| and Water | to 100% by volume | by intimately mixing the ingredients and grinding in a bead mill until the median particle size was less than 3 microns.

COMPOSITION EXAMPLE 5

An emulsifiable suspension concentrate was prepared from

| | |
|---|---|
| 5-Amino-3-cyano-1-(2,6-dichloro-4-trifluoro-methylphenyl)-4-trifluoromethylthiopyrazole | 30% w/v |
| Ethylan BCP | 10% w/v |
| Bentone 38 | 0.5% w/v |
| and Solvesso 150 | to 100% by volume | by intimately mixing the ingredients and grinding in a bead mill until the median particle size was less than 3 microns.

COMPOSITION EXAMPLE 6

Water dispersible granules were prepared from

| | |
|---|---|
| 5-Amino-3-cyano-1-(2,6-dichloro-4-trifluoro-methylphenyl)-4-trifluoromethylthiopyrazole | 30% w/w |
| Darvan No. 2 | 15% w/w |
| Arylan S | 8% w/w |
| and Celite PF | to 100% by weight | by mixing the ingredients, micronizing in a fluid-energy mill, and then granulating in a rotating pelletiser by spraying on sufficient water (up to 10% w/w). The resulting granules were dried in a fluid-bed drier to remove excess water.

Descriptions of commercial ingredients used in the foregoing Composition Examples:

| | |
|---|---|
| Ethylan BCP | nonylphenol ethylene oxide condensate |
| Soprophor BSU | condensate of tristyrylphenol and ethylene oxide |
| Arylan CA | 70% w/v solution of calcium dodecylbenzene-sulphonate |
| Solvesso 150 | light $C_{10}$-aromatic solvent |
| Arylan S | sodium dodecylbenzenesulphonate |
| Darvan | sodium lignosulphonate |
| Celite PF | synthetic magnesium silicate carrier |
| Sopropon T36 | sodium salt of polycarboxylic acid |
| Rhodigel 23 | polysaccharide xanthan gum |
| Bentone 38 | organic derivative of magnesium montmorillonite |

COMPOSITION EXAMPLE 7

A dusting powder may be prepared by intimately mixing:

| | |
|---|---|
| 5-Amino-3-cyano-1-(2,6-dichloro-4-trifluoro-methylphenyl)-4-trifluoromethylthiopyrazole | 1 to 10% w/w (weight/weight) |
| Talc superfine | to 100% by weight |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

COMPOSITION EXAMPLE 8

An edible bait may be prepared by intimately mixing:

| | |
|---|---|
| 5-Amino-3-cyano-1-(2,6-dichloro-4-trifluoro-methylphenyl)-4-trifluoromethylthiopyrazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

COMPOSITION EXAMPLE 9

A solution may be prepared containing:

| | |
|---|---|
| 5-Amino-3-cyano-1-(2,6-dichloro-4-trifluoro-methylphenyl)-4-trifluoromethylthiopyrazole | 15% w/v (weight/volume) |
| Dimethylsulphoxide | to 100% by volume | by dissolving the pyrazole derivative in a portion of the dimethyl-sulphoxide and then adding more dimethylsulphoxide to the desired volume. This solution may be applied to domestic animals infested by arthropods, percutaneously as a pour-on application or, after sterilisation by filtration through a polytetrafluoroethylene membrane (0.22 micrometer pore size), by parenteral injection, at a rate of application of from 1.2 to 12 ml of solution per 100 kg of animal body weight.

COMPOSITION EXAMPLE 10

A wettable powder may be formed from:

| | |
|---|---|
| 5-Amino-3-cyano-1-(2,6-dichloro-4-trifluoromethylphenyl)-4-trifluoromethylthiopyrazole | 50% w/w |
| Ethylan BCP (a nonylphenol/ethylene oxide condensate containing 9 moles of ethylene oxide per mol of phenol) | 5% w/w |
| Aerosil (silicon dioxide of microfine-particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder, which may be diluted with water to a concentration of from 0.001% to 2% w/v of the pyrazole compound and applied to a locus of infestation by arthropods, for example dipterous larvae, or plant nematodes by spraying, or to domestic animals infested by, or at risk of infestation by, arthropods, helminths or protozoa, by spraying or dipping, or by oral administration in drinking water, to control the arthropods, helminths or protozoa.

COMPOSITION EXAMPLE 11

A slow release bolus may be formed from granules containing a density agent, binder, slow-release agent and 5-amino-3-cyano-1-(2,6-dichloro- 4-trifluoromethylphenyl)-4-trifluoromethylthiopyrazole compound at varying percentage compositions. By compressing the mixture a bolus with a specific gravity of 2 or more can be formed and may be administered orally to ruminant domestic animals for retention within the reticulo-rumen to give a continual slow release of pyrazole compound over an extended period of time to control infestation of the ruminant domestic animals by arthropods, helminths or protozoa.

COMPOSITION EXAMPLE 12

A slow release composition may be prepared from:

| | |
|---|---|
| 5-Amino-3-cyano-1-(2,6-dichloro-4-trifluoromethylphenyl)-4-trifluoromethylthiopyrazole | 0.5 to 25% w/w |
| polyvinylchloride base | to 100% w/w | by blending the polyvinylchloride base with the pyrazole compound and a suitable plasticiser, e.g. dioctyl phthalate, and melt-extruding or hot-moulding the homogenous composition into suitable shapes, e.g. granules, pellets, brickettes or strips, suitable, for example, for addition to standing water or, in the case of strips, fabrication into collars or ear-tags for attachment to domestic animals, to control insect pests by slow release of the pyrazole compound.

Similar compositions may be prepared by replacing the 5-amino-3-cyano-1-(2,6-dichloro-4 -trifluoromethylphenyl)-4-trifluoromethylthiopyrazole in the Composition Examples by the appropriate quantity of any other compound of general formula I.

In experiments on activity against arthropods carried out on representative compounds of the second embodiment, the following results have been obtained:

Test 2

One or more of the dilutions of the compounds to be tested were made in 50% aqueous acetone.

Test species: *Spodoptera littoralis* (Egyptian cotton worm)

French bean leaf discs were set in agar in petri dishes and infected with 5 2nd instar larvae. Four replicate dishes were assigned to each treatment and were sprayed under a Potter Tower with the appropriate test dilution. After 2 days, live larvae were transferred to similar dishes containing untreated leaves set in agar. Two or three days later, the dishes were removed from the constant temperature (25° C.) room in which they had been held and the mean percentage mortalities of larvae were determined. These data were corrected against the mortalities in dishes treated with 50% aqueous acetone alone which served as controls.

According to the above method an application of 500 ppm of the following compounds was effective against the larvae of *Spodoptera littoralis*, producing at least 70% mortality: Compounds 102, 103, 104, 105, 106, 107.

The following Composition Examples illustrate compositions for use against arthropod, plant nematode, helminth or protozoan pests which comprise, as active ingredients, compounds of formula XXVI. The compositions described in Composition Examples 13 to 18 can each be diluted in water to give a sprayable composition at concentrations suitable for use in the field.

COMPOSITION EXAMPLE 13

A water-soluble concentrate was prepared from

| | |
|---|---|
| 5-Acetamido-3-cyano-1-(2,6-dichloro-4-trifluoromethylphenyl)-4-nitropyrazole | 7% w/v |
| Ethylan BCP | 10% w/v |
| and N-methylpyrrolodone | to 100% by volume | by dissolving the Ethylan BCP in a portion of N-methylpyrrolidone, and then adding the active ingredient with heating and stirring until dissolved. The resulting solution was made up to volume by adding the remainder of the solvent.

COMPOSITION EXAMPLE 14

An emulsifiable concentrate was prepared from

| | |
|---|---|
| 5-Acetamido-3-cyano-1-(2,6-dichloro-4-trifluoromethylphenyl)-4-nitropyrazole | 7% w/v |
| Soprophor BSU | 4% w/v |
| Arylan CA | 4% w/v |
| N-methylpyrrolidone | 50% w/v |
| and Solvesso 150 | to 100% by volume | by dissolving Soprophor BSU, Arylan CA and the active ingredient in N-methylpyrrolidone, and then adding Solvesso to volume.

COMPOSITION EXAMPLE 15

A wettable powder was prepared from

| | |
|---|---|
| 5-Acetamido-3-cyano-1-(2,6-dichloro-4-trifluoromethylphenyl)-4-nitro pyrazole | 40% w/w |
| Arylan S | 2% w/w |
| Darvan No. 2 | 5% w/w |
| and Celite PF | to 100% by weight | by mixing the ingredients, and grinding the mixture in a hammer-mill to a particle size less than 50 microns.

COMPOSITION EXAMPLE 16

An aqueous flowable formulation was prepared from

| | |
|---|---|
| 5-Acetamido-3-cyano-1-(2,6-dichloro-4-tri-fluoromethylphenyl)-4-nitropyrazole | 30% w/v |
| Ethylan BCP | 1% w/v |
| Sopropon T36 | 0.2% w/v |
| Ethylene glycol | 5% w/v |
| Rhodigel 23 | 0.15% w/v |
| and Water | to 100% by volume | by intimately mixing the ingredients and grinding in a bead mill until the median particle size was less than 3 microns.

COMPOSITION EXAMPLE 17

An emulsifiable suspension concentrate was prepared from

| | |
|---|---|
| 5-Acetamido-3-cyano-1-(2,6-dichloro-4-tri-fluoromethylphenyl)-4-nitropyrazole | 30% w/v |
| Ethylan BCP | 10% w/v |
| Bentone 38 | 0.5% w/v |
| and Solvesso 150 | to 100% by volume | by intimately mixing the ingredients and grinding in a bead mill until the medium particle size was less than 3 microns.

COMPOSITION EXAMPLE 18

Water-dispersible granules were prepared from

| | |
|---|---|
| 5-Acetamido-3-cyano-1-(2,6-dichloro-4-tri-fluoromethylphenyl)-4-nitropyrazole | 30% w/w |
| Darvan No. 2 | 15% w/w |
| Arylan S | 8% w/w |
| and Celite PF | to 100% by weight | by mixing the ingredients, micronizing in a fluid-energy mill, and then granulating in a rotating pelletizer by spraying on sufficient water (up to 10% w/w). The resulting granules were dried in a fluid-bed drier to remove excess water.

Descriptions of commercial ingredients used in the foregoing Composition Examples

| | |
|---|---|
| Ethylan BCP | nonylphenol ethylene oxide condensate |
| Soprophor BSU | condensate of tristyrylphenol and ethylene oxide |
| Arylan CA | 70% w/v solution of calcium dodecylbenzene-sulphonate |
| Solvesso 150 | light C$_{10}$-aromatic solvent |
| Arylan S | sodium dodecylbenzenesulphonate |
| Darvan | sodium lignosulphonate |
| Celite PF | synthetic magnesium silicate carrier |
| Sopropon T36 | sodium salt of polycarboxylic acid |
| Rhodigel 23 | polysaccharide xanthan gum |
| Bentone 38 | organic derivative of magnesium montmorillonite |

COMPOSITION EXAMPLE 19

A dusting powder may be prepared by intimately mixing:

| | |
|---|---|
| 5-Acetamido-3-cyano-1-(2,6-dichloro-4-tri-fluoromethylphenyl)-4-nitropyrazole | 1 to 10% w/w |
| Talc superfine | to 100% by weight |

This powder may be applied to a locus of arthropod infestation, for example refuse tips or dumps, stored products or household goods or animals infested by, or at risk of infestation by arthropods to control the arthropods by oral ingestion. Suitable means for distributing the dusting powder to the locus of arthropod infestation include mechanical blowers, handshakers and livestock self treatment devices.

COMPOSITION EXAMPLE 20

An edible bait may be prepared by intimately mixing:

| | |
|---|---|
| 5-Acetamido-3-cyano-1-(2,6-dichloro-4-tri-fluoromethylphenyl)-4-nitropyrazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

COMPOSITION EXAMPLE 21

A solution may be prepared containing:

| | |
|---|---|
| 5-Acetamido-3-cyano-1-(2,6-dichloro-4-tri-fluoromethylphenyl)-4-nitropyrazole | 15% w/v (weight/volume) |
| Dimethylsulphoxide | to 100% by volume | by dissolving the pyrazole derivative in a portion of the dimethylsulphoxide and then adding more dimethylsulphoxide to the desired volume.

This solution may be applied to domestic animals infested by arthropods, percutaneously as a pour-on application or, after sterilization by filtration through a polytetrafluoroethylene membrane (0.22 micrometer pore size), by parenteral injection, at a rate of application of from 1.2 to 12 ml of solution per 100 kg of animal body weight.

COMPOSITION EXAMPLE 22

A wettable powder may be formed from:

| | |
|---|---|
| 5-Acetamido-3-cyano-1-(2,6-dichloro-4-trifluoro-methylphenyl)-4-nitropyrazole | 50% w/w |
| Ethylan BCP (a nonylphenol/ethylene oxide condensate containing 9 moles of ethylene oxide per mole of phenol) | 5% w/w |
| Aerosil (silicon dioxide of microfine-particle size) | 5% w/w |
| Celite PF (synthetic magnesium silicate carrier) | 40% w/w | by adsorbing the Ethylan BCP onto the Aerosil, mixing with the other ingredients and grinding the mixture in a hammermill to give a wettable powder, which may be diluted with water to a concentration of from 0.001% to 2% w/v of the pyrazole compound and applied to a locus of infestation by arthropods, for example dipterous larvae, or plant nematodes by spraying, or to domestic animals infested by, or at risk of infestation by, arthropods, helminths or protozoa, by spraying or dipping, or by oral administration as drinking water, to control the arthropods, helminths or protozoa.

COMPOSITION EXAMPLE 23

A slow release bolus may be formed from granules containing a density agent, binder, slow-release agent and 5-acetamido-3-cyano-1-(2,6-dichloro-4 -trifluoromethylphenyl)-4-nitropyrazole compound at varying percentage compositions. By compressing the mixture, a bolus with a specific gravity of 2 or more can be formed and may be administered orally to ruminant domestic animals for retention within the reticulo-rumen to give a continual slow release of pyrazole compound over an extended period of time to control infestation of the ruminant domestic animals by arthropods, helminths or protozoa.

COMPOSITION EXAMPLE 24

A slow release composition may be prepared from:

| | |
|---|---|
| 5-Acetamido-3-cyano-1-(2,6-dichloro-4-tri-fluoromethylphenyl)-4-nitropyrazole | 0.5 to 25% w/w |
| polyvinylchloride base | to 100% w/w | by blending the polyvinylchloride base with the pyrazole compound and a suitable plasticizer, e.g. dioctyl phthalate, and melt-extruding or hot-moulding the homogenous composition into suitable shapes, e.g. granules, pellets, brickettes or strips, suitable, for example, for addition to standing water or, in the case of strips, fabrication into collars or ear-tags for attachment to domestic animals, to control insect pests by slow release of the pyrazole compound.

Similar compositions may be prepared by replacing the 5-acetamido-3-cyano-1-(2,6-dichloro-4 -trifluoromethylphenyl)-4-nitropyrazole in the Composition Examples by the appropriate quantity of any other compound of general formula XXVI.

In the third preferred embodiment, the present invention provides an arthropodical, plant nematocidal or anthelmintic composition which comprises at least one compound of formula I, or at salt thereof, in association with one or more compatible diluents or carriers with the provisos that (1) when the composition comprises a single compound of general formula I wherein $R^1$ and $R^3$ both represent methyl, $R^2$ represents thiocyanato and $R^4$—$R^8$ represent 2-, 3- or 4-nitro, 4-methyl, 4-chloro or 2,4-dinitro substitution; or $R^1$ represents methyl, $R^2$ represents cyano, $R^3$ represents unsubstituted amino and $R^4$—$R^8$ represent 4-chloro, 2,4-dichloro, 3,4-dichloro, 3 -chloro-4-methyl or 2-methyl-4-chloro substitution, the composition is not an association of a single compound of formula (I) alone with water or a common organic solvent; (2) when the composition comprises a single compound of general formula I wherein $R^1$ represents methyl, $R^2$ represents cyano or CONH2, $R^3$ represents unsubstituted amino and $R^4$—$R^8$ represent 3- or 4-fluoro substitution; or $R^1$ represents ethyl, $R^2$ represents cyano or CONH2, $R^3$ represents unsubstituted amino and $R^4$—$R^8$ represent 3- or 4-chloro, 2-, 3- or 4-fluoro or methyl, 3-bromo or 3-nitro substitution; or $R^1$ represents propyl, $R^2$ represents cyano or CONH$_2$, $R^3$ represents unsubstituted amino and $R^4$—$R^8$ represent 3-fluoro substitution; or $R^1$ represents methyl, $R^2$ represents sulphamoyl, $R^3$ represents chloro and $R^4$—$R^8$ represent 4-chloro substitution; the composition comprises an agriculturally acceptable surface active agent or a feedstuff; (3) when $R^1$ represents methyl, $R^2$ represents nitro, and $R^3$ represents chloro or $R^1$ represents chloro, $R^2$ represents nitro, and $R^3$ represents methyl and $R^4$—$R^8$ represents 4-nitro substitution, the composition comprises a pharmaceutically acceptable adjuvant or a feedstuff or is substantially sterile and pyrogen-free or is in unit dosage form; and (4) excluding compositions comprising 1-(4 -nitrophenyl)-3-nitro-4-pyrazole-carbonitrile or carboxamide.

Medicated feeds which comprise known compounds of general formula I and arthropodicidally- or anthelmintically-acceptable salts thereof and an edible carrier or diluent form a feature of the present invention.

In experiments on activity against arthropods carried out on representative compounds, the following results (wherein "Dose mg/kg" indicates the dose of test compound administered in mg per kg animal body weight and ppm indicates the concentration of the compound in parts per million of the test solution applied) have been obtained:

Test 3

One or more dilutions of the compounds to be tested were made in 50% aqueous acetone.

a) Test species: *Plutella xylostella* (Diamond-back Moth) and *Phaedon cochleariae* (Mustard Beetle)

Turnip leaf discs were set in agar in petri-dishes and infected with 10 larvae (2nd instar Plutella or 3rd instar Phaedon). Four replicate dishes were assigned to each treatment and were sprayed under a Potter Tower with the appropriate test dilution. Four or five days after treatment the dishes were removed from the constant temperature (25° C.) room in which they had been held and the mean percentage mortalities of larvae were determined. These data were corrected against the mortalities in dishes treated with 50% aqueous acetone alone which served as controls.

b) *Megoura viciae* (Vetch Aphid)

Potted tic bean plants previously infected with mixed stages of Megoura were sprayed to run-off using a laboratory turntable sprayer. Treated plants were held in a greenhouse for 2 days and were assessed for aphid mortality using a scoring system, judging the response in comparison with plants treated with 50% aqueous acetone alone, as controls.

| Score | |
|---|---|
| 3 | all aphids dead |
| 2 | few aphids alive |
| 1 | most aphids alive |
| 0 | no significant mortality |

According to the above method (a) an application of 500 ppm of the following compounds was totally effective against the larvae of *Plutella xylostella*, producing 100% mortality.

Compound Nos.

113, 114, 115, 116, 128, 129, 130, 136, 138, 139, 140, 143, 144, 145, 146, 147, 149, 150, 151, 152, 176, 177, 178, 179, 180, 181, 184, 187, 188, 189, 193, 195, 202, 207, 210, 211, 212, 213, 214, 216, 219, 228, 229.

According to the above method (a) an application of 5 ppm of the following compounds was totally effective against the larvae of *Phaedon cochleariae*, producing 100% mortality.

Compound Nos.

144, 161, 165, 166, 178, 179, 182, 187, 188, 193, 198, 199, 205, 206, 207, 210, 212, 214, 216, 217, 219, 220, 221, 224, 226, 228, 229.

According to the above method (b) an application of 50 ppm of the following compounds was totally effective against *Megoura viciae* producing 100% mortality, that is given a score of 12 from 4 replicates.

Compound Nos.

112, 113, 128, 129, 144, 156, 161, 165, 166, 190, 191, 200, 201, 206, 210, 214, 217, 219, 224, 225, 226, 228.

The data quoted in Tables 1–3 summarize the results from a number of different experiments carried out to the protocols a) and b) above.

TABLE 1

| No. | Plutella % m 500 ppm | Phaedon % m 10 ppm | Megoura score/12 50 ppm |
|---|---|---|---|
| 113 | | 100 | |
| 114 | | 100 | 9 |
| 115 | | 100 | 10 |
| 127 | 100* | 100 | 10 |
| 128 | | 100 | |
| 129 | | 100 | |
| 150 | | 100 | 10 |
| 118 | 73 | 45 | 10 |
| 151 | | 100 | 11 |

TABLE 2

| No. | Plutella % m 500 ppm | Phaedon % m 10 ppm |
|---|---|---|
| 116 | | 93 |
| 110 | 89 | 100 |
| 155 | 96 | 100 |
| 143 | | 100 |
| 130 | | 100 |
| 131 | 58 | 100 |
| 132 | 10 | 100 |
| 138 | | 100 |
| 136 | | 56 |
| 137 | 48 | 100 |
| 133 | 21* | 100 |
| 139 | | 16 |
| 146 | | 85 |
| 149 | | 100 |
| 145 | | 100 |
| 141 | 44 | 100 |
| 152 | | 100 |
| 140 | | 84 |
| 148 | 98 | 21 |
| 147 | | 100 |

TABLE 3

| No. | Phaedon % m 10 ppm | Megoura score/12 50 ppm |
|---|---|---|
| 112 | 98 | |
| 153 | 100 | 11 |
| 117 | 68 | 10+ |

*% mortality at 100 ppm
+score at 10 ppm

Test 4

Some 20 larvae of *Rhipicephalus appendiculatus* were placed in plastic capsules attached to the shaved flank of guinea-pigs. After 3 hours and then at 23 hourly intervals, the guinea-pigs were given a total of 4 subcutaneous injections of the test compound. Approximately 100 hours after infestation, the guinea-pigs were killed and the engorged tick larvae recovered, counter and kept at 23° C. in a humidity cabinet for 14 to 21 days. After this period, the percentage survival through moulting was assessed. Results obtained are given below in Table 4.

TABLE 4

| Compound No. | Dose (mg/kg at each repetition) | Result |
|---|---|---|
| 120 | 5 | No ticks recovered |
| | 4 | No ticks recovered |
| | 3 | Less than five engorged ticks recovered |
| | 2.5 | Ticks engorged normally but only 62.5 percent survived |
| 113 | 5 | No ticks recovered |
| | 4 | No ticks recovered |
| | 3 | Number of engorged ticks reduced, only 8.3 percent survived |
| | 2.5 | Ticks engorged normally but only 30.0 percent survived |
| | 1.0 | Ticks engorged normally but only 47.9 percent survived |
| 134 | 10 | No ticks recovered |
| | 5 | Less than five engorged ticks recovered |
| 133 | 15 | No ticks recovered |
| | 5 | No ticks recovered |
| | 2.5 | No ticks recovered |

Test 5

The high activity of the compounds of the third embodiment of general formula I against the cockroach species *Periplaneta americana* is demonstrated by results from the following experiment.

0.2 microliters of an acetone solution of the compound was injected through the soft cuticle between the leg and thorax of ten insects, to give a dose rate of 5 micrograms per g of insect body weight. Ten cockroaches were similarily injected with 0.2 microliters of acetone alone to serve as controls. After treatment the insects were held in plastic boxes with appropriate food. Five days after treatment the numbers of dead and alive insects were counted and percentage mortalities calculated.

According to the above method a dose of 5 micrograms/g insect body weight of the following compounds was totally effective against the cockroach species *Periplaneta americana* producing 100% mortality.

Compound Nos.

110, 113, 122, 125, 130, 161

The following Examples illustrate compositions for use against arthropod, plant nematode or helminth pests which comprise, as active ingredients, compounds of general formula I.

COMPOSITION EXAMPLE 25

A dusting powder may be prepared by intimately mixing:

| | |
|---|---|
| 5-amino-4-cyano-1-(2,6-dichloro-4-trifluoro-methylphenyl)-3-trifluoromethylpyrazole | 1 to 10% w/w (weight/weight) |
| Talc superfine | to 100% by weight |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

The 5-amino-4-cyano-1-(2,6-dichloro-4-trifluoromethylphenyl)- 3-trifluoromethylpyrazole may, if desired, be replaced in the above dusting powder by any other compound of general formula I.

COMPOSITION EXAMPLE 26

An edible bait may be prepared by intimately mixing:

| | |
|---|---|
| 5-amino-4-cyano-1-(2,6-dichloro-4-trifluoromethylphenyl)-3-trifluoromethylpyrazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

The 5-amino-4-cyano-1-(2,6-dichloro-4 -trifluoromethylphenyl)-3-trifluoromethylpyrazole may, if desired, be replaced in the above edible bait by any other compound of the third embodiment of general formula I.

COMPOSITION EXAMPLE 27

A solution may be prepared containing:

| | |
|---|---|
| 5-amino-4-cyano-1-(2,6-dichloro-4-trifluoromethylphenyl)-3-trifluoromethylpyrazole | 15% w/w (weight/volume) |
| Dimethylsulphoxide | to 100% by volume | by dissolving the pyrazole derivative in a portion of the dimethylsulphoxide and then adding more dimethylsulphoxide to the desired volume. This solution may be applied to domestic animals infesed by arthropods, percutaneously as a pour-on application or, after sterilization by filtration through a polytetrafluoroethylene membrane (0.22 um pore size), by parenteral injection, at a rate of application of from 1.2 to 12 ml of solution per 100 kg of animal body weight.

The 5-amino-4-cyano-1-(2,6-dichloro-4 -trifluoromethylphenyl)-3-trifluoromethylpyrazole may, if desired, be replaced in the above solution by similar amounts of an other compound of the third embodiment of general formula I.

COMPOSITION EXAMPLE 28

A wettable powder may be formed from:

| | |
|---|---|
| 5-amino-4-cyano-1-(2,6-dichloro-4-trifluoromethylphenyl)-3-trifluoromethylpyrazole | 50% w/w |
| Ethylan BCP (a nonylphenol/ethylene oxide condensate containing 9 moles of ethylene oxide per mole of phenol) | 5% w/w |
| Aerosil (silicon dioxide of microfine-particle size) | 5% w/w |
| Celite PF (synthetic magnesium silicate carrier) | 40% w/w | by adsorbing the Ethylan BCP onto the Aerosil, mixing with the other ingredients and grinding the mixture in a hammermill to give a wettable powder, which may be diluted with water to a concentration of from 0.001% to 2% w/v of the pyrazole compound and applied to a locus of infestation by arthropods, for example dipterous larvae, or plant nematodes by spraying, or to domestic animals infested by, or at risk of infestation by, arthropods, by spraying or dipping, or by oral administration as drinking water, to control the arthropods or helminths.

The 5-amino-4-cyano-1-(2,6-dichloro-4 -trifluoromethylphenyl)-3-trifluoromethylpyrazole may, if desired, be replaced in the above wettable powder by any other compound of the third embodiment of general formula I.

COMPOSITION EXAMPLE 29

A slow release bolus may be formed from granules containing a density agent, binder, slow-release agent and 5-amino-4-cyano-1-(2,6-dichloro-4-trifluoromethylphenyl)-3-trifluoromethylpyrazole compound at varying percentage compositions. By compressing the mixture a bolus with a specific gravity of 2 or more can be formed and may be administered orally to ruminant domestic animals for retention within the reticulo-rumen to give a continual slow release of pyrazole compound over an extended period of time to control infestation of the ruminant domestic animals by arthropods or helminths.

The 5-amino-4-cyano-1-(2,6-dichloro-4 -trifluoromethylphenyl)-3-trifluoromethylpyrazole may, if desired, be replaced in the above bolus by any other compound of the third embodiment of general formula I.

COMPOSITION EXAMPLE 30

A slow release composition may be prepared from:

| | |
|---|---|
| 5-amino-4-cyano-1-(2,6-dichloro-4-trifluoromethylphenyl)-3-trifluoromethylpyrazole | 0.5 to 25% w/w |
| polyvinylchloride base | to 100% w/w | by blending the polyvinylchloride base with the pyrazole compound and a suitable plasticizer, e.g. dioctyl phthalate, and melt-extruding or hot-moulding the homogeneous composition into suitable shapes, e.g. granules, pellets, brickettes or strips, suitable, for example, for addition to standing water or, in the case of strips, fabrication into collars or ear-tags for attachment to domestic animals, to control insect pests by slow release of the pyrazole compound.

The compounds of general formula I can be prepared by the application or adaptation of known methods (i.e. methods heretofore used or described in the chemical literature), generally heterocycle (pyrazole ring) formation followed where necessary by changing substituents.

It is to be understood that in the description of the following processes that the sequences for the introduction of the various groups on the pyrazole ring may be performed in a different order and that suitable protecting groups may be required as will be apparent to those skilled in the art: compounds of general formula I may be converted by known methods into other compounds of general formula I.

In the following description when symbols appearing in formulae are not specifically defined it is to be understood that they are "as hereinbefore defined" in accordance with the first definition of each symbol in this specification. Within the process definitions, unless otherwise stated, amino refers to the unsubstituted amino group.

Compounds of the first embodiment of the invention corresponding to general formula I wherein $R^2$ represents an $R'SO_2$, $R'SO$ or $R'S$ group, $R^3$ represents the unsubstituted amino group and $R^1$ represents the cyano or acetyl group may be prepared by a process version "a" in which a compound of formula II wherein $R^9$ represents a cyano or acetyl group is reacted with a compound of formula $R^2CH_2CN$, preferably a molar equivalent thereof, generally in the presence of an anhydrous inert organic solvent, e.g. ethanol, and a molar equivalent of a base, e.g. sodium ethoxide, and at a temperature from 0° to 50° C.

Compounds of general formula I wherein $R^2$ represents an R'S group and $R^3$ represents an amino group —NR"R"' wherein R and R each represent a hydrogen atom or a straight or branched chain alkyl, alkenylalkyl or alkynylalkyl group as hereinbefore defined may be prepared by a process version "b" in which an intermediate corresponding to general formula I in which $R^2$ is replaced by the hydrogen atom is reacted with a compound of formula:

R'—SCl     (III)

(wherein R' is as hereinbefore defined) in an inert organic solvent, preferably chloroform or dichloromethane, optionally in the presence of a base, preferably pyridine, and at temperatures from 0° to 50° C.

Compounds of general formula I wherein $R^1$ represents a chlorine or fluorine atom, $R^2$ represents an $R'SO_2$, R'SO or R'S group, and $R^3$ represents an amino group may be prepared by a process version "c" in which a compound of formula IV wherein X and Y both represent chlorine atoms or both represent fluorine atoms, is reacted with a phenylhydrazine of formula V:

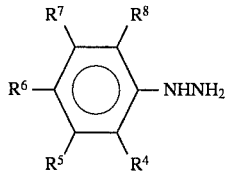     (V)

or an acid addition salt thereof, e.g. the hydrochloride, in an inert solvent, preferably ether or tetrahydrofuran, and optionally in the presence of a base, e.g. triethylamine or sodium acetate, and at a temperature from 0° C. to the reflux temperature of the solvent. When an acid addition salt of the compound of formula (V) is used, the reaction with the compound of formula (IV) is effected in the presence of an alkali metal, e.g. sodium or potassium, acetate, carbonate or bicarbonate.

According to a further process version "d" (1), compounds of general formula I wherein $R^2$ represents an R'S group, $R^1$ represents a chlorine, bromine, iodine or fluorine atom or a cyano or nitro group, and $R^3$ represents an amino group may also be prepared by the reaction of corresponding 4-thiocyanatopyrazoles with an organometallic reagent such as a compound of formula VI:

R'—Mg—X$^1$     (VI)

wherein R' is as hereinbefore defined and $X^1$ represents a halogen atom in an inert solvent, such as diethyl ether ortetrahydrofuran, and at a temperature from −78° C. to the reflux temperature of the reaction mixture or a compound of formula IX:

R$^{10}$—C≡C$^-$Li$^+$     (IX)

wherein $R^{10}$—C≡C$^-$ corresponds to R' in (I), in an inert solvent, such as tetrahydrofuran or diethyl ether, at temperatures from −78° C. to ambient.

Alternatively, according to process version "d" (2), compounds of general formula I in which $R^2$ represents an R'S group wherein R'S is other than a 1-alkenylthio or 1-alkynylthio group may also be prepared by reacting an intermediate corresponding to general formula I in which $R^2$ is replaced by a thiocyanato group, with a base preferably sodium hydroxide, or a reducing agent preferably sodium borohydride, in the presence of a reagent of formula VII:

R'$^a$—X$^2$     (VII)

wherein R'$^a$ is as hereinbefore defined for R' with the exclusion of 1-alkenyl and 1-alkynyl and $X^2$ represents a halogen, preferably bromine or iodine, for example methyl iodide or propargyl bromide, or with a base preferably sodium hydroxide, in the presence of a reagent of formula VIIA:

$F_2C$=C(Z) Z'     (VIIA)

wherein Z represents a fluorine, chlorine or bromine atom and Z' is as hereinbefore defined for Z or represents the trifluoromethyl group in an inert organic or aqueous-organic solvent, such as methanol, ethanol or dioxan or mixtures of these solvents with water, the reaction being performed at a temperature from −40° C. to the reflux temperature.

Alternatively, according to process version "d" (3), compounds of general formula I wherein R'S is other than a 1-alkenylthio or 1-alkynylthio group may be prepared by reductive alkylation of disulphides of formula VIII employing a reducing agent preferably sodium dithionite or sodium borohydride, in the presence of a base, preferably sodium hydroxide or sodium carbonate, and of a halide of formula VII, such as methyl iodide, in an inert organic or aqueous-organic solvent such as ethanol or a mixture of alcohol and water, at a temperature from ambient to reflux.

According to a further process version "e" compounds of general formula I in which $R^2$ represents an R'SO or $R'SO_2$- group may be prepared by oxidation of the sulphur atoms of the corresponding alkylthio, alkenylthio or alkynylthio compounds of formula (I) wherein $R^2$ is a group R'S as defined above; the oxidation may be effected employing oxidants of formula (X):

$R^{11}$—O—O—H     (X)

wherein $R^{11}$ represents the hydrogen atom, or a trifluoroacetyl or preferably 3-chlorobenzoyl group in a solvent e.g. dichloromethane or chloroform or trifluoroacetic acid and at temperatures from 0° C. to 60° C., or with a reagent such as potassium hydrogen persulphate or potassium salt of Caro's acid in a solvent e.g. methanol and water, and at a temperature from −30° C. to 50° C.

According to a further process version "f" (1), compounds of general formula I wherein $R^1$ represents a chlorine, bromine or iodine atom or a cyano or nitro group may be prepared by the diazotisation of an intermediate corresponding to general formula I in which $R^1$ is replaced by the amino group and $R^3$ represents a hydrogen atom or the amino group using sodium nitrite in a mineral acid, for example a mixture of concentrated sulphuric acid and acetic acid, at a temperature from 0° to 60° C., and by subsequent reaction with a copper salt and a mineral acid or with an aqueous solution of potassium iodide (when $R^1$ represents an iodine atom) at a temperature from 0° to 100° C.; or with cuprous cyanide, or sodium nitrite in the presence of a copper salt in an inert solvent e.g. water at pH from 1 to 7 at 25° to 100° C. The diazotisation may alternatively be performed employing an alkyl nitrite e.g. tert-butyl nitrite in the presence of a suitable halogenating agent preferably bromoform or iodine or anhydrous cupric chloride at temperatures from 0° C. to 100° C., and optionally in the presence of an inert solvent, preferably acetonitrile or chloroform.

According to a further process version "f" (2), compounds of formula I wherein $R^1$ represents a fluorine atom and $R^3$ represents a hydrogen atom or the amino group may be prepared by diazotisation of the corresponding amine wherein $R^1$ is replaced by the amino group using for example a solution of sodium nitrite in sulphuric acid and in the presence of fluoroboric acid or its sodium salt and subsequent thermolysis or photolysis of the diazonium fluoroborate derivative by methods known per se.

According to a further process version "g", compounds of formula I wherein $R^1$ represents a fluorine atom or a cyano group, and $R^3$ represents a hydrogen atom or the amino group may be prepared by the reaction of a halide of formula I wherein $R^1$ represents a chlorine or bromine atom with an alkali metal fluoride, preferably cesium fluoride, or with a metal cyanide preferably KCN under anhydrous conditions in an inert solvent, preferably sulpholane, and at a temperature from ambient to 150° C.

According to a further process version "h" compounds of formula I wherein $R^1$ represents a nitro group, and $R^2$ is a group $R'SO_2$ or $R'SO$ may be prepared by the reaction of an intermediate corresponding to general formula I in which $R^1$ is replaced by an unsubstituted amino group, and $R^2$ is a group $R'SO_2$, $R'SO$ or $R'S$, and $R^3$ represents a hydrogen atom or the amino group with an oxidant, preferably trifluoroperacetic acid or m-chloroperbenzoic acid, in an inert solvent, preferably dichloromethane, at a temperature from 0° C. to the reflux temperature. In this process concomitant oxidation at sulphur may occur when $R^2$ is $R'S$.

According to a further process version "i", compounds of general formula I wherein $R^1$ represents the cyano group and $R^3$ represents a hydrogen atom or the amino group may also be prepared by the dehydration of a compound corresponding to general formula I in which $R^1$ is replaced by the carbamoyl group. The compound corresponding to general formula I in which $R^1$ is replaced by the carbamoyl group may be prepared by the reaction of a compound corresponding to general formula I in which $R^1$ is replaced by the carboxy group with a chlorinating agent, preferably thionyl chloride at ambient to reflux temperature, followed by reaction of the intermediate acid chloride with ammonia to give an intermediate amide. The dehydration is generally effected by heating with a dehydrating agent e.g. phosphorus pentoxide or preferably phosphorus oxychloride at a temperature from 50° C. to 250° C.

According to a further process version "j", compounds of general formula I wherein $R^1$ is the acetyl group, and $R^3$ represents a hydrogen atom or the amino group may be prepared by the reaction of the corresponding nitrile of formula (I) wherein $R^1$ is the cyano group, or of esters wherein $R^1$ is replaced by an alkoxycarbonyl group or of carboxylic acids wherein $R^1$ is replaced by a carboxy group with methyl lithium in an inert solvent, e.g. toluene, and at temperatures from –78° C. to ambient. Alternatively the nitrile of formula (I) wherein $R^1$ is the cyano group or ester wherein $R^1$ is replaced by an alkoxycarbonyl group may be reacted with a Grignard reagent $CH_3MgX^3$ wherein $X^3$ represents a halogen, preferably iodine atom, in an inert solvent, e.g. diethyl ether or tetrahydrofuran, and at a temperature from 0° C. to the reflux temperature of the solvent.

According to a further process version "k", compounds of general formula I wherein $R^1$ represents the acetyl group and $R^3$ is as defined above may alternatively be prepared by oxidation of alcohols corresponding to general formula I wherein $R^1$ is replaced by a 1-hydroxyethyl group, with an oxidant, preferably pyridinium chlorochromate, in an inert solvent, e.g. dichloromethane, and at a temperature from 0° C. to the reflux temperature of the solvent.

According to a further process version "1", compounds of the general formula I wherein $R^1$ represents a formyl group and $R^3$ is as defined above may be prepared by the reaction of the corresponding nitriles of general formula I wherein $R^1$ represents a cyano group with (1) a suitable reducing agent preferably diisobutylaluminium hydride in an inert solvent, preferably tetrahydrofuran and at a temperature from –78° C. to the ambient temperature, followed by mild hydrolysis with an acid, e.g. dilute hydrochloric acid, at room temperature; or (2) Raney nickel in formic acid preferably at the reflux temperature of formic acid.

Derivatives of the 5-amino group form a further feature of the present invention and are collectively referred to as process "m". Compounds of general formula I which conform to formula IA wherein R" represents an $R^{12}C(=O)$- group, wherein $R^{12}$ represents a straight or branched-chain alkyl or alkoxy group containing from 1 to 4 carbon atoms, and R"' represents a hydrogen atom or an $R^{12}C(=O)$- group which is identical to the group $R^{12}C(=O)$- represented by R" or —NR"R"' represents a cyclic imide as hereinbefore defined, may be prepared by the reaction of a compound of general formula I wherein $R^3$ represents the unsubstituted amino group, or an alkali metal salt thereof, with a compound of formula XI:

$$R^{12}\text{—CO—X}^4 \qquad (XI)$$

wherein $X^4$ represents a chlorine or bromine atom, or with a compound of formula XII:

$$(R^{12}\text{—CO})_2O \qquad (XII)$$

or with a dicarboxylic acid derivative. The reaction may be conducted in the absence or presence of an inert organic solvent, for example acetonitrile, tetrahydrofuran, a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. to the reflux temperature of the reaction medium, to give a compound of formula IA wherein R" represents an $R^{12}C(=O)$- group wherein $R^{12}$ is as hereinbefore defined and R"' represents a hydrogen atom or an $R^{12}C(=O)$- group, depending upon the reaction conditions chosen and/or the use of an excess of the compound of formula XI or XII, or —NR"R"' represents a cyclic imide as hereinbefore defined.

Compounds of formula IA wherein R" represents a formyl group and R"' represents a hydrogen atom or a formyl group, may be prepared by the reaction of a compound of general formula I, wherein $R^3$ represents the unsubstituted amino group with formylacetic anhydride. Formylacetic anhydride may be prepared from formic acid and acetic anhydride and the reaction with the compound of general formula I may be conducted in the absence or presence of an inert organic solvent, for example a ketone, e.g. acetone, or an aromatic hydrocarbon, e.g. benzene or toluene, and optionally in the presence of an acid-binding agent, for example pyridine, triethylamine or an alkali metal, e.g. sodium or potassium, carbonate or bicarbonate, at a temperature from 0° C. to the reflux temperature of the reaction mixture, to give a compound of formula IA wherein R" represents a formyl group and R'" represents a hydrogen atom or a formyl group, depending upon the reaction conditions chosen and/or the use of an excess of formylacetic anhydride.

Compounds of formula IA wherein R" represents a formyl group or a group $R^{12}C(=O)$- and R'" represents a hydrogen atom may be prepared by the selective removal by hydrolysis of an $R^{12}C(=O)$- group or a formyl group from a compound of formula IA wherein R" and R'" both represent a $R^{12}C(=O)$- group or a formyl group. Hydrolysis is effected under mild conditions, for example by treatment with an aqueous-ethanolic solution or suspension of an alkali metal, e.g. sodium or potassium, bicarbonate, or with aqueous ammonia.

Compounds of formula IA wherein R" represents a straight or branched-chain alkoxycarbonyl group containing from 2 to 5 carbon atoms which is unsubstituted or substituted by one or more halogen atoms, and R'" represents a hydrogen atom may be prepared by the reaction of a compound of the formula IB wherein $R^{13}$ represents an alkoxycarbonyl group $R^{14}C(=O)$, wherein $R^{14}$ represents a straight or branched-chain alkoxy group containing from 1 to 4 carbon atoms (which is unsubstituted or substituted by one or more halogen atoms) or a phenoxy group, with a compound of the formula XIII:

$$R^{14}-H \quad (XIII)$$

(wherein $R^{14}$ is as hereinbefore defined) to replace a first group represented by the symbol $R^{13}$ by a hydrogen atom, and to replace the second group represented by the symbol $R^{13}$ by an alkoxycarbonyl group when $R^{13}$ represents a phenoxycarbonyl group, or, if desired, to replace the second group represented by the symbol $R^{13}$ by another alkoxycarbonyl group when $R^{13}$ in formula (IB) represents an alkoxycarbonyl group. As will be apparent to those skilled in the art, the desired compound of formula IA is obtained by selection of the appropriate compounds of formulae IB and XIII. The reaction may be effected in water or an inert aqueous-organic or organic solvent, for example an alkanol containing 1 to 4 carbon atoms, e.g. ethanol, or an aromatic hydrocarbon, e.g. benzene or toluene, or which is preferably an excess of the compound of formula XIII, at a temperature from ambient temperature to the reflux temperature of the reaction mixture and, if necessary, at elevated pressure, and optionally in the presence of a base, for example an alkali metal alkoxide, e.g. of the compound of formula XIII.

Compounds of formula IA wherein R" and R'", which may be the same or different, each represents a formyl group or $R^{12}C(=O)$- group, may be prepared by the reaction of an alkali metal, e.g. sodium or potassium, derivative of a compound of formula IA wherein R" represents a group $R^{12}C(=O)$- as hereinbefore defined, or a formyl group, and R'" represents a hydrogen atom with formylacetic anhydride or a compound of formula XI. Reaction may be effected in an inert aprotic solvent, e.g. dimethylformamide, at a temperature from laboratory temperature to the reflux temperature of the reaction mixture.

Alkali metal derivatives of compounds of general formula I (wherein $R^3$ represents the unsubstituted amino group) or (IA) wherein R" represents a group $R^{12}CO$ and R'" represents a hydrogen atom may be prepared in situ by reaction with an alkali metal, e.g. sodium or potassium, hydride, in an inert aprotic solvent, e.g. dimethylformamide, at a temperature from laboratory temperature to the reflux temperature of the reaction mixture.

Compounds of formula IB wherein $R^{13}$ represents a group $R^{14}C(=O)$-, may be prepared as hereinbefore described.

Intermediates of formula IB wherein $R^{13}$ represents a phenoxycarbonyl group may be prepared by the reaction of a compound of general formula I (wherein $R^3$ represents the unsubstituted amino group), with a compound of formula XIV:

$$R^{15}-CO-X^4 \quad (XIV)$$

(wherein $R^{15}$ represents a phenoxy group and $X^4$ is as hereinbefore defined, e.g. phenyl chloroformate, or with a compound of formula XV:

$$(R^{15}-CO)_2O \quad (XV)$$

(wherein $R^{15}$ is as hereinbefore defined) using the reaction conditions hereinbefore described for the reaction of a compound of general formula I with a compound of formula XI or XII.

Compounds of formula IA wherein R" represents a group $R^{16}$ which represents a straight or branched-chain alkyl, alkenylalkyl or alkynylalkyl group containing up to 5 carbon atoms and R'" represents a hydrogen atom may be prepared by the removal of the group $R^{12}C(=O)$- of a compound of the formula IA, wherein R" represents a group $R^{16}$ and R'" represents a group $R^{12}C(=O)$-. Removal of the group $R^{12}C(=O)$- may be effected by selective hydrolysis under mild conditions, for example by treatment with an alkali metal, e.g. sodium or potassium, hydroxide in water or an inert organic or aqueous-organic solvent, for example a lower alkanol, e.g. methanol, or a mixture of water and lower alkanol, at a temperature from laboratory temperature up to the reflux temperature of the reaction mixture.

Compounds of formula IA, wherein R represents a group $R^{16}$ and R'" represents a group $R^{12}C(=O)$-, may be prepared:

(1) by reaction of a compound of formula IA wherein R" represents a hydrogen atom and R'" represents a group $R^{12}C(=O)$, or an alkali metal, e.g. sodium or potassium, derivative thereof, with a compound of the formula XVI:

$$R^{16}-X^5 \quad (XVI)$$

wherein $X^5$ represents a chlorine, bromine or iodine atom; the reaction may be effected in an inert organic solvent, e.g. dichloromethane, tetrahydrofuran, or dimethylformamide, at a temperature from laboratory temperature up to the reflux temperature of the reaction mixture and, when a compound of formula IA is used, in the presence of a base, e.g., Triton B; or (2) by reaction of a compound of formula IA wherein R" represents the hydrogen atom and R'" represents a group $R^{16}$ with a compound of formula XI or XII.

Compounds of general formula I wherein $R^3$ represents an N-(alkyl, alkenylalkyl or alkynylalkyl)-N-formylamino group as hereinbefore described may be prepared in a similar manner to the process just described, where appropriate, formylacetic anhydride instead of a compound of formula XI or XII.

Compounds of formula IA wherein one or both of R" and R'" represents a straight or branched-chain alkyl, alkenylalkyl or alkynylalkyl group containing up to 5 carbon atoms, groups represented by R" and R'" being identical, may be prepared by reaction of a compound of formula I, wherein $R^3$ represents the unsubstituted amino group, or an alkali metal, e.g. sodium or potassium, derivative thereof, with a compound of formula XVI, in the absence or presence of an inert organic solvent, for example an aromatic hydrocarbon, e.g. benzene or toluene, chloroform, dichloromethane, tetrahydrofuran or dimethylformamide, and optionally in the presence of an acid-binding agent, for example pyridine, triethylamine or an alkali metal, e.g. sodium or potassium, bicarbonate, at a temperature from 0° C. up to the reflux temperature of the reaction mixture.

According to a further process version "n", compounds of general formula I wherein $R^3$ represents a straight or branched-chain alkoxymethyleneamino group containing from 2 to 5 carbon atoms which may be unsubstituted or substituted on methylene by a straight or branched-chain alkyl group containing from 1 to 4 carbon atoms may be prepared by the reaction of a compound of general formula I (wherein $R^3$ represents the unsubstituted amino group) with a trisalkoxyalkane in the presence of an acidic catalyst, e.g. p-toluenesulphonic acid, at a temperature from ambient temperature to the reflux temperature of the reaction mixture.

According to a further process version "o" compounds of general formula I wherein $R^3$ represents a group —NHCH$_2$R$^{17}$ wherein $R^{17}$ represents the hydrogen atom or a straight or branched-chain alkyl group containing from 1 to 4 carbon atoms may be prepared by reaction of a compound of general formula I wherein $R^3$ represents —N=C(OR$^{18}$)R$^{17}$ wherein $R^{18}$ represents a straight or branched-chain alkyl group containing from 1 to 4 carbon atoms with a reducing agent, preferably sodium borohydride. The reaction may be effected in an inert organic solvent, ethanol or methanol being preferred, at a temperature from 0° C. to the reflux temperature of the reaction mixture.

Compounds of general formula I, wherein $R^3$ represents a halogen atom, may be prepared by diazotisation of the corresponding compound of general formula I wherein $R^3$ represents the amino group, adopting the procedure of process "f" used above to prepare compounds of general formula I wherein $R^1$ represents a halogen atom. Fluorides of general formula I wherein $R^3$ represents a fluorine atom may also be prepared by a halogen exchange reaction of halides of general formula I wherein $R^3$ represents a chlorine or bromine atom, adopting the procedure of process "g" used above to prepare compounds (I) wherein $R^1$ represents a fluorine atom.

According to a further process version "p", compounds of general formula I wherein $R^1$ represents the formyl, acetyl, cyano or nitro group, $R^2$ is as defined, and $R^3$ represents a fluorine atom may be prepared by a halogen exchange reaction with a compound of general formula I wherein $R^3$ represents a chlorine or bromine atom by heating with an alkali metal fluoride preferably caesium fluoride in an inert solvent preferably sulpholane and at a temperature from 50° C. to 150° C.

According to a further process version "q", compounds of general formula I wherein $R^3$ represents a hydrogen atom may be prepared by treatment of a compound of general formula I wherein $R^3$ represents an amino group, with a diazotising agent preferably tertiary butyl nitrite in a solvent, preferably tetrahydrofuran, and at ambient to the reflux temperature.

According to a further process version "r" compounds of formula IA wherein $R^1$ represents a cyano or nitro group, $R^2$ is a group R'SO$_2$, R" and R"' each represents a straight or branched chain alkyl, alkenylalkyl or alkynylalkyl group containing up to 5 carbon atoms and R"' may also represents a hydrogen atom may be prepared by the reaction of a compound of general formula I wherein $R^3$ represents a halogen, preferably bromine, atom with the corresponding amine within formula R"R"'NH, or dimethylhydrazine when R" and R"' are both methyl, in an inert solvent preferably dioxan, tetrahydrofuran, N,N-dimethylformamide, dimethylsulphoxide or sulpholane and at a temperature from 25° to 100° C.

Intermediate compounds of formula II wherein the $R^9$ group represents a cyano or acetyl group may be prepared by diazotization of the aniline of formula IIA (wherein $R^4$—$R^8$ are as hereinbefore defined) generally with a solution of a molar equivalent of sodium nitrite in a mineral acid, e.g. a mixture of concentrated sulphuric acid and acetic acid, at a temperature from 0° to 60° C., and then reacting with a compound of formula CH$_3$COCH(Cl)CN [preparation described in J. Org. Chem 43 (20), 3822 (1978)] or a compound of formula CH$_3$COCH(Cl)COCH$_3$ in the presence of an inert solvent, e.g. a mixture of water and ethanol, optionally buffered, e.g. with excess sodium acetate, and at a temperature from 0° to 50° C.

Intermediates corresponding to general formula I in which $R^3$ represents an amino group, $R^2$ is replaced by the hydrogen atom, and $R^1$ represents the cyano group may be prepared by diazotisation of the aniline of formula IIA generally with a solution of a molar equivalent of sodium nitrite in a mineral acid, e.g. a mixture of concentrated sulphuric and acetic acid, at a temperature from 0° to 60° C., and then reacting with a compound of formula XVII:

NC—CH$_2$—CH(CO—R$^{19}$)CN    (XVII)

wherein $R^{19}$ represents an alkoxy group containing from 1 to 6 carbon atoms, preferably the ethoxy group, or a hydrogen atom in the presence of an inert solvent, e.g. a mixture of water and ethanol, and optionally buffered, e.g. with sodium acetate, and at a temperature from 0° to 50° C. Subsequent mild hydrolysis with a base such as aqueous sodium hydroxide, sodium carbonate or ammonia may be necessary to effect the cyclization.

Intermediates of formula XVII used above, in which $R^{19}$ represents the hydrogen atom, may be employed as alkali metal enolate salts which are converted into the aldehydes under the acidic conditions of the above coupling reaction.

Intermediates corresponding to general formula I in which $R^1$ is as defined with the exclusion of the formyl group, $R^2$ is replaced by the hydrogen atom and $R^3$ represents an amino group may be prepared by decarboxylation of a compound corresponding to general formula I wherein $R^2$ is replaced by the carboxy group, generally performed by heating at a temperature from 100° C. to 250° C. optionally in the presence of an inert organic solvent, particularly N,N-dimethylaniline. Alternatively intermediates corresponding to general formula I in which $R^2$ is replaced by a hydrogen atom, $R^1$ is as defined with the exclusion of the formyl group, and $R^3$ represents an amino group may be prepared directly from esters corresponding to general formula I wherein $R^2$ represents a group —COOR in which R represents a straight or branched chain alkyl group containing from 1 to 6 carbon atoms, by heating in an inert organic solvent preferably acetic acid at a temperature from 50° C. to reflux, in the presence of a strong acid preferably hydrobromic acid. When the $R^1$ group within the definition of this process is a chlorine or fluorine atom concomitant halogen exchange may also occur to give intermediates wherein $R^2$ and $R^3$ are as defined and $R^1$ represents a bromine atom.

Intermediate carboxy compounds corresponding to general formula I in which $R^1$ is as defined with the exclusion of the formyl group, $R^2$ is replaced by the carboxy group and $R^3$ represents an amino group may be prepared by hydrolysis of esters wherein $R^2$ is replaced by a group —COOR as defined above, preferably with an alkali metal hydroxide in a solvent such as an aqueous alcohol at a temperature from 0° C. to the reflux temperature of the reaction mixture.

Intermediate esters corresponding to general formula I in which $R^2$ is replaced by a group —COOR as hereinbefore defined, $R^3$ is the amino group, and $R^1$ represents a cyano or acetyl group may be prepared in a similar manner to process version "a", described hereinbefore, from esters $ROOCCH_2CN$ and intermediates of formula II wherein $R^9$ represents a cyano or acetyl group.

Intermediate esters corresponding to general formula I in which $R^2$ is replaced by a group —COOR as hereinbefore defined, $R^3$ is the amino group and $R^1$ represents a chlorine or fluorine atom may be prepared by the reaction of a phenylhydrazine (V) with a compound of formula XVIII wherein X, Y and R are as hereinbefore defined, in a similar manner to the procedure of process version "c".

Alternatively intermediates corresponding to general formula I in which $R^1$ represents a chlorine or fluorine atom, $R^2$ is replaced by a hydrogen atom, and $R^3$ represents the amino group, may be prepared by reaction of the corresponding aldehydes in which $R^2$ is replaced by the formyl group with an acid, preferably aqueous hydrochloric acid, in a solvent preferably ethanol at a temperature from 50° C. to the reflux temperature.

Intermediates corresponding to general formula I in which $R^2$ is replaced by a formyl group may be prepared by reaction of nitriles wherein $R^2$ is replaced by a cyano group with a suitable reducing agent, preferably diisobutyl aluminium hydride in an inert solvent, preferably tetrahydrofuran at a temperature from −78° C. to ambient temperature.

Intermediates corresponding to general formula I in which $R^2$ is replaced by a cyano group may be prepared by the reaction of a compound of formula XIX wherein X and Y are as hereinbefore defined (i.e. dichlorodicyanoethylene or difluorodicyanoethylene), with a phenylhydrazine (V) in a similar manner to process version "c".

Intermediates of formula XX wherein $R^{20}$ represents an $R^2$ group or a hydrogen atom and $R^3$ represents a hydrogen atom or an amino group may be prepared by performing a Curtius rearrangement of the acid azide corresponding to general formula I in which $R^1$ is replaced by $CON_3$ or in which $R^2$ is replaced by the hydrogen atom and $R^1$ is replaced by $CON_3$ by heating in an inert organic solvent such as toluene at a temperature from 50° C. to 150° C. to give an isocyanate which is then reacted with for example tert-butanol to give a carbamate, which in turn is hydrolysed using dilute acid preferably hydrochloric acid in ethanol at a temperature from ambient to reflux.

Intermediate acid azides may be prepared by reaction of a carboxylic acid corresponding to general formula I in which $R^1$ is replaced by a carboxy group and $R^2$ and $R^3$ are as defined above with an azide transfer reagent such as diphenyl phosphoryl azide in the presence of a base, preferably triethylamine and in an inert solvent preferably N,N-dimethylformamide, and at a temperature from 0° to 60° C.

Intermediate carboxylic acids in which $R^1$ is replaced by a carboxylic acid group may be prepared by hydrolysis of the corresponding esters in which R1 is replaced by an alkoxycarbonyl group e.g. ethoxycarbonyl, using a base such as sodium hydroxide and a solvent such as aqueous alcohol, and at a temperature from 0° C. to the reflux temperature of the solvent.

Intermediate carboxylic esters in which $R^1$ represents an alkoxycarbonyl group and wherein $R^{20}$ represents $R^2$ may be prepared by reaction of an intermediate XXI wherein R and $R^2$ are as hereinbefore defined and $X^6$ is a leaving group, e.g. the chlorine atom, with a phenylhydrazine V, in a similar manner to process version "c".

Intermediate carboxylic esters in which $R^1$ is replaced by an alkoxycarbonyl group as defined above, and $R^2$ is replaced by $R^{20}$, may alternatively be prepared in a similar manner to process version "a" by the reaction of a compound II wherein $R^9$ is replaced by a —COOR group in which R is as hereinbefore defined, with a compound of formula $R^{20}CH_2CN$ wherein $R^{20}$ is as hereinbefore defined.

Intermediates corresponding to formula II in which $R^9$ is replaced by —COOR may be prepared from known compounds (e.g. $CH_3COCH(Cl)COOR$) in a similar manner to that described above for compounds of formula II wherein $R^9$ represents a cyano or acetyl group.

Intermediate halides of formula XXI wherein $X^6$ represents a chlorine atom and R and $R^2$ are as hereinbefore defined, may be prepared by the reaction of the sodium or potassium salts XXI wherein $X^6$ is —O$^-$Na$^+$ or —O$^-$K$^+$ with a suitable chlorinating agent, preferably phosphorus oxychloride, optionally in the presence of an inert solvent, e.g. tetrahydrofuran, and at a temperature from 0° C. to the reflux temperature of the solvent.

Intermediate salts XXI wherein $X^6$ is —O$^-$Na$^+$ or —O$^-$K$^+$ may be prepared by methods described in the literature, wherein active methylene compounds $R^2CH_2CN$ are reacted with dialkyl oxalates, e.g. diethyl oxalate, in the presence of a metal alkoxide, e.g. sodium ethoxide, in. an inert solvent, e.g. an alcohol such as ethanol, and at a temperature from 25° C. to the reflux temperature of the solvent.

Intermediates corresponding to general formula I in which $R^1$ is replaced by a 1-hydroxyethyl group may be prepared by the reaction of aldehydes of general formula I wherein $R^1$ represents a formyl group and $R^3$ represents the hydrogen atom or an amino group with a Grignard reagent, preferably methyl magnesium halide, in an inert solvent, e.g. ether or tetrahydrofuran, and at a temperature from ambient to the reflux temperature of the solvent.

Intermediate 4-thiocyanatopyrazoles corresponding to general formula I in which $R^2$ is replaced by the thiocyanato group and $R^3$ represents the amino group may be prepared by the reaction of a compound corresponding to general formula I in which $R^2$ is replaced by the hydrogen atom with a thiocyanating agent, such as alkali metal or ammonium salts of thiocyanic acid (e.g. NaSCN) and bromine, in an inert organic solvent, such as methanol, and at a temperature from 0° C. to 100° C.

Intermediate disulphides of formula VIII may be prepared by the hydrolysis of thiocyanates in which $R^2$ is replaced by the thiocyanato group and $R^1$ represents a chlorine, bromine or fluorine atom or the cyano or nitro group using hydrochloric acid in the presence of ethanol or by reduction with sodium borohydride in ethanol, both being at a temperature from ambient to reflux. Alternatively the thiocyanates may be converted into compounds of formula VIII by treatment with base, preferably aqueous sodium hydroxide and preferably under phase-transfer conditions with chloroform as co-solvent and in the presence of a phase transfer catalyst e.g. triethylbenzylammonium chloride and at a temperature from ambient to 60° C.

Intermediate diaminoesters corresponding to general formula I in which $R^1$ and $R^3$ represent the amino group and $R^2$ is replaced by an ester group —COOR as hereinbefore defined containing from 2 to 7 carbon atoms, may be prepared by reaction of an appropriately substituted phenylhydrazine of formula V with an alkali metal salt of an alkyl dicyanoacetate of formula XXII:

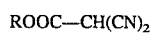

ROOC—CH(CN)$_2$         (XXII)

(wherein R is as hereinbefore defined) preferably potassium ethyl dicyanoacetate using hydrochloric acid, at ambient to reflux temperature. Alkyl dicyanoacetate potassium salts may be prepared by reaction of the appropriate alkyl chloroformate with malononitrile in the presence of potassium hydroxide in tetrahydrofuran at a temperature of 0° to 100° C.

Intermediate diaminosulphonylpyrazoles corresponding to general formula I in which $R^1$ and $R^3$ represent the amino group and $R^2$ represents a sulphonyl group $R'SO_2$ may be prepared in a similar manner to the process just described by reaction of a phenylhydrazine (V) with an alkali metal salt of a suitable alkylsulphonylmalononitrile of formula XXIII:

$$R'SO_2—CH(CN)_2 \quad (XXIII)$$

(wherein R' is as hereinbefore defined).

The preparation of compounds of formula XXIII is described in the literature.

Intermediate esters corresponding to general formula I in which $R^1$ represents a chlorine, bromine or fluorine atom or a nitro group, $R^2$ is replaced by a group —COOR as hereinbefore defined, and $R^3$ is an amino group, may be prepared in a similar manner to process version "f" via diazotisation of compounds corresponding to general formula I in which $R^1$ is replaced by an amino group.

Intermediate esters corresponding to general formula I in which $R^1$ is replaced by a group —COOR as hereinbefore defined, $R^2$ is replaced by the hydrogen atom, and $R^3$ represents an amino group, may also be prepared from the reaction of a phenylhydrazine of formula V with an alkali metal salt of formula XXIV wherein M is sodium or potassium and R is as hereinbefore defined. The reaction is performed in an acidic medium generally dilute sulphuric acid, optionally in the presence of a co-solvent e.g. ethanol, and at a temperature from ambient to the reflux temperature of the solvent.

According to a further feature of the present invention there are provided intermediates of formula XXV, useful in the preparation of compounds of general formula I, wherein $R^{2'}$ is as defined for $R^2$ or represents the hydrogen atom, a thiocyanato, formyl, cyano or carboxy group, a straight- or branched-chain alkoxycarbonyl group containing from 2 to 7 carbon atoms or the dithio group (which joins two pyrazole rings for example as in formula VIII), $R^{3'}$ is as defined for $R^3$ or represents the diphenoxycarbonylamino group, and $R^{1'}$ is as defined for $R^1$ or represents the amino, 1-hydroxyethyl, carboxy or carbamoyl group or a straight- or branched-chain alkoxycarbonyl or alkoxycarbonylamino group containing from 2 to 7 carbon atoms, with the exclusion of compounds of general formula I and of those compounds of formula XXV wherein $R^4$ and $R^8$ are chloro and $R^6$ is trifluoromethyl, i.e., 2,6-dichloro-4-trifluoromethylphenyl, $R^{2'}$ represents the cyano group, $R^{1'}$ represents the cyano group and $R^{3'}$ represents the amino, acetamido, dichloroacetamido, t-butylcarbonylamino, propionamido, pentanamido, bis(ethoxycarbonyl)amino, ethoxycarbonylamino, methylamino or ethylamino group, or $R^{1'}$ represents the chlorine atom and $R^{3'}$ represents the amino, t-butylcarbonylamino, bis(ethoxycarbonyl)amino or ethoxycarbonylamino group, or $R^{1'}$ represents a bromine or iodine atom or an amino or ethoxycarbonyl group and $R^{3'}$ represents the amino group, or $R^{1'}$ represents the fluorine atom-end $R^{3'}$ represents the hydrogen atom or the amino group, or $R^{1'}$ represents a nitro, amino, t-butoxycarbonylamino or ethoxycarbonyl group and $R^{3'}$ represents the hydrogen atom;

the phenyl group with substituents $R^4$—$R^8$ represents a 2,4,6-trichlorophenyl, 2-chloro-4-trifluoromethylphenyl or 2,6-dichloro-4-trifluoromethoxyphenyl group, $R^{2'}$ represents the cyano group, $R^{1'}$ represents the cyano group and $R^{3'}$ represents the amino group;

the phenyl group with substituents $R^4$—$R^8$ represents a 2,6-dichloro-4-trifluoromethoxy group, $R^{2'}$ represents the cyano group, $R^{1'}$ represents the chlorine atom and $R^{3'}$ represents the amino group; and the phenyl group is the 2 6-dichloro-4-trifluoromethylphenyl group, , $R^{2'}$ represents the methanesulphonyl group, $R^{1'}$ represents a carboxy, carbamoyl or ethoxycarbonyl group and $R^{3'}$ represents the amino group.

5-Amino-3-cyano-1-(2,6-dichloro-4-trifluoromethylphenyl)pyrazole is a preferred intermediate.

The following Examples and Reference Examples illustrate the preparation of compounds of general formula I according to the present invention:

[Chromatography was effected on a silica column (May & Baker Ltd 40/60 flash silica) at a pressure of 6.8 $Nm^{-2}$, unless otherwise stated.]

EXAMPLE 1

Compounds Nos. 1, 2, 3, 4, 5, 6, 7, 8, 9, 10, 11, 12, 13, 14, 15, 90

A solution of 5-amino-3-cyano-1-(2,6-dichloro-4-trifluoromethylphenyl)pyrazole (20.0g) in dichloromethane (100 ml) was stirred magnetically and treated dropwise with a solution of trifluoromethylsulphenyl chloride (10.8 g) in dichloromethane (50 ml) during 1 hour. The solution was stirred overnight at room temperature, then washed with water (100 ml), dried over anhydrous magnesium sulphate, filtered, and evaporated in vacuo to give a solid (26.3 g). This solid was recrystallised from toluene/hexane to give 5-amino-3-cyano-1-(2,6-dichloro-4-trifluoromethylphenyl)-4-trifluoromethylthiopyrazole as fawn crystals (24.2 g) m.p. 169°–171° C. By proceeding in a similar manner but replacing the 5-amino-3-cyano-1-(2,6-dichloro-4-trifluoromethylphenyl)pyrazole by the hereinafter indicated appropriately substituted pyrazole there was obtained from trifluoromethyl-sulphenyl chloride unless otherwise stated:

5-Amino-3-cyano-1-(2,6-dichloro-4 -trifluoromethoxyphenyl)-4-trifluoro-methylthiopyrazole, m.p. 125°–126° C., in the form of pale yellow crystals, from 5-amino-3-cyano-1-( 2,6-dichloro-4-trifluoromethoxyphenyl)-pyrazole.

5-Amino-3-cyano-1-(2,6-dichloro-4 -difluoromethoxyphenyl)-4-trifluoromethylthiopyrazole, m.p. 127°–128.5° C., in the form of a buff solid, from 5-amino-3-cyano-1-(2,6 -dichloro-4-difluoromethoxyphenyl)pyrazole.

5-Amino-1-(2-chloro-4-trifluoromethylphenyl)-3 -cyano-4-trifluoromethylthiopyrazole, m.p. 142°–144° C., in the form of a light brown solid, from 5-amino-1-(2-chloro-4 -trifluoromethylphenyl)-3-cyanopyrazole.

5-Amino-3-cyano-1-(2,4,6-trichlorophenyl)-4-trifluoromethylthiopyrazole, m.p. 192°–193° C., in the form of brown crystals, from 5-amino-3-cyano-1-(2,4,6-trichlorophenyl)pyrazole.

5-Amino-3-cyano-1-(2,6-dibromo-4 -trifluoromethylphenyl-4-trifluoromethylthiopyrazole, m.p. 202°–204° C., in the form of orange crystals, from 5-amino-3-cyano-1-(2,6 -dibromo-4-trifluoromethylphenyl)pyrazole.

5-Amino-1-(2-bromo-4-trifluoromethylphenyl)-3-cyano 4-trifluoromethylthiopyrazole, m.p. 136°–138° C., in the form of a pale yellow solid, from 5-amino-1-(2-bromo-4 -trifluoromethylphenyl)-3-cyanopyrazole.

5-Amino-3-cyano-1-(2,6-dichloro-4-trifluoromethylphenyl)-4-difluoromethylthiopyrazole, m.p. 159°–161° C., in the form of a light brown solid, from 5-amino-3-cyano-1-(2,6-dichloro-4-trifluoromethylphenyl)pyrazole and difluoromethylsulphenyl chloride.

5-Amino-3-cyano-1-(2,6-dichloro-4-trifluoromethylphenyl)-4-heptafluoropropylthiopyrazole, m.p. 148°–150° C., in the form of a yellow solid, after dry column flash chromatography on silica eluting with dichloromethane and petroleum ether (2:1), from 5-amino-3-cyano-1-(2,6-dichloro-4-trifluoromethylphenyl) pyrazole and heptafluoropropylsulphenyl chloride.

5-Amino-1-(2-bromo-6-chloro-4-trifluoromethylphenyl)-3-cyano-4-trifluoromethylthiopyrazole, m.p. 183°–185° C., in the form of yellow crystals, from 5-amino-1-(2-bromo-6-chloro-4-trifluoromethylphenyl)-3-cyanopyrazole and employing tetrahydrofuran as solvent.

5-Amino-3-cyano-1-(2,6-dichloro-4-trifluoromethylphenyl)-4-trichloromethylthiopyrazole, m.p. 245°–247° C., in the form of a white solid after purification by chromatography, starting from 5-amino-3-cyano-1-(2,6-dichloro-4-trifluoromethylphenyl)pyrazole and trichloromethylsulphenyl chloride.

By proceeding in a similar manner but replacing the trifluoromethylsulphenyl chloride by dichlorofluoromethylsulphenyl chloride, and by the addition of a molar equivalent of pyridine to the reaction mixture after stirring overnight there was obtained:

5-Amino-3-cyano-4-dichlorofluoromethylthio-1-(2,6-dichloro-4-trifluoromethylphenyl)pyrazole, m.p. 178°–180° in the form of a white solid, after purification by chromatography eluting with diethyl ether/hexane (1:1), from 5-amino-3-cyano-1-(2,6-dichloro-4-trifluoromethylphenyl)pyrazole.

By proceeding in a similar manner but employing a molar equivalent of pyridine in the reaction solution there was obtained:

5-Amino-3-chloro-1-(2,6-dichloro-4-trifluoromethylphenyl)-4-trifluoromethylthiopyrazole. m.p. 149°–150.5° C., in the form of a white solid, after recrystallisation from hexane from 5-amino-3-chloro-1-(2,6-dichloro-4-trifluoromethylphenyl)pyrazole.

5-Amino-3-bromo-1-(2,6-dichloro-4-trifluoromethylphenyl)-4-trifluoromethylthiopyrazole, m.p. 154.5°–156° C., in the form of a white solid, after recrystallisation from hexane/ethyl acetate and then from hexane/cyclohexane, starting from 5-amino-3-bromo-1-(2,6-dichloro-4-trifluoromethylphenyl)pyrazole.

5-Amino-1-(2,6-dichloro-4-trifluoromethylphenyl)-3-fluoro-4-trifluoromethylthiopyrazole, m.p. 123°–126° C., in the form of a white solid, starting from 5-amino-1-(2,6-dichloro-4-trifluoromethylphenyl)-3-fluoropyrazole.

5-Amino-4-chlorodifluoromethylthio-3-cyano1-(2,6-dichloro-4-trifluoromethylphenyl)pyrazole, m.p. 167°–168° C., in the form of a white solid, starting from chlorodifluoromethylsulphenyl chloride. The product was purified by high performance liquid chromatography employing a 8 micron irregular column (21.4mm×25cm) and eluting with acetonitrile/water (3:2)

REFERENCE EXAMPLE 1

5-Amino-3-cyano-1-(2,6-dichloro-4-trifluoromethylphenyl)pyrazole used in the above Example was prepared as follows:

A suspension of nitrosyl sulphuric acid prepared from sodium nitrite (7.0 g) and concentrated sulphuric acid (27.5 ml) was diluted with acetic acid (25 ml), cooled to 25° C., and stirred mechanically. To this was added a solution of 2,6-dichloro-4-trifluoromethylaniline (21.2 g) in acetic acid (50 ml) dropwise over 15 minutes at 25°–32° C. This mixture was heated to 55° C. for 20 minutes and poured onto a stirred solution of ethyl 2,3-dicyanopropionate (14.0 g) in acetic acid (60 ml) and water (125 ml) at 10°–20° C. After 15 minutes, water (200 ml) was added, and the oily layer separated. The aqueous solution was then extracted with dichloromethane (3×70 ml) and the extracts combined with the oil and washed with ammonia solution (to pH9). The organic phase was then stirred with ammonia (20 ml) for 2 hours, and the dichloromethane layer then separated. This was washed with water (1×100 ml), 1N hydrochloric acid (1×100 ml), dried over anhydrous magnesium sulphate, filtered, and evaporated in vacuo to give an oily solid. Crystallisation from toluene/hexane gave the title compound as brown crystals (20.9 g), m.p. 140°–142° C.

By proceeding in a similar manner but replacing the 2,6-dichloro-4-trifluoromethylaniline by the appropriately substituted anilines there was obtained: 5-Amino-3-cyano-1-(2,6-dichloro-4-trifluoromethoxyphenyl)pyrazole in the form of a fawn solid, m.p. 119°–120.5° C., from 2,6-dichloro-4-trifluoromethoxyaniline.

5-Amino-3-cyano-1-(2,6-dichloro-4-difluoromethoxyphenyl)pyrazole, after washing the initially formed product as a solution in dichloromethane with saturated sodium carbonate solution. The title compound was obtained as a yellow solid after recrystallisation from toluene, m.p. 120.5°–122.5° C., from 2,6-dichloro-4-difluoromethoxyaniline.

5-Amino-1-(2-chloro-4-trifluoromethylphenyl)-3-cyanopyrazole in the form of an orange crystalline solid, m.p. 133°–135° C., from 2-chloro-4-trifluoromethylaniline. 5-Amino-3-cyano-1-(2,4,6-trichlorophenyl)pyrazole in the form of a light brown solid, m.p. 155°–156° C., from 2,4,6-trichloroaniline.

5-Amino-3-cyano-1-(2,6-dibromo-4-trifluoromethylphenyl)pyrazole in the form of a yellow crystalline solid, m.p. 142°–146° C., from 2,6-dibromo-4-trifluoromethylaniline. 5-Amino-1-(2-bromo-6-chloro-4-trifluoromethylphenyl)-3cyanopyrazole in the form of a brown crystalline solid, m.p. 146°–148° C., from 2-bromo-6-chloro-4-trifluoromethylaniline 5-Amino-1-(2-bromo-4-trifluoromethylphenyl)-3-cyanopyrazole in the form of a yellow crystalline solid, m.p. 159°–162° C., from 2-bromo-4-trifluoromethylaniline.

5-Amino-3-chloro-1-(2,6-dichloro-4-trifluoromethylphenyl)pyrazole, used in Example 1, was prepared as follows:

A mixture of 5-amino-3-chloro-1-(2,6-dichloro-4 trifluoromethylphenyl)-4-ethoxycarbonylpyrazole (5.0 g) and hydrochloric acid (6N; 75 ml) in glacial acetic acid (75 ml) was heated at reflux for 24 hours. The cooled reaction mixture was evaporated to low bulk and basified to pH 12 with sodium hydroxide (2N) and extracted with diethyl ether (3×75 ml). The ether extracts were combined and evaporated in vacuo to give a mixture of 5-amino and 5-acetamido pyrazoles in the form of a yellow gummy solid (3.5 g). This solid was dissolved in a mixture of hydrochloric acid (6N; 30 ml) and dioxan (60 ml) and heated at reflux for 48 hours. The volatiles were removed in vacuo and the residue purified by column chromatography using dichloromethanehexane (4:1). Evaporation of the eluate containing the major component gave the title compound (1.3 g), m.p. 128°–129° C., in the form of an off-white solid.

5-Amino-3-chloro-1-(2,6-dichloro-4-trifluoromethylphenyl)-4-ethoxycarbonylpyrazole, used above, was prepared as follows:

Tertiary-butyl nitrite (15.0 g) was added dropwise to a stirred and cooled (0° C.) mixture of 3,5-diamino-1-(2,6-dichloro-4-trifluoromethylphenyl)-4-ethoxycarbonyl-pyrazole (50.0 g) and cupric chloride (21.0 g) in acetonitrile (600 ml) over 10 minutes. The reaction mixture was stirred for 2 hours at 0° C. and 2 hours at laboratory temperature then evaporated to low bulk and poured into hydrochloric acid (5N; 1500 ml). The resultant solution was extracted with dichloromethane (3×600 ml), washed with hydrochloric acid (2N; 2×600 ml), dried over anhydrous magnesium sulphate and evaporated to furnish a brown tar. The tarry material was removed from the product using a dry silica chromatography eluted with dichloromethane-hexane (4:1), further purification by column chromatography using hexane containing increasing proportions of dichloromethane (60 to 80%) gave the title compound (15.8 g), m.p. 143°–146.5° C., in the form of an orange solid.

3,5-Diamino-1-(2,6-dichloro-4-trifluoromethylphenyl)-4-ethoxycarbonylpyrazole, used above, was prepared as follows:

Ethyl dicyanoacetate potassium salt (35.2 g) was added to a stirred suspension of 2,6-dichloro-4-trifluoromethylphenylhydrazine (49 g) in hydrochloric acid (0.9N; 220 ml) and the reaction mixture stirred and heated at reflux for 18 hours. The reaction mixture was then cooled to precipitate a solid which was filtered off, triturated with diethyl ether (250 ml) and dried to give an off-white solid (56 g) which was recrystallised from a mixture of ethyl acetate and hexane to give the title compound (29.2 g), m.p. 196°–197° C., in the form of an off-white solid.

Ethyl dicyanoacetate potassium salt was prepared as follows:

A solution of ethyl chloroformate (520 g) and malononitrile (330 g) in tetrahydrofuran (500 ml) was added dropwise over one hour to a stirred solution of potassium hydroxide (560 g) and water (2.01) at a temperature below 40° C. (external ice cooling). The reaction mixture was stirred at laboratory temperature for 1 hour then cooled to 0° C. to precipitate a solid which was filtered off and dried over phosphorus pentoxide to give the title compound, (334.4 g) in the form of an off-white solid.

5-Amino-3-bromo-1-(2,6-dichloro-4-trifluoromethylphenyl)pyrazole, used in the above Example, was prepared as follows:

A mixture of 5-amino-4-carbethoxy-3-chloro-1-(2,6-dichloro-4-trifluoromethylphenyl)pyrazole (3.3 g) and hydrobromic acid (48%, 30 ml) in glacial acetic acid (50 ml) was heated at reflux for 18 hours. The mixture was evaporated to low bulk, basified with sodium hydroxide solution (1N) and the product filtered off and dried (2.9 g). Recrystallisation from a mixture of ethanol and water gave the title compound (2.5 g), m.p. 132.5°–134° C., in the form of a colourless solid.

5-Amino-1-(2,6-dichloro-4-trifluoromethylphenyl)-3-fluoropyrazole, used in the above Example was prepared as follows:

A mixture of 5-amino-1-(2,6-dichloro-4-trifluoromethylphenyl)-3-fluoro-4-formylpyrazole (1.5 g) in methanol (40 ml) and 2N hydrochloric acid (10 ml) was heated under reflux for 24 hours. After evaporation in vacuo, water (100 ml) was added, and the mixture extracted with ethyl acetate (2×100 ml). The extract was washed with saturated sodium bicarbonate solution (50 ml), dried over anhydrous magnesium sulphate, and evaporated in vacuo. Purification by chromatography eluting with dichloromethane gave the title compound, m.p. 128°–129° C., in the form of a white solid.

5-Amino-1-(2,6-dichloro-4-trifluoromethylphenyl)-3-fluoro-4-formylpyrazole, used above, was prepared as follows:

A stirred solution of 5-amino-4-cyano-(2,6-dichloro-4-trifluoromethylphenyl)-3-fluoropyrazole (preparation described in PCT Patent Publication WO 8703-781-A) (2.2 g) in dry tetrahydrofuran (40 ml) was treated at −70° C. under nitrogen with a solution of diisobutylaluminium hydride (13 ml of a 1M toluene solution). The mixture was allowed to warm to room temperature over 2 hours, left overnight, and poured onto a mixture of 2N hydrochloric acid (50 ml) and ice (50 g). After stirring for ½ hour, toluene (25 ml) was added, and the organic layer separated. The aqueous layer was re-extracted with dichloromethane (2×100 ml), and the combined organic solution washed with sodium bicarbonate solution (20 ml) and dried over anhydrous magnesium sulphate. Evaporation in vacuo gave a brown solid (1.5 g), which was purified by chromatography eluting with toluene/ethyl acetate (98:2) to give the title compound (1.0 g), m.p. 137°–139.5° C., in the form of a pale yellow solid.

EXAMPLE 2

Compounds Nos. 16, 17

A mixture of anhydrous cupric chloride (1.15 g) in acetonitrile (20 ml) was stirred whilst tert-butyl nitrite (0.73 g) was added at 0° C. After 10 minutes, a solution of 5-amino-3-cyano-1-(2,6-dichloro-4trifluoromethylphenyl)-4-trifluoromethylthiopyrazole (3.0 g) in acetonitrile (5 ml) was added at 0° C. and the mixture stirred at 0° C. for 2 hours, and then at room temperature overnight. After evaporation in vacuo the residue was dissolved in a mixture of dichloromethane (50 ml) and hydrochloric acid (5M; 50 ml). The organic layer was dried over anhydrous magnesium sulphate, evaporated in vacuo and then purified by chromatography, eluting with petroleum ether (b.p.60°–80° C.)/dichloromethane (2:1). Recrystallisation of the resultant product from petroleum ether (b.p.60°–80° C.) gave 5-chloro-3-cyano-1-(2,6-dichloro-4-trifluoromethylphenyl)-4-trifluoromethylthiopyrazole (0.55 g) as a white crystalline solid, m.p. 131°–132° C. By proceeding in a similar manner but starting from 3,5-diamino-1-(2,6-dichloro-4-trifluoromethylphenyl)-4-methanesulphonylpyrazole and performing the reaction at 0° C. for 2 hours and then warming to reflux temperature there was obtained:

5-Amino-3-chloro-1-(2,6-dichloro-4-trifluoromethylphenyl)-4-methanesulphonylpyrazole, m.p. 177°–179° C., in the form of a white solid, after purification by chromatography eluting with dichloromethane, and then recrystallising from toluene/hexane.

REFERENCE EXAMPLE 2

3,5-Diamino-1-(2,6-dichloro-4-trifluoromethylphenyl) 4-methanesulphonylpyrazole, used in the above Example, was prepared as follows:

Potassium carbonate (11.7 g) was added portionwise to a stirred mixture of methanesulphonylmalononitrile hydrochloride chloride (30.0 g) in water (150 ml). 2,6-Dichloro-4-trifluoromethylphenylhydrazine (41.0 g) was then added and the mixture heated at 100° C. overnight. After cooling the yellow solid was filtered, washed with water, and recrystallised from aqueous methanol. This solid was washed thoroughly with ether, yielding the title compound as a white solid (14.6 g) m.p. 224°–226° C.

EXAMPLE 3

Compounds Nos. 18, 19, 20, 99

5-Amino-3-cyano-1-(2,6-dichloro-4 -trifluoromethylphenyl)-4-trifluoromethylthiopyrazole (4.0 g) was added to triethyl orthoformate (19.0 ml) and p-toluene/-sulphonic acid (0.019 g) added. The mixture was heated under reflux for 21 hours, cooled, and the triethyl orthoformate evaporated in vacuo to give a brown oil as residue. This was purified by chromatography eluting with a mixture of dichloromethane and hexane (1:1). Evaporation of the eluates in vacuo gave 3-cyano-1-(2,6-dichloro-4 -trifluoromethylphenyl)-5-ethoxymethyleneamino-4-trifluoromethylthiopyrazole as a colourless solid, m.p. 70°–71.5° C.

By proceeding in a similar manner but replacing the triethyl orthoformate with triethyl orthoacetate and employing toluene as co-solvent there was obtained: 3-Cyano-1-(2,6-dichloro-4-trifluoromethylphenyl) 5-ethoxyethylideneamino-4-trifluoromethylthiopyrazole as a pale yellow solid, m.p. 71°–73° C.

By proceeding in a similar manner but replacing the 5-amino-3-cyano-1-(2,6-dichloro-4-trifluoromethylphenyl)-4-trifluoromethylthiopyrazole by 5-amino-3-cyano-1-(2,6 -dichloro-4-trifluoromethylphenyl)-4-methanesulphonylpyrazole, and by employing triethyl orthoformate and toluene, there was obtained:

3-Cyano-1-(2,6-dichloro-4-trifluoromethylphenyl)5 -ethoxymethyleneamino-4-methanesulphonylpyrazole, m.p. 145°–147° C., in the form of a cream solid.

By proceeding in a similar manner there was prepared from 5-amino-3-cyano-1-(2,6-dichloro-4 -trifluoromethylphenyl)-4-trifluoromethylsulphonylpyrazole and triethyl orthoformate and in the absence of toluene as co-solvent, 3-Cyano-1-(2,6-dichloro-4-trifluoromethylphenyl)-5 -ethoxymethyleneamino-4-trifluoromethylsulphonylpyrazole, m.p. 118.8°–119.8° C., in the form of a white solid, and after recrystallisation from hexane.

EXAMPLE 4

Compounds Nos. 21, 22, 23, 24, 96

To a stirred solution of 5-amino-3-cyano-1-(2,6 -dichloro-4-trifluoromethylphenyl)-4-trifluoromethylthiopyrazole (4.0 g) and acetyl chloride (2.3 g) in acetonitrile (40 ml) at 0° C. was added pyridine (1.3 ml) dropwise. The yellow solution was warmed to room temperature during 45 minutes and then heated under reflux for 24 hours. The cooled solution was evaporated in vacuo and the residue dissolved in dichloromethane (100 ml), washed with water (2×100 ml), dried over anhydrous magnesium sulphate and evaporated in vacuo to give a buff solid (4.2 g). This was purified by chromatography eluting with dichloromethane to give 5-acetamido-3-cyano-1-(2,6-dichloro-4 -trifluoromethylphenyl)-4-trifluoromethyl-thiopyrazole (2.0 g) as a colourless solid, m.p. 217°–218° C., after recrystallisation from toluene.

By proceeding in a similar manner but replacing the acetyl chloride by propionyl chloride there was obtained the following two compounds:

3-Cyano-1-(2,6-dichloro-4-trifluoromethylphenyl)-5-bis(propionyl)amino-4-trifluoromethylthiopyrazole, m.p. 128°–130° C., in the form of a white crystalline solid, and 3 -cyano-1-(2,6-dichloro-4-trifluoromethylphenyl)-5 -propionamido-4-trifluoromethylthiopyrazole, m.p. 178.5°–182° C., in the form of a pale yellow solid. By proceeding in a similar manner, but replacing the 5-amino-3-cyano-1-(2,6 -dichloro-4-trifluoromethylphenyl)-4-trifluoromethylthiopyrazole by 5-amino-3-cyano-1-(2,6-dichloro-4 -trifluoromethylphenyl)-4-methanesulphonylpyrazole, there was obtained:

5-Acetamido-3-cyano-1-(2,6-dichloro-4 -trifluoromethylphenyl)-4-methanesulphonylpyrazole, m.p. 220°–222° C., in the form of a cream solid.

By proceeding in a similar manner there was obtained 5-acetamido-3-cyano-1-(2,6-dichloro-4 -trifluoromethylphenyl)-4-trifluoromethysulphinylpyrazole, m.p. 208°–211° C., in the form of a white solid, from 5-amino-3-cyano-1-(2,6 -dichloro-4-trifluoromethylphenyl)-4-trifluoromethylsulphinylpyrazole. The reaction mixture was heated at reflux for 3 hours in this instance.

EXAMPLE 5

Compounds Nos. 25, 26, 27 28, 29, 30, 97

To a stirred solution of 5-amino-3-cyano-1-(2,6 -dichloro-4-trifluoromethylphenyl)-4-trifluoromethylthiopyrazole (5.0 g) in dry tetrahydrofuran (80 ml) stirred under nitrogen at room temperature, was added sodium hydride (0.36 g of an 80% oil dispersion) during ½ hour. After a further ½ hour, 2 drops of 15-crown-5 followed by trimethylacetyl chloride (1.6 g) was added, and the mixture heated under reflux for 24 hours. After cooling to 0° C. a further addition of sodium hydride (0.15 g) followed by trimethylacetyl chloride (0.8 g) was made, and the mixture refluxed for another 18 hours. The mixture was cooled, poured onto water (100 ml) and extracted with ether (2×80 ml). The ether extracts were dried over anhydrous magnesium sulphate, and evaporated in vacuo to give a yellow oil (6.2 g), which was purified by chromatography eluting with petroleum ether/dichloromethane (3:2) to give 3-cyano-1-(2,6-dichloro-4-trifluoromethylphenyl)-4 -trifluoromethylthio-5-trimethylacetamidopyrazole (0.82 g), m.p. 172.5°–173.5° C., in the form of a white solid.

By proceeding in a similar manner but replacing the trimethylacetyl chloride by the appropriate acylating agents there was prepared:

3-Cyano-1-(2.6-dichloro-4-trifluoromethylphenyl)- 5-bis-(methoxycarbonyl)amino-4-trifluoromethylthiopyrazole, m.p. 135°–136.5° C., in the form of a white solid, using methyl chloroformate.

3-Cyano-1-(2.6-dichloro-4-trifluoromethylphenyl)-5 -bis(ethoxycarbonyl)amino-4-trifluoromethylthioyrazole, m.p. 83.2°–85.5° C., in the form of a white solid, using ethyl chloroformate and performing the reaction at ambient temperature.

5-Chloroacetamido-3-cyano-1-(2,6-dichloro-4 -trifluoromethylphenyl)-4-trifluoromethylthiopyrazole, m.p. 175°–176° C., in the form of a white solid, using chloroacetyl chloride, and after purification by chromatography and recrystallisation from toluene/hexane.

By proceeding in a similar manner but replacing the 5-amino-3-cyano-1-(2,6-dichloro-4-trifluoromethylphenyl-4-trifluoromethylthiopyrazole by 5-amino-3-cyrano-1-(2,6 -dichloro-4-trifluoromethylphenyl)-4-methanesulphonylpyrazole and by the use of appropriate acylating agents, there was prepared:

3-Cyano-1-(2,6-dichloro-4-trifluoromethylphenyl)-5-bis(ethoxycarbonyl)amino-4-methanesulphonylpyrazole in the form of a white solid, m.p. 195°–198° C., using ethyl chloroformate.

3-Cyano-1-(2,6-dichloro-4-trifluoromethylphenyl)-4-methanesulphonyl-5-trimethylacetamidopyrazole in the form of a white solid, m.p. 245°–247° C., using trimethylacetyl chloride.

By proceeding in a similar manner there was prepared from 5-amino-3-cyano-1-(2,6-dichloro-4-trifluoromethylpheny. 1)-4-trifluoromethylsulphonylpyrazole and ethyl chloroformate:

3-Cyano-1-(2,6-dichloro-4-trifluoromethylphenyl)-5-bis(ethoxycarbonyl)amino-4-trifluoromethylsulphonylpyrazole, m.p. 116°–116.9° C., in the form of a white solid, after recrystallisation from toluene/hexane.

EXAMPLE 6

Compounds Nos. 31, 32, 33, 34, 35, 36, 93

To a mixture of sodium hydride (0.71 g of an 80% oil dispersion) in dry tetrahydrofuran (30 ml) was added 5-amino-3-cyano-1-(2,6-dichloro-4-trifluoromethylphenyl)-4-trifluoromethylthiopyrazole (4.0 g). After 20 minutes, 3 drops of 15-crown-5 was added and the mixture cooled to 0° C. Methyl iodide (3.4 g) was then added and the mixture stirred at 0° C. for ½ hour, then at room temperature overnight. The solvent was evaporated in vacuo and the residue partitioned between dichloromethane (80 ml) and water (80 ml). The organic phase was dried over anhydrous magnesium sulphate, and evaporated in vacuo. to give a pale yellow solid (4.29 g). Purification by chromatography eluting with dichloromethane/petroleum ether (1:1) gave 3-cyano-1-(2,6-dichloro-4-trifluoromethylphenyl)-5-dimethylamino-4-trifluoromethylthiopyrazole (2.11 g), m.p. 109.5°–110.8° C., in the form of a white solid.

By proceeding in a similar manner but replacing the methyl iodide by the appropriate alkyl halides there was prepared:

3-Cyano-1-(2,6-dichloro-4-trifluoromethylphenyl)-5-isopropylamino-4-trifluoromethylthiopyrazole, m.p. 173°–175° C., in the form of a cream solid after purification by chromatography and recrystallisation from toluene/hexane, prepared from isopropyl iodide. 3-Cyano-1-(2,6-dichloro-4-trifluoromethylphenyl)-5-propylamino-4-trifluoromethylthiopyrazole, m.p. 162°–163.5° C., in the form of a white solid, and:

3-Cyano-1-(2,6-dichloro-4-trifluoromethylphenyl)-5-dipropylamino-4-trifluoromethylthiopyrazole, m.p. 72.5°–73° C., in the form of a white solid, both compounds prepared using propyl bromide and performing the reaction initially at 0° C. and then at 70° C.

3-Cyano-1-(2,6-dichloro-4-trifluoromethylphenyl)-5-bis(propargyl)amino-4-trifluoromethylthiopyrazole, m.p. 86°–89° C., in the form of a white solid after recrystallisation from toluene/hexane, prepared from propargyl bromide.

By proceeding in a similar manner but replacing the 5-amino-3-cyano-1-(2,6-dichloro-4-trifluoromethylphenyl)-4-trifluoromethylthiopyrazole by 5-amino-3-cyano-1-(2,6-dichloro-4-trifluoromethylphenyl)-4-methanesulphonylpyrazole, and using methyl iodide as alkylating agent, there was prepared:

3-Cyano-1-(2,6-dichloro-4-trifluoromethylphenyl)-5-methylamino-4-methanesulphonylpyrazole in the form of a yellow solid, m.p. 169°–172° C.

By proceeding in a similar manner but replacing the 5-amino-3-cyano-1-(2,6-dichloro-4-trifluoromethylphenyl)-4-trifluromethylthiopyrazole by 5-amino-3-cyano-1-(2,6-dichloro-4-trifluoromethylphenyl)-4-trifluoromethylsulphinylpyrazole and employing dioxan as solvent and heating under reflux for 5 hours was obtained 3-cyano-1-(2,6-dichloro-4-trifluoromethylphenyl)-5-dimethylamino-4-trifluoromethylsulphinylpyrazole, m.p. 154°–161° C., in the form of a white solid.

EXAMPLE 7

Compounds Nos. 37, 38, 39, 40, 41, 95

A suspension of 5-amino-3-cyano-1-(2,6-dichloro-4-trifluoromethylphenyl)-4-trifluoromethanesulphonylpyrazole (43.8 g) was stirred in a mixture of bromoform (141 ml) and dry acetonitrile (63 ml). Tert-butyl nitrite (29.9 g) was added dropwise during 5 minutes, and the mixture heated at 60°–70° C. for 2.75 hours. After cooling to 25° C. a further addition of tert-butyl nitrite (29.9 g) was made, and the heating resumed for 2 hours. Evaporation in vacuo gave a yellow oily solid which was triturated with hexane and filtered off. Two recrystallisations from toluene/hexane gave 5-bromo-3-cyano-1-(2,6-dichloro-4trifluoromethylphenyl) 4-trifluoromethanesulphonylpyrazole as a yellow solid (34.0 g), m.p. 136°–137° C.

By proceeding in a similar manner but replacing the 5-amino-3-cyano-1-(2,6-dichloro-4-trifluoromethylphenyl)-4trifluoromethanesulphonylpyrazole by the following phenylpyrazoles there was obtained:

5-Bromo-3-cyano-1-(2,6-dichloro-4-trifluoromethylphenyl)-4-trifluoromethylthiopyrazole, m.p. 161.5°–164° C., in the form of a buff solid, from 5-amino-3-cyano-1-(2,6-dichloro-4-trifluoromethylphenyl)-4-trifluoromethylthiopyrazole. Acetonitrile was not employed as co-solvent for this preparation.

5-Bromo-3-cyano-1-(2,6-dichloro-4-trifluoromethylphenyl)-4-methanesulphonylpyrazole, m.p. 160.5°–162° C., in the form of a white solid, from 5-amino-3-cyano-1-(2,6-dichloro-4-trifluoromethylphenyl)-4-methanesulphonylpyrazole.

5-Amino-3-bromo-1-(2,6-dichloro-4-trifluoromethylphenyl)-4-methanesulphonylpyrazole, m.p. 193°–195° C., in the form of a white solid, from 3,5-diaminol-(2,6-dichloro-4-trifluoromethylphenyl)-4-methanesulphonylpyrazole (preparation described in Reference Example 2), and by replacing the bromoform by two equivalents of bromine and by employing chloroform as solvent.

3-Bromo-1-(2,6-dichloro-4-trifluoromethylphenyl)-4-methanesulphonylpyrazole in the form of white crystals, m.p. 178°–180° C. from 3-amino-1-(2,6-dichloro4-trifluoromethylphenyl)-4-methanesulphonylpyrazole. By proceeding in a similar manner there was obtained:

5-Bromo-3-cyano-1-(2,6-dichloro-4-trifluoromethylphenyl)-4-trifluoromethylsulphinylpyrazole, m.p. 147°–148° C., in the form of a yellow solid. The reaction was performed at 52° C. for 2 hours in this instance.

REFERENCE EXAMPLE 3

3-Amino-1-(2,6-dichloro-4-trifluoromethylphenyl)-4-methanesulphonylpyrazole used in the Example above was prepared as follows:

A solution of 3-tert-butoxycarbonylamino-1-(2,6-dichloro-4-trifluoromethylphenyl)4-methanesulphonylpyrazole (6.4 g) in ethanol (150 ml) was treated with 50% v/v hydrochloric acid (20 ml), and the mixture refluxed for 1 hour. The solvent was evaporated in vacuo and the residue dissolved in dichloromethane, washed with sodium bicarbonate solution, then with water, dried over anhydrous magnesium sulphate and evaporated in vacuo. The product was recrystallised from ethyl acetate/hexane to give the title compound (3.0 g) as white crystals, m.p. 222°–223° C.

3-tert-Butoxycarbonylamino-1-(2,6-dichloro-4-trifluoromethylphenyl)-4-methanesulphonylpyrazole was prepared as follows:

A mixture of 3-carboxy-1-(2,6-dichloro-4-trifluoromethylphenyl)-4-methanesulphonylpyrazole (9.4 g), and thionyl chloride (70 ml) and N,N-dimethylformamide (3 drops) was heated under reflux for 2 hours. The solvent was evaporated in vacuo and re-evaporated in vacuo after addition of dry toluene (20 ml). The resultant solid was dissolved in dry acetone (60 ml) and stirred, whilst a solution of sodium azide (2.1 g) in water (15 ml) was added during 5 minutes keeping at 10°–15° C. After 30 minutes the mixture was poured onto water (250 ml) and extracted with dichloromethane (3×80 ml). The combined extract was washed with water, dried over anhydrous magnesium sulphate, and evaporated in vacuo at equal to or below 40° C. to give a fawn solid.

The resulting azide was dissolved in dry toluene (80 ml) and heated under reflux for 0.75 hour, with smooth evolution of nitrogen. After cooling, this was treated with tert-butanol (15 g), and the mixture heated under reflux for two hours. After standing overnight at room temperature and evaporation in vacuo, the resulting brown semi solid (9.2 g) was purified by chromatography on silica (Merck 230–400 mesh, 6.8 Nm$^{-2}$) eluting with dichloromethane and ethyl acetate (98:2) to give the title compound (6.6 g).

3-Carboxy-1-(2,6-dichloro-4-trifluoromethylphenyl)-4-methanesulphonylpyrazole was prepared as follows:

A mixture of 1-(2,6-dichloro-4-trifluoromethylphenyl)-3-ethoxycarbonyl-4-methanesulphonylpyrazole (14.0 g) and 80% sulphuric acid (300 ml) was heated and stirred at 80° C. for 4 hours. After standing at room temperature overnight, the solution was poured onto excess ice and the precipitated solid filtered off. This was dissolved in ethyl acetate, washed with water, dried (anhydrous magnesium sulphate) and evaporated to give the title compound as a buff solid (11.1 g), m.p. 215°–216° C.

1-(2,6-Dichloro-4-trifluoromethylphenyl)-3-ethoxycarbonyl-4-methanesulphonylpyrazole, used above, was prepared as follows:

To a solution of 5-amino-1-(2,6-dichloro-4-trifluoromethylphenyl)-3-ethoxycarbonyl-4-methanesulphonylpyrazole (17.1 g) in dry tetrahydrofuran (130 ml) stirred at room temperature, was added during 2 minutes, tert-butyl nitrite (33 ml). The mixture was heated at reflux for 1.5 hours, the solvent evaporated in vacuo, and the residue dissolved in dichloromethane. After washing with water, drying (anhydrous magnesium sulphate), and evaporation a yellow solid was obtained. Recrystallisation from toluene-petroleum ether (b.p. 60°–80° C.) gave the title compound as yellow crystals (15.2 g), m.p. 183°–185° C.

5-Amino-1-(2,6-dichloro-4-trifluoromethylphenyl)-3-ethoxycarbonyl-4-methanesulphonylpyrazole, used above, was prepared as follows:

To absolute ethanol (20 ml) cooled in an ice-water bath was added sodium hydride (0.25 g of an 80% oil dispersion), followed by methanesulphonylacetonitrile (0.99 g) and the mixture stirred for ½ hour. A solution of ethyl chloro(2,6-dichloro-4-trifluoromethylphenyl)hydrazonoacetate (3.0 g) in absolute ethanol (20 ml) was then added, and stirring continued for 5 hours. The yellow solid was filtered off (2.55 g) and recrystallised from ethanol to give the title compound as a colourless solid, m.p. 255° C. Ethyl chloro(2,6-dichloro-4-trifluoromethylphenyl)hydrazonoacetate was prepared as follows:

Sodium nitrite (3.04 g) was added during 15 minutes to stirred concentrated sulphuric acid (24 ml) at 30°–50° C. The solution was cooled to 20° C., and added dropwise during 15 minutes to a solution of 2,6-dichloro-4-trifluoromethylaniline (9.2 g) in acetic acid (90 ml), maintaining at 35°–40° C. This solution was then cooled to +10°, and added dropwise to a stirred solution of anhydrous sodium acetate (54 g) and ethyl chloroacetoacetate (7.0 g) in a mixture of water (72 ml) and ethanol (48 ml) during 45 minutes with cooling such that the temperature was kept at 10° C. After 1 hour at room temperature the mixture was diluted with water, filtered, and the solid dissolved in dichloromethane. This solution was dried over anhydrous magnesium sulphate, filtered, and evaporated in vacuo to give the title compound as a white solid (11.9 g), m.p. 96°–98° C.

EXAMPLE 8

Compounds Nos. 42, 43, 44, 45

A solution of 5-amino-3-cyano-1-(2,6-dichloro-4-trifluoromethylphenyl)-4-trifluoromethylthiopyrazole (4.0 g) in dry tetrahydrofuran (20 ml) was treated with tert-butyl nitrite (5.76 g) at room temperature. The mixture was then heated under reflux for 3 hours and evaporated in vacuo to give a yellow solid. Purification by chromatography eluting with petroleum ether/dichloromethane (2:1) gave 3-cyano-1-(2,6-dichloro-4-trifluoromethylphenyl)4-trifluoromethylthiopyrazole (3.12 g), m.p. 126.5°–128° C., in the form of a white solid. By proceeding in a similar manner but replacing the 5-amino-3-cyano-1-(2,6-dichloro-4-trifluoromethylphenyl)-4-trifluoromethylthiopyrazole by the following phenylpyrazoles, there was obtained:

3-Cyano-1-(2,6-dichloro-4-trifluoromethylphenyl)4-trifluoromethanesulphonylpyrazole, m.p. 149°–151° C., in the form of a white solid, from 5-amino-3-cyano-(2,6-dichloro-4-trifluoromethylphenyl)-4-trifluoromethanesulphonylpyrazole. The product was obtained after 29 hours heating under reflux, followed by purification by chromatography and recrystallisation from toluene/hexane.

3-Cyano-1-(2,6-dichloro-4-trifluoromethoxyphenyl)4-trifluoromethylthiopyrazole, m.p. 64°–65° C., in the form of a white solid, from 5-amino-3-cyano-(2,6-dichloro-4-trifluoromethoxyphenyl) 4-trifluoromethylthiopyrazole.

3-Cyano-1-(2,6-dichloro-4-trifluoromethylphenyl)4-methanesulphonylpyrazole, m.p. 147°–150° C., in the form of yellow crystals, from 5-amino-3-cyano-1-(2,6-dichloro-4-trifluoromethylphenyl)-4-methanesulphonylpyrazole.

EXAMPLE 9

Compounds Nos. 46, 47, 48, 49, 50, 94

To a solution of 5-amino-3-cyano-1-(2,6-dichloro-4-trifluoromethylphenyl)-4-trifluoromethylthiopyrazole (3.0 g) in chloroform (50 ml) stirred at room temperature, was added iodine (3.61 g). Tert-butyl nitrite (1.43 g) was then added and after ½ hour the mixture was heated under reflux for 2 hours, then left at room temperature overnight. The solid was filtered off, washed with dichloromethane (50 ml) and the combined filtrate washed with sodium thiosulphate solution (2×50 ml) and then with water (50 ml). After drying over anhydrous magnesium sulphate, the solution was evaporated in vacuo to give a yellow solid (3.8 g), which was purified by chromatography eluting with petroleum ether/dichloromethane (2:1). Recrystallisation from toluene/hexane gave 3-cyano-1-(2,6-dichloro-4 -trifluoromethylphenyl)-5-iodo-4-trifluoromethylthiopyrazole, m.p. 187.3°–188.3° C., in the form of a white solid.

By proceeding in a similar manner but replacing the 5-amino-3-cyano-1-(2,6-dichloro-4-trifluoromethylphenyl)-4-trifluoromethylthiopyrazole by the following phenylpyrazoles, there was obtained:

3-Cyano-1-(2,6-dichloro-4-trifluoromethylphenyl)-5 -iodo-4-trifluoromethylsulphonylpyrazole, m.p. 180°–181° C., in the form of a white solid; from 5-amino-3-cyano-1-(2,6 -dichloro-4-trifluoromethylphenyl)-4-trifluoromethanesulphonylpyrazole. In this instance the reaction mixture was heated under reflux for 24 hours.

5-Amino-1-(2,6-dichloro-4-trifluoromethylphenyl)3 -iodo-4-methanesulphonylpyrazole, m.p. 226°–227° C., in the form of a brown solid; from 3,5-diamino-1-(2,6-dichloro-4 -trifluoromethylphenyl)4-methanesulphonylpyrazole. The reaction mixture was heated under reflux for 4½ hours in this case. 1-(2,6-Dichloro-4-trifluoromethylphenyl)-3 -iodo-4-methanesulphonylpyrazole, in the form of a cream solid, m.p. 150°–151° C., prepared from 3-amino-1-(2,6 -dichloro-4-trifluoromethylphenyl)-4-methanesulphonylpyrazole (preparation described in Reference Example 3). 1-(2,6-Dichloro-4-trifluoromethylphenyl)-3-iodo-4-trifluoromethylthiopyrazole, m.p. 80°–81.5° C., in the form of a white solid, prepared from 3-amino-1-(2,6-dichloro-4-trifluoromethylphenyl) 4-trifluoromethyl-thiopyrazole. The reaction was performed using dry acetonitrile as solvent and at a temperature of 0°–5° C. initially and then at ambient temperature for ½ hour. By proceeding in a similar manner there was obtained:

3-Cyano-1-(2,6-dichloro-4-trifluoromethylphenyl)-5 -iodo-4-trifluoromethylsulphinylpyrazole, m.p. 165°–166° C., in the form of a pale yellow solid; from 5-amino-3-cyano-1-( 2,6-dichloro-4-trifluoromethylphenyl)-4-trifluoromethylsulphinyl pyrazole.

REFERENCE EXAMPLE 4

3-Amino-1-(2,6-dichloro-4-trifluoromethylphenyl)-4-trifluoromethylthiopyrazole, used in the above Example was prepared as follows:

3-tert-Butoxycarbonylamino-1-(2,6-dichloro-4 -trifluoromethylphenyl)-4-trifluoromethylthiopyrazole (3.45 g) dissolved in dry acetonitrile (80 ml) was treated with iodotrimethylsilane (2.6 g) added dropwise under nitrogen. After stirring for 45 minutes, methanol (10 ml) was added, and after a further 15 minutes the solution was concentrated in vacuo to give a dark gum. This was dissolved in dichloromethane (100 ml), washed with a solution of sodium sulphite (50 ml), then with water (50 ml) and dried over anhydrous magnesium sulphate. Evaporation of the dichloromethane gave the title compound (2.6 g), m.p. 130°–135° C., as an off white solid.

3-tert-Butoxycarbonylamino-1-(2,6-dichloro-4 -trifluoromethylphenyl)-4-trifluoromethylthiopyrazole used above, was prepared as follows:

1-(2,6-Dichloro-4-trifluoromethylphenyl)-4 -trifluoromethylthiopyrazole-3-carboxylic acid (5.6 g) was dissolved in dry N,N-dimethylformamide (50 ml) and triethylamine (1.33 g) added. After cooling to 5° C., a solution of diphenylphosphorylazide (3.63 g) in N,N-dimethylformamide (20 ml) was added. When the solution had reached ambient temperature, it was heated to 35° C. for 2½ hours. After evaporation in vacuo at a temperature kept below 40° C., a solution of sodium chloride (5 g) in water (100 ml) was added, and the suspension extracted with ether (3×100 ml). The combined extracts were washed with water (50 ml), dried over anhydrous magnesium sulphate and evaporated to give 1-( 2,6-dichloro-4-trifluoromethylphenyl)4 -trifluoromethylthiopyrazole-3-carboxylic acid azide (5.4 g). A solution of this in dry toluene (200 ml) was heated under reflux with stirring for 1.5 hours, tert-butanol (35 ml) was added, and reflux continued for 4 hours. After evaporation in vacuo the residue was purified by chromatography eluting with dichloromethane to give the title compound (3.3 g) as an off-white solid, m.p. 122°–125° C.

1-(2,6-Dichloro-4-trifluoromethylphenyl)-4 -trifluoromethylthiopyrazole-3-carboxylic acid used above, was prepared as follows:

A solution of sodium hydroxide (1.73 g) in water (50 ml) was added to a suspension of 1-(2,6-dichloro-4 -trifluoromethylphenyl)-3-ethoxycarbonyl-4-trifluoromethylthiopyrazole (6.8 g) in ethanol (70 ml), and the mixture heated under reflux for 1½ hours. The solvent was evaporated in vacuo, water (250 ml) added, followed by concentrated sulphuric acid to pH1. The product was filtered off, washed with water (100 ml) and dried at 120° C. in vacuo giving the title compound (5.7 g) as a grey solid, m.p. 175°–177° C.

1-(2,6-Dichloro-4-trifluoromethylphenyl)-3 -ethoxycarbonyl-4-trifluoromethylthiopyrazole used above, was prepared by following the procedure of Example 8 by replacing the 5-amino-3-cyano-1-(2,6-dichloro-4-trifluoromethylphenyl)- 4-trifluoromethylthiopyrazole by 5-amino-1-(2,6 -dichloro-4-trifluoromethylphenyl)3-ethoxycarbonyl-4-trifluoromethylthiopyrazole. The title compound was obtained as an off white solid, m.p. 125.5°–126° C.

5-Amino-1-(2,6-dichloro-4-trifluoromethylphenyl)-3 -ethoxycarbonyl-4-trifluoromethylthiopyrazole used above, was prepared by the procedure described in Example 1, and obtained in the form of a white solid, m.p. 213°–214° C. after purification by chromatography; from 5-amino-1-(2,6 -dichloro-4-trifluoromethylphenyl)3-ethoxycarbonylpyrazole. 5-Amino-1-(2,6-dichloro-4-trifluoromethylphenyl)-3-ethoxycarbonylpyrazole was prepared as follows:

A solution of 3-cyano-2-hydroxyprop-2-enoic acid ethyl ester sodium salt (50.0 g) [C.A.57:16604d N. S. Vulfson et al] in cold water (500 ml) was stirred whilst cold sulphuric acid (2N) was added to pH1. The solution was extracted with ether (2×400 ml) and the extract washed with water (200 ml), dried over anhydrous magnesium sulphate, and evaporated in vacuo to give a yellow oil (29.4 g). A solution of this in ethanol (400 ml) was treated with 2,6-dichloro-4-trifluoromethylphenylhydrazine (51.1 g), and the solution heated under reflux overnight. After cooling, the solution was evaporated in vacuo to give an orange solid. Recrystallisation from toluene/hexane gave the title compound as a fawn solid (40.2 g), m.p. 179°–181° C.

EXAMPLE 10

Compounds Nos. 51, 52, 53, 54, 55, 56, 57, 58, 59, 60, 61, 62, 91

A partial solution of 5-amino-3-cyano-1-(2,6 -dichloro-4-trifluoromethylphenyl)-4-trifluoromethylthiopyrazole (48.0 g) in chloroform (600 ml) was stirred mechanically and treated with m-chloroperbenzoic acid (61.4 g). The mixture was stirred and heated under reflux in an atmosphere of nitrogen for 3.5 hours. After cooling, an additional amount of m-chloroperbenzoic acid (12.3 g) was added, and reflux continued for 1 hour. The cooled mixture was diluted with ethyl acetate (600 ml), washed with a solution of sodium metabisulphite (2×250 ml), then with sodium hydroxide solution (2×250 ml) and finally with water (1×500 ml). The organic layer was dried over anhydrous magnesium sulphate, filtered, and evaporated in vacuo to give a fawn solid.

Recrystallisation from toluene/hexane/ethyl acetate gave 5-amino-3-cyano-1-(2,6-dichloro-4 -trifluoromethylphenyl)-4-trifluoromethanesulphonylpyrazole as white crystals (37.0 g) m.p. 219°–221.5° C.

A stirred solution of 5-amino-3-cyano-1-(2,6 -dichloro-4-trifluoromethylphenyl)-4-trifluoromethylthiopyrazole (10.0 g) in dichloromethane (100 ml) was treated with m-chloroperbenzoic acid (4.5 g). After stirring overnight additional m-chloroperbenzoic acid (1.6 g) was added in 2 portions, and left for 2 days. The reaction product was diluted with ethyl acetate (30 ml) and then washed in turn with sodium sulphite solution (50 ml), sodium carbonate solution (50 ml) and with water (50 ml). After drying over magnesium sulphate, this was filtered and evaporated in vacuo. Purification by chromatography on silica eluting with dichloromethane gave 5-amino-3-cyano-1-(2,6-dichloro-4-trifluoromethylphenyl)-4-trifluoromethylsulphinylpyrazole as a white solid (6.0 g), m.p. 200.5°–201° C.

By proceeding in a similar manner and by replacing the abovementioned phenylpyrazoles by the appropriate phenylpyrazoles there was prepared:

5-Amino-3-cyano-1-(2,6-dichloro-4 -trifluoromethoxyphenyl)-4-trifluoromethanesulphonylpyrazole, m.p. 210°–211.5° C., in the form of a white solid, and 5-amino-3-cyano- 1-(2,6-dichloro-4-trifluoromethoxyphenyl)-4-trifluoromethylsulphinylpyrazole, m.p.179°–180° C., in the form of a white solid.

Both of the above two compounds being prepared from 5-amino-3-cyano-1-(2,6-dichloro-4-trifluoromethoxyphenyl) 4-trifluoromethylthiopyrazole by the use of an appropriate quantity of m-chloroperbenzoic acid.

3-Cyano-1-(2,6-dichloro-4-trifluoromethylphenyl)4-trifluoromethylsulphinylpyrazole, m.p. 142.5°–144.2° C., in the form of a white solid, from 3-cyano-1-(2,6-dichloro-4 -trifluoromethylphenyl)-4-trifluoromethylthiopyrazole and by performing the reaction at 40°–50° C. for 20 hours.

5-Amino-3-cyano-1-(2,6-dichloro-4 -trifluoromethylphenyl)-4-(1-methylprop-2-ynylsulphinyl)pyrazole, 136.6°–137.2° C., in the form of a white solid, from 5-amino-3 -cyano-1-(2,6-dichloro-4-trifluoromethylphenyl)-4-(1 -methylprop-2-ynylthio)pyrazole.

5-Amino-3-cyano-1-(2,6-dichloro-4 -trifluoromethylphenyl)-4-methylsulphinylpyrazole, m.p. 176°–177° C., in the form of a fawn crystalline solid; prepared from 5-amino-3 -cyano-1-(2,6-dichloro-4-trifluoromethylphenyl)-4-methylthiopyrazole.

5-Amino-3-cyano-1-(2,6-dichloro-4 -trifluoromethylphenyl)-4-isopropylsulphinylpyrazole, m.p. 187°–188° C., in the form of a white solid; prepared from 5-amino-3-cyano-1-( 2,6-dichloro-4-trifluoromethylphenyl)-4-isopropylthiopyrazole.

5-Amino-3-bromo-1-(2,6-dichloro-4 -trifluoromethylphenyl)-4-trifluoromethylsulphinylpyrazole, m.p. 179°–180° C., in the form of a white solid; prepared from 5-amino-3 -bromo-1-(2,6-dichloro-4-trifluoromethylphenyl)-4-trifluoromethylthiopyrazole.

5-Amino-4-tert-butanesulphonyl-3-cyano-1-(2,6 -dichloro-4-trifluoromethylphenyl)pyrazole, m.p. 183°–184° C., in the form of a pale yellow solid; prepared from 5-amino- 4-tert-butylthio-3-cyano-1-(2,6-dichloro-4-trifluoromethylphenyl)pyrazole employing 2 molar equivalents of m-chloroperbenzoic acid in chloroform and at room temperature for 4 hours.

By proceeding in a similar manner there was prepared:

5-Amino-3-chloro-1-(2,6-dichloro-4 -trifluoromethylphenyl)-4-trifluoromethanesulphonylpyrazole, m.p. 162°–164° C., in the form of a white solid, from 5-amino-3-chloro-1- (2,6 -dichloro-4-trifluoromethylphenyl)4-trifluoromethylthiopyrazole.

3-Cyano-1-(2,6-dichloro-4-trifluoromethylphenyl)5 -propylamino-4-trifluoromethanesulphonylpyrazole, m.p. 49°–65° C., in the form of a yellow solid; prepared from 3-cyano- 1-(2,6-dichloro-4-trifluoromethylphenyl)-5-propylamino-4-trifluoromethylthiopyrazole at room temperature.

5-Acetamido-3-cyano-1-(2,6-dichloro-4 -trifluoromethylphenyl)-4-trifluoromethanesulphonylpyrazole, m.p. 174°–175.9° C., in the form of a white solid; prepared from 5 -acetamido-3-cyano-1-(2,6-dichloro-4-trifluoromethylthiopyrazole employing 2 molar equivalents of m-chloroperbenzoic acid and heating under reflux in chloroform for 20 hours.

EXAMPLE 11

Compounds Nos. 63, 64

Trifluoroacetic anhydride (6.0 ml) was added dropwise during 15 minutes to a stirred mixture of 85% hydrogen peroxide (0.96 ml) in dichloromethane (20 ml) at 0°–10° C. The mixture was warmed to 20° C. for 5 minutes, and a suspension of 3-amino-1-(2,6-dichloro-4-trifluoromethylphenyl)-4methanesulphonylpyrazole (2.0 g) in dichloromethane (20 ml) was added during 5 minutes. The solution was then heated under reflux for 1 hour and left at room temperature overnight. This was poured onto water (100 ml) and the organic layer washed in turn with sodium metabisulphite solution (30 ml) and sodium bicarbonate solution (30 ml), and then dried over anhydrous magnesium sulphate. Evaporation in vacuo gave, after recrystallization from dichlormethane/toluene/hexane, 1-(2,6-dichloro-4-trifluoromethylphenyl)- 4-methanesulphonyl-3-nitropyrazole, m.p. 190°–192° C., in the form of a white solid.

By proceeding in a similar manner but replacing the 3-amino-1-(2,6-dichloro-4-trifluoromethylphenyl)-4-methanesulphonylpyrazole by 3,5-diamino-1-(2,6-dichloro-4 -trifluoromethylphenyl)-4-methanesulphonylpyrazole there was prepared:

5-Amino-1-(2,6-dichloro-4-trifluoromethylphenyl)-4 -methanesulphonyl-3-nitropyrazole in the form of a cream solid, m.p. 190°–192° C. The oxidation was performed initially at 0° C. and then warmed to room temperature for 1.5 hours. Purification by chromatography eluting with dichloromethane, and recrystallisation from toluene was necessary in this case.

EXAMPLE 12

Compound No. 65

A stirred mixture of 85% hydrogen peroxide(0.31 g) and dichloromethane (20 ml) was treated with trifluoroacetic anhydride (2.1 g) dropwise at −10° C. After 15 minutes the mixture was allowed to reach room temperature, and stirred for a further 15 minutes. After re-cooling to 0° C., a solution of 3-amino-1-(2,6-dichloro-4 -trifluoromethylphenyl)-4-trifluoromethylthiopyrazole (1.0 g) [preparation described in Reference Example 4] in dichloromethane (20 ml) was added, and the solution allowed to warm to room temperature. After 2 hours, an additional quantity of trifluoroperacetic acid [prepared as above using 85% hydrogen peroxide (0.31 g); dichloromethane (20 ml) and trifluoroacetic anhydride (2.1 g)] was added. The mixture was stirred overnight, then poured onto water (50 ml), and the dichloromethane layer washed in turn with 5% sodium sulphite solution (30 ml), sodium bicarbonate solution (30 ml) and with water (30 ml). This solution was then dried over anhydrous magnesium sulphate, and evaporated in vacuo to give a green gum (0.8 g). Purification by chromatography eluting with dichloromethane/hexane (3:2) gave 1-(2,6 -dichloro-4-trifluoromethylphenyl)-3-nitro-4 -trifluoromethyl-sulphinylpyrazole (0.3 g), m.p. 124°–130° C., in the form of a pale green solid.

EXAMPLE 13

Compounds Nos. 66, 67

Phosphorus oxychloride (20 ml) was added to 5-amino-1-(2-bromo-6-chloro-4-trifluoromethylphenyl)-3-carbamoyl-4-methanesulphonylpyrazole (4.0 g) and the solution heated at 50°–60° C. for 3.25 hours, and left at room temperature overnight. The mixture was cautiously added to vigorously stirred water (200 ml), and the precipitated solid collected and dried in vacuo. Recrystallisation from toluene/ethanol gave 5-amino-1-(2-bromo-6-chloro-4-trifluoromethylphenyl)-3 -cyano-4-methanesulphonylpyrazole as buff crystals, m.p. 235°–238° C.

By proceeding in a similar manner to that described above but replacing the 5-amino-1-(2-bromo-6-chloro-4 -trifluoromethylphenyl)-3-carbamoyl-4-methylsulphonylpyrazole by 5-amino-3-carbamoyl-1-(2,6-dichloro-4 -trifluoromethoxyphenyl)-4-methanesulphonylpyrazole there was obtained:

5-Amino-1-(2,6-dichloro-4-trifluoromethoxyphenyl)-3 -cyano-4-methanesulphonylpyrazole in the form of a white solid, m.p. 202.5°–203.5° C.

REFERENCE EXAMPLE 5

5-Amino-3-carbamoyl-1-(2,6-dichloro-4 -trifluoromethoxyphenyl)-4-methanesulphonylpyrazole, used above, was prepared as follows:

A suspension of 5-amino-3-carboxy-1-(2,6-dichloro-4 -trifluoromethoxyphenyl)-4-methanesulphonylpyrazole (40.0 g) in toluene (160 ml) was treated with thionyl chloride (150 ml) and the mixture heated under reflux with stirring for 3 hours. The solution was evaporated in vacuo and re-evaporated after addition of toluene (100 ml). The resultant acid chloride was dissolved in tetrahydrofuran (200 ml) and this solution added dropwise during 15 minutes to stirred ammonia solution (300 ml), with cooling at 5°–10° C. throughout. After standing overnight, water (250 ml) was added and the solution extracted with ethyl acetate (3×100 ml). The combined extract was washed with water (2×250 ml), dried over anhydrous magnesium sulphate, and evaporated in vacuo to give a solid (34.9 g). The title compound (19.3 g) was obtained in the form of a white solid, m.p. 219°–220° C., after recrystallisation from ethyl acetate/hexane.

By proceeding in a similar manner but replacing the 5-amino-3-carboxy-1-(2,6-dichloro-4 -trifluoromethoxyphenyl)-4-methanesulphonylpyrazole by 5-amino-1-(2-bromo-6 -chloro-4-trifluoromethylphenyl)3-carboxy-4-methanesulphonylpyrazole there was obtained:

5-Amino-1-(2-bromo-6-chloro-4 -trifluoromethylphenyl)-3-carbamoyl-4-methanesulphonylpyrazole, m.p. 250°–253° C., in the form of a grey-brown powder.

5-Amino-3-carboxy-1-(2,6-dichloro-4 -trifluoromethoxyphenyl)-4-methanesulphonylpyrazole, used above, was prepared by using the method employed to prepare 3-carboxy- 1-(2,6-dichloro-4-trifluoromethylphenyl)-4-methanesulphonylpyrazole by replacing the 1-(2,6-dichloro-4 -trifluoromethylphenyl)-4-ethoxycarbonyl-4-methanesulphonylpyrazole (Reference Example 3) by 5-amino-1-(2,6-dichloro- 4-trifluoromethoxyphenyl)-3-ethoxycarbonyl-4-methanesulphonylpyrazole. It was obtained in the form of a white solid, m.p. 195°–196° C.

5-Amino-1-(2-bromo-6-chloro-4 -trifluoromethylphenyl)-3-carboxy-4-methanesulphonylpyrazole, used above, was prepared as follows:

5-Amino-1-(2-bromo-6-chloro-4 -trifluoromethylphenyl)-3-ethoxycarbonyl-4-methanesulphonylpyrazole (8.0 g) was heated under reflux with 48% hydrobromic acid (75 ml) in acetic acid (75 ml) for 3 hours. After cooling overnight, this was evaporated in vacuo, and the residue triturated with aqueous sodium bicarbonate. The title compound was obtained as a grey powder (6.6 g), m.p. 130°–133° C., after drying in vacuo.

5-Amino-1-(2,6-dichloro-4-trifluoromethoxyphenyl)-3 -ethoxycarbonyl-4-methanesulphonylpyrazole, used above, was prepared by the procedure of Reference Example 3 by replacing ethyl chloro (2,6-dichloro-4-trifluoromethylphenyl)hydrazonoacetate by ethyl chloro (2,6-dichloro-4-trifluoromethoxyphenyl)hydrazonoacetate. It was obtained in the form of a light brown solid, m.p. 207° C.

5-Amino-1-(2-bromo-6-chloro-4 -trifluoromethylphenyl)-3-ethoxycarbonyl-4-methanesulphonylpyrazole, used above, was prepared similarly from ethyl chloro (2-bromo-6 -chloro-4-trifluoromethylphenyl)hydrazonoacetate. It was obtained as a white solid, m.p. 255.5°–256.5° C.

Ethyl chloro (2,6-dichloro-4-trifluoromethoxyphenyl)hydrazonoacetate, used above, was prepared by the procedure of Reference Example 3 by replacing 2,6-dichloro- 4-trifluoromethylaniline by 2,6-dichloro-4-trifluoromethoxyaniline, and was obtained as a brown solid, m.p. 55°–58° C.

Ethyl chloro (2-bromo-6-chloro-4-trifluoromethylphenyl)hydrazonoacetate, used above, was prepared similarly from 2-bromo-6-chloro-4-trifluoromethylaniline, and was obtained as a buff solid, m.p. 116.5°–117.5° C.

EXAMPLE 14

Compound No. 68

A solution of sodium ethoxide prepared from sodium (0.36 g) and absolute ethanol (50 ml) was treated at room temperature with methanesulphonyl acetonitrile (1.88 g) and stirred for 1 hour. To this was then added dropwise with stirring, a solution of 1-chloro-1-(2,6-dichloro-4 -trifluoromethylphenyl)hydrazonopropan-2-one (5.0 g) in ether (50 ml). After stirring overnight the solution was diluted with water (100 ml), extracted with ether (3×50 ml), and the combined ethereal extracts dried over anhydrous magnesium sulphate, and evaporated in vacuo to give a brown solid.

Recrystallisation from toluene/hexane gave 3-acetyl-5-amino-1-(2,6-dichloro-4-trifluoromethylphenyl)-4-methanesulphonylpyrazole (2.56 g) in the form of a buff solid, m.p. 176.7°–178.9° C.

1-Chloro-1-(2,6-dichloro-4-trifluoromethylphenyl) hydrazonopropan-2-one, used above, was prepared by the procedure described in Reference Example 3, but replacing the ethyl chloroacetoacetate by 3-chloropentan-2,4-dione. It was obtained in the form of a light brown solid, m.p. 77°–79° C., after recrystallisation from petroleum ether b.p. 60°–80° C.

EXAMPLE 15

Compounds Nos. 69, 70, 71, 72, 73, 74, 75, 76, 77, 78, 100

A solution of 5-amino-3-cyano-1-(2,6-dichloro-4-trifluoromethylphenyl)-4-thiocyanatopyrazole (3.1 g) in methanol (50 ml) was stirred under nitrogen at −7° C. and methyl iodide (5.25 ml) added. A solution of potassium hydroxide (0.92 g) in water (10 ml) was then added dropwise during 10 minutes, keeping the mixture below 0° C. After stirring at room temperature for 3 hours, the mixture was neutralised by the addition of carbon dioxide pellets, followed by water (180 ml). The precipitated solid was filtered off, and recrystallised from toluene/hexane (2:1).

5-Amino-3-cyano-1-(2,6-dichloro-4 -trifluoromethylphenyl)-4-methylthiopyrazole was obtained as a brown crystalline solid (1.94 g), m.p. 170°–172° C.

By proceeding in a similar manner but replacing the methyl iodide by the following alkyl halides there was obtained:

5-Amino-3-cyano-1-(2,6-dichloro-4 -trifluoromethylphenyl)-4-ethylthiopyrazole in the form of a yellow solid, m.p. 158°–160° C., by using ethyl iodide and aqueous ethanol as solvent.

5-Amino-3-cyano-1-(2,6-dichloro-4 -trifluoromethylphenyl)-4-propylthiopyrazole in the form of a pale brown solid, m.p. 123°–124° C., by using propyl bromide and aqueous dioxan as solvent.

5-Amino-3-cyano-1-(2,6-dichloro-4 -trifluoromethylphenyl)-4-isopropylthiopyrazole in the form of a pale brown solid, m.p. 168°–169° C., by using isopropyl bromide and aqueous isopropyl alcohol as solvent.

5-Amino-3-cyano-1-(2,6-dichloro-4 -trifluoromethylphenl)-4-(2-methylpropylthio)pyrazole in the form of a pale brown solid, m.p. 134°–137° C., by using 1-iodo-2-methylpropane and aqueous dioxan as solvent.

5-Amino-3-cyano-1-(2,6-dichloro-4 -trifluoromethylphenll)-4-(1-methylpropylthio)pyrazole in the form of a pale brown solid, m.p. 152.5°–154° C., by using 2-iodobutane and aqueous dioxan as solvent. The product was purified by dry column chromatography on silica eluting with hexane/diethylether (1:1). 4-Allylthio-5-amino-3-cyano-1-(2,6 -dichloro-4-trifluoromethylphenyl)pyrazole in the form of a pale brown solid, m.p. 140°–141° C., by using allyl bromide and aqueous dioxan as solvent. The product was purified by chromatography eluting with hexane/diethyl ether (1:1), followed by recrystallisation from toluene. 5-Amino-3 -cyano-1-(2,6-dichloro-4-trifluoromethylphenyl)-4-(prop-2-ynylthio)pyrazole in the form of a brown solid, m.p. 161°–163° C., by using propargyl bromide and aqueous methanol as solvent.

5-Amino-3-cyano-1-(2,6-dichloro-4 -trifluoromethylphenyl)-4-(1-methylprop-2-ynylthio)pyrazole in the form of a white solid, m.p. 134°–135.6° C., by using 3-bromobut-1-yne and aqueous methanol as solvent. The product was purified by chromatography eluting with diethyl ether/hexane (1:1), followed by recrystallisation from toluene/hexane.

5-Amino-3-bromo-1-(2,6-dichloro-4 -trifluoromethylphenyl)-4-methylthiopyrazole in the form of a white solid, m.p. 117°–119° C., by using methyl iodide and aqueous methanol as solvent. The product was purified by chromatography eluting with dichloromethane.

By proceeding in a similar manner there was prepared:

5-Amino-4-(2-chloro-1,1,2-trifluoroethylthio)-3 -cyano-1-(2,6-dichloro-4-trifluoromethylphenyl)pyrazole, m.p. 116°–118° C., in the form of a white solid, by using chlorotrifluoroethylene and aqueous dioxan as solvent. The product was purified by chromatography eluting with dichloromethane, and subsequent recrystallisation from toluene/hexane (3:10).

REFERENCE EXAMPLE 6

5-Amino-3-cyano-1-(2,6-dichloro-4 -trifluoromethylphenyl)-4-thiocyanatopyrazole, used above, was prepared as follows:

A suspension of potassium thiocyanate (4.99 g) in methanol (75 ml) was stirred at −78° C. Bromine (0.8 ml) dissolved in methanol (10 ml) was then added dropwise during 25 minutes. After a further 20 minutes, a solution of 5 -amino-3-cyano-1-(2,6-dichloro-4-trifluoromethylphenyl)pyrazole (5.0 g) in methanol (50 ml) was then added over 30 minutes. The mixture was stirred at −78° C. and then. allowed to warm to room temperature for 3 hours, before pouring onto water (250 ml). The precipitated solid was filtered off, washed with water, and recrystallised from toluene/hexane to give the title compound (3.1 g) as a white solid, m.p. 179°–182° C.

By proceeding in a similar manner but replacing the 5-amino-3-cyano-1-(2,6-dichloro-4-trifluoromethylphenyl)pyrazole in the above Reference Example by 5-amino-3-bromo- 1-(2,6-dichloro-4-trifluoromethylphenyl)pyrazole, there was obtained:

5-Amino-3-bromo-1-(2,6-dichloro-4 -trifluoromethylphenyl)-4-thiocyanatopyrazole in the form of a white solid, m.p. 162°–163.5° C., after purification by chromatography, eluting with dichloromethane. The preparation of 5-amino- 3-bromo-1-(2,6-dichloro-4-trifluoromethylphenyl)pyrazole, used above, is described in Reference Example 1.

EXAMPLE 16

Compound No. 79

To a stirred solution of 5-amino-3-cyano-1-(2,6 -dichloro-4-trifluoromethylphenyl)-4-thiocyanatopyrazole (5.0 g) in dry diethyl ether (70 ml) at 0° C. under an atmosphere of nitrogen, was added dropwise a solution of tert-butylmagnesium chloride (7.92 ml of a 2M solution in dry ether). The solution was then allowed to reach room temperature, and the stirring continued for 3 hours. Water (40 ml) was then added and the mixture stirred for 15 minutes. The ethereal layer was separated, washed with water (50 ml), dried over anhydrous magnesium sulphate, and evaporated in vacuo to give a brown solid. Purification by chromatography eluting with dichloromethane/petroleum ether (3:1) gave 5-amino- 3-cyano-1-(2,6-dichloro-4-trifluoromethylphenyl) -4-tert-butylthiopyrazole (2.62 g), m.p. 196°–198.5° C., in the form of a pale yellow solid.

EXAMPLE 17

Compounds Nos. 80, 81

A solution of 5-amino-3-bromo-1-(2,6-dichloro-4 -trifluoromethylphenyl)-4-methylthiopyrazole (2.0 g) [preparation described in Example 15] in methanol (45 ml) at –25° C. was treated with a rapidly added solution of potassium hydrogen persulphate (1.66 g), followed immediately by the addition of water (22 ml). The mixture was stirred for 30 minutes at 0° C., and potassium hydrogen persulphate (0.4 g) added. After 2½ hours stirring at room temperature, the mixture was poured onto water (300 ml) and saturated sodium bisulphite solution (35 ml) added. This was extracted with dichloromethane (2×150 ml) and the extract washed with water (2×50 ml), dried over anhydrous magnesium sulphate, and evaporated in vacuo. The crude product was purified by chromatography eluting with dichloromethane/ethyl acetate (4:1) to give 5-amino-3-bromo-1-(2,6-dichloro-4 -trifluoromethylphenyl)-4-methylsulphinylpyrazole (0.9 g) as a white solid, m.p. 135°–136° C.

By proceeding in a similar manner but replacing the 5-amino-3-bromo-1-(2,6-dichloro-4-trifluoromethylphenyl)-4-methylthiopyrazole by 5-amino-3-cyano-1-(2,6-dichloro-4-trifluoromethylphenyl) 4-ethylthiopyrazole and by utilising an appropriate quantity of potassium hydrogen persulphate there was obtained:

5-Amino-3-cyano-1-(2,6-dichloro-4 -trifluoromethylphenyl)-4-ethanesulphonylpyrazole in the form of a yellow solid, m.p. 180°–183° C. In this case the reaction mixture was kept at room temperature for 20 hours, and gave the title compound without chromatographic purification.

EXAMPLE 18

Compound No. 82

A solution of 3-cyano-1-(2,6-dichloro-4 -trifluoromethylphenyl)-5-ethoxymethyleneamino-4-trifluoromethylthiopyrazole (1.7 g) in methanol (30 ml) was stirred, and sodium borohydride (1.08 g) added portionwise. The solution was allowed to reach room temperature, and after a further 7 hours was poured onto water (200 ml). This was extracted with dichloromethane (3×50 ml), dried over anhydrous magnesium sulphate, and evaporated in vacuo to give a white solid (1.4 g). Purification by chromatography eluting with dichloromethane/petroleum ether (4:1) gave 3 -cyano-1-(2,6-dichloro-4-trifluoromethylphenyl)-5-methylamino-4-trifluoromethylthiopyrazole (0.42 g) in the form of a white solid, m.p. 208.5°–209.5° C.

EXAMPLE 19

Compound No. 83

To a solution of 3-cyano-1-(2,6-dichloro-4 -trifluoromethylphenyl)-5-ethoxycarbonylamino-4-trifluoromethylthiopyrazole (1.0 g) in dry tetrahydrofuran (20 ml) was added sodium hydride (0.095 g) with stirring at 0°–10° C. After stirring at room temperature for 2½ hours, methyl iodide (0.6 g) was added dropwise with cooling at 0°–10° C., and the mixture stirred overnight. Additional methyl iodide (0.6 g) was added and stirring continued for 8½ hours. The solution was poured onto water (100 ml) and extracted with dichloromethane (2×50 ml).

The extracts were dried over anhydrous magnesium sulphate and evaporated in vacuo to give 3-cyano-1-(2,6 -dichloro-4-trifluoromethylphenyl)-5 -(N-ethoxycarbonyl-N-methyl)amino-4-trifluoromethylthiopyrazole (0.81 g), m.p. 86.2°–88.5° C., in the form of a white solid.

EXAMPLE 20

Compound No. 84

A mixture of 5-amino-3-cyano-1-(2,6-dichloro-4 -trifluoromethylphenyl)-4-trifluoromethylthiopyrazole (3.0 g) and trifluoroacetic anhydride (15.0 g) in tetrahydrofuran (25 ml) was heated under reflux for 6 hours. After standing overnight the mixture was evaporated in vacuo, dissolved in dichloromethane (50 ml) and washed with sodium bicarbonate solution (50 ml) and with water (50 ml). The solution was dried over anhydrous magnesium sulphate and evaporated in vacuo to give a brown oil (2.9 g). Trituration with hexane then gave 3-cyano-1-(2,6-dichloro-4-trifluoromethylphenyl)- 5-trifluoroacetamido-4-trifluoromethylthiopyrazole (1.86 g), m.p. 138.2°–139.8° C., in the form of a white solid.

EXAMPLE 21

Compounds Nos. 85, 98

A solution of 3-cyano-1-(2,6-dichloro-4 -trifluoromethylphenyl)-5-bisethoxycarbonyl)amino-4-trifluoromethylthiopyrazole (1.8 g) in ethanol (20 ml) was treated with a saturated solution of sodium bicarbonate (20 ml), and the mixture heated under reflux for 1½ hours. After evaporation in vacuo the yellow oil was distributed between dichloromethane (70 ml) and water (70 ml). The aqueous layer was re-extracted with dichloromethane (50 ml) and the combined organic solution dried over anhydrous magnesium sulphate, and evaporated in vacuo. Trituration with hexane then gave 3-cyano-1-(2,6-dichloro-4 -trifluoromethylphenyl)-5-ethoxycarbonylamino-4-trifluoromethylthiopyrazole (1.23 g), m.p. 108.7°–109.7° C., in the form of a white solid.

By proceeding in a similar manner there was prepared from 3-cyano-1-(2,6-dichloro-4-trifluoromethylphenyl)-5 -bis(ethoxycarbonyl)amino-4-trifluoromethylsulphonylpyrazole:

3-Cyano-1-(2,6-dichloro-4-trifluoromethylphenyl)-5 -ethoxycarbonylamino-4-trifluoromethylsulphonylpyrazole, m.p. 112.4°–113° C., in the form of a white solid, and after purification by chromatography eluting with dichloromethane/hexane (1:1).

EXAMPLE 22

Compound No. 86

To a solution of 1-(2,6-dichloro-4 -trifluoromethylphenyl)-3-(1-hydroxyethyl)-4-trifluoromethylthiopyrazole (1.1 g) in dichloromethane (40 ml) was added pyridinium chlorochromate (0.62 g), and the mixture stirred at room temperature overnight. Ether (50 ml) was added and the mixture filtered on diatomaceous earth. Evaporation of the filtrate in vacuo gave a brown solid, which was triturated with hexane and filtered. The filtrate was evaporated in vacuo to give a yellow solid, which recrystallised from cyclohexane to give 3-acetyl-1-(2,6-dichloro-4 -trifluoromethylphenyl)-4-trifluoromethylthiopyrazole (0.4 g) in the form of a yellow solid, m.p. 89°–91° C.

REFERENCE EXAMPLE 7

1-(2,6-Dichloro-4-trifluoromethylphenyl)3-(1-hydroxyethyl)-4-trifluoromethylthiopyrazole used in the above Example was prepared as follows: A stirred solution of 1-(2,6-dichloro-4-trifluoromethylphenyl)-3-formyl-4-trifluoromethylthiopyrazole (1.64 g) in dry ether (20 ml) was treated with a solution of methyl magnesium-iodide (1.35 ml of a 3M solution in ether) added dropwise during 5 minutes under nitrogen. The solution was then heated under reflux for 1½ hours, after which time it was cooled and treated with an additional portion of methyl magnesium iodide solution (0.2 ml) in the same manner as before. After another 1 hour of reflux, the mixture was poured onto excess ice and dilute hydrochloric acid (100 ml) and extracted with ether (2×50 ml). The extract was washed with sodium bicarbonate solution (50 ml), and with water (50 ml) and dried over anhydrous magnesium sulphate. Evaporation in vacuo gave the title compound (1.46 g), in the form of a yellow oil.

EXAMPLE 23

Compound No. 87

A stirred solution of 3-cyano-1-(2,6-dichloro-4-trifluoromethylphenyl)-4-trifluoromethylthiopyrazole (2.03 g) in dry tetrahydrofuran (20 ml) was treated with a solution of diisobutyl aluminium hydride (10 ml of a 1.0M solution in toluene) which was added dropwise under nitrogen at −60° to 70° C. during 10 minutes. The solution was allowed to warm to room temperature for 3 hours and then at −10° C. overnight. After pouring onto ice and 2N sulphuric acid (100 ml) and stirring for ½ hour, the mixture was extracted into dichloromethane (3×25 ml). The extract was washed with water (50 ml), dried over anhydrous magnesium sulphate, and evaporated in vacuo to give a yellow oil (1.8 g). Purification by chromatography eluting with dichloromethane/hexane (1:1) gave 1-(2,6-dichloro-4-trifluoromethylphenyl)-3-formyl-4-trifluoromethylthiopyrazole (1.5 g) in the form of a white solid, m.p. 79°–81° C.

EXAMPLE 24

Compound No. 88

A solution of 5-amino-3-cyano-1-(2,6-dichloro-4-trifluoromethylphenyl)-4-trifluoromethylthiopyrazole (2.0 g) in formic acid (90%, 50 ml) was heated under reflux with Raney nickel (2.0 g), cooled and heating continued for 5 hours after a further addition of Raney nickel (2.0 g). The filtered mixture was diluted with water (250 ml) and extracted with dichloromethane (4×50 ml). The extract was washed with sodium bicarbonate solution (2×50 ml), dried over anhydrous magnesium sulphate, and evaporated in vacuo to give a solid (1.0 g). Purification by chromatography eluting with dichloromethane gave 5-amino-1-(2,6-dichloro-4-trifluoromethylphenyl)-3-formyl-4-trifluoromethylthiopyrazole (0.05 g), m.p. 140°–143° C., in the form of yellow crystals, after recrystallisation from toluene/hexane.

EXAMPLE 25

Compound No. 89

A mixture of dry sulpholane (15 ml) and 4 Å molecular sieve (3.0 g) was stirred under nitrogen with caesium fluoride (2.4 g) at 60° C. for ½ hour. To this was added 5-bromo-3-cyano-1-(2,6-dichloro-4-trifluoromethylphenyl)-4-trifluoromethanesulphonylpyrazole (2.0 g) and the mixture stirred at 60° C. for 2 hours, and left overnight at room temperature. This was diluted with ether (50 ml), filtered, and washed with water (100 ml). The aqueous layer was re-extracted with ether (3×50 ml) and the combined organic solution re-washed with water (4×50 ml), dried over anhydrous magnesium sulphate, and evaporated in vacuo to give an oil. Purification by chromatography, eluting with ether/hexane (1:4) gave 3-cyano-1-(2,6-dichloro-4-trifluoromethylphenyl)-5-fluoro-4-trifluoromethanesulphonylpyrazole (0.17 g), m.p. 95°–98° C., in the form of a white solid, after recrystallisation from hexane.

EXAMPLE 26

Compound No. 92

A solution of pentafluoroethyl iodide (5.0 g) in dry ether (30 ml) was stirred at −78° C., whilst a solution of phenylmagnesium bromide (0.02mol) in dry ether (20 ml) and a separate solution of 5-amino-3-cyano-1-(2,6-dichloro-4-trifluoromethylphenyl)-4-thiocyanatopyrazole (7.6 g) in dry ether (75 ml) were added simultaneously dropwise during 2.5 hours. The mixture was allowed to reach room temperature, and after a further 0.5 hour, was treated with a solution of hydrochloric acid (2M,15 ml) at 0° C. The ethereal layer was dried over anhydrous magnesium sulphate, and evaporated in vacuo to give a brown gum (8.8 g). Purification by dry column flash chromatography eluting with dichloromethane/-petroleum ether (1:1) gave 5-amino-3-cyano-1-(2,6-dichloro-4-trifluoromethylphenyl)-4-pentafluoroethylthiopyrazole, m.p. 134°-5°–136.5° C., in the form of a yellow solid.

EXAMPLE 27

Compound No. 101

To a solution of 5-bromo-3-cyano-1-(2,6-dichloro-4-trifluoromethylphenyl)-4-trifluoromethylsulphonylpyrazole (1.5 g) in dioxan (20 ml) there was added 1,1-dimethylhydrazine (0.62 g) and the mixture heated to 60° C. for 4.25 hours. After pouring onto water (20 ml) the aqueous layer was extracted with dichloromethane (2×50 ml) and this extract combined with the dioxan layer, washed with water (1×50 ml) dried over anhydrous magnesium sulphate, and evaporated in vacuo to give a solid (1.4 g). Purification by chromatography eluting with dichloromethane/hexane (1:1) gave 3-cyano-1-(2,6-dichloro-4-trifluoromethylphenyl)-5-dimethylamino-4-trifluoromethylsulphonylpyrazole (0.35 g), m.p. 178°–179° C., in the form of a white solid.

EXAMPLE 28

Compounds Nos 1, 13 and Intermediate in Reference Example 4

To a stirred solution of 5-amino-3-cyano-1-(2,6-dichloro-4-trifluoromethylphenyl)pyrazole (2.23 g) and pyridine (0.55 g) in chloroform (50 ml) was added dropwise at 0° C., a solution of trifluoromethylsulphenyl chloride (1.24 g) in chloroform (15 ml) during 20 minutes. The mixture was stirred at 0° C. for 3 hours, and the solvent evaporated in vacuo to give a yellow solid (3.1 g). This was purified by chromatography on silica (Merck, 230–400 mesh, 0.7 kgcm$^{-2}$) eluting with dichloromethane and petroleum ether b. 40°–60° (3:1) to give 5-amino-1-(2,6-dichloro-4-trifluoromethylphenyl)-3-cyano-4-trifluoromethylthiopyrazole in the form of a white solid (2.33 g), m.p. 169.5°–170.5° C.

By proceeding in a similar manner to that described above but replacing the 5-amino-1-(2,6-dichloro-4-trifluoromethylphenyl)-3-cyanopyrazole by the following phenylphyrazoles there was obtained:

5-Amino-3-bromo-1-(2,6-dichloro-4-trifluoromethylphenyl)-4-trifluoromethylthiopyrazole in the form of a colourless solid, m.p. 154.5°–156° C., from 5-amino-3-bromo-1-(2,6-dichloro-4-trifluoromethylphenyl)-pyrazole.

5-Amino-1-(2,6-dichloro-4-trifluoromethylphenyl)-4-trifluoromethylthiopyrazole-3-carboxylic acid ethyl ester in the form of a white solid, m.p. 213°–215° C. from 5-amino-1-(2,6-dichloro-4-trifluoromethylphenyl-3-ethoxycarbonylpyrazole.

5-Amino-1-(2,6-dichloro-4-trifluoromethylphenyl)-3-ethoxycarbonylpyrazole used in the above example was prepared as follows:

A solution of 3-cyano-2-hydroxyprop-2-enoic acid ethyl ester sodium salt (50.0 g) in cold water (500 ml) was stirred and acidified to pH 1 with cold dilute sulphuric acid. Sodium chloride (50 g) was added and the solution extracted with ether (2×200 ml). This extract was washed with water (50 ml), dried (anhydrous magnesium sulphate), and evaporated to give a yellow liquid (30.2 g). This was dissolved in ethanol (400 ml) and stirred whilst 2,6-dichloro-4-trifluoromethylphenylhydrazine (51.5 g) was quickly added. The solution was then heated under reflux overnight, cooled, and evaporated in vacuo to give an orange solid. After trituration with hexane (300 ml), the filtered solid was recrystallized from toluene-hexane with charcoaling to give the title compound (43.4 g), m.p. 177°–179° C. as buff crystals.

REFERENCE EXAMPLE 8

A solution of 2,6-dichloro-4-trifluoromethylphenylhydrazine (10.1 g) in tetrahydrofuran (50 ml) was stirred at room temperature, and potassium carbonate (anhydrous, 8.5 g) added. To this was added, dropwise at 0° C., a solution of 2-chloro-3-cyano-3-(1-methyl)ethylsulphonylprop-2-enoic acid ethyl ester (11.0 g) in tetrahydrofuran (100 ml). After stirring for 2 hours, the mixture was filtered, and the filtrate evaporated in vacuo to give a brown oil. After trituration with hexane (100 ml) this gave an off white solid (11.7 g). After refluxing this in ethanol and cooling there was obtained 5-amino-1-(2,6-dichloro-4-trifluoromethylphenyl)-3-ethoxycarbonyl-4-(1-methyl)ethylsulphonyl pyrazole (8.5 g), m.p. 255.5°–256.5° C. as white crystals.

REFERENCE EXAMPLE 9

2-Chloro-3-cyano-3-(1-methyl)ethylsulphonylprop-2-enoic acid ethyl ester used above was prepared as follows:

3-Cyano-2-hydroxy-3-(1-methyl)ethylsulphonylprop-2-enoic acid ethyl ester sodium salt (10.0 g) was added to the stirred phosphorus oxychloride (28.5 g) at room temperature. After 3 hours, the mixture was heated at 50° C. for 1 hour, and then evaporated in vacuo. The residue was re-evaporated after addition of toluene to give the title compound as a brown oil.

3-Cyano-2-hydroxy-3-(1-methyl) ethylsulphonylprop-2-enoic acid ethyl ester sodium salt was prepared as follows:

A solution of sodium ethoxide prepared from sodium (4.0 g) and ethanol (80 ml) was treated with propane-2-sulphonylacetonitrile (24.5 g) with stirring. After complete dissolution diethyl oxalate (24.8 g) was added dropwise over 10 minutes giving a heavy precipitate. After heating under reflux for 1 hour, the yellow solid was filtered, washed with hexane, and dried in a vacuum dessicator (41.3 g). This was the title compound, m.p. 195°–197.50° C.

EXAMPLE 29

Compounds Nos. 59 and 52 and an Intermediate for No. 52

By proceeding in a similar manner to that described below but replacing 5-amino-1-(2,6-dichloro-4-trifluoromethylphenyl)-4-methylthio-3-trifluoromethylpyrazole by the following phenylpyrazoles, there was obtained:

5-Amino-1-(2,6-dichloro-4-trifluoromethylphenyl)-3-ethoxycarbonyl-4-trifluoromethylsulphinylpyrazole as an off white solid, m.p. 210°–214° C. from 5-amino-1-(2,6-dichloro-4-trifluoromethylphenyl)-3-ethoxycarbonyl-4-trifluoromethylthiopyrazole.

5-Amino-1-(2,6-dichloro-4-trifluoromethylphenyl)-3-bromo-4-trifluoromethylsulphinylpyrazole in the form of a white solid, m.p. 179°–180° C. from 5-amino-1-(2,6-dichloro-4-trifluoromethylphenyl)-3-bromo-4-trifluoromethylthiopyrazole.

5-Amino-1-(2,6-dichloro-4-trifluoromethylphenyl)-3-cyano-4-trifluoromethylsulphinylpyrazole in the form of a white solid, m.p. 203°–203.5° C. from 5-amino-1-(2,6-dichloro-4-trifluoromethylphenyl)-3-cyano-4-trifluoromethylthiopyrazole.

A stirred solution of 5-amino-1-(2,6-dichloro-4-trifluoromethylphenyl)-4-methylthio-3-trifluoromethylpyrazole (1.0 g) in chloroform (40 ml) was treated with m-chloroperbenzoic acid (0.42 g), portionwise at room temperature. After stirring for 6 hours, the solution was diluted with dichloromethane and washed in turn with solidum sulphite solution, sodium hydroxide solution, and water. The solution was dried over anhydrous magnesium sulphate, and evaporated in vacuo to give a yellow oil. Purification by chromatography on silica (Merck, 230°–400 mesh, 0.7 kg cm$^{-2}$) eluting with dichloromethane-ethylacetate (4:1) gave 5-amino-1-(2,6-dichloro-4-trifluoromethylphenyl)-4-methylsulphinyl-3-trifluoromethylpyrazole in the form of a white solid, m.p. 142°–145° C. with decomposition.

REFERENCE EXAMPLE 10

5-Carbamoyl-4-cyano-1-(2,6-dichloro-4-trifluoromethylphenyl)-3-trifluoromethylpyrazole (3.57 g) was heated to 200° C. with phosphorus pentoxide (2.82 g) 0.with stirring. After 3 hours, the cooled product was treated with ice, and extracted with dichloromethane (3×50 ml). The organic solution was washed with water, dried over anhydrous magnesium sulphate, and evaporated in vacuo to give a solid. Recrystallization from hexane gave 1-(2,6-dichloro-4-trifluoromethylphenyl)-4,5-dicyano-3-trifluoromethylpyrazole in the form of white crystals (1.8 g), m.p. 80° C.

By proceeding in a similar manner to that described above but replace the 5-carbamoyl-4-cyano-1-(2,6-dichloro-4-trifluoromethylphenyl)-3-trifluoromethylpyrazole by 5-amino-3-carbamoyl-1-(2,6-dichloro-4-trifluoromethylphenyl)-4-methanesulphonylpyrazole there was prepared: -5-Amino-3-cyano-1-(2,6-dichloro-4-trifluoromethylphenyl)-4methanesulphonylpyrazole in the form of a white solid, m.p. 214° C.

REFERENCE EXAMPLE 11

5-Carbamoyl-4-cyano-1-(2,6-dichloro-4-trifluoromethylphenyl)-3-trifluoromethylpyrazole used in the above Reference Example 10, was prepared as follows:

5-Carboxy-4-cyano-1-(2,6-dichloro-4 -trifluoromethylphenyl)-3-trifluoromethylpyrazole (6.0 g) was added to thionyl chloride (30 ml) and the stirred solution heated to reflux for 4 hours. The solvent was evaporated in vacuo, and re-evaporated after addition of dry toluene (30 ml). The resultant orange oil was dissolved in dry ether (10 ml) and added dropwise to a stirred solution of ammonia (0.88, 20 ml) cooled by an ice bath. After stirring overnight, water (150 ml) was added, and the mixture extracted with dichloromethane (3×50 ml). The combined extract was washed with water, dried over anhydrous magnesium sulphate, and evaporated in vacuo to give a white solid (7.0 g). Recrystallization from a mixture of ethyl acetate and petroleum ether gave the title compound (4.3 g), in the form of white crystals, m.p. 180°–181° C.

5-Amino-3-carbamoyl-1-(2,6-dichloro-4 -trifluoromethylphenyl)-4-methanesulphonylpyrazole used in the above Reference Example 10 was prepared by the same procedure, but by replace the 5-carboxy-4-cyano-1-(2,6-dichloro-4 -trifluoromethylphenyl)-3-trifluoromethylpyrazole by 5-amino-3-carboxy-1-(2,6-dichloro-4-trifluoromethylphenyl)-4 -methanesulphonylpyrazole. The title compound was obtained in the form of an off-white solid, m.p. 223°–224° C.

5-Amino-3-carboxy-1-(2,6-dichloro-4 -trifluoromethylphenyl)-4-methanesulphonylpyrazole used above was prepared as follows:

5-Amino-1-(2,6-dichloro-4-trifluoromethylphenyl)-3 -ethoxycarbonyl-4-methanesulphonylpyrazole (8.15 g; Reference Example 3) was added to stirred 80% sulphuric acid (80 ml), and heated at 100° C. for 5 hours. After cooling, the solution was poured onto ice, the solid filtered off and dried over phosphorus pentoxide in a vacuum desiccator. Recrystallization from a mixture of methanol and petroleum ether gave the title compound as a white solid, m.p. 203°–205° C.

Processes for producing compounds of the second embodiment of the invention, wherein the various substituents are as defined above for the second embodiment, are described hereinafter According to process version "aa" which is a further feature of the present invention, compounds of the second embodiment of the invention, having formula XXVI, wherein $R^3$ represents an amino group —$NHR'''^a$ wherein $R'''^a$ represents the hydrogen atom or a straight- or branched-chain alkyl group containing from 1 to 6 carbon atoms may be prepared from compounds of formula XXVI, wherein $R^3$ represents an amino group —$NR''^a R'''^b$, wherein $R''^a$ represents the formyl group or a straight- or branched-chain alkanoyl group containing from 2 to 7 carbon atoms which may be unsubstituted or substituted by one or more halogen atoms, or a straight- or branched-chain alkoxycarbonyl group containing from 2 to 7 carbon atoms, which may be unsubstituted or substituted by one or more halogen atoms, and $R'''^b$ is as hereinbefore defined for $R'''$ except that $R''^a$ and $R'''^b$ together do not form a 5 or 6 membered cyclic imide with the nitrogen atom to which they are attached, by hydrolysis. The hydrolysis is generally effected with an acid such as hydrochloric acid or hydrobromic acid in a solvent such as acetic acid or dioxan, or with an alkali metal, e.g. sodium or potassium, hydroxide in water or an inert organic or aqueous-organic solvent, e.g. a lower alkanol such as methanol or a mixture of water and a lower alkanol, at a temperature from laboratory temperature to the boiling point of the reaction mixture.

According to process version "bb", which is a further feature of the present invention, compounds of formula XXVI, wherein $R^3$ is as hereinbefore defined but does not represent an unsubstituted amino or alkylamino group, may be prepared from the corresponding compounds within formula XXVII, wherein $R^1$, $R^4$, $R^6$ and $R^8$ are as hereinbefore defined and $R^3$ is replaced by $R^{3a}$ which is as hereinbefore defined for $R^3$ but does not represent an unsubstituted amino or alkylamino group (such compounds are referred to as of formula XXVIIA), by treatment with a nitrating agent, preferably nitric acid, optionally in the presence of sulphuric acid, or nitric acid in a solvent such as acetic acid or acetic anhydride, at a temperature from 0° C. to 100° C.

The preparation of derivatives of the 5-amino group form a further feature of the present invention and are collectively referred to as process "cc". Compounds of formula XXVI which conform to formula XXVIB, wherein R" represents an $R^{21}C(=O)$- group, wherein $R^{21}$ represents a straight- or branched-chain alkyl or alkoxy group containing from 1 to 6 carbon atoms which is unsubstituted or substituted by one or more halogen atoms, and R''' represents a hydrogen atom or an $R^{21}C(=O)$- group which is identical to the group $R^{21}C(O)$- represented by R", or —NR"R''' represents a cyclic imide as hereinbefore defined, may be prepared by the reaction of a compound of formula XXVI wherein $R^3$ represents the unsubstituted amino group, or an alkali metal salt thereof, with a compound of the formula XXVIII:

$$R^{21}COX^7 \qquad \text{XXVIII}$$

wherein $X^7$ represents a chlorine or bromine atom, or with a compound of the formula XXIX:

$$(R^{21}CO)_2O \qquad \text{XXIX}$$

or with a dicarboxylic acid derivative. The reaction may be conducted in the absence or presence of an inert organic solvent, for example acetonitrile, tetrahydrofuran, a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkalimetal, e.g. sodium or potassium, carbonate or bicarbonate, at a temperature from 0° C. to the reflux temperature of the reaction medium, to give a compound of formula XXVIB, wherein R" represents an $R^{21}C(=O)$- group wherein $R^{21}$ is as hereinbefore defined and R''' represents a hydrogen atom or an $R^{21}C(=O)$- group, depending upon the reaction conditions chosen and/or the use of an excess of the compound of formula XXVIII or XXIX, or —NR"R''' represents a cyclic imide as hereinbefore defined.

Compounds of formula XXVIB, wherein R" represents a formyl group and R''' represents a hydrogen atom or a formyl group, may be prepared by the reaction of a compound of formula XXVI, wherein $R^3$ represents the unsubstituted amino group with formylacetic anhydride. Formylacetic anhydride may be prepared from formic acid and acetic anhydride and the reaction with the compound of formula XXVI may be conducted in the absence or presence of an inert organic solvent, for example a ketone, e.g. acetone, or an aromatic hydrocarbon, e.g. benzene or toluene, and optionally in the presence of an acid-binding agent, for example pyridine, triethylamine or an alkali metal, e.g. sodium or potassium, carbonate or bicarbonate, at a temperature from 0° C. to the reflux temperature of the reaction mixture, to give a compound of formula XXVIB wherein R" represents a formyl group and R''' represents a hydrogen atom or a formyl group, depending upon the reaction conditions chosen and/or the use of an excess of formylacetic anhydride.

Compounds of formula XXVIB wherein R" represents a formyl group or a group $R^{21}C(=O)-$ and R"' represents a hydrogen atom may be prepared by the selective removal by hydrolysis of an $R^{21}C(=O)-$ group or a formyl group from a compound of formula XXVIB wherein R" and R"' both represent a $R^{21}C(=O)-$ group or a formyl group. Hydrolysis is effected under mild conditions, for example by treatment with an aqueous-ethanolic solution or suspension of an alkali metal, e.g. sodium or potassium, bicarbonate, or with aqueous ammonia.

Compounds of formula XXVIB, wherein R" represents a straight- or branched-chain alkoxycarbonyl group containing from 2 to 7 carbon atoms which is unsubstituted or substituted by one or more halogen atoms, and R"' represents a hydrogen atom may be prepared by the reaction of a compound of the formula XXX wherein $R^{22}$ represents an alkoxycarbonyl group $R^{23}C(=O)$, wherein $R^{23}$ represents a straight- or branched-chain alkoxy group containing from 1 to 6 carbon atoms (which is unsubstituted or substituted by one or more halogen atoms) or a phenoxy group, with a compound of the formula XXXI:

$R^{23}H$                         XXXI to replace a first group represented by the symbol $R^{22}$ by a hydrogen atom, and to replace the second group represented by the symbol $R^{22}$ by an alkoxycarbonyl group when $R^{22}$ represents a phenoxycarbonyl group, or, if desired, to replace the second group represented by the symbol $R^{22}$ by another alkoxycarbonyl group when $R^{22}$ in formula XXX represents an alkoxycarbonyl group. As will be apparent to those skilled in the art, the desired compound of formula XXVIB is obtained by selection of the appropriate compounds of formulae XXX and XXXI. The reaction may be effected in water or an inert aqueous organic or organic solvent, for example an alkanol containing 1 to 4 carbon atoms, e.g. ethanol, or an aromatic hydrocarbon, e.g. benzene or toluene, which is preferably an excess of the compound of formula XXXI, at a temperature from ambient temperature to the reflux temperature of the reaction mixture and, if necessary, at elevated pressure, and optionally in the presence of a base, for example an alkali metal alkoxide, e.g. of the compound of formula XXXI.

Compounds of formula XXVIB wherein R" and R"', which may be the same or different, each represents a formyl group or a $R^{21}C(=O)-$ group, may be prepared by the reaction of an alkali metal, e.g. sodium or potassium, derivative of a compound of formula XXVIB wherein R" represents a group $R^{21}C(=O)-$ as hereinbefore defined, or a formyl group, and R"' represents a hydrogen atom with formylacetic anhydride or a compound of formula XXVIII. Reaction may be effected in an inert aprotic solvent, e.g. dimethylformamide, at a temperature from laboratory temperature to the reflux temperature of the reaction mixture.

Alkali metal derivatives of compounds of formula XXVI (wherein $R^3$ represents the unsubstituted amino group) or XXVIB wherein R"' represents a hydrogen atom may be prepared in situ by reaction with an alkali metal, e.g. sodium or potassium, hydride, in an inert aprotic solvent, e.g. dimethylformamide, at a temperature from laboratory temperature to the reflux temperature of the reaction mixture.

Compounds of formula XXX wherein $R^{22}$ represents a group $R^{23}C(=O)-$, may be prepared as hereinbefore described. Compounds of formula XXX wherein $R^{22}$ represents a phenoxycarbonyl group may be prepared by the rection of a compound of formula XXVI (wherein $R^3$ represents the unsubstituted amino group), with phenyl chloroformate using the reaction conditions hereinbefore described for the reaction of a compound of formula XXVI with a compound of formula XXVIII.

Compounds of formula XXVIB wherein R" represents a group $R^{24}$ which represents a straight- or branched-chain alkyl group containing from 1 to 6 carbon atoms and R"' represents a hydrogen atom may be prepared by the removal of the group $R^{21}C(=O)-$ of a compound of the formula XXVIB, wherein R" represents a group $R^{24}$ and R"' represents a group $R^{21}C(=O)-$. Removal of the group $R^{21}C(=O)-$ may be effected by selective hydrolysis under mild conditions, for example by treatment with an alkali metal, e.g. sodium or potassium, hydroxide in water or an inert organic or aqueous-organic solvent, for example a lower alkanol, e.g. methanol, or a mixture of water and lower alkanol, at a temperature from laboratory temperature up to the reflux temperature of the reaction mixture.

Compounds of formula XXVIB, wherein R represents a group $R^{24}$ and R"' represents a group $R^{21}C(=O)-$, may be prepared by reaction of a compound of formula XXVIB, wherein R" represents a hydrogen atom, or an alkali metal, e.g. sodium or potassium, derivative thereof, with a compound of the formuala XXXII:

$R^{24}X^8$                        XXXII wherein $X^8$ represents a chlorine, bromine or iodine atom. Reaction may be effected in an inert organic solvent, e.g. dichloromethane, tetrahydrofuran, or dimethylformamide, at a temperature from ambient up to the boiling point of the reaction mixture and, when a compound of formula XXVIB is used, in the presence of a base, e.g. Triton B; or by reaction of a compound of formula XXVIB wherein R" represents the hydrogen atom and R"' represents a group $R^{24}$ with a compound of formula XXVIII or XXIX.

Compounds of formula XXVI, wherein $R^3$ represents an N-alkyl-N-formylamino group as hereinbefore described may be prepared in a similar manner to the process above using, where appropriate, formylacetic anhydride instead of a compound of formula XXVIII or XXIX.

Compounds of formula XXVIB, wherein one or both of R" and R"' represent a straight- or branched-chain alkyl group containing from 1 to 6 carbon atoms, groups represented by R" and R"' being identical, may be prepared by reaction of a compound of formula XXVI, wherein $R^3$ represents the unsubstituted amino group, or an alkali metal, e.g. sodium or potassium, derivative thereof, with a compound of formula XXXII, in the absence or presence of an inert organic solvent, for example an aromatic hydrocarbon, e.g. benzene or toluene, chloroform, dichloromethane, tetrahydrofuran or dimethylformamide, and optionally in the presence of an acid-binding agent, for example pyridine, triethylamine or an alkali metal, e.g. sodium or potassium, bicarbonate, at a temperature from 0° C. up to the boiling point of the reaction mixture.

Compounds of formula XXVI, wherein $R^3$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms may be prepared by the reaction of a compound of formula XXVI (wherein $R^3$ represents the unsubstituted amino group) with a trisalkoxyalkane in the presence of an acidic catalyst, e.g. p-toluenesulphonic acid, at a temperature from ambient to the boiling point of the reaction mixture.

Compounds of formula XXVI wherein $R^3$ represents —$NHCH_2R^{25}$ wherein $R^{25}$ represents the hydrogen atom or a straight- or branched-chain alkyl group containing from 1 to 4 carbon atoms may be prepared by reaction of a compound of formula XXVI, wherein $R^3$ represents —$N=C(OR^{26})R^{25}$ wherein $R^{26}$ represents a straight- or branched-chain alkyl group containing from 1 to 4 carbon atoms, with a reducing agent, preferably sodium borohydride. The reaction may be effected in an inert organic solvent, ethanol or methanol being preferred, at a temperature from 0° C. to the boiling point of the reaction mixture.

According to process version "dd", which is a further feature of the present invention, compounds of formula XXVI, wherein $R^1$ represents a fluorine, chlorine, bromine or iodine atom, may be prepared by the replacement by known methods of an amino group by a halogen atom, for example by diazotization of a compound corresponding to formula XXVII wherein $R^1$ is replaced by the amino group and the hydrogen atom in the 4-position of the pyrazole ring is replaced by the nitro group, using sodium nitrite in tetrafluoroboric acid and sulphuric acid at a temperature of −10° to +10° C. followed by photolysis in an excess of tetrafluoroboric acid at a temperature of −30° to +30° C. to obtain a compound wherein $R^1$ represents a fluorine atom, or with an alkyl nitrite, preferably tertiary butyl nitrite, in the presence of a halogenating agent, preferably anhydrous copper chloride, bromoform or iodine respectively, at a temperature from 0° C. to 100° C. to obtain a compound wherein $R^1$ represents a chlorine, bromine or iodine atom.

According to process version "ee", which is a further feature of the present invention compounds of formula XXVI, wherein $R^3$ represents a halogen atom, may be prepared by diazotization of the corresponding compound of formula XXVI wherein $R^3$ represents the amino group, in a similar manner to that hereinbefore described in process version "dd".

Compounds of the formula XXVII, wherein $R^1$ represents the nitro group and $R^3$ is as hereinbefore defined but not the unsubstituted amino group may be prepared by oxidation of a compound of formula XXXIII, wherein $R^{1a}$ represents the amino group, $R^{3a}$ is as hereinbefore defined for $R^3$ except that $R^{3a}$ does not represent the unsubstituted amino group, and $R^8$, $R^6$ and $R^4$ are as hereinbefore defined, with trifluoroacetic peracid (which is prepared in situ from trifluoroacetic anhydride and hydrogen peroxide (85% w/w)) in dichloromethane at a temperature between ambient and the boiling point of the solvent.

Compounds of formula XXXIII, wherein $R^{1a}$ represents the amino group and $R^8$, $R^6$, $R^4$ and $R^{3a}$ are as hereinbefore defined, can be prepared by performing a Curtius rearrangement of the corresponding acid azide by heating in an inert solvent such as toluene at a temperature from 50° to 150° C. to give an isocyanate which is then treated with tertiary butanol at a temperature between 50° and 150° C. to give a carbamate which in turn is hydrolyzed using dilute hydrochloric acid in ethanol or using iodotrimethylsilane in an inert solvent such as acetonitrile at a temperature between ambient and the boiling point of the solvent.

The intermediate acid azide may be prepared from compounds corresponding to formula XXXIII, wherein $R^{1a}$ is replaced by the carboxy group (prepared by hydrolysis of the corresponding ester) with an azide transfer agent preferably diphenylphosphonylazide in a solvent such as dimethyl formamide in the presence of triethylamine at a temperature from ambient to 100° C.

The intermediate ester is prepared by treating a phenylhydrazine of formula XXXIV with a compound of formula XXXV wherein $R^{27}$ preferably represents ethyl, by treatment with dilute mineral acid e.g. sulphuric acid, followed by reaction in a lower alkanol solvent, preferably ethanol, at ambient temperature to the boiling point of the solvent.

According to process version "ff" which is a further feature of the present invention, compounds of the formula XXVI, wherein $R^3$ represents a hydrogen atom may be prepared by treatment of a compound of formula XXVI wherein $R^3$ represents the amino group, with an alkyl nitrite, preferably tertiary butyl nitrite, in an inert organic solvent, preferably tetrahydrofuran, at ambient to reflux temperature.

Intermediates of formula XXXVI, wherein $R^{1b}$ represents the cyano group or a chlorine or fluorine atom, may be prepared by reaction of an appropriately substituted phenylhydrazine (or acid addition salt thereof) of formula XXXIV with tetracyanoethylene or dichloromethylenemalononitrile or difluoromethylenemalononitrile, in an inert solvent, for example ethanol or acetic acid, at a temperature from ambient to reflux, optionally (or in the case of an acid addition salt) in the presence of a base, i.e. potassium carbonate or triethylamine.

Intermediates corresponding to formula XXVII, wherein $R^1$ represents a fluorine, chlorine, bromine or iodine atom and the hydrogen atom in the 4-position of the pyrazole ring is replaced by a group $R^{2a}$ which represents a cyano or formyl group or the group $R^{27}OC(=O)$, wherein $R^{27}$ represents an alkyl group containing from 1 to 8 carbon atoms, preferably the ethyl group, may be prepared by diazotization of a compound corresponding to formula XXVII wherein $R^1$ is replaced by the amino group and the hydrogen atom in the 4-position of the pyrazole ring is replaced by a group $R^{2a}$, using sodium nitrite in tetrafluoroboric acid and sulphuric acid at a temperature of −10° to +10° C. followed by photolysis in an excess of tetrafluoroboric acid at a temperature of −30° to +30° C. to obtain a compound wherein $R^1$ represents a fluorine atom, or with an alkyl nitrite, preferably tertiary butyl nitrite, in the presence of a halogenating agent, preferably anhydrous copper chloride, bromoform or iodine respectively, at a temperature from 0° C. to 100° C. to obtain a compound wherein $R^1$ represents a chlorine, bromine or iodine atom.

Intermediate esters corresponding to formula XXVII, wherein $R^1$ represents a chlorine, bromine or iodine atom, or $R^1$ represents the fluorine atom, $R^3$ represents the amino group and the hydrogen atom in the 4-position of the pyrazole ring is replaced by a group $R^{27}OC(=O)$- wherein $R^{27}$ is as hereinbefore defined, may be prepared by diazotization of a compound of formula XXXVII wherein $R^{27}$ is as hereinbefore defined in a similar manner to process version "dd", as hereinbefore described Intermediate diaminoesters of formula XXXVII wherein $R^{27}$ is as hereinbefore defined may be prepared by reaction of an appropriately substituted phenylhydrazine (or acid addition salt thereof) of formula XXXIV with an alkali metal salt of an alkyl dicyanoacetate, preferably potassium ethyl dicyanoacetate, in hydrochloric acid at ambient to reflux temperature. Alkyl dicyanoacetate potassium salts may be prepared by reaction of the appropriate alkyl chloroformate with malononitrile in the presence of potassium hydroxide in tetrahydrofuran at a temperature between 0° and 100° C.

Intermediate aldehydes corresponding to formula XXVII, wherein $R^1$ represents the cyano group or a chlorine or fluorine atom and the hydrogen atom in the 4-position of the pyrazole ring is replaced by the formyl group, may be prepared by reduction of a compound of formula XXXVI, wherein $R^{1b}$ is as defined above, with Raney nickel in formic acid, at reflux or with di-isobutylaluminum hydride in an inert solvent such as tetrahydrofuran at −78° to 0° C.

Intermediates of formula XXVII, wherein $R^3$ represents the hydrogen atom, may be prepared by treatment of the corresponding compound of formula XXVII, wherein $R^3$ represents the amino group, in a similar manner to process version "ff" as hereinbefore described.

Intermediates of formula XXXVIII wherein $R^1$ represents a halogen atom or the nitro group may be prepared by reaction of compounds corresponding to formula XXVII, wherein $R^1$ represents a halogen atom or the nitro group, $R^3$ represents the amino group and the hydrogen atom in the 4-position of the pyrazole ring is replaced by a formyl or $R^{27}OC(=O)$- group, by heating at reflux in a mixture of a mineral acid, e.g. hydrochloric acid, and acetic acid.

Intermediates of formula XXVII, wherein $R^1$ represents bromine or iodine can be prepared by refluxing compounds of formula XXVII wherein $R^1$ represents chlorine in a mixture of acetic acid and either hydrobromic or hydroiodic acid respectively.

Intermediates of formula XXXVIII wherein $R^1$ represents the cyano group may be prepared by diazotization of the appropriate aniline with a solution of a molar equivalent of sodium nitrite in a mineral acid, e.g. a mixture of concentrated sulphuric acid and acetic acid at a temperature from 0° to 60° C., and then reacting with the compound of formula $NCCH_2CH(CN)COR°$ wherein $R°$ represents an alkoxy, preferably ethoxy, group in the presence of an inert solvent, e.g. a mixture of water and ethanol, buffered, e.g. with excess sodium acetate, and at a temperature from 0° to 50° C.

Intermediates of formula XXXVIII wherein $R^1$ represents the cyano group may also be prepared by reacting the corresponding carboxylic acid with a chlorinating agent, preferably thionyl chloride at ambient to reflux temperature, followed by reaction of the intermediate acid chloride with ammonia to give an intermediate amide which is then dehydrated by heating with a dehydrating reagent, preferably phosphorus oxychloride at a temperature from 50°–250° C.

Intermediate carboxylic acids above may be prepared by hydrolysis of the corresponding esters preferably using a base such as sodium hydroxide and a solvent such as aqueous alcohol, and at a temperature from 0° C. to the reflux temperature of the reaction mixture.

Compounds of formula XXXIV can be prepared by methods known per se.

The following Examples and Reference Examples illustrate the preparation of compounds of the second embodiment of the invention of formula XXVI:

[Chromatography was effected on a silica column (Merck 0.040–0.063 mm) at a pressure of $6.8Nm^{-2}$ unless otherwise stated.]

EXAMPLE 30

Compounds 102, 103 and 104

Fuming nitric acid (1.7 ml) was added dropwise to a stirred solution of 5-acetamido-3-bromo-1-(2,6-dichloro-4 -trifluoromethylphenyl)-pyrazole (4.7 g) and acetic anhydride (1 ml) in glacial acetic acid (60 ml). After 1.5 h the reaction mixture was heated to 60° C. and stirred at this temperature for 5 h. The reaction mixture was cooled, poured into water (200 ml), basified with saturated potassium carbonate solution (to pH 12) and extracted with diethyl ether. The extracts were washed with saturated sodium bicarbonate solution (2×100 ml), dried and evaporated to give a brown gum (4.0 g). This was purified by column chromatography using dichloromethane as eluent to give 5-acetamido-3-bromo-1-(2,6-dichloro-4 -trifluoromethylphenyl)-4-nitropyrazole (2.9 g), m.p. 179°–180.5° C., in the form of colorless crystals.

By proceeding in a similar manner but replacing 5 -acetamido-3-bromo-1-(2,6-dichloro-4-trifluoromethylphenyl)pyrazole by the hereinafter indicated substituted pyrazole, there were obtained:

5-Acetamido-3-chloro-1-(2,6-dichloro-4 -trifluoromethylphenyl)-4-nitropyrazole, m.p. 177°–178.5° C., in the form of colorless crystals, from 5-acetamido-3-chloro-1-( 2,6-dichloro-4-trifluoromethylphenyl)-pyrazole.

5-Acetamido-3-cyano-1-(2,6-dichloro-4 -trifluoromethylphenyl)-4-nitropyrazole, m.p. 226°–228.5° C., in the form of a cream-colored solid, from 5-acetamido-3-cyano-1-( 2,6-dichloro-4-trifluoromethylphenyl)-pyrazole.

EXAMPLE 31

Compounds 105, 106 and 107

A mixture of 5-acetamido-3-bromo-1-(2,6-dichloro-4 -trifluoromethylphenyl)-4-nitropyrazole (1.0 g), hydrobromic acid (48%; 5 ml) and dioxan (15 ml) was boiled under reflux for 18 h. The reaction mixture was cooled and evaporated in vacuo and the residue treated with water to precipitate a solid which was filtered off and dried at 100° C. to give 5 -amino-3-bromo-1-2,6-dichloro-4-trifluoromethylphenyl)-4-nitropyrazole (0.8 g), m.p. 235°–236° C., in the form of a colorless solid.

By proceeding in a similar manner but replacing 5 -acetamido-3-bromo-1-(2,6-dichloro-4-trifluoromethylphenyl)- 4-nitropyrazole by the hereinafter indicated substituted pyrazole and replacing hydrobromic acid by 6M hydrochloric acid, there were obtained:

5-Amino-3-chloro-1-(2,6-dichloro-4 -trifluoromethylphenyl)-4-nitropyrazole, m.p. 219°–220.5° C., in the form of colorless crystals from 5-acetamido-3-chloro-1-(2,6 -dichloro-4-trifluoromethylphenyl)-4-nitropyrazole after purification by chromatography using dichloromethane as eluant followed by recrystallization from dichloromethane-hexane.

5-Amino-3-cyano-1-(2,6-dichloro-4 -trifluoromethylphenyl)-4-nitropyrazole, m.p. 255.5°–256.5° C., in the form of a cream-colored solid, from 5-acetamido-3-cyano-1-(2,6 -dichloro-4-trifluoromethylphenyl)-4-nitropyrazole after purification by recrystallization from toluene.

EXAMPLE 32

Compound 108

Tertiary butyl nitrite (6.6 ml) was added at room temperature to a solution of 5-amino-3-cyano-1-(2,6 -dichloro-4-trifluoromethylphenyl)-4-nitropyrazole (3.7 g), bromoform (13.3 ml) and acetonitrile (10 ml). The mixture was heated at 50°–60° C. for 4.5 hours and the solvents were evaporated to give an orange oil. This was purified by medium pressure liquid chromatography (eluant hexane/ether 2:1) to give 5-bromo-3-cyano-1-(2,6-dichloro-4 -trifluoromethylphenyl)-4-nitropyrazole (3.4 g) as a solid, m.p. 147°–150° C.

REFERENCE EXAMPLE 12

Pyridine (4.0 ml) was added dropwise to a stirred solution of 5-amino-3-bromo-1-(2,6-dichloro-4-trifluoromethylphenyl)-pyrazole (5.0 g), acetyl chloride (3.0 g) and dry chloroform (30 ml), causing an exothermic reaction (maximum temperature 60° C.). The reaction mixture was stirred at laboratory temperature for 2 h and evaporated to dryness. The residue was dissolved in ethanol (25 ml), ammonia solution (d. 0.880; 25 ml) was added, and the solution was boiled under reflux for 1 h. The cooled reaction mixture was evaporated to dryness, dissolved in dichloromethane (100 ml), washed with dilute hydrochloric acid (3×50 ml) and water (50 ml), dried over anhydrous magnesium sulphate, filtered, and evaporated to give 5-acetamido-3-bromo-1-(2,6-dichloro-4-trifluoromethylphenyl)pyrazole (5.3 g), m p 180°–187° C. in the form of a pale brown solid.

By proceeding in a similar manner but replacing 5-amino-3-bromo-1-(2,6-dichloro-4-trifluoromethylphenyl)pyrazole by the hereinafter indicated substituted pyrazole, there were obtained:

5-Acetamido-3-chloro-1-(2,6-dichloro-4-trifluoromethylphenyl)-pyrazole, m.p. 195°–197° C., in the form of a colorless solid after chromatography using dichloromethane as eluent from 5-amino-3-chloro-1-(2,6-dichloro-4-trifluoromethylphenyl)-pyrazole.

5-Acetamido-3-cyano-1-(2,6-dichloro-4-trifluoromethylphenyl)-pyrazole, m.p. 200.5°–201.5° C., in the form of an orange solid, from 5-amino-3-cyano-1-(2,6-dichloro-4-trifluoromethylphenyl)-pyrazole.

REFERENCE EXAMPLE 13

A mixture of 5-amino-4-carboethoxy-3-chloro-1-(2,6-dichloro-4-trifluoromethylphenyl)-pyrazole (3.3 g), hydrobromic acid (45%; 30 ml) and acetic acid (50 ml) was boiled under reflux for 18 h. The mixture was evaporated to low bulk and basified with sodium hydroxide solution (2M), and the product was filtered off, dried (2.9 g) and recrystallized from a mixture of ethanol and water to give 5-amino-3-bromo-1-(2,6-dichloro-4-trifluoromethylphenyl)-pyrazole (2.5 g), m.p. 132.5°–134° C. in the form of a colorless solid.

REFERENCE EXAMPLE 14

Tertiary butyl nitrite (15.0 g) was added dropwise to a stirred mixutre of 4-carboethoxy-3,5-diamino-1-(2,6-dichloro-4-trifluoromethylphenyl)-pyrazole (50.0 g), copper (II) chloride (21.0 g) and acetonitrile (600 ml) over a period of 10 min., with the temperature kept at 0° C. by external cooling. The reaction mixture was stirred at this temperature for 2 h and for a further 2 h at laboratory temperature, evaporated to low bulk, and poured into hydrochloric acid (5M; 1.5l). The resultant solution was extracted with dichloromethane (3×100 ml) and the extracts were washed with hydrochloric acid (2M; 2×600 ml), dried over magnesium sulphate, filtered and evaporated to give a brown tar. The material was purified by dry-column chromatography on a silica gel column with dichloromethane:hexane (4:1) as eluent, followed by medium-pressure chromatography with the same solvents to give 5-amino-4-carboethoxy-3-chloro-1-(2,6-dichloro-4-trifluoromethylphenyl)-pyrazole (15.8 g), m.p. 143°–146 5° C. in the form of an orange solid.

REFERENCE EXAMPLE 15

A mixture of 5-amino-4-carboethoxy-3-chloro-1-(2,6-dichloro-4-carboethoxy-3-chloro-1-(2,6-dichloro-4-trifluoromethylphenyl)-pyrazole (5.0 g), hydrochloric acid (6M; 75 ml) and acetic acid (75 ml) was boiled under reflux for 24 h. The mixture was evaporated to low bulk and basified to pH 12 with sodium hydroxide solution (2M), and the product was extracted with diethyl ether (3×75 ml). The combined extracts were evaporated to give a yellow, gummy solid (3.5 g). This was dissolved-in a mixture of hydrochloric acid (6M; 30 ml) and dioxan (60 ml) and boiled under reflux for 48 h. Volatile materials were removed in vacuo and the residue was purified by chromatography with dichloromethane:hexane (4:1) as eluent to give 5-amino-3-chloro-1-(2,6-dichloro-4-trifluoromethylphenyl)-pyrazole (1.3 g), m.p. 128°–129° C. in the form of an off-white solid.

REFERENCE EXAMPLE 16

Ethyl dicyanoacetate potassium salt (35.2 g) was added to a stirred suspension of 2,6-dichloro-4-trifluoromethylphenylhydrazine (49 g) in hydrochloric acid (0.9M; 220 ml) and the mixture was stirred and boiled under reflux for 18 h, then cooled to precipitate a solid which was filtered off, triturated with diethyl ether (250 ml) and dried to give an off-white solid which was recrystallized from ethyl acetate-hexane to give 4-carboethoxy-3,5-diamino-1-(2,6-dichloro-4-trifluoromethylphenyl)-pyrazole (29.2 g), m.p. 196°–197° C. in the form of an off-white solid.

REFERENCE EXAMPLE 17

Sodium nitrite (8.8 g) was added slowly to stirred concentrated sulphuric acid (90 ml) and the resultant solution, when cool, was added dropwise, over a period of 20 min., to a solution of 2,6-dichloro-4-trifluoromethylaniline (23.0 g) in acetic acid (180 ml) with the temperature kept below 30° C. Thie mixture was then cooled to 5° C. and added dropwise over 35 min. to a stirred solution of ethyl 2,3-dicyanopropanoate (17.1 g), sodium acetate (300 g), water (1.2l) and ethanol (1.5 ml), with the temperature maintained at 17°–22° C. The mixture was stirred at room temperature for 2.5 h, left overnight, diluted with water (2.0l) and extracted with dichloromethane (3×500 ml). The combined extracts were washed three times with dilute sodium hydroxide solution and once with brine, dried over anhydrous magnesium sulphate and evaporated in vacuo to give a brown oil (25.2 g). The residue was dissolved in a minimum amount of a hot toluene-hexane mixture and treated with charcoal. The solution was filtered and on cooling it gave 5-amino-3-cyano-1-(2,6-dichloro-4-trifluoromethylphenyl)-pyrazole (8.7 g), m.p. 141°–142° C., in the form of a pale brown solid.

REFERENCE EXAMPLE 18

A solution of ethyl chloroformate (520 g), malononitrile (330 g) and tetrahydrofuran (500 ml) was added dropwise over 1 h to a stirred solution of potassium hydroxide (560 g) and water (2.0l) at a temperature kept below 40° C. by external ice-cooling. The reaction mixture was stirred at laboratory temperature for 1 h, then cooled to 0° C. to precipitate a solid which was filtered off and dried over phosphorus pentoxide to give ethyl dicyanoacetate potassium salt (334.4 g) in the form of an off-white solid.

Compounds of the third embodiment of general formula I conforming to formula XL wherein $Y^1$ represents the cyano or nitro group or a group $R'SO_2$, $R'SO$ or $R'S$, a straight- or branched-chain alkoxycarbonyl group containing from 2 to 7 carbon atoms, or a straight- or branched-chain alkyl group containing from 1 to 6 carbon atoms which may be unsubstituted or substituted by one or more halogen atoms, $Z^1$ represents the unsubstituted amino group or a straight- or branched-chain alkyl group containing from 1 to 4 carbon atoms, and $R^{28}$ represents a fluorine, chlorine or bromine atom, the cyano group or a straight- or branched-chain alkyl group containing from 1 to 4 carbon atoms which may be unsubstituted or substituted by one or more halogen atoms, or a cycloalkyl group containing from 3 to 6 carbon atoms, may be prepared by the process which comprises (i) the reaction of a compound of the formula XLI, or an acid addition salt thereof, e.g. the hydrochloride, with (1), when $R^{28}$ in the compound of formula XL represents a fluorine, chlorine or bromine atom, an optionally halogenated straight- or branched-chain alkyl group containing from 1 to 4 carbon atoms or a cycloalkyl group containing from 3 to 6 carbon atoms, a compound of the formula XLII, wherein $R^{29}$ represents the cyano group or a straight- or branched-chain alkanoyl group containing from 2 to 5 carbon atoms and $R^{30}$ represents a straight- or branched-chain alkoxy group containing from 1 to 4 carbon atoms, preferably ethoxy, the hydroxy group or a fluorine, chlorine or bromine atom, or (2), when $R^{28}$ in the compound of formula XL represents the cyano group (and $Y^1$ represents the cyano group and $Z^1$ represents the unsubstituted amino group), tetracyanoethylene.

The reaction of a compound of formula XLI with a compound of formula XLII (optionally prepared in situ) or tetracyanoethylene may be effected in the presence of an inert organic solvent, for example an alkanol containing from 1 to 4 carbon atoms, e.g. ethanol, acetic acid, ethoxyethanol or an ether, and at a temperature from ambient temperature to the reflux temperature of the reaction mixture and optionally in the presence of an alkali metal, e.g. sodium or potassium, acetate, carbonate or bicarbonate or organic base, e.g. triethylamine. When an acid addition salt of the compound of formula XLI is used, the reaction with the compound of formula XLII is effected in the presence of an alkali metal, e.g. sodium or potassium, acetate, carbonate or bicarbonate.

(ii) Compounds of formula XL wherein $Z^1$ represents the unsubstituted amino group may alternatively be prepared directly by reacting a compound of formula $Y^1CH_2CN$ with a compound of formula XLI in the presence of a compound of formula $R^{31}C(R°)_3$ wherein $R^{31}$ represents a straight- or branched-chain alkyl group containing from 1 to 4 carbon atoms which may be unsubstituted or substituted by one or more halogen atoms or a cycloalkyl group containing from 3 to 6 carbon atoms and R° represents an alkoxy group which may be straight- or branched-chain and preferably contains from 1 to 4 carbon atoms, in an inert organic solvent, preferably ethanol, at a temperature from ambient to reflux.

(iii) Compounds of formula XL wherein $Z^1$ represents the unsubstituted amino group and $R^{28}$ represents the cyano group may be obtained by the reaction of a compound of the formula XLIII with a molar equivalent of compound of formula $Y^1CH_2CN$, i.e. malononitrile when $Y^1$ represents the cyano group, generally in the presence of an ahydrous inert organic solvent, e.g. ethanol, and a molar equivalent of a base, e.g. sodium hydride, and at a temperature from 0° to 50° C.

The compounds of formula XL may be prepared by reaction of a compound of formula XLI with a compound of formula XLII or tetracyanoethylene with isolation of an intermediate compound of formula (XLIV) from the reaction mixture. When the reaction of a compound of formula XLI with a compound of formula XLII is effected in acetic acid, in the absence or presence of an alkali metal, e.g. sodium or potassium, acetate, the intermediate compound of formula XLIV may separate from the reaction mixture, depending upon its solubility in the reaction medium, and may, if desired, be isolated before being cyclized as hereinbefore described to a compound of formula XL. The cyclization of a compound of formula XLIV, which constitutes a feature of the invention may be effected in the presence of an inert organic solvent, for example an alkanol containing from 1 to 4 carbon atoms, e.g. ethanol, acetic acid or ethoxyethanol, at a temperature of from ambient temperature up to the reflux temperature of the reaction mixture, and optionally in the presence of sodium ethoxide when the solvent is ethanol.

It will be appreciated that in the preparation of compounds of general formula I corresponding to the third embodiment of the invention the following subsidiary processes or adaptations thereof may be performed in an appropriate combination to achieve the compound sought.

Compounds of general formula I which conform to formula XLV wherein R" represents an $R^{33}C(=O)-$ group, wherein $R^{33}$ represents a straight- or branched-chain alkyl or alkoxy group containing from 1 to 6 carbon atoms, or a cycloalkyl group containing from 3 to 6 carbon atoms and R"' represents a hydrogen atom or an $R^{33}C(=O)-$ group which is identical to the group $R^{33}C(=O)-$ represented by R" or $-NR^{32}R$"' represents a cyclic imide as hereinbefore defined, may be prepared by the reaction of a compound of general formula I wherein $R^3$ represents the unsubstituted amino group, or an alkali metal salt thereof, with a compound of the formula XLVI:

$R^{33}COX^9$  XLVI wherein $X^9$ represents a chlorine or bromine atom, or with a compound of the formula XLVII:

$(R^{33}CO)_2O$  XLVII or with a dicarboxylic acid derivative. The reaction may be conducted in the absence or presence of an inert organic solvent, for example acetonitrile, tetrahydrofuran, a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. to the reflux temperature of the reaction medium, to give a compound of formula XLV wherein R" represents an $R^{33}C(=O)-$ group wherein $R^{33}$ is as hereinbefore defined and R"' represents a hydrogen atom or an $R^{33}C(=O)-$ group, depending upon the reaction conditions chosen and/or the use of an excess of the compound of formula XLVI or XLVII.

Compounds of formula XLV wherein R" represents a formyl group and R"' represents a hydrogen atom may be prepared by reaction of a compound of general formula I of the third embodiment of the invention, wherein $R^3$ represents the unsubstituted amino group with formic acid. The reaction may be conducted in an inert organic solvent, for example a ketone, e.g. methylisobutylketone, or an aromatic hydrocarbon, e.g. benzene or toluene, at the reflux temperature of the reaction mixture.

Compounds of formula XLV wherein R" represents a formyl group and R"' represents a hydrogen atom or a formyl group, may be prepared by the reaction of a compound of general formula I, wherein $R^3$ represents the unsubstituted amino group with formylacetic anhydride. Formylacetic anhydride may be prepared from formic acid and acetic anhydride and the reaction with the compound of general formula I may be conducted in the absence or prsence of an inert organic solvent, for example a ketone, e.g. acetone, or an aromatic hydrocarbon, e.g. benzene or toluene, and optinally in the presence of an acid-binding agent, for example pyridine, triethylamine or an akali metal, e.g. sodium or potassium, carbonate or bicarbonate, at a temperature from 0° C. to the reflux temperature of the reaction mixture, to give a compound of formula XLV wherein R" represents a formyl group and R"' represents a hydrogen atom or a formyl group, depending upon the reaction conditions chosen and/or the use of an excess of formylacetic anhydride.

Compounds of formula XLV wherein R" represents a formyl group or a group $R^{33}C(=O)$- and R"' represents a hydrogen atom may be prepared by the selective removal by hydrolysis of an $R^{33}C(=O)$- group or a formyl group from a compound of formula XLV wherein R" and R"' both represent a $R^{33}C(=O)$- group or a formyl group. Hydrolysis is effected under mild conditions, for example by treatment with an aqueous-ethanolic solution or suspension of an alkali metal, e.g. sodium or potassium, bicarbonate, or with aqueous ammonia.

Compounds of formula XLV wherein R" represents a straight- or branched-chain alkoxycarbonyl group containing from 2 to 7 carbon atoms which is unsubstituted or substituted by one or more halogen atoms, and R"' represents a hydrogen atom may be prepared by the reaction of a compound of the formula XLVIII, wherein $R^{35}$ represents an alkoxycarbonyl group $R^{36}C(=O)$-, wherein $R^{36}$ represents a straight- or branched-chain alkoxy group containing from 1 to 6 carbon atoms (which is unsubstituted or substituted by one or more halogen atoms) or a phenoxy group, with a compound of the formula XLIX:

$R^{36}H$                                  XLIX to replace a first group represented by the symbol $R^{35}$ by a hydrogen atom, and to replace the second group represented by the symbol $R^{35}$ by an alkoxycarbonyl group when $R^{35}$ represents a phenoxycarbonyl group, or, if desired, to replace the second group represented by the symbol $R^{35}$ by another alkoxycarbonyl group when $R^{35}$ in formula XLVIII represents an alkoxycarbonyl group. As will be apparent to those skilled in the art, the desired compound of formula XLV is obtained by selection of the appropriate compounds of formulae XLVIII and XLIX. The reaction may be effected in water or an inert aqueous-organic or organic solvent, for example an alkanol containing 1 to 4 carbon atoms, e.g. ethanol, or an aromatic hydrocarbon, e.g. benzene or toluene, or which is preferably an excess of the compound of formula XLIX, at a temperature from ambient temperature to the reflux temperature of the reaction mixture and, if necessary, at elevated pressure, and optionally in the presence of a base, for example an alkali metal alkoxide, e.g. of the compound of formula XLIX.

Compounds of formula XLV wherein R" and R"', which may be the same or different, each represents a formyl group or a $R^{33}C(=O)$- group, may be prepared by the reaction of an alkali metal, e.g. sodium or potassium, derivative of a compound of formula XLV wherein R" represents a group $R^{33}C(=O)$- as hereinbefore defined, or a formyl group, and R"' represents a hydrogen atom with formic acid, formylacetic anhydride or a compound of formula XLVI. Reaction may be effected in an inert aprotic solvent, e.g. dimethylformamide, at a temperature from laboratory temperature to the reflux temperature of the reaction mixture.

Alkali metal derivatives of compounds of general formula I (wherein $R^3$ represents the unsubstituted amino group) or formula XLV wherein R" represents a group $R^{33}C(=O)$- and R"' represents a hydrogen atom may be prepared in situ by reaction with an alkali metal, e.g. sodium or potassium, hydride, in an inert aprotic solvent, e.g. dimethylformamide, at a temperature from laboratory temperature to the reflux temperature of the reaction mixture.

Compounds of formula XLVIII wherein $R^{35}$ represents a group $R^{36}C(=O)$-, may be prepared as hereinbefore described. Compounds of formula XLVIII wherein $R^{35}$ represents a phenoxycarbonyl group may be prepared by the reaction of a compound of general formula I (wherein $R^3$ represents the unsubstituted amino group), with a compound of the formula XLVIA:

$R^{37}$ $COX^9$                           XLVIA wherein $R^{37}$ represents a phenoxy group, or with a compound of the formula XLVIIA:

$(R^{37}CO)_2O$                            XLVIIA using the reaction conditions hereinbefore described for the reaction of a compound of general formula I with a compound of formula XLVI or XLVII.

Compounds of formula XLV wherein R" represents a group $R^{38}$ which represents a straight- or branched-chain alkyl group containing from 1 to 6 carbon atoms (which may be unsubstituted or substituted by alkoxycarbonyl groups containing from 2 to 5 carbon atoms) or a cycloalkyl group containing from 3 to 6 carbon atoms, and R"' represents a hydrogen atom may be prepared by the removal of the group $R^{33}C(=O)$- of a compound of the formula XLV, wherein $R^1$ represents a group $R^{38}$ and R"' represents a group $R^{33}C(=O)$-. Removal of the group $R^{33}C(=O)$- may be effected by selective hydrolysis under mild conditions, for example by treatment with an alkali metal, e.g. sodium or potassium, hydroxide in water or an inert organic or aqueous-organic solvent, for example a lower alkanol, e.g. methanol, or a mixture of water and lower alkanol, at a temperature from laboratory temperature up to the reflux temperature of the reaction mixture.

Compounds of the formula XLV, wherein R" represents a group $R^{38}$ and R"' represents a group $R^{33}C(=O)$, may be prepared by reaction of a compound of formula XLV wherein R" represents a hydrogen atom, or an alkali metal, e.g., sodium or potassium, derivative thereof, with a compound of the formula L:

$R^{38}X^{10}$                             L wherein $X^{10}$ represents a chlorine, bromine or iodine atom. Reaction may be effected in an inert organic solvent, e.g. dichloromethane, tetrahydrofuran, or dimethylformamide, at a temperature from laboratory temperature up to the reflux temperature of the reaction mixture and, when a compound of formula XLV is used, in the presence of a base, e.g. Triton B; or by reaction of a compound of formula XLV wherein R"' represents the hydrogen atom and R" represents a group $R^{38}$ with a compound of formula XLVI or XLVII.

Compounds of general formula I wherein $R^3$ represents an N-(alkyl or cycloalkyl)-N-formylamino group as hereinbefore described may be prepared in a similar manner to the process above using, where appropriate, formylacetic anhydride instead of a compound of formula XLVI or XLVII.

Compounds of formula XLV wherein one of R" and R"' or both of R" and R"' represent a straight- or branched-chain alkyl group containing from 1 to 6 carbon atoms or cycloalkyl group containing from 3 to 6 carbon atoms, groups represented by R" and R'" being identical, may be prepared by reaction of a compound of general formula I, wherein $R^3$ represents the unsubstituted amino group, or an alkali metal, e.g. sodium or potassium, derivative thereof, with a compound of formula L, in the absence or presence of an inert organic solvent, for example an aromatic hydrocarbon, e.g. benzene or toluene, chloroform, dichloromethane, tetrahydrofuran or dimethylformamide, and optionally in the presence of an acid-binding agent, for example pyridine, triethylamine or an alkali metal, e.g. sodium or potassium, bicarbonate, at a temperature from 0° C. up to the reflux temperature of the reaction mixture.

Alkali metal derivatives of compounds of formulae XLV (wherein R" represents a hydrogen atom) and I (wherein $R^3$ represents the unsubstituted amino group) may be prepared in situ by the reaction of the compounds, with an alkali metal, e.g. sodium or potassium, hydride, at a temperature from laboratory temperature to the reflux temperature of the reaction mixture.

Compounds of general formula I wherein $R^3$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms may be prepared by the reaction of a compound of general formula I (wherein $R^3$ represents the unsubstituted amino group) with a trisalkoxyalkane in the presence of an acidic catalyst, e.g. p-toluenesulphonic acid, at a temperature from ambient temperature to the reflux temperature of the reaction mixture.

Compounds of general formula I, wherein $R^3$ represents a straight- or branched-chain alkylsulphenylamino group containing from 1 to 4 carbon atoms, may be prepared by the reaction of compounds of general formula I (wherein $R^3$ represents the unsubstituted amino group) with an alkanesulphenyl chloride in the presence of a base, e.g. sodium hydride, and optionally in the presence of a crown ether catalyst, e.g. 15-crown-5.

The reaction may be performed in a solvent, e.g. tetrahydrofuran, at a temperature from 0° C. to the reflux temperature of the reaction mixture.

Compounds of general formula I wherein $R^3$ represents —NHCH$_2^{R39}$ wherein $R^{39}$ represents the hydrogen atom or a straight- or branched-chain alkyl group containing from 1 to 4 carbon atoms may be prepared by reaction of a compound of general formula I wherein $R^3$ represents —N=C(OR$^{40}$)R$^{39}$ wherein $R^{40}$ represents a straight- or branched-chain alkyl group containing from 1 to 4 carbon atoms with a reducing agent, preferably sodium borohydride. The reaction may be effected in an inert organic solvent, ethanol or methanol being preferred, at a temperature from 0° C. to the reflux temperature of the reaction mixture.

Compounds of general formula I wherein $R^2$ represents —C(=O)NH$_2$ may be prepared by partial hydrolysis of a compound of general formula I wherein $R^2$ represents —CN preferably with sulphuric acid at a temperature from ambient temperature to 100° C.

Compounds of general formula I wherein $R^2$ represents the chlorine, bromine or iodine atom may be prepared by reaction of a compound of formula LI with a halogenating agent, preferably N-halosuccinimide in an inert solvent, preferably carbon tetrachloride, at a temperature from ambient temperature to the reflux temperature of the reaction mixture.

Compounds of general formula I wherein $R^3$ represents the chlorine, bromine or iodine atom may be prepared by diazotization of a compound of general formula I wherein $R^3$ represents —NH$_2$ with an alkyl nitrite, preferably tert-butyl nitrite, in the presence of a halogenating agent preferably bromoform, iodine or anhydrous copper chloride at a temperature from 0° C. to 100° C.

Compounds of general formula I wherein $R^2$ represents the nitro group may be prepared by reacting a compound of formula LI with a nitrating agent, preferably nitric acid optionally in the presence of sulphuric acid or nitric acid in a solvent such as acetic acid or acetic anhydride at a temperature from 0° C. to 100° C.

Compounds of general formula I wherein $R^2$ represents —SO$_2$NR$^{41}$R$^{42}$ wherein $R^{41}$ and $R^{42}$, which may be the same or different, each represent the hydrogen atom or a straight- or branched-chain alkyl group containing from 1 to 6 carbon atoms may be prepared by reacting a compound of formula LIV with an amine of the formula $R^{41}R^{42}$NH in a solvent such as toluene or water at a temperature from 0° C. to the reflux temperature of the reaction mixture.

Compounds of general formula I wherein $R^2$ represents —CONR$^{41}$R$^{42}$ may be prepared by reacting a compound of formula LV wherein $X^{11}$ represents a chlorine or bromine atom or activated ester moiety, e.g. 4-nitrophenoxy group, especially the chlorine atom, with an amine of the formula $R^{41}R^{42}$NH in a solvent such as toluene or water, at a temperature from 0° C. to the reflux temperature of the reaction mixture.

Intermediates of formula LI may be prepared by decarboxylation of a compound of formula LVI, performed by heating at a temperature from 100° C. to 250° C., optionally in the presence of an inert organic solvent, particularly N,N-dimethylaniline.

Intermediates of formula LI wherein $R^3$ is the unsubstituted amino group and $R^1$ represents a straight- or branched-chain alkyl group containing from 1 to 4 carbon atoms which may be unsubstituted or substituted by one or more halogen atoms may also be prepared by reaction of an appropriate β-ketonitrile or derivative thereof, e.g. the imine with an arylhydrazine in an inert organic solvent such as ethanol optionally in the presence of an acidic or basic catalyst at a temperature from ambient to 100° C.

Alternatively, intermediates of formula LI may be prepared directly from esters of compounds of formula LVI by heating in an inert organic solvent preferably acetic acid at a temperature from 50° C. to reflux, in the presence of a strong acid preferably hydrobromic acid.

Intermediates of formula LVI may be prepared by hydrolysis of esters of general formula I wherein $R^2$ represents —COOR$^{43}$ wherein $R^{43}$ represents a straight- or branched-chain alkyl group containing from 1 to 6 carbon atoms, preferably with an alkali metal hydroxide in a solvent such as an aqueous alcohol at a temperature from 0° C. to the reflux temperature of the reaction mixture.

Intermediates of formula LIV may be prepared by reacting a compound of formula LI with chlorosulphonic acid at a temperature from 0° C. to 150° C.

Intermediates of formula LV are prepared by reacting a compound of formula LVI with a chlorinating or brominating agent or e.g. 4-nitrophenol (preferably thionyl chloride) at a temperature from ambient temperature to the reflux temperature of the reaction mixture.

Compounds of general formula I wherein $R^2$ represents —C(=O)R$^{43}$ wherein $R^{43}$ represents a straight- or branched-chain alkyl group containing from i to 6 carbon atoms may be prepared by the reaction of a compound of formula LI with an acylating agent such as $R^{43}$COCl in the presence of a catalyst such as aluminum chloride and in an inert organic solvent such as 1,1,2,2-tetrachloroethane and at a temperature from 0° C. to the reflux temperature of the reaction mixture.

When $R^3$ is an amino group it may also be acylated and subsequent hydrolysis using an acid such as hydrochloric or hydrobromic acid in a solvent such as dioxan or acetic acid may be necessary.

Compounds of general formula I wherein $R^2$ represents —C(=O)$R^{43}$ may also be prepared by the reaction of nitriles of the general formula I wherein $R^2$ represents —CN with an organometallic reagent such as a compound of formula $R^{43}MgX^{10}$ in an inert organic solvent such as diethyl ether or tetrahydrofuran, at a temperature from 0° C. to reflux.

Compounds of formula LVII may be prepared by the reaction of a compound of formula I wherein $R^2$ represents the thiocyanato group with an organometallic reagent such as a compound of formula R'Mg$X^{10}$ in an inert organic solvent such as diethyl ether or tetrahydrofuran, and at a temperature from ambient temperature to the reflux temperature of the reaction mixture.

Compounds of formula LVII wherein R'S is other than a 1-alkenylthio group may also be prepared by reacting a compound of general formula I wherein $R^2$ represents the thiocyanato group with a base, preferably sodium hydroxide, or a reducing agent, preferably sodium borohydride, in the presence of a reagent of formula Ra$X^{10}$ wherein $R^a$ is as hereinbefore defined for R' with the exclusion of 1-alkenyl groups, for example methyl iodide in an inert organic or aqueous-organic solvent such as an alcohol, e.g. ethanol or a mixture of an alcohol and water, the reaction being performed at a temperature from ambient to reflux.

Alternatively, compounds of formula LVII wherein R'S is other than a 1-alkenylthio group may be prepared by reductive alkylation of disulphides of formula LVIII employing a reducing agent preferably sodium dithionite or sodium borohydride, in the presence of a base, preferably sodium hydroxide or sodium carbonate, and of a reagent of formula $R^aX^{10}$ such as methyl iodide in an inert organic or aqueous-organic solvent such as an alcohol, e.g. ethanol or a mixture of an alcohol and water, at a temperature from ambient to reflux.

Alternatively, compounds of formula LVII may be prepared from a halide of general formula I wherein $R^2$ represents a bromine or iodine atom by metal exchange using a strong base, preferably butyl lithium, and subsequent addition of the appropriate disulphide of formula R'—S—S—R' in an inert organic solvent such as tetrahydrofuran, and the reaction is performed at a temperature from −78° C. to ambient.

Alternatively, compounds of formula LVII wherein R'S represents a straight- or branched-chain alkylthio group containing from 1 to 6 carbon atoms which may be unsubstituted or substituted by one or more halogen atoms may be prepared by reacting a compound of formula LI with an alkanesulphenyl halide (which may be optionally substituted by one or more halogen atoms) in an inert organic solvent, preferably chloroform, in the presence of a base such as pyridine, and at temperatures from 0° C. to reflux.

Compounds of formula LVII wherein R'S represents a methylthio group which is substituted by three halogen atoms which may be the same or different may also be prepared by the reaction of a compound of general formula I wherein $R^2$ represents the thiocyanato group with a source of halogenocarbene, such as chloroform and sodium hydroxide, preferably with phase transfer catalysis using for example benzyltriethylammonium chloride or tetrabutylammonium chloride.

Compounds of formula LVII wherein R'S represents a straight- or branched-chain alkylthio group containing from 1 to 6 carbon atoms which is substituted by one or more fluorine atoms may also be prepared by a halogen exchange reaction of a compound of formula LVII wherein R'S represents a straight- or branched-chain alkylthio group containing from 1 to 6 carbon atoms which is substituted by one or more chlorine atoms with a fluorinating agent such as a mixture of antimony trifluoride and antimony pentachloride, KF or CsF in an aprotic solvent such as sulfolane at a temperature from 50° C. to reflux.

Compounds of general formula I wherein $R^2$ represents the thiocyanato group may be prepared by the reaction of a compound of formula LI with a thiocyanating agent such as alkali metal or ammonium salts of thiocyanic acid (e.g. NaSCN) and bromine in an inert organic solvent such as methanol, and at a temperature from 0° C. to 100° C.

Intermediates of formula LVIII may be prepared by hydrolysis of thiocyanates of general formula I wherein $R^2$ represents the thiocyanato group, preferably using hydrochloric acid in the presence of ethanol at a temperature from ambient to reflux temperature; they may also be prepared by reduction of the thiocyanates by sodium borohydride in an alcohol preferably ethanol at a temperature from ambient to reflux.

Compounds of general formula I wherein $R^2$ represents a group R SO may be prepared by the oxidation of compounds of formula LVII by an oxidizing reagent preferably 3-chloroperbenzoic acid in an inert organic solvent such as dichloromethane or by hydrogen peroxide in acetic acid at a temperature from 0° C. to the reflux temperature of the reaction medium.

Compounds of general formula I wherein $R^2$ represents a group R'$SO_2$ may also be prepared by the above process, by employing an excess of the oxidizing agent.

Compounds of general formula I wherein $R^2$ represents a group R'$SO_2$ wherein R represents a straight- or branched-chain alkyl group containing from 1 to 6 carbon atoms which is substituted by one or more fluorine atoms may also be prepared by a halogen exchange reaction of a compound of general formula I wherein $R^2$ represents a group R'$SO_2$ wherein R represents a straight- or branched-chain alkyl group containing from 1 to 6 carbon atoms which is substituted by one or more chlorine atoms with a fluorinating agent such as a mixture of antimony trifluoride and antimony pentachloride, KF or CsF at a temperature from 50° C. to 200° C.

Compounds of general formula I wherein $R^2$ represents a group R'$SO_2$ may also be prepared by reaction of a compound of general formula LI with the appropriate sulphonic anhydride of general formula (R'$SO_2)_2$O for example trifluoromethanesulphonic or methanesulphonic anhydride and in the presence of aluminum chloride as catalyst, and employing an inert organic solvent such as 1,1,2,2-tetrachloroethane at a temperature from ambient to 150° C.

Compounds of general formula I wherein $R^3$ represents a straight- or branched-chain alkyl group containing from 1 to 4 carbon atoms, the carboxy group, a group $R^{44}$S wherein $R^{44}$ represents a straight- or branched-chain alkyl group containing from 1 to 6 carbon atoms which may be unsubstituted or substituted by one or more halogen atoms or $R^3$ represents a trialkylsilyl group containing from 1 to 6 carbon atoms in each alkyl group which may be the same or different may be prepared by the reaction of a compound of general formula I wherein $R^3$ represents a hydrogen, bromine or iodine atom with a lithiating agent preferably lithium diisopropylamide or n-butyl lithium, and reaction with the appropriate substrate from alkyl halide, carbon dioxide, dialkylsulphides or trialkylsilyl halides respectively at a temperature from −78° C. to ambient temperature, and in an inert solvent, preferably tetrahydrofuran.

Compounds of general formula I wherein $R^3$ represents a hydrogen atom may be prepared by diazotization of an amine of general formula I wherein $R^3$ represents the unsubstituted amino group using an alkyl nitrite, preferably tert-butyl nitrite, in an inert solvent preferably tetrahydrofuran, at a temperature from ambient temperaure to the reflux temperature of the reaction mixture.

Compounds of general formula I wherein $R^3$ represents a group $R^{44}SO$ may be prepared by the reaction of a compound of general formula I wherein Z represents a group $R^{44}S$ with an oxidizing agent, preferably 3-chloroperbenzoic acid in a solvent such as dichloromethane, or by hydrogen peroxide in acetic acid at a temperature from 0° C. to the reflux temperature of the reaction mixture.

Compounds of general formula I wherein $R^3$ represents a group $R^{44}SO_2$ may also be prepared by the above process, by employing an excess of the oxidizing agent.

Compounds of general formula I wherein $R^3$ represents the fluorine atom or the cyano group may be prepared by the reaction of a halide of formula I wherein $R^3$ represents the chlorine or bromine atom with an alkali metal fluoride, preferably cesium fluoride, or with an alkali metal cyanide preferably KCN, under anhydrous conditions in an inert solvent, preferably sulfolane, and at a temperature from ambient temperature to 150° C.

Compounds of general formula I wherein $R^3$ represents the nitro group may be prepared by oxidation of amines of general formula I wherein $R^3$ represents the unsubstituted amino group with an oxidant, preferably trifluoroperacetic acid or m-chloroperbenzoic acid and in an inert organic solvent preferably dichloromethane at a temperature from 0° C. to reflux.

Compounds of general formula I wherein $R^3$ represents the cyano group may be prepared by dehydration of the corresponding amide preferably by heating with phosphorous pentoxide at a temperature from 50° C. to 250° C.

The amides may be prepared (i) by reacting a carboxylic acid of general formula I wherein $R^3$ represents a carboxy group with a chlorinating agent preferably thionyl chloride, and (ii) reacting the resultant acid chloride of formula LIX with ammonia:

(i) the reaction with a chlorinating agent preferably thionyl chloride is generally conducted at a temperature from ambient temperature to the reflux temperature of the reaction mixture;

(ii) the reaction with ammonia is generally conducted in a solvent which may be inert, preferably toluene, or in the presence of water, and at a temperature from 0° C. to 100° C.

Compounds of general formula I wherein $R^2$ represents a group $R'SO_2$ is other than a 1-alkenylsulphonyl group may be prepared alternatively by reaction of sulphinate metal (e.g. sodium) salts with a reagent of formula $RaX^{10}$ or preferably a sulphate of formula $(Ra)_2SO_4$, in a solvent such as water and in the presence of sodium bicarbonate at a temperature from 0° C. to 100° C.

The intermediate sulphinate sodium salts may be prepared by reaction of sulphonyl chlorides of formula LIV with sodium sulphite in the presence of sodium bicarbonate and water as solvent, at a temperature from 50° C. to reflux.

Intermediates of formula LIV may also be prepared from the thiocyanates of general formula I wherein $R^2$ represents a thiocyanato group by chlorination using chlorine in a solvent, preferably water, at a temperature from ambient to reflux.

Compounds of general formula I wherein one of the substituents $R^4$—$R^8$ represents a haloalkylsulphinyl group may be prepared by oxidation of a haloalkylthio derivative of general formula I, preferably with m-chloroperbenzoic and in an inert organic solvent preferably dichloromethane, at a temperature from 0° C. to reflux.

Compounds of general formula I wherein one of the substituents $R^4$—$R^8$ represents a haloalkylsulphonyl group may be prepared in a similar manner, by employing two molar equivalents of oxidant.

Compounds of general formula I wherein $R^2$ represents the fluorine atom may be prepared by diazotization of corresponding amines using sodium nitrite in tetrafluoroboric acid and sulphuric acid at a temperature from −10° C. to +10° C., followed by photolysis in the presence of excess sodium tetrafluoroboric acid at a temperature from −30° C. to ambient.

Intermediate amines above may be prepared by reduction of nitro compounds of general formula I wherein $R^2$ represents a nitro group, preferably with zinc in ethanol at a temperature from ambient to reflux.

Compounds of general formula I wherein $R^2$ represents the methyl group may be prepared by reduction of an acid of general formula LVI using a reducing agent, preferably borane-tetrahydrofuran complex in a solvent preferably tetrahydrofuran at a temperature from −30° C. to reflux.

Compounds of general formula I Wherein $R^3$ represents a trialkylsilylmethyl group as hereinbefore defined may be prepared by the reaction of a compound of general formula I wherein $R^3$ represents the methyl group with a lithiating agent preferably lithium diisopropylamide or n-butyl lithium, and reaction with a trialkylsilyl halide at a temperature from −78° C. to ambient, and in an inert organic solvent preferably tetrahydrofuran, optionally in an inert atmosphere.

The following processes optionally followed by the subsidiary processes hereinbefore described permit the preparation of the remaining compounds of general formula I not described above, as well as some whose preparation is described above.

Compounds of general formula I wherein $R^1$ represents a chlorine, bromine or iodine atom and $R^3$ represents the unsubstituted amino group, may be prepared by the diazotization of the (diamino) compounds of general formula I in which $R^3$ represents and $R^1$ is replaced by amino, using a molar equivalent of sodium nitrite in a mineral acid, for example a mixture of concentrated sulphuric acid and acetic acid, at a temperature from 0° to 60° C., and by subsequent reaction with the appropriate copper salt and appropriate mineral acid or with an aqueous solution of potassium iodide (when $R^1$ represents an iodine atom) at a temperature from 0° to 100° C.

The diamino compounds above wherein $R^2$ represents the cyano group may be prepared by the reaction of potassium cyanoform KC(CN) 3 with a phenylhydrazine of formula XLI in the presence of hydrochloric acid, at a temperature from 50° C. to the reflux temperature of the reaction mixture.

Compounds of general formula I wherein $R^1$ represents the fluoromethyl group may be prepared by reacting a compound of formula LII with a fluorinating agent, preferably diethylaminosulphur trifluoride, in an inert organic solvent, preferably dichloromethane, at a temperature from −78° C. to the reflux temperature of the reaction mixture.

Intermediates of formula LII may be prepared by reduction of compounds of formula LX preferably with lithium borohydride in an inert organic solvent, e.g. tetrahydrofuran at a temperature from 0° C. to the reflux temperature of the reaction mixture.

Intermediates of formulae LX (wherein $R^{45}$ represents an alkyl group) and LXI wherein $R^3$ represents the unsubstituted amino group may be obtained by the reaction of a compound of the formula LIII (wherein $R°$ represents an alkoxy group) with a molar equivalent of compound of formula $Y^1CH_2CN$, i.e. malononitrile when $Y^1$ represents the cyano group, in the presence of an anhydrous solvent, e.g. ethanol, and a molar equivalent of a base, e.g. sodium hydride, and at a temperature from 0° to 50° C. followed, if desired, by hydrolysis of the esters of formula LX with an aqueous base, e.g. sodium hydroxide, with a co-solvent, e.g. ethanol, at a temperature from 0° C. to the reflux temperature of the reaction mixture.

Intermediates of formulae XLIII and LIII may be prepared by chlorination of the appropriate unsubstituted compound using chlorine or other chlorinating agent.

Intermediates of formulae XLIII and LIII may be prepared by diazotization of the appropriate aniline with a solution of a molar equivalent of sodium nitrite in a mineral acid, e.g. a mixture of concentrated sulphuric acid and acetic acid at a temperature from 0° to 60° C., and then reacting with the compound of formula $CH_3COCH(Cl)CN$ or a compound of formula $CH_3COCH(Cl)COR°$ wherein $R°$ represents an alkoxy group in the presence of an inert solvent, e.g. a mixture of water and ethanol, buffered, e.g. with excess sodium acetate, and at a temperature from 0° to 50° C.

Compounds of general formula I wherein $R^1$ represents the nitro group may be prepared by oxidation of the corresponding amine with an oxidant, preferably trifluoroperacetic acid or m-chloro-perbenzoic acid in an inert organic solvent preferably dichloromethane at a temperature from 0° C. to reflux. By employing known protecting agents in this process compounds of general formula I wherein $R^3$ represents the amino group may be prepared.

Compounds of general formula I wherein $R^1$ represents the fluorine atom may be prepared by the diazotization of the corresponding amine of general formula I in which $R^1$ is replaced by —$NH_2$ using for example a solution of sodium nitrite in a mineral acid, for example sulphuric acid and in the presence of fluoroboric acid or its sodium salt and subsequent thermolysis or photolysis of the diazonium fluoroborate derivative by methods known per se.

Amine intermediates above wherein $R^3$ represents the hydrogen atom may be prepared by performing a Curtius rearrangement of the corresponding acid azide by heating in an inert organic solvent such as toluene at a temperature from 50° to 150° C. to give an isocyanate which is then reacted with for example tert.-butanol to give a carbamate, which in turn is hydrolyzed using dilute acid preferably hydrochloric acid in ethanol at a temperature from ambient to reflux.

Intermediate acid azides may be prepared by reaction of a carboxylic acid of formula LXI wherein $R^3$ represents the hydrogen atom with a chlorinating agent, preferably thionyl chloride at temperatures from ambient to reflux, followed by reaction of the intermediate acid chloride with sodium azide in a polar solvent, preferably acetone and water at a temperature from 0° C. to ambient.

Compounds of general formula I wherein $R^1$ represents the cyano group may also be prepared by reacting a carboxylic acid of formula LXI with a chlorinating agent, preferably thionyl chloride at ambient to reflux temperature, followed by reaction of the intermediate acid chloride with ammonia to give an intermediate amide which is then dehydrated by heating with a dehydrating reagent, preferably phosphorus pentoxide at a temperature from 50°–250° C.

Intermediates of formula LXI may be prepared by hydrolysis of the corresponding esters of formula LX preferably using a base such as sodium hydroxide and a solvent such as aqueous alcohol, and at a temperature from 0° C. to the reflux temperature of the reaction mixture.

Compounds of general formula I wherein $R^2$ represents a 1,1-difluoroalkyl group which may be substituted by one or more additional halogen atoms may be prepared by the reaction of a compound of general formula I wherein $R^2$ represents a straight- or branched-chain alkanoyl group containing from 2 to 6 carbon atoms or the corresponding compound in which $R^2$ is replaced by the formyl group or a straight- or branched-chain alkanoyl group containing from 2 to 6 carbon atoms which is substituted by one or more halogen atoms with a fluorinating agent, preferably diethylaminosulphur trifluoride or sulphur tetrafluoride in an inert organic solvent, preferably dichloromethane, at a temperature from −78° C. to ambient.

Compounds of general formula I wherein $R^2$ represents the trifluoromethyl group or a trifluoromethylalkyl group containing from 2 to 6 carbon atoms which may be substituted by one or more additional halogen atoms may be prepared by the reaction of a fluorinating agent, e.g. sulphur tetrafluoride, with an acid of formula LVI or the corresponding carboxyalkyl compound (it being understood that the carboxy group may be attached to any position of the alkyl moiety) at a temperature from ambient to 150° C.

Salts with pesticidally-acceptable bases of compounds of general formula I wherein $R^3$ represents the carboxy group may be prepared from the corresponding compounds of general formula I by methods known per se, for example by reacting stoichiometric quantities of the compound of general formula I and the appropriate base, for example an alkali metal hydroxide, carbonate or bicarbonate, an alkaline earth metal hydroxide or carbonate, ammonia or an amine (e.g. diethanolamine, triethanolamine, octylamine, morpholine or dioctylamine), in a suitable solvent. The salts may, if necessary, be purified by recrystallization from one, two or more suitable solvents.

Compounds of the third embodiment of the invention according to general formula I not hitherto disclosed or described in the chemical literature, together with their processes of preparation form further features of the present invention.

The present invention accordingly provides the compounds of general formula I, wherein the various symbols are as hereinbefore defined for the third embodiment of the invention, and salt thereof, with the exclusion of the compounds wherein: $R^1$ and $R^3$ both represent methyl, $R^2$ represents thiocyanato and $R^4$-$R^8$ represent 2-, 3- or 4-nitro, 4-methyl, 4-chloro or 2,4-dinitro substitution; $R^1$ represents methyl, $R^2$ represents cyano, $R^3$ represents unsubstituted amino and $R^4$—$R^8$ represent 4-chloro, 2,4-dichloro, 3,4-dichloro, 3-chloro-4-methyl or 2-methyl-4-chloro substitution; $R^1$ represents methyl, $R^2$ represents cyano or $CONH_2$, $R^3$ represents unsubstituted amino and $R^4$—$R^8$ represent 3- or 4-fluoro substitution; $R^1$ represents ethyl, $R^2$ represents cyano or $CONH_2$, $R^3$ represents unsubstituted amino and $R^4$—$R^8$ represent 3- or 4-chloro, 2-, 3- or 4-fluoro or methyl, 3-bromo or 3-nitro substitution; $R^1$ represents propyl, $R^2$ represents cyano or $CONH_2$, $R^3$ represents unsubstituted amino and $R^4$—$R^8$ represent 3-fluoro substitution; $R^1$ represents methyl, $R^2$ represents sulphamoyl, $R^3$ represents chloro and $R^4$—$R^8$ represent 4-chloro substitution; $R^1$ represents methyl, $R^2$ represents nitro, and $R^3$ represents chloro or $R^1$ represents chloro, $R^2$ represents nitro, and $R^3$ represents methyl and $R^4$—$R^8$ represent 4-nitro; and $R^1$ represents nitro, $R^2$ represents cyano or $CONH_2$, $R^3$ represents hydrogen and $R^4$—$R^8$ represent 4-nitro substitution.

According to a further feature of the present invention there are provided intermediates for the preparation of certain compounds of general formula I according to the third embodiment of the invention, i.e. compounds for which in their alternative meanings $R^2$ represents the hydrogen atom, the formyl or carboxy group, a straight- or branched-chain alkanoyl group containing from 2 to 6 carbon atoms which is substituted by one or more halogen atoms, the dithio group (which joins two pyrazole rings), the amino group, the —$SO_2Cl$ group, a straight- or branched-chain carboxyalkyl group containing from 2 to 6 carbon atoms, $R^3$ represents the carbamoyl group or a straight- or branched-chain alkoxycarbonyl group containing from 2 to 7 carbon atoms or the diphenoxycarbonylamino group, $R^4$—$R^8$ substitution is a preferred combination given earlier in the specification or $R^1$ represents the amino, hydroxylethyl, carboxy or carbamoyl group or a straight- or branched-chain alkoxycarbonyl or alkoxycarbonylamino group containing from 2 to 7 carbon atoms.

The following Examples and Reference Examples illustrate the preparation of compounds of general formula I according to the present invention:

EXAMPLE 33

Compound No. 109

A mixture of 2,4,6-trichlorophenylhydrazine (21.1 g) and tetracyanoethylene (13.3 g) in ethanol (100 ml) was heated at reflux for 15 minutes. The reaction mixture was cooled and the solid precipitate was filtered off and washed with diethyl ether to give 5-amino-3,4-dicyano-1-(2,4,6-trichlorophenyl)pyrazole (13 g), as a buff colored solid, m.p. 267°–271° C.

EXAMPLE 34

Compounds Nos. 110 and 111

Tetracyanoethylene (1.9 g) and 2,6-dichloro-4-trifluoromethylphenylhydrazine (3.7 g) was added to a magnetically-stirred solution of sodium acetate (0.6 g) in glacial acetic acid (15 ml) at laboratory temperature. After stirring for 15 minutes, a colorless solid precipitated from the solution and stirring was continued overnight. The mixture was then filtered. The solid obtained was washed successively with acetic acid, water, aqueous sodium bicarbonate solution and water, to give 5-amino-1-(2,6-dichloro-4-trifluoromethylphenyl)-3,4-dicyanopyrazole (2.5 g), as beige crystals, m.p. 221°–222° C.

By proceeding in a similar manner, but replacing the 2,6-dichloro-4-trifluoromethylphenylhydrazine by 2,3,5,6-tetrachlorophenylhydrazine, there was obtained:

5-Amino-3,4-dicyano-1-(2,3,5,6-tetrachlorophenyl)pyrazole, m.p. greater than 330° C., in the form of a buff-colored powder.

REFERENCE EXAMPLE 19

Phenylhydrazines used as starting materials in Examples 33, 34 and 43, not hitherto described in the chemical literature were prepared as follows:

2,6-Dichloro-4-trifluoromethylphenylaniline (4.3 g) was dissolved with stirring, in glacial acetic acid (23 ml). A solution of sodium nitrite (1.5 g) in concentrated sulphuric acid (11 ml) was then added at 55°–60° C. The solution thus obtained was cooled to 0°–5° C. and a solution of stannous chloride (16.4 g) in concentrated hydrochloric acid (14 ml) was added with vigorous stirring. A cream-colored solid precipitated. The mixture was filtered and the solid obtained was added to a mixture of aqueous ammonia solution and ice. The mixture thus obtained was extracted with diethyl ether (6×500 ml) and the combined ethereal extracts were dried over sodium sulphate, filtered and evaporated to dryness to give 2,6-dichloro-4-trifluoromethylphenylhydrazine (3.7 g) m p 54°–56° C. in the form of a colorless crystalline solid.

By proceeding in a similar manner, but replacing the 2,6-dichloro-4-trifluoromethylaniline by the hereinafter indicated aniline there were prepared:

2-Chloro-4-trifluoromethylphenylhydrazine, m.p. 38°–39° C. in the form of a colorless solid, from 2-chloro-4-trifluoromethylaniline.

EXAMPLE 35

Compound No. 112

Ethoxyethylenemalononitrile (44.5 g) and 2,6-dichloro-4-trifluoromethylphenylhydrazine (80.0 g) were added to a stirred solution of sodium acetate (13.4 g) in glacial acetic acid (110 ml) at laboratory temperature. A thick suspension was obtained and was stirred overnight, after which a dark solution had formed. The solvent was evaporated in vacuo, and the residue was diluted with aqueous sodium bicarbonate solution (100 ml) and extracted with dichloromethane (3×100 ml), and the combined extracts were washed with sodium bicarbonate solution (50 ml), then with water (100 ml), dried over anhydrous magnesium sulphate and evaporated in vacuo to give a dark syrup. This was heated at reflux with 2-ethoxyethanol (200 ml) for 1 hour, and then evaporated in vacuo to give a dark oil. The oil was dissolved in dichloromethane, washed with sodium bicarbonate solution (50 ml), then with water (100 ml), dried over anhydrous magnesium sulphate, treated with charcoal, and evaporated in vacuo to give a black solid. The solid was recrystallized twice from a mixture of toluene and petrolum ether (b.p. 60°–80° C.) to give 5-amino- 4-cyano-1-(2,6-dichloro-4-trifluoromethylphenyl)-3-methylpyrazole (49.3 g), m.p. 194°–196° C., in the form of pale brown crystals.

EXAMPLE 36

Compounds Nos. 113, 130, 132 and 144

To a mechanically stirred solution of 2,6-dichloro-4-trifluoromethylphenylhydrazine (180.3 g) in dry diethyl ether (700 ml) was added anhydrous potassium carbonate (112 g), and the mixture was cooled to 0° C. To this mixture was added dropwise during half-an-hour a solution of 2-chloro-1,1-dicyano-2-trifluoromethylethylene (132.1 g) in dry diethyl ether (350 ml). The ice-bath was removed at the end of the reaction, and the mixture was left overnight and then poured onto water (2000 ml). The ethereal layer was separated and the aqueous solution extracted with diethyl ether (2×300 ml). The combined extracts were dried over anhydrous magnesium sulphate, filtered, and evaporated in vacuo to give a buff solid (350 g).

Recrystallization from toluene/hexane gave white crystals (169.5 g) m.p. 202°–204° C. of 5-amino-4-cyano-1-(2,6-dichloro-4-trifluoromethylphenyl)-3-trifluoromethylpyrazole.

By proceeding in a similar manner, but replacing the 2-chloro-1,1-dicyano-2-trifluoromethylethylene by 2-chloro-1-cyano-1-methanesulphonyl-2-trifluoromethylethylene there was prepared:

5-Amino-1-(2,6-dichloro-4-trifluoromethylphenyl)-4-methanesulphonyl-3-trifluoromethylpyrazole in the form of buff crystals m.p. 215°–218° C., from toluene-hexane.

By proceeding in a similar manner, but replacing the 2-chloro-1,1-dicyano-2-trifluoromethylethylene by 2-chloro-1-cyano-1-methoxycarbonyl-2-trifluoromethylethylene there was prepared:

5-Amino-1-(2,6-dichloro-4-trifluoromethylphenyl)-4-methoxycarbonyl-3-trifluoromethylpyrazole in the form of fawn crystals, m.p. 114°–115° C., from hexane.

By proceeding in a similar manner, but replacing the 2,6-dichloro-4-trifluoromethylphenylhydrazine by 2,6-dichloro-4-trifluoromethoxyphenylhydrazine there was prepared:

5-Amino-4-cyano-1-(2,6-dichloro-4-trifluoromethoxyphenyl)-3-trifluoromethylpyrazole in the form of white crystals, m.p. 160°–160.5° C. from toluene-hexane.

EXAMPLE 37

Compounds Nos. 127, 128, 129 and 155

Anhydrous sodium acetate (0.246 g) was added to a stirred solution of 2-chloro-1,1-dicyano-2-pentafluoroethylethylene (1.38 g) in acetic acid (5 ml). To this mixture was added 2,6-dichloro-4-trifluoromethylphenylhydrazine (1.47 g) during 5 minutes. After stirring overnight the mixture was neutralized with sodium bicarbonate solution, and extracted with dichloromethane (2×50 ml). The combined extracts were washed with water, dried over anhydrous magnesium sulphate, filtered, and evaporated in vacuo to give a buff solid )2.1 g). This solid was heated under reflux with 2-ethoxyethanol (10 ml) for 1 hours, and evaporated in vacuo to give a brown oil (2.2 g). This oil was chromatographed on silica (Merck, 230°–400 mesh, 0.7 kg cm$^{-2}$) using a mixture of dichloromethane and ethyl acetate (98:2) to give a yellow solid. Recrystallization from a mixture of dichloromethane and petroleum ether gave 5-amino-4-cyano-1-(2,6-dichloro-4-trifluoromethylphenyl)-3-pentafluoroethylpyrazole as white crystals, m.p. 160°–162° C.

By proceeding in a similar manner, but replacing the 2-chloro-1,1-dicyano-2-pentafluoroethyl-ethylene by 2-chloro-1,1-dicyano-2-chlorodifluoromethylethylene there was prepared:

5-Amino-3-chlorodifluoromethyl-1-(2,6-dichloro-4-trifluoromethylphenyl)-4-cyanopyrazole in the form of white prisms, m.p. 192° C. from toluenehexane By proceeding in a similar manner, but replacing the 2-chloro-1,1-dicyano-2-pentafluoroethylethylene by 2-chloro-1,1-dicyano-2-difluoromethylethylene there was prepared:

5-Amino-1-(2,6-dichloro-4-trifluoromethylphenyl)-4-cyano-3-difluoromethylpyrazole in the form of a colorless solid, m.p. 184.5° C. (from toluene-petroleum ether).

By proceeding in a similar manner, but replacing the 2-chloro-1,1-dicyano-2-pentafluoroethylethylene by 2-chloro-1,1-dicyano-2-heptafluoropropylethylene there was prepared:

5-Amino-1-(2,6-dichloro-4-trifluoromethylphenyl)-4-cyano-3-heptafluoropropylpyrazole in the form of colorless prisms, m.p. 139°–140° C. (from toluene-petroleum ether).

REFERENCE EXAMPLE 20

Chloro-dicyanoethylenes used as starting materials in the above Examples, not hitherto described in the chemical literature were prepared by follows:

A suspension of 2-cyano-3-hydroxy-4-chloro-4,4-difluorobut-2-enenitrile sodium salt (18.56 g) in dichloromethane (60 ml) was stirred at room temperature and treated with phosphorus pentachloride (19.27 g). The suspension was heated under reflux for 6 hours, cooled and filtered, and the filtrate was distilled. A Widmer fractionating column was used to give 2-chloro-1,1-dicyano-2-chlorodifluoromethylethylene as a liquid, b.p. 88° C. (44 mmHg) (71 g).

By proceeding in a similar manner, but replacing 2-cyano-3-hydroxy-4-chloro-4,4-difluorobut-2-enenitrile sodium salt by 2-cyano-3-hydroxy-4,4-difluorobut-2-enenitrile sodium salt there was prepared 2-chloro-1,1-dicyano-2-difluoromethyl-ethylene as a liquid, b.p. 94° C. (46 mmHg).

By replacing 2-cyano-3-hydroxy-4-chloro-4,4-difluorobut-2-enenitrile sodium salt by 3-hydroxy-2-methanesulphonyl-4,4,4-trifluorobut-2-enenitrile sodium salt and proceeding in a similar manner there was prepared 2-chloro-1-cyano-1-methanesulphonyl-2-trifluoromethylethylene as a pale brown liquid.

By replacing 2-cyano-3-hydroxy-4-chloro-4,4-difluorobut-2-enenitrile sodium salt by 3-hydroxy-2-methoxycarbonyl-4,4,4-trifluorobut-2-enenitrile sodium salt and proceeding in a similar manner there was prepared 2-chloro-1-cyano-1-methoxycarbonyl-2-trifluoromethylethylene as a colorless oil, b.p. 86°–92° C. at 23°–25 mm Hg.

By replacing 2-cyano-3-hydroxy-4-chloro-4,4-difluorobut-2-enenitrile sodium salt by 2-cyano-3-hydroxy-4,4,5,5,6,6,6-heptafluorohex-2-enenitrile sodium salt and proceeding in a similar manner there was prepared 2-chloro-1,1-dicyano-2-heptafluoropropylethylene as a pale yellow liquid, b.p. 110° C. at 60 mm Hg.

REFERENCE EXAMPLE 21

The sodium salts used in the above Reference Examples as starting materials, not hitherto described in the chemical literature, were prepared as follows:

To a solution of sodium methoxide (5.61 g) in anhydrous methanol (70 ml) was added malononitrile (6.85 g) and the yellow solution treated with methyl chlorodifluoroacetate (15 g). The mixture was heated under reflux for 4 hours, the solvent was evaporated in vacuo and re-evaporated after addition of toluene to give 2-cyano-3-hydroxy-4-chloro-4,4-difluoro-but-2-enenitrile sodium salt as a brown solid (18.9 g). This was dried in a vacuum desiccator.

By proceeding in a similar manner, but replacing methyl chlorodifluoroacetate by ethyl difluoroacetate there was obtained 2-cyano-3-hydroxy-4,4-difluorobut-2-enenitrile sodium salt as a light brown solid.

By proceeding in a similar manner, but replacing methyl chlorodifuloroacetate by methyl trifluoroacetate, and the malononitrile by methanesulphonylacetonitrile there was obtained 3-hydroxy-2-methanesulphonyl-4,4,4-trifluorobut-2-enenitrile sodium salt as a brown solid.

By proceeding in a similar manner, but replacing methyl chlorodifuloroacetate by methyltrifluoroacetate, and the malononitrile by methylcyanoacetate there was obtained 3-hydroxy-2-methoxycarbonyl-4,4,4-trifluorobut-2-enenitrile sodium salt as a buff solid.

By proceeding in a similar manner, but replacing methyl chlorodifluoroacetate by methylheptafluorobutyrate there was obtained 2-cyano-3-hydroxy-4,4,5,5,6,6,6 -heptafluorohex-2-enenitrile sodium salt as a light brown hygroscopic solid.

EXAMPLE 38

Compound No. 131

To stirred 80% sulphuric acid (22 ml) was added 5-amino-4-cyano-1-(2,6-dichloro-4-trifluoromethylphenyl)-3-trifluoromethylpyrazole (3.98 g) at 80° C. After 1 hour, the cooled solution was poured onto ice and extracted with dichloromethane (3×). The combined extracts were washed with water, dried over anhydrous magnesium sulphate, filtered, and evaporated in vacuo to give a white solid. This solid was recrystallized from ethyl acetate-petroleum ether to give 5-amino-4-carbamoyl-1-(2,6-dichloro-4 -trifluoromethylphenyl)-3-trifluoromethylpyrazole (3.5 g), m.p. 169°–171° C. in the form of white crystals.

EXAMPLE 39

Compounds Nos. 114, 115 and 116

3,5-Diamino-4-cyano-1-(2,6-dichloro-4-trifluoromethylphenyl)pyrazole (3.9 g); prepared as described below) was dissolved with stirring in glacial acetic acid (60 ml) at 15° C. A solution of sodium nitrite (0.88 g) in concentrated sulphuric acid (5.85 ml) was then added over 5 minutes, maintaining at 15° C. After 15 minutes longer at this temperature, the dark red oil solution was poured during 1 minute onto a stirred solution of cuprous chloride (2.32 g) in concentrated hydrochloric acid (26 ml). After 15 minutes at laboratory temperature, by which time the evolution of nitrogen had completely subsided, the reaction mixture was poured onto excess ice and water, and extracted with dichloromethane (3×50 ml). The combined extracts were washed with water (2×50 ml), then with sodium bicarbonate solution (50 ml), dried over anhydrous magnesium sulphate, and evaporated in vacuo to give a brown semi-solid (4.1 g). Chromatography on silica (Merck, 230–400 mesh, 0.7 kg cm$^{-2}$) using a mixture of dichloromethane and ethyl acetate (98:2) as eluent gave after evaporation of the eluate and recrystallization of the residue from a mixture of dichloromethane and petroleum ether (b.p. 60°–80° C.) 5-amino-3-chloro-4-cyano-1-(2,6-dichloro-4-trifluoromethylphenyl)pyrazole (0.95 g), m.p. 189°–191° C. in the form of white crystals.

By proceeding in a similar manner but replacing the cuprous chloride and concentrated hydrochloric acid by cuprous bromide and 48% w/v hydrobromic acid respectively there was prepared:

5-Amino-3-bromo-4-cyano-1-(2,6-dichloro-4-trifluoromethylphenyl)pyrazole, m.p. 182°–183° C., in the form of white crystals.

By replacing the cuprous chloride and concentrated hydrochloric acid by a solution of potassium iodide in water there was prepared:

5-Amino-3-iodo-4-cyano-1-(2,6-dichloro-4-trifluoromethylphenyl)pyrazole, m.p. 208°–210° C., in the form of white crystals.

REFERENCE EXAMPLE 22

A suspension of 2,6-dichloro-4-trifluoromethylphenylhydrazine (14.7 g) in water (40 ml) was stirred with concentrated hydrochloric acid (5.2 ml), and potassium cyanoform (8.52 g) added. The suspension was stirred and heated under reflux for 16 hours, and left to cool overnight. The mixture was washed into a separating funnel with the aid of ethyl acetate and water, and the organic phase collected. The aqueous phase was re-extracted with ethyl acetate (2×80 ml), and the combined organic solutions washed with water (2×50 ml), dried over anhydrous magnesium sulphate, and evaporated in vacuo to give an orange solid (20.9 g). Two recrystallizations from a mixture of ethyl acetate and petroleum ether (b.p.60°–80° C.) gave 3,5-diamino-4-cyano-1-(2,6-dichloro-4-trifluoromethylphenyl)pyrazole (7.75 g), m.p. 208°–210° C. in the form of white crystals.

EXAMPLE 40

Compound No. 117

A solution of ethanethiol (2.1 g) in toluene (10 ml) was added dropwise at 5°–10° C. to a stirred suspension of N-chlorosuccinimide (4.7 g) in toluene (40 ml). The reaction mixture was filtered after 20 minutes to give a solution of ethanesulphenyl chloride. This filtrate was added dropwise with stirring to a solution of 5-amino-4-cyano-1-(2,6 -dichloro-4-trifluoromethylphenyl)-3-methylpyrazole sodium salt [prepared in situ by reaction of 5-amino-4-cyano-1-( 2,6-dichloro-4-trifluoromethylphenyl)-3-methylpyrazole (5 g) with sodium hydride (0.4 g)] in tetrahydrofuran (50 ml) containing 15-crown-5 (3 drops) at a temperature of 5°–10° C. After 2 hours, aqueous sodium bicarbonate solution (50 ml) was added, and the organic phase was separated and washed with water (2×50 ml), and dried over anhydrous magnesium sulphate. Evaporation of the solvent in vacuo gave a dark brown gum, which was chromatographed on silica (Merck 230–400 mesh, 0.7 kg cm$^{-2}$) using dichloromethane as eluent. Evaporation of the eluates gave an orange gum, which then recrystallized from a mixture of ethyl acetate and hexane to give 4-cyano-1-(2, 6-dichloro-4-trifluoromethylphenyl)-3 -methyl-5-ethanesulphenylaminopyrazole (2.3 g), m.p. 160°–161° C., in the form of a pale yellow solid.

EXAMPLE 41

Compounds Nos. 118, 119 and 135

A mixture of 5-amino-4-cyano-1-(2,6-dichloro-4 -trifluoromethylphenyl)-3-methylpyrazole (5 g) and p-toluenesulphonic acid hydrate (0.1 g) in trimethylorthoformate (20 ml) was heated at reflux for 4.5 hours. After cooling, the reaction mixture was evaporated to dryness in vacuo. The residue was dissolved in diethyl ether and left to crystallize at 0° C. The dark colored solid was recrystallized from a mixture of ethanol and water to give 4 -cyano-1-(2,6-dichloro-4-trifluoromethylphenyl)-3-methyl-5-methoxymethyleneaminopyrazole (4.67 g), m.p. 75°–78° C. in the form of buff crystals.

By proceeding in a similar manner but replacing the trimethylorthoformate by tripropylorthoformate there was prepared:

4-Cyano-1-(2,6-dichloro-4-trifluoromethylphenyl)-3-methyl-5-propoxymethyleneaminopyrazole, m.p. 77°–79° C., in the form of buff crystals.

By proceeding in a similar manner but replacing the 5-amino-4-cyano-1-(2,6-dichloro-4-trifluoromethylphenyl)-3 —the form of a white solid, from 3-cyano-1-(2,6-dichloro-4 -trifluoromethylphenyl)-4-trifluoromethylthiopyrazole and by performing the reaction at 40°–50° C. for 20 hours.

5-Amino-3-cyano-1-(2,6-dichloro-4 -trifluoromethylphenyl)-4-(1-methylprop-2-ynylsulphinyl)pyrazole, 136.6°–137.2° C., in the form of a white solid, from 5-amino-3 -cyano-1-(2,6-dichloro-4-trifluoromethylphenyl)-4-(1 -methylprop-2-ynylthio)pyrazole.

5-Amino-3-cyano-1-(2,6-dichloro-4 -trifluoromethylphenyl)-4-methylsulphinylpyrazole, m.p. 176°–177° C., in the form of a fawn crystalline solid; prepared from 5-amino-3 -cyano-1-(2,6-dichloro-4-trifluoromethylphenyl)-4-methylthiopyrazole.

5-Amino-3-cyano-1-(2,6-dichloro-4 -trifluoromethylphenyl)-4-isopropylsulphinylpyrazole, m.p. 187°–188° C., in the form of a white solid; prepared from 5-amino-3-cyano-1-( 2,6-dichloro-4-trifluoromethylphenyl)-4-isopropylthiopyrazole.

5-Amino-3-bromo-1-(2,6-dichloro-4 -trifluoromethylphenyl)-4-trifluoromethylsulphinylpyrazole, m.p. 179°–180° C., in the form of a white solid; prepared from 5-amino-3 -bromo-1-(2,6-dichloro-4-trifluoromethylphenyl)-4-trifluoromethylthiopyrazole.

5-Amino-4-tert-butanesulphonyl-3-cyano-1-(2,6-dichloro-4-trifluoromethylphenyl)pyrazole, m.p. 183°–184° C., in the form of a pale yellow solid; prepared from 5-amino-amido- 1-(2,6-dichloro-4-trifluoromethylphenyl)-3,4-dicyanopyrazole, m.p. 208°–209° C. in the form of white crystals.

By proceeding in a similar manner, the following phenylpyrazoles were obtained by acylation of 5-amino-1-( 2,6-dichloro-4-trifluoromethylphenyl)-3,4-dicyanopyrazole with the appropriate acid chloride:

5-Dichloroacetamido-1-(2,6-dichloro-4 -trifluoromethylphenyl)-3,4-dicyanopyrazole, m.p. 186°–187° C. after purification by trituration with carbon tetrachloride and subsequent recrystallization from a mixture of ethanol and water, in the form of an off-white solid. The reaction was performed at laboratory temperature.

5-Cyclopropylcarbonamido-1-(2,6-dichloro-4 -trifluoromethylphenyl)-3,4-dicyanopyrazole, m.p. 217°–218° C. after recrystallization from a mixture of ethanol and water, in the form of an off-white solid. The reaction was performed at laboratory temperature.

5-Pentanamido-1-(2,6-dichloro-4 -trifluoromethylphenyl)-3,4-dicyanopyrazole in the form of a pale yellow glass. Infra-Red Absorption bands: 3260, 3100, 2960, 2940, 2880, 2240, 1730, 1700, 1315, 880 820 cm$^{-1}$ (liquid film). The reaction was performed at 0° C. during the addition, and at laboratory temperature thereafter.

5-Propionamido-1-(2,6-dichloro-4 -trifluoromethylphenyl)-3,4-dicyanopyrazole, m.p. 188°–189° C. after purification by chromatography on silica (Merck, 230–400 mesh, 0.7 kg cm$^{-2}$) using a mixture of acetone and hexane (2:3) as eluent, and subsequent trituration with toluene, in the form of a white powder. The reaction was performed at laboratory temperature.

By proceeding in a similar manner, but replacing the solvent by acetonitrile, the following phenylpyrazole was obtained by acylation of 5-amino-1-(2,6-dichloro-4 -trifluoromethylphenyl)-3,4-dicyanopyrazole with trimethylacetyl chloride:

1-(2,6-Dichloro-4-trifluoromethylphenyl)-3,4 -dicyano-5-(2,2-dimethylpropionamido)pyrazole as white crystals, m.p. 202°–203° C. from toluene-hexane, and after purification by chromatography on silica (Merck 230–400 mesh, 0.7 kg cm$^{-2}$) using a mixture of dichloromethane and ethyl acetate (9:1) as eluent.

By proceeding in a similar manner but replacing 5 -amino-1-(2,6-dichloro-4-trifluoromethylphenyl)-3,4-dicyanopyrazole by 5-amino-4-cyano-1-(2,6-dichloro-4 -trifluoromethylphenyl)-3-trifluoromethylpyrazole and by heating under reflux for 18 hours there was obtained:

5-Acetamido-4-cyano-1-(2,6-dichloro-4 -trifluoromethylphenyl)-3-trifluoromethylpyrazole, m.p. 225°–227° C. from ethyl acetate-hexane, in the form of white crystals.

EXAMPLE 43

Compounds Nos. 125 and 126

Anhydrous sodium acetate (1.0 g) was dissolved in stirred acetic acid (40 ml), and tetracyanoethylene (3.5 g) was added at laboratory temperature. 2-Chloro-4-trifluoromethylphenylhydrazine (5.25 g) was added in one portion, and the mixture was stirred overnight. After dilution with water, the precipitated solid was filtered off to give, after drying, 5-amino-1-(2-chloro-4 -trifluoromethylphenyl)-3,4-dicyanopyrazole, m.p. 209°–210° C. in the form of a white powder.

By proceeding in a similar manner but replacing the 2-chloro-4-trifluoromethylphenylhydrazine by 2,3,5,6 -tetrafluoro-4-trifluoromethylphenylhydrazine and with cooling during addition of the phenylhydrazine to the tetracyanoethylene solution, there was prepared:

5-amino-3,4-dicyano-1-(2,3,5,6-tetrafluoro-4-trifluoromethylphenyl)pyrazole, m.p. 262°–263° C. in the form of a buff powder.

EXAMPLE 44

Compounds Nos. 136 and 137

Sodium hydride (80%, 0.25 g) was added to a stirred solution of 5-amino-4-cyano-1-(2,6-dichloro-4 -trifluoromethylphenyl)-3-trifluoromethylpyrazole (2.9 g) in dry tetrahydrofuran (50 ml). After 3 hours at room temperature, 15-crown-5 (1 drop) and methyl iodide (2 g) was added at 0° C., and the mixture left overnight at room temperature. The solution was evaporated in vacuo, and the residue was dissolved in dichloromethane (50 ml), washed with water, dilute hydrochloric acid and water. After drying over anhydrous magnesium sulphate, filtration, and evaporation in vacuo a yellow oil was obtained. Purification by chromatography using Merck silica (230–400 mesh, 0.7 kg cm$^{-2}$) with dichloromethane as eluent gave 4-cyano-1-( 2,6-dichloro-4-trifluoromethylphenyl)-5-dimethylamino-3-trifluoromethylpyrazole as a white solid, m.p. 105°–107° C.

By proceeding in a similar manner but replacing the methyl iodide by ethyl bromoacetate, and employing dioxan as solvent in place of tetrahydrofuran there was obtained 4-cyano-1-(2,6-dichloro-4-trifluoromethylphenyl)-5 -ethoxycarbonylmethylamino-3-trifluoromethylpyrazole as white crystals, m.p. 104°–106° C. from ethyl acetate-petroleum ether.

EXAMPLE 45

Compound No. 138

To a suspension of 4-cyano-1-(2,6-dichloro-4-trifluoromethylphenyl)-5-ethoxymethyleneamino-3-trifluoromethylpyrazole (1.0 g) in methanol (10 ml) stirred at room temperature was added sodium borohydride (0.17 g). After 2 hours an additional 0.17 g of sodium borohydride was added, and another 0.34 g added after 1 hours. One hour later the mixture was poured onto water (80 ml). The combined extracts were dried over anhydrous magnesium sulphate, filtered, and evaporated in vacuo. The white solid thus obtained was purified by chromatography on silica (Merck, 230–400 mesh, 0.7 kg cm$^{-2}$) with dichloromethane as eluent, to furnish 4-cyano-5-methylamino-1-(2,6-dichloro-4-trifluoromethylphenyl)-3-trifluoromethylpyrazole as a white solid )0.6 g), m.p. 200°–202° C.

EXAMPLE 46

Compounds Nos. 139, 145 and 146

Sodium hydride (80%, 0.3 g) was added to a stirred solution of 5-amino-4-cyano-1-(2,6-dichloro-4-trifluoromethylphenyl)-3-trifluoromethylpyrazole (2.9 g) in dry tetrahydrofuran (50 ml). After 3 hours, 15-crown-5 (1 drop) and trimethylacetyl chloride (1.8 g) was added, and the mixture stirred overnight. Evaporation in vacuo gave a buff semisolid, which was dissolved in dichloromethane. This solution was washed with water, dilute hydrochloric acid and with water again and finally dried over anhydrous magnesium sulphate. Filtration followed by evaporation in vacuo gave a yellow oil, which was purified by chromatography on silica (Merck, 40–230 mesh, 0.7 kg cm$^{-2}$). Elution with dichloromethane gave after evaporation 4-cyano-1-(2,6-dichloro-4-trifluoromethylphenyl)-5-(2,2-dimethylpropionamido)-3-trifluoromethylpyrazole as a white solid, m.p. 198°–200° C.

By proceeding in a similar manner but replacing the trimethylacetyl chloride by ethyl chloroformate there was obtained, after recrystallization from toluene, 4-cyano-1-(2,6-dichloro-4-trifluoromethylphenyl)-5-bis(ethoxycarbonyl)amino-3-trifluoromethylpyrazole as white crystals, m.p. 62° C.

By proceeding in a similar manner but replacing the trimethylacetyl chloride by cyclopropanecarboxylic acid chloride there was obtained 4-cyano-1-(2,6-dichloro-4-trifluoromethylphenyl)-5-bis-(cyclopropanecarbonyl)amino-3-trifluoromethylpyrazole as a pale yellow solid, m.p. 126°–127° C.

EXAMPLE 47

Compound No. 147

A solution of 4-cyano-1-(2,6-dichloro-4-trifluoromethylphenyl)-5-bis(cyclopropanecarbonyl)amino-3-trifluoromethylpyrazole (1.0 g) in ethanol (50 ml) was heated under reflux with saturated sodium bicarbonate solution (25 ml) for 45 minutes. After cooling, and evaporation of the solvent in vacuo, the residue was diluted with water and extracted with dichloromethane. The extract was dried over anhydrous magnesium sulphate, filtered, and evaporated in vacuo to give 4-cyano-1-(2,6-dichloro-4-trifluoromethylphenyl)-5-cyclopropanecarbonamido-3-trifluoromethylpyrazole as a white solid m.p. 210°–212° C.

EXAMPLE 48

Compound No. 141

A stirred mixture of 5-amino-4-cyano-1-(2,6-dichloro-4-trifluoromethylphenyl)-3-trifluoromethylpyrazole (3.89 g) and bromoform (13 ml) was treated with tert-butyl nitrite (2.26 ml) at room temperature. After 15 minutes the mixture was heated to 50° C. for 1 hour, and evaporated in vacuo to yield a red oil. This was purified by chromatography on silica (Merck, 40–230 mesh, 0.7 kg cm$^{-2}$) eluting with a mixture of dichloromethane and petroleum ether (1:2) to furnish 5-bromo-4-cyano-1-(2,6-dichloro-4-trifluoromethylphenyl)-3-trifluoromethylpyrazole as a fawn solid m.p. 85°–87° C. (3.7 g).

EXAMPLE 49

Compound No. 142

A solution of 5-amino-4-cyano-1-(2,6-dichloro-4-trifluoromethylphenyl)-3-hydroxymethylpyrazole (1.25 g) in dichloromethane (10 ml) was added slowly to a stirred solution of diethylaminosulphur trifluoride (0.66 g) in dichloromethane (6 ml) cooled to −78° C. After 30 minutes at this temperature the solution was warmed to room temperature and stirred for 2 hours. The mixture was then poured onto water (20 ml) and the dichloromethane layer was separated, dried over anhydrous magnesium sulphate, filtered and evaporated in vacuo. The product was purified by chromatography on silica (Merck, 40–230 mesh, 0.7 kg cm$^{-2}$) eluting with a mixture of dichloromethane and ethyl acetate (98:2), and subsequent recrystallization from dichloromethane-petroleum ether to give 5-amino-4-cyano-1-(2,6-dichloro-4-trifluoromethylphenyl)-3-fluoromethylpyrazole as a white solid m.p. 139°–141° C.

REFERENCE EXAMPLE 23

5-Amino-4-cyano-1-(2,6-dichloro-4-trifluoromethylphenyl)-3-hydroxymethylpyrazole was prepared as follows:

A solution of 5-amino-4-cyano-1-(2,6-dichloro-4-trifluoromethylphenyl)-3-ethoxycarbonylpyrazole (1.0 g) in dry tetrahydrofuran (15 ml) was treated under nitrogen with lithium borohydride (0.06 g) with stirring at room temperature for 18 hours. Ethyl acetate (5 ml) followed by saturated sodium chloride solution (5 ml) was added, and the mixture was acidified with dilute hydrochloric acid and extracted with dichloromethane. The extract was dried over anhydrous magnesium sulphate, filtered, and evaporated in vacuo. The residual oil was purified by chromatography on silica (Merck, 40–230 mesh, 0.7 kg cm$^{-2}$) eluting with a mixture of dichloromethane and ethyl acetate (1:1), and the pure fractions were evaporated in vacuo and recrystallized from ethyl acetate-petroleum ether to give the title compound as a white solid m.p. 159°–161° C.

5-Amino-4-cyano-1-(2,6-dichloro-4-trifluoromethylphenyl)-3-ethoxycarbonylpyrazole was prepared as follows:

To sodium hydride (80%, 0.9 g) in dry ethanol (30 ml) was added, with stirring, malononitrile (1.98 g). Ethyl chloro-(2,6-dichloro-4-trifluoromethylphenyl)hydrazonoacetate (11.0 g) was then added with stirring and cooling. The internal temperature quickly rose to 20° C. and was kept at that for 1 hour, before filtration of the pale yellow solid. The filtrate was evaporated in vacuo to give an orange solid. The combined solids were dissolved in ethyl acetate, washed twice with water, dried over anhydrous magnesium sulphate, filtered and evaporated in vacuo to give an orange solid (11.0 g). Recrystallization from ethyl acetate-petroleum ether gave the title compound as fawn crystals (8.3 g) m.p. 208°–209° C.

Ethyl chloro-(2,6-dichloro-4-trifluoromethylphenyl)hydrazonoacetate was prepared as follows:

Sodium nitrite (3.04 g) was added during 15 minutes to stirred concentrated sulphuric acid (24 ml) at 30°–50° C. The solution was cooled to 20° C., and added dropwise during 15 minutes to a solution of 2,6-dichloro-4-trifluoromethylaniline (9.2 g) in acetic acid (90 ml), maintaining at 35°–40° C. This solution was then cooled to +10°, and added dropwise to a stirred solution of anhydrous sodium acetate (54 g) and ethyl chloroacetoacetate (7.0 g) in a mixture of water (72 ml) and ethanol (48 ml) during 45 minutes with cooling such that the temperature was kept at 10° C. After 1 hour at room temperature the mixture was diluted with water, filtered, and the solid dissolved in dichloromethane. This solution was dried over anhydrous magnesium sulphate, filtered, and evaporated in vacuo to give tht title compound as a white solid (11.9 g) m.p. 96°–98° C.

EXAMPLE 50

Compounds 140 and 148

A mixture of 5-amino-1-(2,6-dichloro-4 -trifluoromethylphenyl)-3-trifluoromethylpyrazole (3.64 g) and N-bromosuccinimide (1.78 g) in carbon tetrachloride (30 ml) was stirred and heated under reflux for 1 hour. Further N-bromosuccinimide (0.89 g) was added, and reflux was continued for a further 1 hour. The mixture was cooled, filtered, and the filtrate was evaporated in vacuo to give an orange solid. Recrystallization from petroleum ether gave 5-amino-4-bromo-1-(2,6-dichloro-4 -trifluoromethylphenyl)-3-trifluoromethylpyrazole in the form of white crystals (2.6 g) m.p. 119°–120° C.

By proceeding in a similar manner but replacing N-bromosuccinimide by N-chlorosuccinimide there was obtained 5-amino-4-chloro-1-(2,6-dichloro-4-trifluoromethylphenyl)- 3-trifluoromethylpyrazole as white crystals m.p. 99°–100° C. No excess of chlorinating agent was required in this case.

REFERENCE EXAMPLE 24

5-Amino-1-(2,6-dichloro-4-trifluoromethylphenyl)-3-trifluoromethylpyrazole was prepared as follows:

A solution of 5-amino-4-carboxy-1-(2,6-dichloro-4 -trifluoromethylphenyl)-3-trifluoromethylpyrazole (10.5 g) in N,N-dimethylaniline (13 ml) was heated under reflux for 3 hours. The cooled mixture was poured onto concentrated hydrochloric acid (15 ml) and extracted with ether (4×30 ml). The combined extract was washed with 6N hydrochloric acid (3×30 ml), with water (2×30 ml), dried over anhydrous magnesium sulphate, filtered, and evaporated in vacuo. The product was recrystallized from cyclohexene to give the title compound (5.7 g) as white needles m.p. 126°–128° C.

5-Amino-4-carboxy-1-(2,6-dichloro-4 -trifluoromethylphenyl)-3-trifluoromethylpyrazole was prepared as follows:

A mixture of 5-amino-1-(2,6-dichloro-4 -trifluoromethylphenyl)-4-methoxycarbonyl-3-trifluoromethylpyrazole (101.2 g; hereinbefore described in Example 36) and sodium hydroxide (48 g) in water (170 ml) and methanol (550 ml) was stirred at room temperature for 2 days, evaporated in vacuo, and the residue triturated with dilute hydrochloric acid. The solid was filtered, dissolved in ethyl acetate, and the resulting solution was washed with sodium chloride solution. After drying over anhydrous magnesium sulphate, filtration, and evaporation in vacuo a semisolid residue was obtained. This residue was triturated with hexane and the solid was recrystallized from toluene-hexane to give the title compound as a cream solid, m.p. 212°–215° C.

EXAMPLE 51

Compound No. 149

Ethyl chloroformate (1.6 g) was added to a stirred solution of 5-amino-4-cyano-1-(2,6-dichloro-4 -trifluoromethylphenyl)-3-trifluoromethylpyrazole (3.9 g) in pyridine (15 ml). After stirring overnight another addition of ethyl chloroformate (1.0 ml) was made, and the mixture was left for a further 12 hours. The solvent was evaporated in vacuo and the residue was acidified with dilute hydrochloric acid, and extracted with dichloromethane. This extract was washed with water (3×), dried over anhydrous magnesium sulphate, filtered, and evaporated in vacuo. Purification by chromatography on silica (Merck, 40–230 mesh, 0.7 kg cm$^{-2}$) eluting with ethyl acetate-petroleum ether (1:1) gave a white solid, which was recrystallized from a mixture of dichloromethane and hexane to furnish white crystals of 4-cyano-1-(2,6-dichloro-4 -trifluoromethylphenyl)-5-ethoxycarbonylamino-3-trifluoromethylpyrazole, m.p. 177°–179° C.

EXAMPLE 52

Compound No. 143

A solution of 5-amino-1-(2,6-dichloro-4 -trifluoromethylphenyl)-3-trifluoromethylpyrazole (3.0 g) in concentrated sulphuric acid (10 ml) at 0° C. was treated with fuming nitric acid (9 ml) during 15 minutes, keeping the temperature at 5°–15° C. After 30 minutes the mixture was poured onto excess ice, and the precipitated solid was filtered off and dissolved in ethyl acetate. After drying over anhydrous magnesium sulphate, filtration, and evaporation in vacuo a brown oil was obtained. This oil was dissolved in the minimum of ethyl acetate and diluted with hexane. A pale yellow solid crystallized and this was discarded. The filtrate was evaporated in vacuo to give a solid which was recrystallized from toluene-hexane to furnish a yellow solid. One further recrystallization from the same solvent pair gave 5-amino-1-(2,6-dichloro-4 -trifluoromethylphenyl)-4-nitro-3-trifluoromethylpyrazole as white crystals, m.p. 214°–215° C.

EXAMPLE 53

Compound No. 150

To a solution of 5-amino-4-cyano-1-(2,6-dichloro-4 -trifluoromethylphenyl)-3-trifluoromethylpyrazole (2.33 g) in dry tetrahydrofuran (30 ml) was added with stirring at room temperature, a solution of tert-butyl nitrite (1.36 ml) in dry tetrahydrofuran (5 ml) during 2 minutes. The solution was then heated under reflux for 1 hour and cooled, and additional tert-butyl nitrite (2.72 ml) was added. The solution was heated under reflux for 30 minutes, and left to cool overnight. Evaporation in vacuo gave an orange oil, which was purified by chromatography on silica (Merck, 40–230 mesh, 0.7 kg cm$^{-2}$) eluting with dichloromethane-hexane (1:1). The product was finally recrystallized from hexane to give 4-cyano-1-(2,6-dichloro-4-trifluoromethylphenyl)-3-trifluoromethylpyrazole, m.p. 121°–123° C., as white crystals.

EXAMPLE 54

Compound No. 151

To a solution of 5-amino-4-cyano-1-(2,6-dichloro-4-trifluoromethylphenyl)-3-trifluoromethylpyrazole (2.33 g) in chloroform (30 ml) stirred at room temperature, was added iodine (3.0 g) followed by tert-butyl nitrite (1.1 g). After 2 hours the mixture was heated under reflux for 1.5 hours, cooled and filtered, and the filtrate was washed with sodium thiosulphate solution to remove excess iodine. After washing with water, drying over anhydrous magnesium sulphate and evaporation in vacuo, a yellow solid was obtained. This was chromatographed on silica (Merck, 40–230 mesh, 0.7 kg cm$^{-2}$) eluting with dichloromethane-hexane (1:2) to give a yellow oil. Dissolution in hot hexane gave, on cooling, 4-cyano-1-(2,6-dichloro-4-trifluoromethylphenyl)-5-iodo-3-trifluoromethylpyrazole as white crystals, m.p. 86°–87° C.

EXAMPLE 55

Compound No. 152

To dry diisopropylamine (0.135 g) in dry tetrahydrofuran (4 ml) stirred at −78° C. under nitrogen, was added via a syringe, a solution of n-butyl lithium (0.52 ml of a 2.6 M solution in hexane). After warming to room temperature during 1 minute, the solution was re-cooled to −78° C. and added via a syringe to a stirred solution of 4-cyano-1-(2,6-dichloro-4-trifluoromethylphenyl)-3-trifluoromethylpyrazole (0.5 g) in dry tetrahydrofuran (4 ml) under nitrogen at −78° C. The addition, during 2 minutes, was exothermic and the internal temperature was maintained at −60° C. for a further 15 minutes. Methyl iodide (0.1 ml) was added. After 1.5 hours at this temperature the solution was poured onto excess water and extracted with dichloromethane (3×). The combined organic phase was washed with water, dried over anhydrous magnesium sulphate, and evaporated in vacuo to give a solid. Chromatography on silica (Merck, 40–230 mesh, 0.7 kg cm$^{-2}$) eluting with dichloromethane-hexane (1:3) gave a white solid (0.2 g). Recrystallization from hexane furnished 4-cyano-1-(2,6-dichloro-4-trifluoromethylphenyl)-5-methyl-3-trifluoromethylpyrazole as white crystals, m.p. 90°–92° C.

EXAMPLE 56

Compound No. 153

A mixture of 5-amino-4-chlorosulphonyl-1-(2,6-dichloro-4-trifluoromethylphenyl)-3-trifluoromethylpyrazole (1.2 g) and dimethylamine (17.6 ml of a 40% aqueous solution) was heated on a steambath for 1 hour, cooled, and poured onto crushed ice (50 g) to give a brown solid. This solid was filtered, dried, and recrystallized from toluene to give 5-amino-1-(2,6-dichloro-4-trifluoromethylphenyl)-4-(N,N-dimethylsulphamoyl)-3-trifluoromethylpyrazole (0.8 g) as light brown crystals, m.p. 177.6°–178.6° C.

REFERENCE EXAMPLE 25

5-Amino-4-chlorosulphonyl-1-(2,6-dichloro-4-trifluoromethylphenyl)-3-trifluoromethylpyrazole used in the above example was prepared as follows:

5-Amino-1-(2,6-dichloro-4-trifluoromethylphenyl)-3-trifluoromethylpyrazole (9.1 g) was added portion-wise to stirred cooled chlorosulphonic acid (16.2 ml), keeping the internal temperature below 10° C. The orange solution was stirred at room temperature for 30 minutes, then at 120° C. for 5 hours, and poured onto iced water (300 ml) to give a pale brown solid. This solid was filtered, dried, and recrystallized from cyclohexane to give the title compound as yellow crystals.

EXAMPLE 57

Compound No. 154

A solution of 2,6-dichloro-4-trifluoromethylphenylhydrazine (3.8 g) and 1,1-dicyano-2-cyclopropyl-2-methoxyethylene (2.23 g) in methanol (30 ml) was stirred and treated with sodium hydride (80%, 30 mg). After 4 hours the solution was evaporated in vacuo and the residue was dissolved in ethyl acetate (40 ml), treated with charcoal and washed with water. The organic phase was evaporated in vacuo, the residual oil was dissolved in petroleum ether and crystals of 5-amino-4-cyano-3-cyclopropyl-1-(2,6-dichloro-4-trifluoromethylphenyl)pyrazole, m.p. 197°–199° C., were obtained.

EXAMPLE 58

Compound Nos. 156, 157 and 158

By proceeding in a similar manner to that hereinbefore described in Example 33, but replacing 2,4,6-trichlorophenylhydrazine by 2,6-dichloro-4-trifluoromethylthiophenylhydrazine, there was obtained:

5-Amino-3,4-dicyano-1-(-2,6-dichloro-4-trifluoromethylthiophenyl)pyrazole, m.p. 226°–227° C., in the form of an off-white solid, after recrystallization from toluene.

By employing 2-chloro-3,5,6-trifluoro-4-trifluoromethylphenylhydrazine there was prepared:

5-Amino-1-(2-chloro-3,5,6-trifluoro-4-trifluoromethylphenyl)-3,4-dicyanopyrazole, m.p. 242°–243° C., in the form of an orange solid, after recrystallization from a mixture of ethanol and water.

By employing 2,6-dichloro-3,5-difluoro-4-trifluoromethylphenylhydrazine there was prepared:

5-Amino-1-(2,6-dichloro-3,5-difluoro-4-trifluoromethylphenyl)-3,4-dicyanopyrazole, m.p. 245°–247° C., in the form of an off-white solid.

REFERENCE EXAMPLE 26

2,6-Dichloro-4-trifluoromethylthiophenylhydrazine was prepared by following the procedure of Reference Example 19, by proceeding in a similar manner, but replacing the 2,6-dichloro-4-trifluoromethylaniline by 2,6-dichloro-4-trifluoromethylthioaniline.

REFERENCE EXAMPLE 27

2-Chloro-3,5,6-trifluoro-4-trifluoromethylphenylhydrazine was prepared as follows:

3-Chloro-2,4,5,6-tetrafluorobenzotrifluoride (12.1 g) and hydrazine hydrate (3.4 g) were heated under reflux with ethanol (50 ml) for 3.5 hours. The mixture was poured onto ice/water mixture (500 ml), stirred, and the product was filtered. After washing with water and drying in a desiccator the title compound was obtained in the form of white crystals, m.p. 91°–92° C.

By proceeding in a similar manner but replacing 3-chloro-2,4,5,6-tetrafluorobenzotrifluoride by 3,5-dichloro-2,4,6-trifluorobenzotrifluoride there was prepared 2,6-dichloro-3,5-difluoro-4-trifluoromethylphenylhydrazine in the form of pale yellow crystals, m.p. 78°–80° C.

EXAMPLE 59

Compound No. 159

By proceeding in a similar manner to that hereinbefore described in Example 2, but employing 2,6-dichloro- 4-trifluoromethoxyphenylhydrazine there was obtained:

5-Amino-1-(2,6-dichloro-4-trifluoromethoxyphenyl)-3,4-dicyanopyrazole, m.p. 231°–232° C. in the form of a brown solid, after recrystallization from toluene.

REFERENCE EXAMPLE 28

2,6-Dichloro-4-trifluoromethoxyphenylhydrazine used in the above Example 59 was prepared by following the procedure of Reference Example 19, by proceeding in a similar manner, but replacing the 2,6-dichloro-4-trifluoromethylaniline by 2,6-dichloro-4-trifluoromethoxyaniline. The title compound was obtained as fawn crystals, m.p. 64°–65° C.

EXAMPLE 60

Compounds Nos. 160, 161, 162 and 163

By proceeding in a similar manner to that hereinbefore described in Example 35, but replacing the ethoxyethylenemalononitrile by ethoxypropylenemalononitrile there was prepared:

5-Amino-4-cyano-3-ethyl-1-(2,6-dichloro-4 -trifluoromethylphenyl)pyrazole in the form of white crystals, m.p. 158°–160° C., after recrystallization from a mixture of ethyl acetate and hexane.

By proceeding in a similar manner but replacing the ethoxyethylenemalononitrile by ethoxyethylenemethanesulphonylacetonitrile, and by replacing the sodium acetate and glacial acetic acid by ethanol containing 10 mole percent of triethylamine at reflux, there was prepared:

5-Amino-1-(2,6-dichloro-4-trifluoromethylphenyl)-4-methanesulphonyl-3-methylpyrazole in the form of a white solid, m.p. 195° C., after recrystallization from a mixture of ethyl acetate and hexane.

By proceeding in a similar manner but replacing the ethoxyethylenemalononitrile by ethoxyethylenecyanoacetic acid ethyl ester there was prepared:

5-Amino-1-(2,6-dichloro-4-trifluoromethylphenyl)-3-methyl-4-ethoxycarbonylpyrazole in the form of white crystals, m.p. 115°–118° C. after recrystallization from a mixture of toluene and petroleum ether.

By proceeding in a similar manner but replacing the ethoxyethylenemalononitrile by ethoxyethylenemethanesulphonylacetonitrile, and by replacing the 2,6-dichloro-4-trifluoromethylphenylhydrazine by 2,6-dichloro-4-trifluoromethoxyphenylhydrazine and by performing the reaction in a 1:1 v/v mixture of ethanol and triethylamine at ambient temperature, there was obtained:

5-Amino-1-(2,6-dichloro-4-trifluoromethoxyphenyl)-4-methanesulphonyl-3-methylpyrazole, in the form of a fawn solid, m.p. 180°–181° C.

REFERENCE EXAMPLE 29

3-Ethoxy-2-methanesulphonylbut-2-ene-nitrile, used in the above Example 60 was prepared as follows:

A mixture of methanesulphonylacetonitrile (200 g), triethylorthoacetate (348 g) and zinc chloride (21 g) was stirred in hexane (1200 ml) with heating under reflux. The distillate was collected via a Mcintyre head, with additional hexane added to the reaction mixture as necessary. Hexane (2800 ml) was collected during 8 hours. After cooling, the mixture was evaporated in vacuo, and re-evaporated after addition of toluene (100 ml). The residue was dissolved in ethyl acetate and recrystallized from a mixture of ethyl acetate with hexane, twice,, to give white crystals, m.p. 99° C., of the title compound.

EXAMPLE 61

Compounds Nos. 164, 165, 166 and 167

By proceeding in a similar manner to that hereinbefore described in Example 36, but replacing the 2,6 -dichloro-4-trifluoromethylphenylhydrazine by 2-chloro- 3,5,6-trifluoro-4-trifluoromethylphenylhydrazine there was obtained:

5-Amino-1(2-chloro-3,5,6-trifluoro-4 -trifluoromethylphenyl)-4-cyano-3-trifluoromethylpyrazole, in the form of white crystals, m.p. 187°–189° C., after recrystallization from toluene.

By employing 2,6-dichloro-4-trifluoromethylthiophenylhydrazine there was obtained:

5-Amino-4-cyano-1-(2,6-dichloro-4 -trifluoromethylthiophenyl)-3-trifluoromethylpyrazole, in the form of pale yellow crystals, m.p. 133.5°–134.5° C., after recrystallization from hexane.

By replacing the 2-chloro-1,1-dicyano-2-trifluoromethylethylene by 2,3-dichloro-1,1-dicyano-3-fluoromethylethylene there was obtained:

5-Amino-3-chlorofluoromethyl-4-cyano-1-(2,6 -dichloro-4-trifluoromethylphenyl)pyrazole in the form of a cream solid, m.p. 186°–188° C., after recrystallization from a mixture of toluene and hexane.

By employing 2,6-dichloro-3,5-difluoro-4-trifluoromethylphenylhydrazine there was obtained:

5-Amino-4-cyano-1-(2,6-dichloro-3,5-difluoro-4 -trifluoromethylphenyl)-3-trifluoromethylpyrazole in the form of a light brown solid, m.p. 176°–177° C.

REFERENCE EXAMPLE 30

Chloro-dicyanoethylene used as starting material in the above Example 61, not hitherto described in chemical literature was prepared as follows:

By proceeding in a similar manner to that hereinbefore described in Reference Example 20, but replacing 2 -cyano-3-hydroxy-4-chloro-4,4-difluorobut-2-enenitrile sodium salt by 2-cyano-3-hydroxy-4-chloro-4-fluorobut-2-enenitrile sodium salt there was prepered 2-chloro-2 -chlorofluoromethyl-1,1-dicyanoethylene as a liquid, b.p. 90° C. (46 mmHg).

By proceeding in a similar manner to that hereinbefore described in Reference Example 21, but replacing methyl chlorodifluoroacetate by ethyl chlorofluoroacetate, there was obtained 2-cyano-3-hydroxy-4-chloro-4-fluorobut-2-enenitrile sodium salt as an orange-red solid.

EXAMPLE 62

Compound 168

By proceeding in a similar manner to that hereinbefore described in Example 41, but replacing the trimethylorthoformate by triethylorthoacetate there was prepared:

4-Cyano-1-(2,6-dichloro-4-trifluoromethylphenyl)-5-(1-ethoxyethylideneamino)-3-methylpyrazole as a white solid, m.p. 50°–53° C., after purification by chromatography on silica (Merck 230–400 mesh, 0.7 kg cm$^{-2}$) using dichloromethane as eluent.

EXAMPLE 63

Compounds Nos. 169, 170 and 171

By proceeding in a similar manner to that hereinbefore described in Example 42, but replacing the 5-amino- 1-(2,6-dichloro-4-trifluoromethylphenyl)-3,4-dicyanopyrazole by 5-amino-1-(2,6-dichloro-4-trifluoromethylphenyl)-4-cyano-3-methylpyrazole and acylating with succinyl dichloride there was obtained:

4-Cyano-1-(2,6-dichloro-4-trifluoromethylphenyl)-3-methyl-5-succinimidopyrazole in the form of a white solid, m.p. 202°–204° C., after purification by chromatography on silica (Merck 230–400 mesh, 0.7 kg cm$^{-2}$) using dichloromethane/ethyl acetate (98:2) as eluent.

By proceeding in a similar manner but replacing the 5-amino-1-(2,6-dichloro-4-trifluoromethylphenyl)-3,4-dicyanopyrazole by 5-amino-1-(2,6-dichloro-4-trifluoromethylphenyl)-4-methanesulphonyl-3-trifluoromethylpyrazole, and employing acetonitrile as solvent for the acylation, there was prepared:

5-Acetamido-1-(2,6-dichloro-4-trifluoromethylphenyl)-4-methanesulphonyl-3-trifluoromethylpyrazole in the form of a white solid, m.p. 194°–195° C., after recrystallization from toluene.

By proceeding in a similar manner (to Example 42) but replacing the 5-amino-1-(2,6-dichloro-4-trifluoromethylphenyl)-3,4-dicyanopyrazole by 5-amino-1-(2,6-dichloro-4-trifluoromethylphenyl)-3-methyl-4-methanesulphonylpyrazole there was prepared 5-acetamido-1-(2,6-dichloro-4-trifluoromethylphenyl)-3-methyl-4-methanesulphonylpyrazole in the form of yellow crystals, m.p. 202°–203° C.

EXAMPLE 64

Compound No. 172

By proceeding in a similar manner to that hereinbefore described in Example 43, but replacing the 2-chloro- 4-trifluoromethylphenylhydrazine by 2,6-dichloro-4-nitrophenylhydrazine there was prepared:

5-Amino-1-(2,6-dichloro-4-nitrophenyl)-3,4-dicyanopyrazole, in the form of a pale brown solid, m.p. 289°–290° C.

EXAMPLE 65

Compounds Nos. 173 and 174

By proceeding in a similar manner to that hereinbefore described in Example 44, but replacing the 5-amino- 4-cyano-1-(2,6-dichloro-4-trifluoromethylphenyl)-3-trifluoromethylpyrazole by 5-amino-1-(2,6-dichloro-4-trifluoromethylphenyl)-3,4-dicyanopyrazole and using an appropriate quantity of methyl iodide there was prepared:

1-(2,6-Dichloro-4-trifluoromethylphenyl)-3,4-dicyano-5-methylaminopyrazole in the form of a pale yellow solid, m.p. 165°–166° C., after recrystallization from toluene.

By proceeding as above, but employing ethyl iodide, there was prepared:

1-(2,6-Dichloro-4-trifluoromethylphenyl)-3,4-dicyano-5-ethylaminopyrazole in the form of an off-white solid, m.p. 245°–246° C., after purification by chromatography on silica (Merck 230–400 mesh, 0.7 kg cm$^{-2}$) using a mixture of ethyl acetate and petroleum ether (15:85).

EXAMPLE 66

Compounds Nos. 175, 176, 177, 178, 179, 180, 181, 182, 183, 184, 185 and 186

By proceeding in a similar manner to that hereinbefore described in Example 46, but replacing the 5-amino- 4-cyano-1-(2,6-dichloro-4-trifluoromethylphenyl)-3-trifluoromethylpyrazole and the trimethylacetyl chloride by the following phenylpyrazoles and acylating agents, there were prepared:

4-Cyano-1-(2,6-dichloro-4-trifluoromethylphenyl)-5-(N-methyl-N-ethoxycarbonylamino)-3-trifluoromethylpyrazole in the form of a white solid, m.p. 88°–90° C., after recrystallization from hexane, using 4-cyano-1-(2,6-dichloro-4-trifluoromethylphenyl)-5-methylamino-3-trifluoromethylpyrazole and ethyl chloroformate;

4-Cyano-1-(2,6-dichloro-4-trifluoromethylphenyl)-5-(N-acetyl-N-trimethylacetylamino)-3-trifluoromethylpyrazole in the form of an off-white solid, m.p. 83.5°–34° C., after recrystallization from hexane, using 4-cyano-1-(2,6-dichloro-4-trifluoromethylphenyl)-5-trimethylacetylamino-3-trifluoromethylpyrazole and acetyl chloride;

4-Cyano-1-(2,6-dichloro-4-trifluoromethylphenyl)-5-(N-propionyl-N-trimethylacetylamino)-3-trifluoromethylpyrazole in the form of a white solid, m.p. 56°–56.5° C., after recrystallization from hexane, using 4-cyano-1-(2,6-dichloro-4-trifluoromethylphenyl)-5-trimethylacetylamino-3-trifluoromethylpyrazole and prop ionyl chloride;

1-(2,6-Dichloro-4-trifluoromethylphenyl)-4-nitro-3-trifluoromethyl-5-trimethylacetylaminopyrazole in the form of a white solid, m.p. 219° C., using 5-amino-1-(2,6-dichloro-4-trifluoromethylphenyl)-4-nitro-3-trifluoromethylpyrazole and trimethylacetyl chloride;

1-(2,6-Dichloro-4-trifluoromethylphenyl)-5-ethoxycarbonylamino-4-nitro-3-trifluoromethylpyrazole in the form of pale yellow crystals, m.p. 124° C., using 5-amino-1-(2,6-dichloro-4-trifluoromethylphenyl)-4-nitro-3-trifluoromethylpyrazole and ethyl chloroformate;

and 3-Chloro-1-(2,6-dichloro-4-trifluoromethylphenyl)-4-cyano-5-trimethylacetylaminopyrazole, in the form of a white solid, m.p. 203°–204° C.;

3-Chloro-1-(2,6-dichloro-4-trifluoromethylphenyl)-4-cyano-5-bis(ethoxycarbonyl)aminopyrazole, in the form of an orange crystalline solid, m.p. 67°–69° C.;

and 3-Chloro-1-(2,6-dichloro-4-trifluoromethylphenyl)-4-cyano-5-ethoxycarbonylaminopyrazole, in the form of a yellow solid m.p. 175°–179° C.;

[(The latter three compounds were obtained by reaction of 5-amino-3-chloro-1-(2,6-dichloro-4-trifluoromethylphenyl)-4-cyanopyrazole with the appropriate acyl chlorides)]

4-Cyano-5-diacetylamino-1-(2,6-dichloro-4-trifluoromethylphenyl)-3-trifluoromethylpyrazole in the form of white crystals, m.p. 138°–139° C.; and 5-(N-Acetyl-N-ethoxycarbonylamino)-4-cyano-1-(2,6-dichloro-4-trifluoromethylphenyl)-3-trifluoromethylpyrazole in the form of a white solid, m.p. 101°–102° C.;

[(The above two compounds were obtained by reaction of 5-acetylamino-1-(2,6-dichloro-4-trifluoromethyl)-4-cyano-3-trifluoromethylpyrazole and the appropriate acyl chlorides] and 1-(2,6-Dichloro-4-trifluoromethylphenyl)-5-bis(ethoxycarbonyl)amino-3,4-dicyanopyrazole and 1-(2,6-dichloro-4-trifluoromethylphenyl)-5-bis(ethoxycarbonyl)amino-4-methanesulphonyl-3-trifluoromethylpyrazole were prepared in a similar manner to the procedure described in Example 46, but replacing the 5-amino-4-cyano-1-(2,6-dichloro-4-trifluoromethylphenyl)-3-trifluoromethylpyrazole by 5-amino-1-(2,6-dichloro-4-trifluoromethylphenyl)-3,4-dicyanopyrazole and by 5-amino-1-(2,6-dichloro-4-trifluoromethylphenyl)-4-methanesulphonyl-3-trifluoromethylpyrazole respectively. The trimethylacetyl chloride was replaced by the appropriate quantity of ethyl chloroformate (two equivalents) and 2 equivalents of sodium hydride were also used. The products were white crystals with m.p. 74°–76° C., and 148°–151° C., respectively.

EXAMPLE 67

Compounds Nos. 187 and 188

By proceeding in a similar manner to that hereinbefore described in Example 47, but replacing the 4-cyano-1-(2,6-dichloro-4-trifluoromethylphenyl)-5-bis(cyclopropanecarbonyl)amino-3-trifluoromethylpyrazole by 1-(2,6-dichloro-4-trifluoromethylphenyl)-5-bis(ethoxycarbonyl)amino-4-methanesulphonyl-3-trifluoromethylpyrazole there was obtained:

1-(2,6-Dichloro-4-trifluoromethylphenyl)-5-ethoxycarbonylamino-4-methanesulphonyl-3-trifluoromethylpyrazole in the form of a white solid, m.p. 138°–141° C.

By proceeding in a similar manner but replacing the 4-cyano-1-(2,6-dichloro-4-trifluoromethylphenyl)-5-bis(cyclopropanecarbonyl)amino-3-trifluoromethylpyrazole by 1-(2,6-dichloro-4-trifluoromethylphenyl)-5-bis(ethoxycarbonyl)amino-3,4-dicyanopyrazole there was obtained:

1-(2,6-Dichloro-4-trifluoromethylphenyl)-3,4-dicyano-5-ethoxycarbonylaminopyrazole in the form of a white solid, m.p. 161°–163° C.

EXAMPLE 68

Compounds Nos. 189 and 190

By proceeding in a similar manner to that hereinbefore described in Example 50, but replacing N-bromosuccinimide by N-iodosuccinimide there was obtained:

5-Amino-1-(2,6-dichloro-4-trifluoromethylphenyl)-4-iodo-3-trifluoromethylpyrazole in the form of a white solid, m.p. 129° C.

By replacing N-bromosuccinimide by N-iodosuccinimide, and replacing 5-amino-1-(2,6-dichloro-4-trifluoromethylphenyl)-3-trifluoromethlypyrazole by 5-amino-1-(2,6-dichloro-4-trifluoromethylphenyl)-3-methylpyrazole (hereinafter described in Reference Example 31), there was obtained:

5-Amino-1-(2,6-dichloro-4-trifluoromethylphenyl)-4-iodo-3-methylpyrazole in the form of a buff solid, m.p. 108°–109° C., after recrystallization from hexane.

REFERENCE EXAMPLE 31

5-Amino-1-(2,6-dichloro-4-trifluoromethylphenyl)-3-methylpyrazole was prepared as follows:

5-Amino-4-carboxy-1-(2,6-dichloro-4-trifluoromethylphenyl)-3-methylpyrazole (28 g) was heated to 190° C. under nitrogen, and maintained at this temperature until gas evolution ceased. After cooling, the title compound was obtained (22 g) as a yellow gum.

5-Amino-4-carboxy-1-(2,6-dichloro-4-trifluoromethylphenyl)-3-methylpyrazole used above was prepared by proceeding in a similar manner to Reference Example 24 but replacing 5-amino-1-(2,6-dichloro-4-trifluoromethylphenyl)-4-methoxycarbonyl-3-trifluoromethylpyrazole by 5-amino-1-(2,6-dichloro-4-trifluoromethylphenyl)-4-ethoxycarbonyl-3-methylpyrazole (hereinbefore described in Example 60), and by performing the base hydrolysis at the reflux temperature in ethanol for 13 hours. The title compound was obtained as a white solid, m.p. 183°–184° C.

EXAMPLE 69

Compounds Nos. 191, 192 and 193

By proceeding in a similar manner to that herein before described in Example 52, but replacing 5-amino-1-(2,6-dichloro-4-trifluoromethylphenyl)-3-trifluoromethylpyrazole by 5-amino-1-(2,6-dichloro-4-trifluoromethylphenyl)-3-methylpyrazole, and replacing the mixture of concentrated sulphuric and fuming nitric acids by concentrated nitric acid alone, there was obtained:

5-Amino-1-(2,6-dichloro-4-trifluoromethylphenyl)-3-methyl-4-nitropyrazole in the form of orange crystals, m.p. 229°–231° C., after recrystallization from a mixture of toluene and petroleum ether.

By proceeding in a similar manner but replacing 5-amino-1-(2,6-dichloro-4-trifluoromethylphenyl)-3-trifluoromethylpyrazole by 5-acetamido-1-(2,6-dichloro-4-trifluoromethylphenyl)-3-trifluoromethylpyrazole, and replacing the mixture of concentrated sulphuric and fuming nitric acids by a mixture of acetic acid and acetic anhydride to which was added fuming nitric acid, there was obtained:

5-Acetamido-1-(2,6-dichloro-4-trifluoromethylphenyl)-4-nitro-3-trifluoromethylpyrazole in the form of a cream solid, m.p. 194°–195° C.

By proceeding in a similar manner but replacing 5-amino-1-(2,6-dichloro-4-trifluoromethylphenyl)-3-trifluoromethylpyrazole by 1-(2,6-dichloro-4-trifluoromethylphenyl)-3-trifluoromethylpyrazole, and replacing the mixture of concentrated sulphuric and fuming nitric acids by acetic anhydride to which was added fuming nitric acid, there was obtained:

1-(2,6-Dichloro-4-trifluoromethylphenyl)-4-nitro-3-trifluoromethylpyrazole in the form of an orange solid, m.p. 110°–112° C., after recrystallization from a mixture of toluene and hexane.

REFERENCE EXAMPLE 32

1-(2,6-Dichloro-4-trifluoromethylphenyl)-3-trifluoromethylpyrazole used in the above Example 69 was prepared by the procedure described in Example 53 by replacing 5-amino-4-cyano-1-(2,6-dichloro-4-trifluoromethylphenyl)-3-trifluoromethlpyrazole by 5-amino-1-(2,6-dichloro-4-trifluoromethylphenyl)-3-trifluoromethylpyrazole. The title compound was obtained as a pale yellow oil.

5-Acetamido-1-(2,6-dichloro-4-trifluoromethylphenyl)-3-trifluoromethylpyrazole used in the above Example 69 was prepared by the procedure described in Example 47, but replacing the 4-cyano-1-(2,6-dichloro-4-trifluoromethylphenyl)-5-bis(cyclopropanecarbonyl)amino-3-trifluoromethylpyrazole by 5-bis(acetyl)amino-1-(2,6-dichloro-4-trifluoromethylphenyl)-3-trifluoromethylpyrazole. The title compound was obtained as white crystals, m.p. 142°–144° C., after recrystallization from ethyl acetate and hexane.

5-Bis(acetyl)amino-1-(2,6-dichloro-4-trifluoromethylphenyl)-3-trifluoromethylpyrazole, used above, was prepared by the procedure of Example 51 but replacing 5-amino-4-cyano-1-(2,6-dichloro-4-trifluoromethylphenyl)-3-trifluoromethylpyrazole by 5-amino-1-(2,6-dichloro-4-trifluoromethylphenyl)-3-trifluoromethylpyrazole, and the ethyl chloroformate by acetyl chloride. The title compound was obtained as a white solid, m.p. 130°–131° C.

EXAMPLE 70

Compounds Nos. 194, 195 and 196

By proceeding in a similar manner to that hereinbefore described in Example 53, but replacing the 5-amino-4-cyano-1-(2,6-dichloro-4-trifluoromethylphenyl)-3-trifluoromethylpyrazole by 5-amino-1-(2,6-dichloro-4-trifluoromethylphenyl)-3-methyl-4-methanesulphonylpyrazole, there was obtained 1-(2,6-dichloro-4-trifluoromethylphenyl)-3-methyl-4-methylsulphonylpyrazole in the form of yellow crystals, m.p. 168°–169° C.

By proceeding in a similar manner but replacing the 5-amino-4-cyano-1-(2,6-dichloro-4-trifluoromethylphenyl)-3-trifluoromethylpyrazole by 5-amino-4-cyano-1-(2,6-dichloro-4-trifluoromethylphenyl)-3-fluoropyrazole, there was obtained 4-cyano-1-(2,6-dichloro-4-trifluoromethylphenyl)-3-fluoropyrazole in the form of white crystals, m.p. 120°–121° C.

1-(2,6-Dichloro-4-trifluoromethylphenyl)-4-methanesulphonyl-3-trifluoromethylpyrazole was prepared in a similar manner by replacing 5-amino-4-cyano-1-(2,6-dichloro-4-trifluoromethylphenyl)-3-trifluoromethylpyrazole by 5-amino-1-(2,6-dichloro-4-trifluoromethylphenyl)-4-methanesulphonyl-3-trifluoromethylpyrazole. The title compound was obtained in the form of white needles, m.p. 154°–155° C.

EXAMPLE 71

Compound No. 197

By proceeding in a similar manner to that hereinbefore described in Example 54, but replacing the iodine by anhydrous cupric chloride, and by replacing the chloroform by anhydrous acetonitrile, there was obtained:

5-Chloro-1-(2,6-dichloro-4-trifluoromethylphenyl)-4-cyano-3-trifluoromethylpyrazole in the form of a yellow oil, after purification by chromatography on silica (Merck, 40–230 mesh, 0.7 kg cm$^{-2}$) eluting with a mixture of dichloromethane and hexane (1:2) Infra-Red Absorption bands: 2260, 1495, 1405, 1325, 1160 cm$^{-1}$ (liquid film).

EXAMPLE 72

Compounds Nos. 198 and 199

By proceeding in a similar manner to that hereinbefore described in Example 56, but replacing the dimethylamine by the appropriate amines there was prepared the following phenylpyrazoles:

5-Amino-1-(2,6-dichloro-4-trifluoromethylphenyl)-4-(N-ethylsulphamoyl)-3-trifluoromethylpyrazole in the form of a cream solid, m.p. 200° C., after recrystallization from a mixture of toluene and petroleum ether.

5-Amino-1-(2,6-dichloro-4-trifluoromethylphenyl)-4-(N-methylsulphamoyl)-3-trifluoromethylpyrazole in the form of a light brown solid, m.p. 199°–200° C., after recrystallization from toluene.

EXAMPLE 73

Compounds Nos. 200 and 201

Trifluoroacetic anhydride (3.5 ml) was added dropwise to a stirred mixture of 85% w/v hydrogen peroxide solution (0.56 ml) in dichloromethane (15 ml) maintaining at 0°–10° C. After warming to 20° C. during 5 minutes, a solution of 3-amino-1-(2,6-dichloro-4-trifluoromethylphenyl)-4-cyanopyrazole (1.0 g; hereinafter described in Reference Example 33) in dichloromethane (10 ml) was added dropwise over 5 minutes. A temperature rise of 10° C. was observed during the addition, and the mixture heated under reflux for 1.5 hours. After cooling, the solution was poured onto excess water, and the organic solution washed in turn with solutions of sodium bicarbonate and sodium bisulphite. Drying over anhydrous magnesium sulphate, followed by evaporation in vacuo gave a buff solid, which was purified by chromatography on silica (Merck, 40–230 mesh, 0.7 kg cm$^{-2}$) eluting with dichloromethane. The resultant white solid was recrystallized from a mixture of dichloromethane and hexane to give 1-(2,6-dichloro-4-trifluoromethylphenyl)-4-cyano-3-nitropyrazole as white crystals (0.7 g), m.p. 163°–165° C.

By proceeding in a similar manner but replacing 3-amino-1-(2,6-dichloro-4-trifluoromethylphenyl)-4-cyanopyrazole by 5-amino-1-(2,6-dichloro-4-trifluoromethylphenyl)-3,4-dicyanopyrazole (hereinbefore described in Example 34), there was obtained:

1-(2,6-Dichloro-4-trifluoromethylphenyl)-3,4-dicyano-5-nitropyrazole as orange crystals, m.p. 138°–140° C., after recrystallization from cyclohexane.

REFERENCE EXAMPLE 33

3-Amino-1-(2,6-dichloro-4-trifluoromethylphenyl)-4-cyanopyrazole was prepared as follows:

A solution of 3-tert-butoxycarbonylamino-1-(2,6-dichloro-4-trifluoromethylphenyl)-4-cyanopyrazole (2.8 g) in ethanol (100 ml) was treated with 50% v/v hydrochloric acid (10 ml), and the mixture heated under reflux for 1 hour. After standing overnight at room temperature, sodium carbonate was added to pH 8, and the mixture extracted three times with dichloromethane. The extract was washed with water, dried over anhydrous magnesium sulphate, and evaporated in vacuo to give a buff solid. Recrystallization from a mixture of ethyl acetate and petroleum ether gave the title compound (1.4 g) in the form of white crystals, m.p. 159°–160° C.

3-tert-Butoxycarbonylamino-1-(2,6-dichloro-4-trifluoromethylphenyl)-4-cyanopyrazole was prepared as follows:

A mixture of 3-carboxy-4-cyano-1-(2,6-dichloro-4trifluoromethylphenyl)pyrazole (11 g) and thionyl chloride (35 ml) and N,N-dimethylformamide (3 drops) was heated under reflux for 2 hours. The solvent was evaporated in vacuo, and re-evaporated in vacuo after addition of dry toluene (20 ml).

The resultant gum was dissolved in dry acetone (50 ml) and stirred, while a solution of sodium azide (2.9 g) in water (15 ml) was added during 5 minutes keeping at 10°–15° C. After 30 minutes the mixture was poured onto water (250 ml) and extracted with dichloromethane (3×80 ml). The combined extract was washed with water, dried over anhydrous magnesium sulphate, and evaporated in vacuo at equal to or below 40° C. to give a buff solid (13 g).

The resulting azide was dissolved in dry toluene (200 ml) and heated under reflux for half-an-hour, with smooth evolution of nitrogen. After cooling, this was treated with tert-butanol (40 g), and the mixture heated under reflux overnight. After evaporation in vacuo, the resulting brown oil (15 g) was purified by chromatography on silica (Merck 230–400 mesh, 0.7 kg cm$^{-2}$) eluting with dichloromethane and ethyl acetate (98:2) to give the title compound (8.0 g) as a white solid, m.p. 154°–155° C.

3-Carboxy-4-cyano-1-(2,6-dichloro-4-trifluoromethylphenyl)pyrazole was prepared as follows:

A suspension of 4-cyano-1-(2,6-dichloro-4 -trifluoromethylphenyl)-3-ethoxycarbonylpyrazole (5.0 g) in ethanol (100 ml) was treated with a solution of sodium hydroxide (0.63 g) in water 15 ml) and stirred at room temperature for 1.5 hours. After evaporation in vacuo at equal to or below 40° C., the residue was dissolved in water (150 ml) and extracted with dichloromethane (1×100 ml). This extract was back-washed with water (2×50 ml), and the combined aqueous solutions brought to pH 1 with dilute hydrochloric acid, and then extracted with ethyl acetate (3×50 ml). This extract was dried over anhydrous magnesium sulphate, and evaporated in vacuo to give a buff solid (4.6 g). Recrystallization from a mixture of toluene and hexane gave the title compound in the form of buff crystals (4.4 g), m.p. 203°–205° C.

4-Cyano-1-(2,6-dichloro-4-trifluoromethylphenyl)-3-ethoxycarbonylpyrazole was prepared by following the method described in Example 53, and replacing 5-amino-4-cyano-1-( 2,6-dichloro-4-trifluoromethylphenyl)-3-trifluoromethylpyrazole by 5-amino-4-cyano-1-(2,6-dichloro-4 -trifluoromethylphenyl)-3-ethoxycarbonylpyrazole. The title compound was obtained in the form of buff crystals, m.p. 198°–199° C.

EXAMPLE 74

Compounds Nos. 202, 203 and 204

Silver (I) fluoride (5 g) was added in portions during 40 minutes to a vigorously stirred solution of 1,1 -dichloro-2,2-dicyanoethylene in acetonitrile (15 ml), maintained at 0°–10° C. by external cooling. The stirring was continued at room temperature for 1 hour and the solid filtered off. The filtrate containing 1,1-difluoro-2,2-dicyanoethylene was stirred and cooled while a solution of 2,6-dichloro-4-trifluoromethylphenylhydrazine (4.9 g) in acetonitrile (15 ml) was added dropwise at 5° C. After stirring overnight the solid was filtered off and the filtrate evaporated in vacuo to give a dark orange oil (6 g). This was purified by chromatography or silica (Merck, 230–400 mesh, 10 lb in$^{-2}$) eluting with dichloromethane to give a white solid. Recrystallization from a mixture of cyclohexane and ethyl acetate gave 5-amino-1-(2,6-dichloro- 4-trifluoromethylphenyl)-4-cyano-3-fluoropyrazole (0.9 g) as a white solid, m.p. 193°–194° C.

By proceeding in a similar manner but replacing the 2,6-dichloro-4-trifluoromethylphenylhydrazine by 2,6 -dichloro-4-trifluoromethoxyphenylhydrazine and by employing 1,1-dichloro-2,2-dicyanoethylene instead of 1,1 -difluoro-2,2-dicyanoethylene, and by using diethyl ether as solvent, there was prepared 5-amino-3-chloro-1-(2,6 -dichloro-4-trifluoromethoxyphenyl)-4-cyanopyrazole in the form of a yellow solid, m.p. 175°–177° C.

By proceeding as immediately above but replacing the 2,6-dichloro-4-trifluoromethoxyphenylhydrazine by 2,6 -dichloro-3,5-difluoro-4-trifluoromethylphenylhydrazine, there was prepared 5-amino-3-chloro-4-cyano-l(2,6-dichloro- 3,5-difluoro-4-trifluoromethylphenyl)pyrazole, in the form of yellow crystals, m.p. 206°–208° C.

EXAMPLE 75

Compounds Nos. 205, 206, 207, 208, 209, 210 and 211

A stirred solution of 4-cyano-1-(2,6-dichloro-4 -trifluoromethylphenyl)-3-trifluoromethylpyrazole (1.5 g) in dry tetrahydrofuran cooled to −78° C. was treated with a solution of n-butyl lithium (2.6M in hexane, 1.71 ml) dropwise under nitrogen. The temperature was kept below −65° C. during the addition, and the resultant solution kept at −78° C. for 1 hour. A solution of trimethylsilyl chloride (0.56 ml) in dry tetrahydrofuran (2 ml) was then added, dropwise, during 2 minutes. The mixture was allowed to reach room temperature over 2 hours, left overnight and evaporated in vacuo to give a pale yellow solid. This was dissolved in dichloromethane, washed with water, dried over anhydrous magnesium sulphate, and evaporated in vacuo. The product was recrystallized from hexane to give 4-cyano-1-( 2,6-dichloro-4-trifluoromethylphenyl)-3-trifluoromethyl-5 -trimethylsilylpyrazole as white crystals, m.p. 108°–110° C.

By proceeding in a similar manner but replacing the trimethylsilyl chloride by the reagents listed below, the following phenylpyrazoles were obtained:

5-tert-Butyldimethylsilyl-4-cyano-1-(2,6-dichloro-4 -trifluoromethylphenyl)-3-trifluoromethylpyrazole in the form of white crystals, m.p. 113°–115° C.; from tert butyldimethylsilyl chloride.

4-Cyano-1-(2,6-dichloro-4-trifluoromethylphenyl)-5 -methylthio-3-trifluoromethylpyrazole, in the form of a white power, m.p. 73°–74° C.; from methylthiocyanate.

4-Cyano-1-(2,6-dichloro-4-trifluoromethylphenyl)-3 -trifluoromethyl-5-trifluoromethylthiopyrazole, in the form of white crystals, m.p. 120°–122° C.; from bis(trifluoromethyl)disulphide.

5-Carboxy-4-cyano-1-(2,6-dichloro-4 -trifluoromethylphenyl)-3-trifluoromethylpyrazole, in the form of a white solid, m.p. 177°–179° C., by pouring the lithiated pyrazole solution onto a large excess of powdered solid carbon dioxide.

By proceeding in a similar manner but replacing the 4-cyano-1-(2,6-dichloro-4-trifluoromethylphenyl)-3-trifluoromethylpyrazole by 1-(2,6-dichloro-4-trifluoromethylphenyl)- 4-nitro-3-trifluoromethylpyrazole, there was prepared:

1-(2,6-Dichloro-4-trifluoromethylphenyl)-4-nitro-3 -trifluoromethyl-5-trimethylsilylpyrazole, in the form of a pale green solid, m.p. 101°–103° C.

By proceeding in a similar manner but replacing the 4-cyano-1-(2,6-dichloro-4-trifluoromethylphenyl)-3-trifluoromethylpyrazole by 4-cyano-1-(2,6-dichloro-4 -trifluoromethylphenyl)-5-methyl-3-trifluoromethylpyrazole (hereinbefore described in Example 55), there was prepared:

4-Cyano-1-(2,6-dichloro-4-trifluoromethylphenyl)-3 -trifluoromethyl-5-trimethylsilylmethylpyrazole, in the form of a colorless oil. Infra-Red Absorption bands: 2250, 1400, 1325, 1260, 1180, 1150, 860cm$^{-1}$ (liquid film) Nuclear Magnetic Resonance: chemical shift (delta) for —Si—CH$_2$— 2.8 ppm in dimethylsulphoxide-D$^6$.

EXAMPLE 76

Compound No. 212

Sodium methoxide (0.3 g) was added to an ice cold stirred mixture of 4-cyano-1-(2,6-dichloro-4 -trifluoromethylphenyl)-5-bis(phenoxycarbonyl)amino-3-trifluoromethylpyrazole (3.1 g) in methanol (30 ml), and heated under reflux for 2 hours. This was poured onto water (200 ml) and extracted with dichloromethane. The organic solution was washed with sodium carbonate solution, then with water, dried over anhydrous magnesium sulphate, and evaporated in vacuo. The resultant white solid was 4 -cyano-1-(2,6-dichloro-4-trifluoromethylphenyl)-5 -methoxycarbonylamino-3-trifluoromethylpyrazole, m.p. 182°–183° C.

REFERENCE EXAMPLE 34

4-Cyano-1-(2,6-dichloro-4-trifluoromethylphenyl)-5 -bis-(phenoxycarbonyl)amino-3-trifluoromethylpyrazole used in the above Example 76 was prepared by following the procedure of Example 46, but replacing trimethylacetyl chloride by phenyl chloroformate. The title compound was obtained as a white solid, m.p. 168°–169° C.

EXAMPLE 77

Compounds Nos. 213 and 214

5-Carbamoyl-4-cyano-1-(2,6-dichloro-4 -trifluoromethylphenyl)-3-trifluoromethylpyrazole (3.57 g) was heated to 200° C. with phosphorus pentoxide (2.82 g) with stirring. After 3 hours, the cooled product was treated with ice, and extracted with dichloromethane (3×50 ml). The organic solution was washed with water, dried over anhydrous magnesium sulphate, and evaporated in vacuo to give a solid. Recrystallization from hexane gave 1-(2,6-dichloro-4-trifluoromethylphenyl)-4,5-dicyano-3-trifluoromethylpyrazole in the form of white crystals (1.8 g), m.p. 80° C.

By proceeding in a similar manner but replacing the 5-carbamoyl-4-cyano-1-(2,6-dichloro-4 -trifluoromethylphenyl)-3-trifluoromethylpyrazole by 5-amino-3-carbamoyl-1-( 2,6-dichloro-4-trifluoromethylphenyl)-4-methanesulphonylpyrazole there was prepared:

5-Amino-3-cyano-1-(2,6-dichloro-4 -trifluoromethylphenyl)-4-methanesulphonylpyrazole in the form of a white solid, m.p. 214° C.

REFERENCE EXAMPLE 35

5-Carbamoyl-4-cyano-1-(2,6-dichloro-4 -trifluoromethylphenyl)-3-trifluoromethylpyrazole used in the above Example 77, was prepared as follows:

5-Carboxy-4-cyano-1-(2,6-dichloro-4 -trifluoromethylphenyl)-3-trifluoromethylpyrazole (6.0 g; hereinbefore described in Example 75) was added to thionyl chloride (30 ml) and the stirred solution heated to reflux for 4 hours. The solvent was evaporated in vacuo, and re-evaporated after addition of dry toluene (30 ml). The resultant orange oil was dissolved in dry ether (10 ml) and added dropwise to a stirred solution of ammonia (0.88, 20 ml) cooled by an ice bath. After stirring overnight, water (150 ml) was added, and the mixture extracted with dichloromethane (3×50 ml). The combined extract was washed with water, dried over anhydrous magnesium sulphate, and evaporated in vacuo to give a white solid (7.0 g). Recrystallization from a mixture of ethyl acetate and petroleum ether gave the title compound (4.3 g), in the form of white crystals, m.p. 180°–181° C.

5-Amino-3-carbamoyl-1-(2,6-dichloro-4 -trifluoromethylphenyl)-4-methanesulphonylpyrazole used in the above Example 77 was prepared by the same procedure, but by replacing the 5-carboxy-4-cyano-1-(2,6-dichloro-4 -trifluoromethylphenyl)-3-trifluoromethylpyrazole by 5-amino-3 -carboxy-1-(2,6-dichloro-4-trifluoromethylphenyl)-4-methanesulphonylpyrazole. The title compound was obtained in the form of an off-white solid, m.p. 223°–224° C.

5-Amino-3-carboxy-1-(2,6-dichloro-4 -trifluoromethylphenyl)-4-methanesulphonylpyrazole used above was prepared as follows:

5-Amino-1-(2,6-dichloro-4-trifluoromethylphenyl)-3 -ethoxycarbonyl-4-methanesulphonylpyrazole (8.15 g) was added to stirred 80% sulphuric acid (80 ml), and heated at 100° C. for 5 hours. After cooling, the solution was poured onto ice, the solid filtered off and dried over phosphorous pentoxide in a vacuum desiccator. Recrystallization from a mixture of methanol and petroleum ether gave the title compound as a white solid, m.p. 203°–205° C.

5-Amino-1-(2,6-dichloro-4-trifluoromethylphenyl)-3 -ethoxycarbonyl-4-methanesulphonylpyrazole, used above, was prepared by the procedure of Reference Example 23, by replacing malononitrile by methanesulphonylacetonitrile. The title compound was obtained in the form of a white solid, m.p. 255° C., after recrystallization from ethanol.

EXAMPLE 78

Compound No. 215

A solution of methylmagnesium iodide (prepared from magnesium (0.26 g) and methyl iodide (1.5 g) in diethyl ether (25 ml)), was treated with a solution of 1-(2,6 -dichloro-4-trifluoromethylphenyl)-4-cyano-3-trifluoromethylpyrazole (2 g) in diethyl ether (20 ml), dropwise. The resulting pale yellow solution was refluxed for 24 hours, cooled, and treated with hydrochloric acid (2N, 10 ml). After stirring for 0.5 hour at room temperature, the reaction mixture was diluted with ether (50 ml). The ethereal extract was washed with water (50 ml), dried over anhydrous magnesium sulphate, and evaporated in vacuo to give a yellow gum. This was purified by chromatography on silica (Merck 230–400 mesh, 0.7 kg cm$^{-2}$) eluting with a mixture of dichloromethane and petroleum ether (4:1) to give 4-acetyl-1-(2,6-dichloro-4-trifluoromethylphenyl)-3-trifluoromethylpyrazole as a white solid, m.p. 134° C.

EXAMPLE 79

Compounds Nos. 216–224

A stirred solution of 5-amino-1-(2,6-dichloro-4 -trifluoromethylphenyl)-4-methylthio-3-trifluoromethylpyrazole (1.0 g) in chloroform (40 ml) was treated with m-chloroperbenzoic acid (0.42 g), portionwise at room temperature. After stirring for 6 hours, the solution was diluted with dichloromethane and washed in turn with sodium sulphite solution, sodium hydroxide solution, and water. The solution was dried over anhydrous magnesium sulphate, and evaporated in vacuo to give a yellow oil. Purification by chromatography on silica (Merck 230–400 mesh, 0.7 kg cm$^{-2}$) eluting with dichloromethane-ethylacetate (4:1) gave 5-amino-1-(2,6-dichloro-4-trifluoromethylphenyl)-4 -methylsulphinyl-3-trifluoromethylpyrazole in the form of a white solid, m.p. 142°–145° C. with decomposition.

By proceeding in a similar manner but replacing 5 -amino-1-(2,6-dichloro-4-trifluoromethylphenyl)-4 -methylthio-3-trifluoromethylpyrazole by the appropriate alkylthio phenylpyrazoles there were prepared:

5-Amino-1-(2,6-dichloro-4-trifluoromethylphenyl)-4 -ethylsulphinyl-3-trifluoromethylpyrazole in the form of a white solid, m.p. 170° C. from 5-amino-1-(2,6-dichloro-4 -trifluoromethylphenyl)-4-ethylthio-3-trifluoromethylpyrazole.

5-Amino-1-(2,6-dichloro-4-trifluoromethylphenyl)-4 -ethylsulphinyl-3-methylpyrazole in the form of a buff solid, m.p. 157°–158° C. from 5-amino-1-(2,6-dichloro-4 -trifluoromethylphenyl)-4-ethylthio-3-methylpyrazole.

5-Amino-4-cyano-1-(2,6-dichloro-4 -trifluoromethylsulphinylphenyl)-3-trifluoromethylpyrazole, in the form of an orange solid, m.p. 76° C., from 5-amino-4-cyano-1-(2,6 -dichloro-4-trifluoromethylthiophenyl)-3-trifluoromethylpyrazole.

4-Cyano-1-(2,6-dichloro-4-trifluoromethylphenyl)-5 -methylsulphinyl-3-trifluoromethylpyrazole, in the form of white crystals, m.p. 97°–98° C., from 4-cyano-1-(2,6-dichloro- 4-trifluoromethylphenyl)-5-methylthio-3-trifluoromethylpyrazole.

By proceeding in a similar manner but replacing 5 -amino-1-(2,6-dichloro-4-trifluoromethylphenyl)-4 -methylthio-3-trifluoromethylpyrazole by the appropriate alkylthiophenylpyrazoles, and employing 2 molar equivalents of m-chloroperbenzoic acid there was prepared:

5-Amino-1-(2,6-dichloro-4-trifluoromethylphenyl)-4 -ethylsulphonyl-3-trifluoromethylpyrazole, 1N the form of white crystals, m.p. 206°–207° C., from 5-amino-1-(2,6 -dichloro-4-trifluoromethylphenyl)-4-ethylthio-3-trifluoromethylpyrazole.

5-Amino-1-(2,6-dichloro-4-trifluoromethylphenyl)-4 -ethylsulphonyl-3-methylpyrazole, in the form of a white solid, m.p. 193° C., from 5-amino-1-(2,6-dichloro-4 -trifluoromethylphenyl)-4-ethylthio-3-methylpyrazole.

By proceeding in a similar manner but replacing the 5-amino-1-(2,6-dichloro-4-trifluoromethylphenyl)-4 -methylthio-3-trifluoromethylpyrazole by 5-amino-1-(2,6-dichloro- 4-trifluoromethylphenyl)-4-n-propylthio-3-methylpyrazole, there was obtained 5-amino-1-(2,6-dichloro-4 -trifluoromethylphenyl)-3-methyl-4-propanesulphonylpyrazole in the form of a white solid, m.p. 145.5°–147° C.

By proceeding in a similar manner there was prepared:

5-Amino-1-(2,6-dichloro-4-trifluoromethylphenyl)-4 -trichloromethanesulphonyl-3-methylpyrazole in the form of a pale pink solid, m.p. 183°–184° C., from 5-amino-1-(2,6 -dichloro-4-trifluoromethylphenyl)-4-trichloromethylthio-3-methylpyrazole.

EXAMPLE 80

Compounds Nos. 225, 226 and 227

A mixture of bis[5-amino-1-(2,6-dichloro-4 -trifluoromethylphenyl)-3-methylpyrazol-4-yl]-disulphide (4.0 g), sodium dithionite (2.02 g) and sodium hydroxide (0.46 g) was stirred and heated under reflux in a mixture of ethanol and water (60 ml, 1:1) for 4 hours. The cooled yellow solution was treated with ethyl iodide (2.17 g) and the mixture stirred and heated under reflux for 2 hours. After evaporation in vacuo, the yellow gum was dissolved in ether (100 ml), washed with water, dried over anhydrous magnesium sulphate, and re-evaporated in vacuo. The resultant gum was purified by chromatography on silica (Merck 230–400 mesh, 0.7 kg cm$^{-2}$) eluting with dichloromethane, to furnish 5-amino-1-(2,6-dichloro-4 -trifluoromethylphenyl)-4-ethylthio-3-methylpyrazole in the form of a white solid, m.p. 117° C., after recrystallization from hexane.

By proceeding in a similar manner, but replacing the ethyl iodide by methyl iodide there was prepared:

5-Amino-1-(2,6-dichloro-4-trifluoromethylphenyl)-3 -methyl-4-methylthiopyrazole, in the form of a white solid, m.p. 112° C., after recrystallization from hexane.

By proceeding in a similar manner but replacing the sodium hydroxide by sodium carbonate, and the methyl iodide by n-propyl iodide, there was obtained 5-amino-1-(2,6 -dichloro-4-trifluoromethylphenyl)-4-n-propylthio-3-methylpyrazole in the form of a white solid, m.p. 100°–102° C.

REFERENCE EXAMPLE 36

Bis[5-Amino-1-(2,6-dichloro-4 -trifluoromethylphenyl)-3-methylpyrazol-4-yl]disulphide was prepared as follows:

A solution of 5-amino-1-(2,6-dichloro-4 -trifluoromethylphenyl)-3-methyl-4-thiocyanatopyrazole (3.0 g; hereinafter described in Example 82) in a mixture of ethanol and water (1:1, 100 ml) was acidified by the addition of hydrochloric acid (10N, 20 ml). The mixture was heated under reflux for 8 hours, concentrated to half volume in vacuo, cooled in an ice bath, and sodium hydroxide solution added until the pH reached 9–10. The precipitated product was filtered, washed with water, and dried in vacuo to furnish the title compound (2.68 g) as an amorphous yellow powder, m.p. 211°–213° C.

EXAMPLE 81

Compounds Nos. 228 and 229

A solution of ethyl magnesium bromide, prepared from magnesium (0.57 g) and ethyl bromide (2.6 g) in dry diethyl ether (25 ml), was added dropwise to a stirred solution of 5-amino-1-(2,6-dichloro-4-trifluoromethylphenyl)-4 -thiocyanato-3-trifluoromethylpyrazole (5.0 g) in dry ether (50 ml) at −20° C. After stirring for a further 2 hours at room temperature, water (130 ml) was carefully added, and stirring maintained for 0.25 hour. The ether layer was separated, dried over anhydrous magnesium sulphate, and evaporated in vacuo to give a yellow gum. Purification by chromatography on silica (Merck 230–400 mesh, 0.7 kg cm$^{-2}$) eluting with dichloromethane-petroleum ether (1:1) gave a product, which recrystallized from hexane to furnish 5 -amino-1-(2, 6-dichloro-4-trifluoromethylphenyl)-4-ethylthio- 3-trifluoromethylpyrazole, in the form of white needles, m.p. 116°–116.5° C.

By proceeding in a similar manner, but replacing the ethyl magnesium iodide by methyl magnesium iodide there was obtained:

5-Amino-1-(2,6-dichloro-4-trifluoromethylphenyl)-4-methylthio-3-trifluoromethylpyrazole, in the form of a white solid, m.p. 108° C., after recrystallization from hexane.

EXAMPLE 82

Compounds Nos. 230 and 231

A stirred mixture of 5-amino-1-(2,6-dichloro-4 -trifluoromethylphenyl)-3-trifluoromethylpyrazole (0.7 g) and potassium thiocyanate (0.55 g) in methanol (15 ml) was treated with a solution of bromine (0.3 g) in methanol (2 ml) at 0°–5° C. Stirring was maintained at this temperature for 1.5 hours, and the mixture was poured onto ice water, and brought to pH 9 by the addition of sodium carbonate. The product was filtered, washed with water and dried. Purification by chromatography on silica (Merck 230–400 mesh, 0.7 kg cm$^{-2}$) eluting with dichloromethane gave 5 -amino-1-(2,6-dichloro-4-trifluoromethylphenyl)-4 -thiocyanato-3-trifluoromethylpyrazole, in the form of a white solid, m.p. 49°–50° C.

By proceeding in a similar manner but replacing 5 -amino-1-(2,6-dichloro-4-trifluoromethylphenyl)-3-trifluoromethylpyrazole by 5-amino-1-(2,6-dichloro-4 -trifluoromethylphenyl)-3-methylpyrazole there was obtained 5 -amino-1-(2,6-dichloro-4-trifluoromethylphenyl)-3-methyl-4-thiocyanatopyrazole in the form of a white solid, m.p. 133.5° C., after recrystallization from a mixture of hexane and ethyl acetate.

EXAMPLE 83

Compound No. 232

By proceeding in a similar manner to that hereinbefore described in Example 36, but replacing the 2,6 -dichloro-4-trifluoromethylphenylhydrazine by 2,6-dichloro- 4-methanesulphonylphenylhydrazine there was obtained:

5-Amino-4-cyano-1-(2,6-dichloro-4 -methanesulphonylphenyl)-3-trifluoromethylpyrazole in the form of white crystals, m.p. 270°–272° C.

REFERENCE EXAMPLE 37

By proceeding in a similar manner to that hereinbefore described in Reference Example 19, but replacing the 2,6-dichloro-4-trifluoromethylaniline by 2,6-dichloro-4methanesulphonylaniline, there was prepared:

2,6-Dichloro-4-methanesulphonylphenylhydrazine in the form of white crystals, m.p. 163°–166° C.

EXAMPLE 84

Compound No. 233

To a stirred ice cold solution of 5-amino-1-(2,6 -dichloro-4-trifluoromethylphenyl)-3-methylpyrazole (2.0 g) in chloroform (40 ml) and pyridine (0.51 g) was added dropwise a solution of trichloromethanesulphenyl chloride (1.2 g) in chloroform (10 ml). The resulting brown solution was stirred at 0° C. for 2 hours, then at room temperature for 2 hours. A further addition of trichloromethanesulphenyl chloride (0.5 g) was made and the mixture stirred for 2 hours at room temperature. Water (100 ml) and dichloromethane (100 ml) was then added and the organic layer washed with water (1×100 ml), dried over anhydrous magnesium sulphate and evaporated in vacuo to give a yellow gum (2.9 g). This was purified by chromatography on silica (Merck, 100–230 mesh, 0.7 kg cm$^{-2}$) eluting with dichloromethane petroleum ether (3:2) to give a white solid (0.98 g). Recrystallization from hexane gave 5-amino-1-(2,6 -dichloro-4-trifluoromethylphenyl)-3-methyl-4-trichloromethylthiopyrazole in the form of white crystals, m.p. 156° C.

EXAMPLE 85

Compound No. 234 m-Chloroperbenzoic acid (2.1 g) was added to a solution of 5-amino-4-cyano-1-(2,6-dichloro-4 -trifluoromethylphenyl)-3-trifluoromethylpyrazole (2.3 g) in dichloromethane (20 ml) cooled to 10° C. After stirring overnight at room temperature, the solution was heated under reflux for 4 hours, cooled, and a further addition of m-chloroperbenzoic acid (2.1 g) made. The mixture was stirred at room temperature for 4 hours and heated under reflux for 4 hours. The cooled solution was washed with sodium bicarbonate solution (20×20 ml), then with water (2×20 ml), dried over anhydrous magnesium sulphate, filtered, and evaporated in vacuo to give an orange solid. Purification by chromatography on silica (Merck, 100–230 mesh, 0.7 kg cm$^{-2}$) eluting with ethyl acetate-petroleum ether (1:9) gave 4-cyano-1-(2,6-dichloro-4-trifluoromethanesulphonylphenyl)- 5-nitro-3-trifluoromethylpyrazole (0.5 g) in the form of an orange solid, m.p. 168°–169° C.

EXAMPLE 86

Compound No. 235

To a stirred solution of diethylaminosulphur trifluoride (1.5 g) in dichloromethane (13 ml) cooled to −70° C., was added dropwise under nitrogen a solution of 1-( 2,6-dichloro-4-trifluoromethylphenyl)-4-formyl-3-trifluoromethylpyrazole (3.1 g) in dichloromethane (17 ml). After 1 hour at −70° C., the mixture was allowed to stand at room temperature overnight, then poured onto excess iced water. Extraction with dichloromethane gave a solution which was washed with water (2×), dried over anhydrous magnesium sulphate and evaporated in vacuo to give a brown oil (3.26 g). Purification by chromatography on silica (Merck, 40–230 mesh, 0.7 kg cm$^{-2}$) eluting with hexane-ethyl acetate (5:1) gave 1-(2,6-dichloro-4 -trifluoromethylphenyl)-4-difluoromethyl-3-trifluoromethylpyrazole (1.15 g) (from ethyl acetate-hexane) in the form of a pale yellow solid, m.p. 88°–90° C.

REFERENCE EXAMPLE 38

A mixture of 4-cyano-1-(2,6-dichloro-4 -trifluoromethylphenyl)-3-trifluoromethylpyrazole (5.0 g; hereinbefore described in Example 53) and formic acid (120 ml) was treated with Raney nickel (5.1 g) and the mixture heated under reflux overnight. After cooling, the mixture was filtered, and the filtrate diluted with water (900 ml) and extracted with dichloromethane (4×100 ml). The combined extract was washed with sodium bicarbonate solution (2×), then with water (1×), dried over anhydrous magnesium sulphate, and evaporated in vacuo to give a brown solid (3.7 g), m.p. 80°–82° C. This was 1-(2,6-dichloro-4 -trifluoromethylphenyl)-4-formyl-3-trifluoromethylpyrazole.

EXAMPLE 87

Compound 236

To a stirred solution of 5-amino-4-carboxy-1-(2,6-dichloro-4-trifluoromethylphenyl)-3-trifluoromethylpyrazole (15.0 g; hereinbefore described in Reference Example 24) in dry tetrahydrofuran (50 ml) was added, under nitrogen, a solution of boranetetrahydrofuran complex (1 Molar, 27.5 g) during 10 minutes keeping at −20° C. The solution was allowed to reach room temperature and stirred overnight. A further addition of the borane was made (10 ml), and the solution heated under reflux overnight. After cooling, a further addition of the borane (20 ml) was made, and the solution again heated under reflux for 4 hours. After cooling, sodium hydroxide (6N) solution was added to pH 11, and the solution extracted with dichloromethane. The organic phase was washed with water, dried over anhydrous magnesium sulphate, and evaporated in vacuo to give a brown oil. Purification by chromatography on silica (Merck, 40–230 mesh, 0.7 kg cm$^{-2}$) eluting with hexane-ethyl acetate (2:1) gave 5-amino-1-(2,6-dichloro-4-trifluoromethylphenyl)-4-methyl-3-trifluoromethylpyrazole (2.0 g) from toluene-hexane, m.p. 97°–100° C., in the form of white crystals.

List of Formula

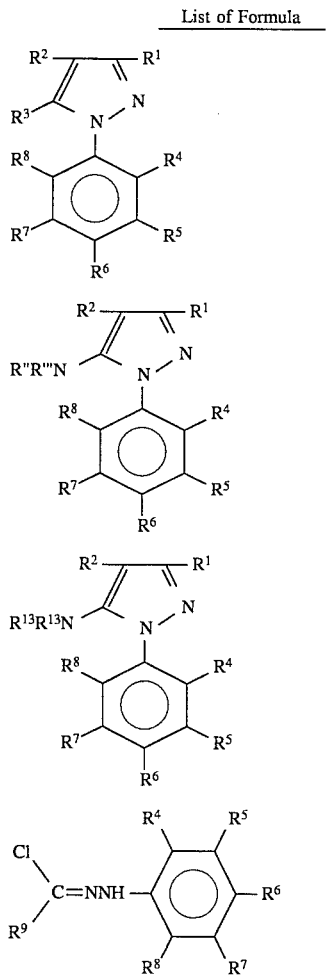

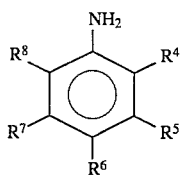 (IIA)

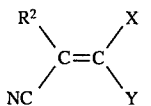 (IV)

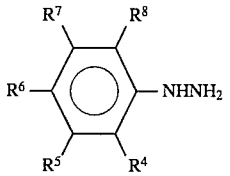 (V)

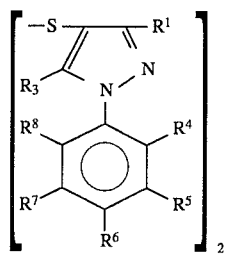 (VIII)

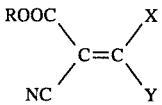 (XVIII)

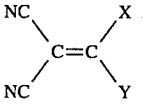 (XIX)

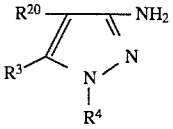 (XX)

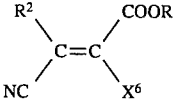 (XXI)

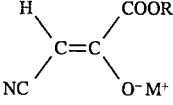 (XXIV)

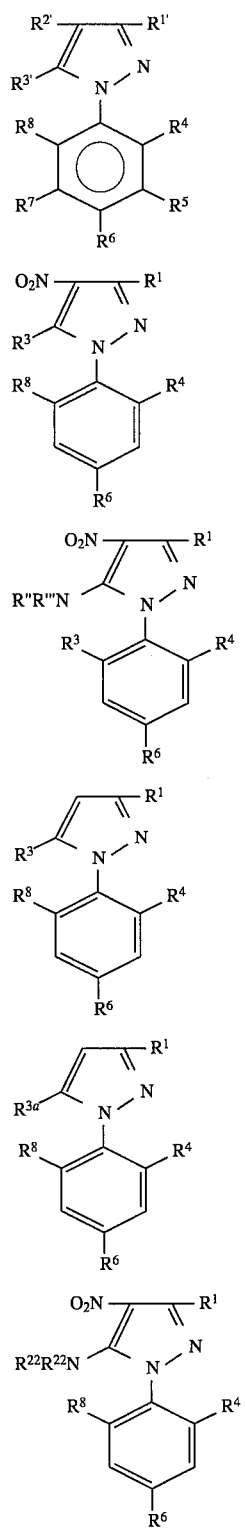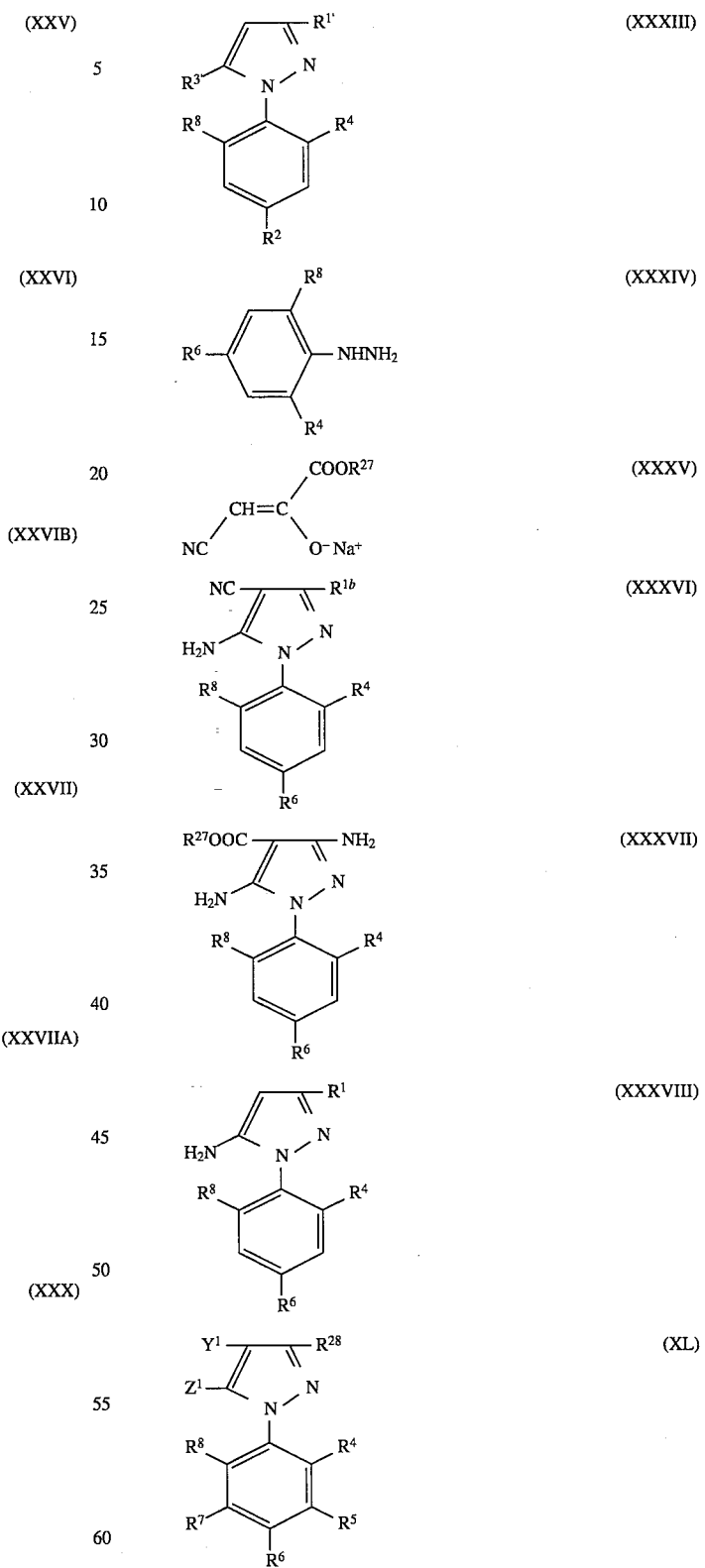

127
-continued
List of Formula

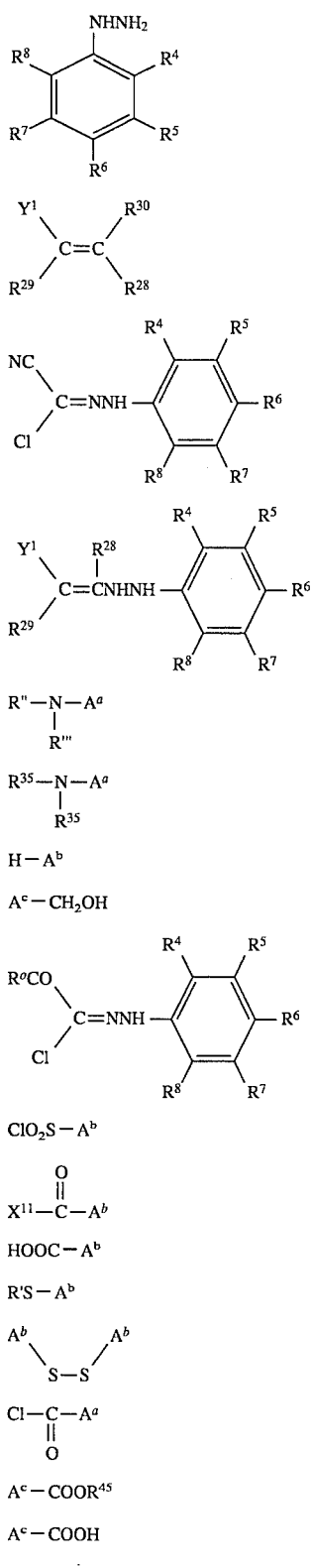

(XLI)
(XLII)
(XLIII)
(XLIV)
(XLV)
(XLVIII)
(LI)
(LII)
(LIII)
(LIV)
(LV)
(LVI)
(LVII)
(LVIII)
(LIX)
(LX)
(LXI)

128

In the above formulae it is to be understood that: $A^a$ represents

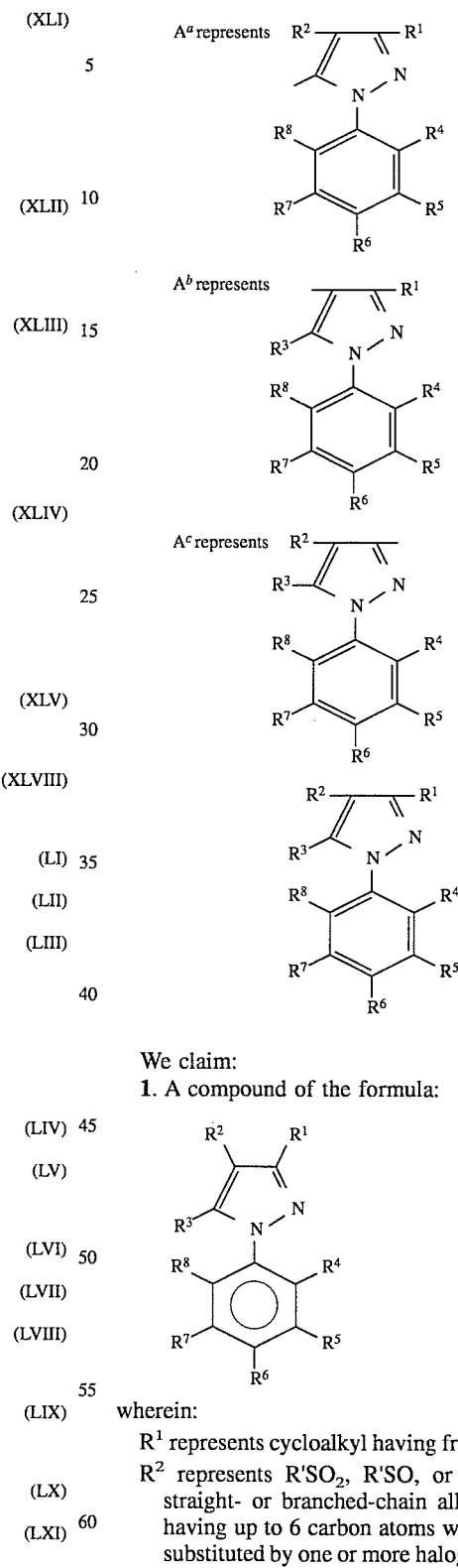

We claim:
1. A compound of the formula:

(I)

wherein:
$R^1$ represents cycloalkyl having from 3 to 6 carbon atoms;
$R^2$ represents $R'SO_2$, $R'SO$, or $R'S$ or wherein $R'$ is straight- or branched-chain alkyl, alkenyl or alkynyl having up to 6 carbon atoms which is unsubstituted or substituted by one or more halogen atoms which are the same or different; or R² is cyano, cycloalkyl having from 3 to 5 carbon atoms, straight- or branched-chain alkenyl having from 2 to 6 carbon atoms, thiocyanato, sulphamoyl which is unsubstituted or substituted by one or two straight- or branched-chain alkyl which are the same or different and which have from 1 to 6 carbon atoms, carbamoyl which is unsubstituted or substituted by one or two straight- or branched-chain alkyl which are the same or different and which have from 1 to 6 carbon atoms, straight- or branched-chain alkoxycarbonyl having from 2 to 7 carbon atoms, straight- or branched-chain alkanoyl having from 2 to 7 carbon atoms, or straight- or branched-chain alkyl having from 1 to 6 carbon atoms which is substituted by one or more halogen atoms;

R³ represents hydrogen, or an amino group —NR"R'" wherein R" and R'", which are the same or different, each represents hydrogen, straight- or branched-chain alkenylalkyl or alkynylalkyl having up to 5 carbon atoms, straight- or branched-chain alkyl having from 1 to 6 carbon atoms, and which are unsubstituted or substituted by straight- or branched-chain alkoxycarbonyl of 2 to 5 carbon atoms, formyl, or straight- or branched-chain alkanoyl having from 2 to 7 carbon atoms and being unsubstituted or substituted with one or more halogen atoms; or R" and R'", together with the nitrogen atom to which they are attached, form a 5 or 6 membered cyclic imide and are themselves unsubstituted or substituted by one or more halogen atoms; or R³ represents straight- or branched-chain alkoxycarbonyl having from 2 to 7 carbon atoms and being unsubstituted or substituted by one or more halogen atoms, or R³ represents straight- or branched-chain alkoxymethyleneamino having from 2 to 5 carbon atoms which is unsubstituted or substituted on methylene by a straight- or branched-chain alkyl having from 1 to 4 carbon atoms; or R³ represents halogen, cycloalkyl having from 3 to 6 carbon atoms, cycloalkylcarbonyl having from 4 to 7 carbon atoms or straight- or branched-chain alkoxycarbonyl having from 2 to 7 carbon atoms and which are unsubstituted or substituted by one or more halogen atoms; or R³ represents straight- or branched-chain alkylsulphenylamino having from 1 to 4 carbon atoms, straight- or branched-chain alkoxymethyleneamino having from 2 to 5 carbon atoms which is unsubstituted or substituted on methylene by a straight- or branched-chain alkyl having from 1 to 4 carbon atoms; or R³ represents straight- or branched-chain alkyl having from 1 to 4 carbon atoms, carboxy, or straight- or branched-chain alkylthio, alkylsulphinyl or alkylsulphonyl having from 1 to 6 carbon atoms which is unsubstituted or substituted by one or more halogen atoms; or R³ represents straight- or branched-chained trialkylsilylmethyl having from 1 to 6 carbon atoms in each alkyl group which are the same or different, trialkylsilyl having from 1 to 6 carbon atoms in each alkyl group which are the same or different, or a cyano or nitro group;

and R⁴, R⁵, R⁶, R⁷ and R⁸ are the same or different and represent halogen, straight- or branched-chain alkyl or alkoxy having from 1 to 4 carbon atoms which is unsubstituted or substituted by one or more halogen atoms, straight- or branched-chain alkylthio or alkylsulphinyl having from 1 to 4 carbon atoms which is substituted by one or more halogen atoms, nitro, cyano, or straight- or branched-chain alkylsulphonyl having from 1 to 4 carbon atoms which is unsubstituted or substituted by one or more halogen atoms.

2. A method for the control of arthropod, plant nematode or helminth pests at a locus which comprises treating the locus with a pesticidally effective amount of a compound of the formula:

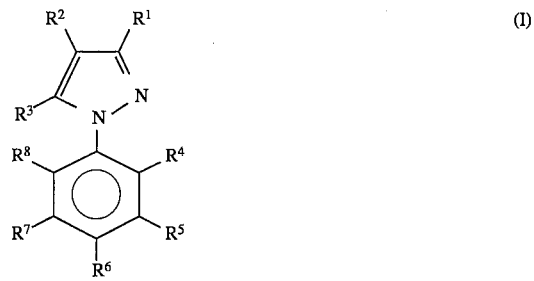

wherein:

R² represents halogen, cyano, a group R'SO₂, R'SO or R'S in which R' represents straight- or branched-chain alkyl having from 1 to 6 carbon atoms which is unsubstituted or substituted by one or more halogen atoms, cycloalkyl having from 3 to 5 carbon atoms, straight- or branched-chain alkenyl having from 2 to 6 carbon atoms, thiocyanato, sulphamoyl which is unsubstituted or substituted by one or two straight- or branched-chain alkyl which are the same or different and have from 1 to 6 carbon atoms, carbamoyl which is unsubstituted or substituted by one or two straight- or branched-chain alkyl which are the same or different and have from 1 to 6 carbon atoms, straight- or branched-chain alkoxycarbonyl having from 2 to 7 carbon atoms, straight- or branched-chain alkanoyl having from 2 to 7 carbon atoms, or straight- or branched-chain alkyl having from 1 to 6 carbon atoms which is unsubstituted or substituted by one or more halogen atoms;

R³ represents hydrogen, or an amino group —NR"R'" wherein R" and R'", which are the same or different, each represents hydrogen, straight- or branched-chain alkyl (having from 1 to 6 carbon atoms, and which is unsubstituted or substituted by straight- or branched-chain alkoxycarbonyl of 2 to 5 carbon atoms), cycloalkyl having from 3 to 6 carbon atoms, formyl, straight- or branched-chain alkanoyl (which has from 2 to 7 carbon atoms or together form a 5- or 6-membered cyclic imide with the nitrogen atom to which they are attached and themselves are unsubstituted or substituted by one or more halogen atoms), cycloalkylcarbonyl (which has from 4 to 7 carbon atoms) or straight- or branched-chain alkoxycarbonyl (which has from 2 to 7 carbon atoms and themselves are unsubstituted or substituted by one or more halogen atoms); or R³ represents straight- or branched-chain alkylsulphenylamino having from 1 to 4 carbon atoms, straight- or branched-chain alkoxymethyleneamino having from 2 to 5 carbon atoms which is unsubstituted or substituted on methylene by a straight- or branched-chain alkyl having from 1 to 4 carbon atoms, or represents halogen, straight- or branched-chain alkyl having from 1 to 4 carbon atoms, carboxy, or straight- or branched-chain alkylthio, alkylsulphinyl or alkylsulphonyl having from 1 to 6 carbon atoms which is unsubstituted or substituted by one or more halogen atoms, or represents straight- or branched-chain trialkylsilylmethyl having from 1 to 6 carbon atoms in each alkyl group which are the same or different, trialkylsilyl having from 1 to 6 carbon atoms in each alkyl group which are the same or different, cyano or nitro;

R⁴—R⁸ each represents hydrogen, halogen, straight- or branched-chain alkyl or alkoxy having from 1 to 4 carbon atoms which is unsubstituted or substituted by one or more halogen atoms, straight- or branched-chain alkylthio or alkylsulphinyl having from 1 to 4 carbon atoms which is substituted by one or more halogen atoms, nitro, cyano or straight- or branched-chain alkylsulphonyl having from 1 to 4 carbon atoms which is unsubstituted or substituted by one or more halogen atoms;

and $R^1$ represents cycloalkyl having from 3 to 6 carbon atoms;

or, when $R^3$ represents carboxy, a salt thereof with a pesticidally acceptable base.

3. A method according to claim 2 for the control of arthropod pests wherein, in formula (I), $R^2$ is other than a group R'SO or R'S in which R' represents straight- or branched-chain alkyl having from 1 to 6 carbon atoms which is substituted by one or more halogen atoms or the thiocyanato group; $R^3$ is other than an amino group —NR"R"' wherein R" or R"' represents cycloalkyl having from 3 to 6 carbon atoms, or straight- or branched-chain alkylthio, alkylsulphinyl or alkylsulphonyl which is substituted by one or more halogen atoms, trialkylsilylmethyl, trialkylsilyl or nitro; and $R^4$—$R^8$ each represent hydrogen, halogen, straight- or branched-chain alkyl or alkoxy having from 1 to 4 carbon atoms, trifluoromethyl, trifluoromethoxy, trifluoromethylthio, trifluoromethylsulphinyl, trifluoromethylsulphonyl, nitro, cyano or straight- or branched-chain alkylsulphonyl having from 1 to 4 carbon atoms.

4. A method according to claim 2 for the control of arthropods or helminths which are parasitic internally or externally upon vertebrates.

5. A method according to claim 2 for the control of arthropod or nematode pests of plants at a locus which comprises applying to the locus of a pesticidally effective amount of a compound of formula (I) or a pesticidally acceptable salt thereof.

6. A method according to claim 2 for the control of arthropods or helminths in man or domestic animals by oral, parenteral, percutaneous or topical administration.

7. A method according to claim 2, wherein, in formula (I), $R^4$—$R^8$ represent 2,4,6-trichloro, 2,3,5,6-tetrachloro, 2-chloro-4-trifluoromethyl, 2,3,5,6-tetrafluoro-4-trifluoromethyl, 2,6-dichloro-4-trifluoromethylthio, 2-chloro-3,5,6-trifluoro-4-trifluoromethyl, 2,6-dichloro-3,5-difluoro-4-trifluoromethyl, 2,6-dichloro-4-nitro, 2,6 -dichloro-4-trifluoromethylsulphinyl, 2,6-dichloro-4-methanesulphonyl or 2,6-dichloro-4 -trifluoromethanesulphonyl substitution.

8. A method according to claim 2 wherein, in formula (I), $R^4$—$R^8$ represent 2,6-dichloro-4-trifluoromethyl or 2,6-dichloro-4-trifluoromethoxy substitution.

9. A method according to claim 2 wherein the compound of formula (I) is 5 -amino-4-cyano-3-cyclopropyl-1-(2,6-dichloro-4-trifluoromethylphenyl)pyrazole.

10. An arthropodicidal, plant nematocidal or anthelmintic composition comprising a pesticidally effective amount of a compound of formula (I) as defined in claim 1, or a pesticidally acceptable salt thereof, in association with one or more compatible carriers.

11. A composition according to claim 10 suitable for administration to vertebrates or man by oral, parenteral, percutaneous or topical administration to control arthropod or helminth pests.

12. A composition according to claim 10 for application to growing crops and crop growing loci or as a seed dressing.

13. A solid or liquid composition according to claim 10 for application topically to animals, timber, stored products or household goods which comprises from 0.001% to 10% by weight of a compound of formula (I) or a pesticidally acceptable salt thereof.

14. A solid or liquid composition according to claim 10 for oral or parenteral, including percutaneous, administration to animals which comprises from 0.1% to 90% by weight of a compound of formula (I) or a pesticidally-acceptable salt thereof.

15. A dust or liquid composition according to claim 10 for application to livestock, persons, goods, premises or outdoor areas which comprises from about 0.005 % to about 2.0% by weight of a compound of formula (I) or a pesticidally-acceptable salt thereof.

16. A compound according to claim 1 wherein $R^4$—$R^8$ represent 2,4,6-trichloro, 2,3,5,6-tetrachloro, 2-chloro-4-trifluoromethyl, 2,3,5,6-tetrafluoro-4-trifluoromethyl, 2,6-dichloro-4-trifluoromethylthio, 2-chloro-3,5,6-trifluoro-4-trifluoromethyl, 2,6-dichloro-3,5-difluoro-4-trifluoromethyl, 2,6-dichloro-4-nitro, 2,6 -dichloro-4-trifluoromethylsulphinyl, 2,6-dichloro-4-methanesulphonyl or 2,6-dichloro-4-trifluoromethanesulphonyl substitution.

17. A compound according to claim 1 wherein $R^4$—$R^8$ represent 2,6-dichloro- 4-trifluorolethyl or 2,6-dichloro-4-trifluoromethoxy substitution.

18. The compound according to claim 1, which is 5-amino-4-cyano-3 -cyclopropyl- 1-(2,6-dichloro-4-trifluoromethylphenyl)pyrazole.

\* \* \* \* \*